United States Patent
Labadie et al.

(10) Patent No.: US 9,969,732 B2
(45) Date of Patent: May 15, 2018

(54) TETRAHYDROISOQUINOLINE ESTROGEN RECEPTOR MODULATORS AND USES THEREOF

(71) Applicant: Genentech, Inc., South San Francisco, CA (US)

(72) Inventors: Sharada Labadie, Sunnyvale, CA (US); Jun Liang, Palo Alto, CA (US); Daniel Fred Ortwine, San Ramon, CA (US); Maia Vinogradova, South San Francisco, CA (US); Xiaojing Wang, Foster City, CA (US); Jason Zbieg, South San Francisco, CA (US); Birong Zhang, Union City, CA (US); Tao Wang, Shanghai (CN)

(73) Assignee: Genentech, Inc., South San Francisco, CA (US)

( * ) Notice: Subject to any disclaimer, the term of this patent is extended or adjusted under 35 U.S.C. 154(b) by 0 days. days.

(21) Appl. No.: 15/481,757

(22) Filed: Apr. 7, 2017

(65) Prior Publication Data

US 2017/0320871 A1    Nov. 9, 2017

Related U.S. Application Data

(63) Continuation of application No. PCT/CN2016/078807, filed on Apr. 8, 2016.

(51) Int. Cl.
| | |
|---|---|
| *C07D 401/04* | (2006.01) |
| *C07D 217/00* | (2006.01) |
| *A61K 31/4725* | (2006.01) |
| *C07D 471/04* | (2006.01) |
| *C07D 401/12* | (2006.01) |
| *A61K 31/4745* | (2006.01) |
| *C07D 403/12* | (2006.01) |
| *A61K 31/55* | (2006.01) |
| *C07D 401/14* | (2006.01) |
| *A61K 31/5377* | (2006.01) |

(52) U.S. Cl.
CPC ........ *C07D 471/04* (2013.01); *A61K 31/4725* (2013.01); *A61K 31/4745* (2013.01); *A61K 31/5377* (2013.01); *A61K 31/55* (2013.01); *C07D 401/12* (2013.01); *C07D 401/14* (2013.01); *C07D 403/12* (2013.01)

(58) Field of Classification Search
None
See application file for complete search history.

(56) References Cited

U.S. PATENT DOCUMENTS

| | | | |
|---|---|---|---|
| 5,981,521 A * | 11/1999 | Haviv | ............. C07D 217/04 514/213.01 |
| 6,774,122 B2 | 8/2004 | Evans | |
| 7,456,160 B2 | 11/2008 | Evans | |
| 8,329,680 B2 | 12/2012 | Evans | |
| 8,466,139 B2 | 6/2013 | Evans | |

FOREIGN PATENT DOCUMENTS

WO    96/21656    7/1996

OTHER PUBLICATIONS

Ashby et al., "Activity of raloxifene in immature and ovariectomized rat uterotrophic assays" Regul Toxicol Pharmacol. 25(3):226-31 (Jun. 1997).
Bencze et al., "Synthetic estrogens, implantation inhibitors, and hypocholesterolemic agents. I. Tetrahydronaphthalene series" J Med Chem. 10(2):138-44 (Mar. 1967).
Cheng et al., "Relationship Between the Inhibition Constant (KI) and the Concentration of Inhibitor Which Causes 50 Per Cent Inhibition (I50) of an Enzymatic Reaction" Biochemical Pharmacology 22:3099-3108 (1973).

(Continued)

*Primary Examiner* — Zinna Northington Davis
(74) *Attorney, Agent, or Firm* — Kevin M. Clark

(57) ABSTRACT

Described herein are tetrahydroisoquinoline compounds with estrogen receptor modulation activity or function having the Formula I structure:

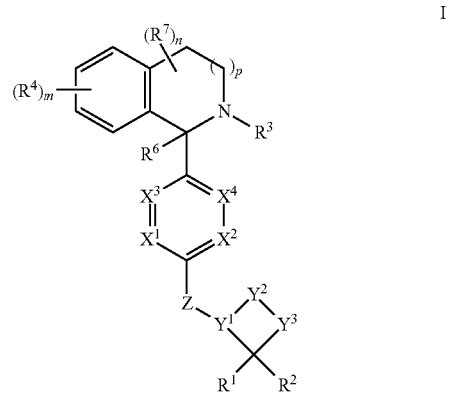

and stereoisomers, tautomers, or pharmaceutically acceptable salts thereof, and with the substituent and structural features described herein. Also described are pharmaceutical compositions and medicaments that include the Formula I compounds, as well as methods of using such estrogen receptor modulators, alone and in combination with other therapeutic agents, for treating diseases or conditions that are mediated or dependent upon estrogen receptors.

33 Claims, No Drawings

(56) References Cited

OTHER PUBLICATIONS

Dan R Robinson et al., "Activating ESR1 mutations in hormone-resistant metastatic breast cancer" Nature Genetics 45(12):1446-1451 (Nov. 3, 2013).
Ferroni et al., "Cyclic guanidines: Synthesis and antiplatelet activity of 4,6,7,8-tetrahydro-1H-imidazo[1,2-a]pyrazolo[3,4-d]pyrimidin-7-ones and 1,4,6,7,8,9-hexahydropyrazolo[3',4':4,5]pyrimido[2,1-c] 1,2,4]triazin-7-ones" Anzneim.-Forsch./Drug Res 40 (ii)( Suppl 12):1328-1331 ( 1990).
Howell, "Pure oestrogen antagonists for the treatment of advanced breast cancer" Endocr Relat Cancer 13(3):689-706 (Sep. 2006).
Jacob, "Resolution of (+/−)-5-Bromonornicitine. Synthesis of (R)- and (S)-Nornicotine of High Enantiomeric Purity" J Org Chem 47:4165-67 ( 1982).
Jeselsohn et al., "Emergence of constitutively active estrogen receptor-α mutations in pretreated advanced estrogen receptor-positive breast cancer" Clin Cancer Res. 20(7):1757-1767 (Apr. 2014).
Klinge, et al., "Estrogen receptor interaction with co-activators and co-repressors" Steroids 65(5):227-251 (May 2000).
Lednicer et al., "Mammalian antifertility agents. VI. A novel sequence for the preparation of 1,2-disubstituted 3,4-dihydronaphthalenes" J Med Chem. 12(5):881-5 (Sep. 1969).
Li et al., "Endocrine-therapy-resistant ESR1 variants revealed by genomic characterization of breast-cancer-derived xenografts" Cell Rep. 4(6):1116-30 (Sep. 2013).
Lochmuller et al., "Chromatographic resolution of enantiomers selective review" J Chromatogr 113(3):283-302 (Oct. 1975).
Merenbakh-Lamin et al., "D538G mutation in estrogen receptor-α: A novel mechanism for acquired endocrine resistance in breast cancer" Cancer Res. 73(23):6856-64 (Dec. 2013).
Okamoto et al., "Optical Resolution of Dihydropyridine Enantiomers by High-Performance Liquid Chromatography Using Phenylcarbamates of Polysaccharides as a Chiral Stationary Phase" Journal of Chromatography 513:375-378 ( 1990).
Prakash et al., "Disposition of lasofoxifene, a next-generation selective estrogen receptor modulator, in healthy male subjects" Drug Metab Dispos. 36(7):1218-26 (Jul. 2008).
Puhalla et al., "Hormonal therapy in breast cancer: a model disease for the personalization of cancer care" Mol Oncol. 6(2):222-36 (Apr. 2012).
Reid et al., "Cyclic, Proteasome-Mediated Turnover of Unliganded and Liganded ERα on Responsive Promoters Is an Integral Feature of Estrogen Signaling" Molecular Cell 11:695-707 ( 2003).
Renaud et al., "Estrogen receptor modulators: identification and structure-activity relationships of potent ERalpha-selective tetrahydroisoquinoline ligands" J Med Chem. 46(14)::2945-5 (Jul. 2003).
Renaud et al., "Selective estrogen receptor modulators with conformationally restricted side chains. Synthesis and structure-activity relationship of ERalpha-selective tetrahydroisoquinoline ligands" J Med Chem. 48(2):364-79 (Jan. 2005).
Rosati et al., "Discovery and preclinical pharmacology of a novel, potent, nonsteroidal estrogen receptor agonist/antagonist, CP-336156, a diaryltetrahydronaphthalene" J Med Chem. 41(16):2928-31 (Jul. 1998).
Schmidt et al., "Heilmittelchemische Studien in der heterocyclischen Reihe. 22. Mitteilung. Pyrazolo-pyrimidine II. Pyrazolo[3,4-d]pyrimidine mit Koffein-ähnlicher Struktur und Wirkung" Helvetica Chimica Acta (with English Summary), 41(4):1052-1060 ( 1958).
Tamrazi et al., "Molecular sensors of estrogen receptor conformations and dynamics" Mol Endocrinol. 17(12):2593-602 (Dec. 2003).
Toy et al., "ESR1 ligand-binding domain mutations in hormone-resistant breast cancer" Nat Genet. 45(12):1439-45 (Dec. 2013).
Wamhoff et al., "Heterocyclic B-Enamino Esters, 39.—Synthesis of 1H-Pyrazolo[3,4-d]Pyrimidines" Liebigs Annalen der Chemie 9:1910-1916 ( 1985).
Welboren et al., "Genomic actions of estrogen receptor α: what are the targets and how are they regulated?" Endocrine-Related Cancer, 16:1073-1089 ( 2009).

* cited by examiner

TETRAHYDROISOQUINOLINE ESTROGEN RECEPTOR MODULATORS AND USES THEREOF

CROSS REFERENCE TO RELATED APPLICATIONS

This non-provisional application filed under 37 CFR § 1.53(b), claims the benefit under 35 USC § 119(a) and § 365 of International Application No. PCT/CN2016/078807 filed on 8 Apr. 2016, which is incorporated by reference in its entirety.

FIELD OF THE INVENTION

Described herein are compounds, including pharmaceutically acceptable salts, solvates, metabolites, prodrugs thereof, pharmaceutical compositions comprising such compounds, and methods of using such compounds to treat, prevent or diagnose diseases or conditions that are estrogen sensitive, estrogen receptor dependent or estrogen receptor mediated in combination with other therapeutic agents.

BACKGROUND OF THE INVENTION

The estrogen receptor ("ER") is a ligand-activated transcriptional regulatory protein that mediates induction of a variety of biological effects through its interaction with endogenous estrogens. Endogenous estrogens include 17β (beta)-estradiol and estrogens. ER has been found to have two isoforms, ER-α (alpha) and ER-β (beta). Estrogens and estrogen receptors are implicated in a number of diseases or conditions, such as breast cancer, lung cancer, ovarian cancer, colon cancer, prostate cancer, endometrial cancer, uterine cancer, as well as others diseases or conditions. There is a need for new ER-α targeting agents that have activity in the setting of metastatic disease and acquired resistance.

SUMMARY OF THE INVENTION

The invention relates generally to tetrahydroisoquinoline (THIQ) compounds with estrogen receptor modulation activity or function and having the Formula I structure:

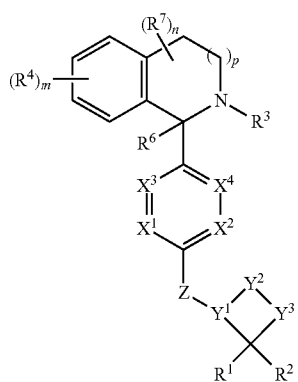

I and stereoisomers, tautomers, or pharmaceutically acceptable salts thereof, with the substituent and structural features described herein.

An aspect of the invention is a pharmaceutical composition of a Formula I compound and a pharmaceutically acceptable carrier, glidant, diluent, or excipient.

An aspect of the invention is a process for making a Formula I compound or a pharmaceutical composition comprising a Formula I compound.

An aspect of the invention is a method of treating an ER-related disease or disorder in a patient comprising administering a therapeutically effective amount of the pharmaceutical composition to a patient with an ER-related disease or disorder.

An aspect of the invention is a kit for treating a condition mediated by an estrogen receptor, comprising:

a) a pharmaceutical composition comprising a Formula I compound; and b) instructions for use.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. The nomenclature used in this Application is based on IUPAC systematic nomenclature, unless indicated otherwise.

Definitions

When indicating the number of sub students, the term "one or more" refers to the range from one substituent to the highest possible number of substitution, i.e. replacement of one hydrogen up to replacement of all hydrogens by substituent. The term "substituent" denotes an atom or a group of atoms replacing a hydrogen atom on the parent molecule. The term "substituted" denotes that a specified group bears one or more substituent. Where any group may carry multiple substituent and a variety of possible substituent is provided, the substituent are independently selected and need not to be the same. The term "unsubstituted" means that the specified group bears no substituent. The term "optionally substituted" means that the specified group is unsubstituted or substituted by one or more substituent, independently chosen from the group of possible sub students. When indicating the number of substituent, the term "one or more" or "one or more groups" means from one substituent to the highest possible number of substitution, i.e. replacement of one hydrogen up to replacement of all hydrogens by sub students, and in particular by one to three substituent.

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituent described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkyldiyl" as used herein refers to a saturated linear or branched-chain divalent hydrocarbon radical of about one to twelve carbon atoms ($C_1$-$C_{12}$), wherein the alkyldiyl radical may be optionally substituted independently with one or more substituent described below. In another embodiment, an alkyldiyl radical is one to eight carbon atoms ($C_1$-$C_8$), or one to six carbon atoms ($C_1$-$C_6$). Examples of alkyldiyl groups include, but are not limited to, methylene (—$CH_2$—), ethylene (—$CH_2CH_2$—), propylene (—$CH_2CH_2CH_2$—), and the like. An alkyldiyl group may also be referred to as an "alkylene" group.

The term "fluoroalkyldiyl" as used herein refers to an alkyldiyl radical substituted with one or more fluorine atoms.

The term "alkenyl" refers to linear or branched-chain monovalent hydrocarbon radical of two to eight carbon atoms ($C_2$-$C_8$) with at least one site of unsaturation, i.e., a carbon-carbon, sp$^2$ double bond, wherein the alkenyl radical may be optionally substituted independently with one or more substituent described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The terms "alkenylene" or "alkyldiyl" refer to a linear or branched-chain divalent hydrocarbon radical of two to eight carbon atoms ($C_2$-$C_8$) with at least one site of unsaturation, i.e., a carbon-carbon, sp$^2$ double bond, wherein the alkenylene radical may be optionally substituted independently with one or more substituent described herein, and includes radicals having "cis" and "trans" orientations, or alternatively, "E" and "Z" orientations. Examples include, but are not limited to, ethenylene or vinylene (—CH=CH—), allyl (—$CH_2$CH=CH—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituent described herein. Examples include, but are not limited to, ethynyl (—≡CH), propynyl (propargyl, —$CH_2$C≡CH), and the like.

The term "alkynylene" or "alkyldiyl" refer to a linear or branched divalent hydrocarbon radical of two to eight carbon atoms ($C_2$-$C_8$) with at least one site of unsaturation, i.e., a carbon-carbon, sp triple bond, wherein the alkynylene radical may be optionally substituted independently with one or more substituent described herein. Examples include, but are not limited to, ethynylene (—C≡C—), propynylene (propynylene, —$CH_2$C≡CH—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo [2.2.2]octane and bicyclo[3.2.2]nonane. Spiro carbocyclyl moieties are also included within the scope of this definition. Examples of spiro carbocyclyl moieties include [2.2]pentanyl, [2.3]hexanoyl, and [2.4]heptenyl. Examples of monocyclic carbocycles include, but are not limited to, cyclopropyl, cyclobutyl, cyclopentyl, 1-cyclopentyl-1-enyl, 1-cyclopentyl-2-enyl, 1-cyclopentyl-3-enyl, cyclohexyl, 1-cyclohexyl-1-enyl, 1-cyclohexyl-2-enyl, 1-cyclohexyl-3-enyl, cyclohexadiene, cycloheptyl, cyclooctyl, cyclo nonyl, cyclo decyl, cyclo undecyl, cyclo dodecyl, and the like. Carbocyclyl groups are optionally substituted independently with one or more substituent described herein.

The term "carbocyclyl" refers to a divalent non-aromatic, saturated or partially unsaturated ring having 3 to 12 carbon atoms ($C_3$-$C_{12}$) as a monocyclic ring or 7 to 12 carbon atoms as a bicyclic ring.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituent described herein.

The terms "arylene" or "aryldiyl" mean a divalent aromatic hydrocarbon radical of 6-20 carbon atoms ($C_6$-$C_{20}$) derived by the removal of two hydrogen atom from a two carbon atoms of a parent aromatic ring system. Some aryldiyl groups are represented in the exemplary structures as "Ar". Aryldiyl includes bicyclic radicals comprising an aromatic ring fused to a saturated, partially unsaturated ring, or aromatic carbocyclic ring. Typical aryldiyl groups include, but are not limited to, radicals derived from benzene (phenyldiyl), substituted benzenes, naphthalene, anthracene, biphenylene, indenylene, indanylene, 1,2-dihydronaphthalene, 1,2,3,4-tetrahydronaphthyl, and the like. Aryldiyl groups are also referred to as "arylene", and are optionally substituted with one or more substituent described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituent described below. A heterocycle may be a mono cycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholine-4-yl, piperidine-1-yl, piperazinyl, piperazine-4-yl-2-one, piperazine-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyclo[3.1.0]hexanoyl, 3-azabicyclo[4.1.0]heptenyl, azabicyclo[2.2.2]hexanoyl, 3H-indolyl quinolizinyl and N-pyridyl ureas. Spiro heterocyclyl moieties are also included within the scope of this definition. Examples of spiro heterocyclyl moieties include azaspiro[2.5]octanyl and azaspiro[2.4]heptenyl. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituent described herein.

The term "heterocyclyldiyl" refers to a divalent, saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituent as described.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituent described herein.

The term "heteroaryldiyl" refers to a divalent aromatic radical of 5-, 6-, or 7-membered rings, and includes fused ring systems (at least one of which is aromatic) of 5-20 atoms, containing one or more heteroatoms independently selected from nitrogen, oxygen, and sulfur.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The terms "treat" and "treatment" refer to therapeutic treatment, wherein the object is to slow down (lessen) an undesired physiological change or disorder, such as the development or spread of arthritis or cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those with the condition or disorder.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

"Hematological malignancies" (British spelling "Haematological" malignancies) are the types of cancer that affect blood, bone marrow, and lymph nodes. As the three are intimately connected through the immune system, a disease affecting one of the three will often affect the others as well: although lymphoma is a disease of the lymph nodes, it often spreads to the bone marrow, affecting the blood. Hematological malignancies are malignant neoplasms ("cancer"), and they are generally treated by specialists in hematology and/or oncology. In some centers "Hematology/oncology" is a single subspecialty of internal medicine while in others they are considered separate divisions (there are also surgical and radiation oncologists). Not all hematological disorders are malignant ("cancerous"); these other blood conditions may also be managed by a hematologist. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin. Leukemias include Acute lymphoblastic leukemia (ALL), Acute myelogenous leukemia (AML), Chronic lymphocytic leukemia (CLL), Chronic myelogenous leukemia (CML), Acute monocytic leukemia (AMOL) and small lymphocytic lymphoma (SLL). Lymphomas include Hodgkin's lymphomas (all four subtypes) and Non-Hodgkin's lymphomas (NHL, all subtypes).

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: ibrutinib (IMBRUVICA™, APCI-32765, Pharmacyclics Inc./Janssen Biotech Inc.; CAS Reg. No. 936563-96-1, U.S. Pat. No. 7,514,444), idelalisib (ZYDELIG®, CAL-101, GS 1101, GS-1101, Gilead Sciences Inc.; CAS Reg. No. 1146702-54-6), erlotinib (TARCEVA®, Genentech/OSI Pharm.), docetaxel (TAXOTERE®, Sanofi-Aventis), 5-FU (fluorouracil, 5-fluorouracil, CAS Reg. No. 51-21-8), gemcitabine (GEMZAR®, Lilly), PD-0325901 (CAS No. 391210-10-9, Pfizer), cisplatin (Platinol®, (SP-4-2)-diamminedichloroplatinum(II), cis-diamine, dichloroplatinum (II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®, CAS No. 23214-92-8), Akti-1/2, HPPD, and rapamycin.

Chemotherapeutic agents include inhibitors of B-cell receptor targets such as BTK, Bcl-2 and JAK inhibitors.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chlorambucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate) and selective estrogen receptor modulators (SERDs) such as fulvestrant (FASLODEX®, Astra Zeneca); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors, such as cobimetinib (WO 2007/044515); (v) lipid kinase inhibitors, such as taselisib (GDC-0032, Genentech Inc.); (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (PERJETA™, 2C4, Genentech), trastuzumab (HERCEPTIN®, Genentech), trastuzumab emtansine (KADCYLA®, Genentech Inc.), and tositumomab (BEXXAR, Corixia).

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a Formula I compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative as depicted in Table 1 structures for illustrative purposes, while stereochemistry is definitively established, such as from x-ray crystallographic data.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "pharmaceutically acceptable salts" denotes salts which are not biologically or otherwise undesirable. Pharmaceutically acceptable salts include both acid and base addition salts. The phrase "pharmaceutically acceptable" indicates that the substance or composition must be compatible chemically and/or toxicologically, with the other ingredients comprising a formulation, and/or the mammal being treated therewith.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, aryl-aliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenyl acetic acid, methanesulfonic acid "mesylate", ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, and polyamine resins A "solvate" refers to an association or complex of one or more solvent molecules and a compound of the invention. Examples of solvents that form solvates include, but are not limited to, water, isopropanol, ethanol, methanol, DMSO, ethylacetate (EtOAc), acetic acid (AcOH), and ethanolamine.

The term "$EC_{50}$" is the half maximal effective concentration" and denotes the plasma concentration of a particular compound required for obtaining 50% of the maximum of a particular effect in vivo.

The term "Ki" is the inhibition constant and denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

The term "$IC_{50}$" is the half maximal inhibitory concentration and denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed, and can be converted to an absolute inhibition constant (Ki) using the Cheng-Prusoff equation (Biochem. Pharmacol. (1973) 22:3099). Other percent inhibition parameters, such as $IC_{70}$, $IC_{90}$, etc., may be calculated.

The terms "compound of this invention," and "compounds of the present invention" and "compounds of Formula I" include compounds of Formulas I and stereoisomers, geometric isomers, tautomers, solvates, metabolites, and pharmaceutically acceptable salts and prodrugs thereof.

Any formula or structure given herein, including Formula I compounds, is also intended to represent hydrates, solvates, and polymorphs of such compounds, and mixtures thereof.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I, Various isotopically labeled compounds of the present invention, for example those into which radioactive isotopes such as 3H, 13C, and 14C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labeled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

Estrogen Receptor

Estrogen receptor alpha (ER-α; NR3A1) and estrogen receptor beta (ER-β; NR3A2) are steroid hormone receptors, which are members of the large nuclear receptor superfamily. Nuclear receptors share a common modular structure, which minimally includes a DNA binding domain (DBD) and a ligand binding domain (LBD). Steroid hormone receptors are soluble, intracellular proteins that act as ligand-regulated transcription factors. Vertebrates contain five closely related steroid hormone receptors (estrogen receptor, androgen receptor, progesterone receptor, glucocorticoid receptor, mineralcorticoid receptor), which regulate a wide spectrum of reproductive, metabolic and developmental activities. The activities of ER are controlled by the binding of endogenous estrogens, including 17β-estradiol and estrogens.

The ER-α (alpha) gene is located on 6q25.1 and encodes a 595 AA protein. The ER-β gene resides on chromosome 14q23.3 and produces a 530 AA protein. However, due to alternative splicing and translation start sites, each of these genes can give rise to multiple isoforms. In addition to the DNA binding domain (called C domain) and ligand binding domain (E domain) these receptors contain an N-terminal (AB) domain, a hinge (D) domain that links the C and E domains, and a C-terminal extension (F domain) (Gronemeyer and Laudet; Protein Profile 2: 1173-1308, 1995). While the C and E domains of ER-α and ER-β are quite conserved (95% and 55% amino acid identity, respectively), conservation of the A, B, D and F domains is poor (below 30% amino acid identity). Both receptors are involved in the regulation and development of the female reproductive tract but also play various roles in the central nervous system, cardiovascular systems and bone metabolism.

The ligand binding pocket of steroid hormone receptors is deeply buried within the ligand binding domain. Upon binding, the ligand becomes part of the hydrophobic core of this domain. Consequently most steroid hormone receptors are instable in the absence of hormone and require assistance from chaperones, such as Hsp90, in order to maintain hormone-binding competency. The interaction with Hsp90 also controls nuclear translocation of these receptors. Ligand-binding stabilizes the receptor and initiates sequential conformational changes that release the chaperones, alter the interactions between the various receptor domains and remodel protein interaction surfaces that allow these receptors to translocate into the nucleus, bind DNA and engage in interactions with chromatin remodeling complexes and the transcriptional machinery. Although ER can interact with Hsp90, this interaction is not required for hormone binding and, dependent on the cellular context, apo-ER can be both cytoplasmic and nuclear. Biophysical studies indicated that DNA binding rather than ligand binding contributes to the stability of the receptor (Greenfield et al., 2001) (Biochemistry 40: 6646-6652).

ER can interact with DNA either directly by binding to a specific DNA sequence motif called estrogen response element (ERE) (classical pathway), or indirectly via protein-protein interactions (nonclassical pathway) (Welboren et al., Endocrine-Related Cancer 16: 1073-1089, 2009). In the nonclassical pathway, ER has been shown to tether to other transcription factors including SP-1, AP-1 and NF-κB. These interactions appear to play critical roles in the ability of ER to regulate cell proliferation and differentiation.

Both types of ER DNA interactions can result in gene activation or repression dependent on the transcriptional coregulators that are recruited by the respective ER-ERE complex (Klinge, Steroid 65: 227-251, 2000). The recruitment of coregulators is primarily mediated by two protein interaction surfaces, the AF2 and AF1. AF2 is located in the ER E-domain and its conformation is directly regulated by the ligand (Brzozowski et al., (1997) Nature 389: 753-758,). Full agonists appear to promote the recruitment of co-activators, whereas weak agonists and antagonists facilitate the binding of co-repressors. The regulation of protein with the AF1 is less well understood but can be controlled by serine phosphorylation (Ward and Weigel, (2009) Biofactors 35: 528-536). One of the involved phosphorylation sites (S118) appears to control the transcriptional activity of ER in the presence of antagonists such as tamoxifen, which plays an important role in the treatment of breast cancer. While full agonists appear to arrest ER in certain conformation, weak agonists tend to maintain ER in equilibrium between different conformations, allowing cell-dependent differences in co-regulator repertoires to modulate the activity of ER in a cell-dependent manner (Tamrazi et al., Mol. Endocrinol. 17: 2593-2602, 2003). Interactions of ER with DNA are dynamic and include, but are not limited to, the degradation of ER by the proteasome (Reid et al., Mol Cell 11: 695-707, 2003). The degradation of ER with ligands provides an attractive treatment strategy for diseases or conditions that are estrogen-sensitive and/or resistant to available anti-hormonal treatments. ER signaling is crucial for the development and maintenance of female reproductive organs including breasts, ovulation and thickening of the endometrium. ER signaling also has a role in bone mass, lipid metabolism, cancers, etc. About 70% of breast cancers express ER-α (alpha) (ER-α positive) and are dependent on estrogens for growth and survival. Other cancers also are thought to be dependent on ER-α signaling for growth and survival, such as for example ovarian and endometrial cancers. The ER-α antagonist tamoxifen has been used to treat early and advanced ER-α positive breast cancer in both pre- and post-menopausal women. Fulvestrant (FASLODEX®, AstraZeneca) a steroid-based ER antagonist is used to treat breast cancer in women which have progressed despite therapy with tamoxifen (Howell A. (2006) Endocr Relat Cancer; 13:689-706; U.S. Pat. No. 6,774,122; U.S. Pat. No. 7,456,160; U.S. Pat. No. 8,329,680; U.S. Pat. No.

8,466,139). Steroidal and non-steroidal aromatase inhibitors are also used to treat cancers in humans. In some embodiments, the steroidal and non-steroidal aromatase inhibitors block the production of estrogen from androstenedione and testosterone in post-menopausal women, thereby blocking ER dependent growth in the cancers. In addition to these anti-hormonal agents, progressive ER positive breast cancer is treated in some cases with a variety of other chemotherapeutics, such as for example, the anthracylines, platins, taxanes. In some cases, ER positive breast cancers that harbor genetic amplification of the ERB-B/HER2 tyrosine kinase receptor are treated with the monoclonal antibody trastuzumab (Herceptin®, Genentech Inc.) or the small molecule pan-ERB-B inhibitor lapatinib (TYKERB®, GlaxoSmith Kline Corp.). Despite this battery of anti-hormonal, chemotherapeutic and small-molecule and antibody-based targeted therapies, many women with ER-α positive breast develop progressive metastatic disease and are in need of new therapies. Importantly, the majority of ER positive tumors that progress on existing anti-hormonal, as well as and other therapies, are thought to remain dependent on ER-α for growth and survival. Thus, there is a need for new ER-α targeting agents that have activity in the setting of metastatic disease and acquired resistance. In one aspect, described herein are compounds that are selective estrogen receptor modulators (SERMs). In specific embodiments, the SERMs described herein are selective estrogen receptor degraders (SERDs). In some embodiments, in cell-based assays the compounds described herein result in a reduction in steady state ER-α levels (i.e. ER degradation) and are useful in the treatment of estrogen sensitive diseases or conditions and/or diseases or conditions that have developed resistant to anti-hormonal therapies.

Most breast cancer patients are treated with agents that either block estrogen synthesis (e.g., aromatase inhibitors; AIs) or antagonize the effects of estradiol via competitive ER binding (e.g., tamoxifen) (Puhalla S, et al Mol Oncol 2012; 6(2):222-236). Despite the well documented therapeutic utility of these agents in various stages of disease, many ER+ breast cancers recur and patients eventually succumb. Recently, next generation whole genome and targeted sequencing has identified ESR1 (estrogen receptor alpha gene) mutations in up to 20% of tumors from patients with advanced breast cancer who have progressed on endocrine therapies, largely aromatase inhibitors (Li S, et al. Cell Rep (2013); 4(6): 1116-1130; Merenbakh-Lamin K, et al. Cancer Res (2013); 73(23): 6856-6864; Robinson D R, et al. Nat Genet (2013); 45(12): 1446-1451; Toy W, et al. Nat Genet (2013); 45(12): 1439-1445; Jeselsohn R, et al. Clin Cancer Res (2014); 20: 1757-1767). These ligand-binding domain (LBD) mutations confer high basal activity of the apo-receptor rendering them ligand-independent and thus active in the setting of low estradiol. There is a need for therapies that target ER signaling with robust activity in the setting of progressive disease post AI or tamoxifen treatment including the subset of patients harboring ESR1 mutant tumors.

In some embodiments, Formula I compounds disclosed herein are used in methods for treating a hormone resistant-estrogen receptor (ER) positive breast cancer in a patient characterized as having a mutation in the ESR1 gene, comprising administering a therapeutically-effective amount of a Formula I compound. In some embodiments, the mutation in the ESR1 gene results in an ER polypeptide having an amino acid substitution at a position selected from among amino acids positions 6, 118, 269, 311, 341, 350, 380, 392, 394, 433, 463, 503, 534, 535, 536, 537, 538 and 555 of SEQ ID NO:2. In some embodiments the mutation results in an ER polypeptide having an amino acid substitution selected from among H6Y, S118P, R269C, T311M, S341L, A350E, E380Q, V392I, R394H, S433P, S463P, R503W, V534E, P535H, L536R, L536P, L536Q, Y537N, Y537C, Y537S, D538G, and R555C. In some embodiments, the patient has two or more mutations in the ESR1 gene.

Given the central role of ER-α in breast cancer development and progression, compounds disclosed herein are useful in the treatment of breast cancer, either alone or in combination with other agent agents that can modulate other critical pathways in breast cancer, including but not limited to those that target IGF1R, EGFR, CDK 4/6, erB-B2 and 3, the PI3K/AKT/mTOR axis, HSP90, PARP or histone deacetylases.

Given the central role of ER-α in breast cancer development and progression, Formula I compounds disclosed herein are useful in the treatment of breast cancer, either alone or in combination with other agent used to treat breast cancer, including but not limited to aromatase inhibitors, anthracyclines, platins, nitrogen mustard alkylating agents, taxanes. Illustrative agent used to treat breast cancer, include, but are not limited to, PI3K inhibitors such as taselisib (GDC-0032, Genentech Inc.), paclitaxel, anastrozole, exemestane, cyclophosphamide, epirubicin, fulvestrant, letrozole (FEMARA®, Novartis, Corp.), gemcitabine, trastuzumab, pegfilgrastim, filgrastim, tamoxifen, docetaxel, toremifene, vinorelbine, capecitabine (XELODA®, Roche), ixabepilone, as well as others described herein.

ER-related diseases or conditions include ER-α dysfunction is associated with cancer (bone cancer, breast cancer, lung cancer, colorectal cancer, endometrial cancer, prostate cancer, ovarian and uterine cancer), central nervous system (CNS) defects (alcoholism, migraine), cardiovascular system defects (aortic aneurysm, susceptibility to myocardial infarction, aortic valve sclerosis, cardiovascular disease, coronary artery disease, hypertension), hematological system defects (deep vein thrombosis), immune and inflammation diseases (Graves' Disease, arthritis, multiple sclerosis, cirrhosis), susceptibility to infection (hepatitis B, chronic liver disease), metabolic defects (bone density, cholestasis, hypospadias, obesity, osteoarthritis, osteopenia, osteoporosis), neurological defects (Alzheimer's disease, Parkinson's disease, migraine, vertigo), psychiatric defects (anorexia nervosa, attention deficit hyperactivity disorder (ADHD), dementia, major depressive disorder, psychosis) and reproductive defects (age of menarche, endometriosis, infertility.

In some embodiments, compounds disclosed herein are used in the treatment of an estrogen receptor dependent or estrogen receptor mediated disease or condition in mammal.

In some embodiments, compounds disclosed herein are used to treat cancer in a mammal. In some embodiments, the cancer is breast cancer, ovarian cancer, endometrial cancer, prostate cancer, or uterine cancer. In some embodiments, the cancer is breast cancer, lung cancer, ovarian cancer, endometrial cancer, prostate cancer, or uterine cancer. In some embodiments, the cancer is breast cancer. In some embodiments, the cancer is a hormone dependent cancer. In some embodiments, the cancer is an estrogen receptor dependent cancer. In some embodiments, the cancer is an estrogen-sensitive cancer. In some embodiments, the cancer is resistant to anti-hormonal treatment. In some embodiments, the cancer is an estrogen-sensitive cancer or an estrogen receptor dependent cancer that is resistant to anti-hormonal treatment. In some embodiments, the cancer is a hormone-sensitive cancer or a hormone receptor dependent cancer that is resistant to anti-hormonal treatment. In some embodiments, anti-hormonal treatment includes treatment with at least one agent selected from tamoxifen, fulvestrant, steroidal aromatase inhibitors, and non-steroidal aromatase inhibitors.

In some embodiments, compounds disclosed herein are used to treat hormone receptor positive metastatic breast cancer in a postmenopausal woman with disease progression following anti-estrogen therapy.

In some embodiments, compounds disclosed herein are used to treat a hormonal dependent benign or malignant disease of the breast or reproductive tract in a mammal. In some embodiments, the benign or malignant disease is breast cancer.

In some embodiments, the compound used in any of the methods described herein is an estrogen receptor degrader; is an estrogen receptor antagonist; has minimal or negligible estrogen receptor agonist activity; or combinations thereof.

In some embodiments, methods of treatment with compounds described herein include a treatment regimen that includes administering radiation therapy to the mammal.

In some embodiments, methods of treatment with compounds described herein include administering the compound prior to or following surgery.

In some embodiments, methods of treatment with compounds described herein include administering to the mammal at least one additional anti-cancer agent.

In some embodiments, compounds disclosed herein are used to treat cancer in a mammal, wherein the mammal is chemotherapy-näve.

In some embodiments, compounds disclosed herein are used in the treatment of cancer in a mammal. In some embodiments, compounds disclosed herein are used to treat cancer in a mammal, wherein the mammal is being treated for cancer with at least one anti-cancer agent. In one embodiment, the cancer is a hormone refractory cancer.

In some embodiments, compounds disclosed herein are used in the treatment or prevention of diseases or conditions of the uterus in a mammal. In some embodiments, the disease or condition of the uterus is leiomyoma, uterine leiomyoma, endometrial hyperplasia, or endometriosis. In some embodiments, the disease or condition of the uterus is a cancerous disease or condition of the uterus. In some other embodiments, the disease or condition of the uterus is a non-cancerous disease or condition of the uterus.

In some embodiments, compounds disclosed herein are used in the treatment of endometriosis in a mammal.

In some embodiments, compounds disclosed herein are used in the treatment of leiomyoma in a mammal. In some embodiments, the leiomyoma is a uterine leiomyoma, esophageal leiomyoma, cutaneous leiomyoma, or small bowel leiomyoma. In some embodiments, compounds disclosed herein are used in the treatment of fibroids in a mammal. In some embodiments, compounds disclosed herein are used in the treatment of uterine fibroids in a mammal.

Tetrahydroisoquinoline Compounds

The present invention provides tetrahydroisoquinoline compounds of Formula I, including Formulas Ia-Ii, and pharmaceutical formulations thereof, which are potentially useful in the treatment of diseases, conditions and/or disorders modulated by Estrogen Receptor alpha (ERa).

Formula I compounds have the structure:

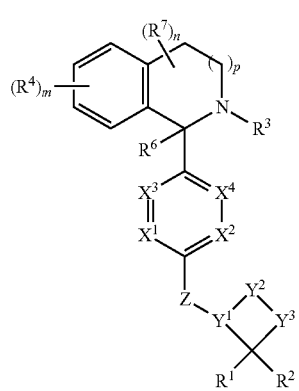

I and stereoisomers, tautomers, or pharmaceutically acceptable salts thereof, wherein:
$Y^1$ is —C($R^b$)— or N;
$Y^2$ is —CH$_2$— or —N($R^a$)—;
$Y^3$ is —N($R^a$)— or —C($R^b$)$_2$—;
where one of $Y^1$, $Y^2$ and $Y^3$ is N or —N($R^a$)—;
$R^a$ and $R^c$ are independently selected from H, $C_1$-$C_6$ alkyl, $C_1$-$C_6$ fluoroalkyl, allyl, propargyl, $C_3$-$C_6$ cycloalkyl, and $C_3$-$C_6$ heterocyclyl, optionally substituted with one or more groups independently selected from F, Cl, Br, I, CN, OH, OCH$_3$, and SO$_2$CH$_3$;
$R^b$ is independently selected from H, —O($C_1$-$C_3$ alkyl), $C_1$-$C_6$ alkyl, $C_1$-$C_6$ fluoroalkyl, allyl, propargyl, $C_3$-$C_6$ cycloalkyl, and $C_3$-$C_6$ heterocyclyl, optionally substituted with one or more groups independently selected from F, Cl, Br, I, CN, OH, OCH$_3$, and SO$_2$CH$_3$;
where at least one of $R^a$ and $R^b$ is —CH$_2$Cl, —CH$_2$F, —CHF$_2$, —CF$_3$, —CH$_2$CH$_2$F, —CH$_2$CHF$_2$, —CH$_2$CF$_3$, CH$_2$CH$_2$Cl, CH$_2$CH$_2$CH$_2$F, CH$_2$CH$_2$CHF$_2$, CH$_2$CH$_2$CF$_3$, or CH$_2$CH$_2$CH$_2$Cl;
$X^1$, $X^2$, $X^3$, and $X^4$ are independently selected from CR$^5$ and N; where none, one, or two of $X^1$, $X^2$, $X^3$, and $X^4$ is N;
Z is selected from O, S, S(O), S(O)$_2$, C(=O), CH(OH), $C_1$-$C_6$ alkyldiyl, CH(OH)—($C_1$-$C_6$ alkyldiyl), $C_1$-$C_6$ fluoroalkyldiyl, NR$^c$, NR$^c$—($C_1$-$C_6$ alkyldiyl), NR$^c$—($C_1$-$C_6$ fluoroalkyldiyl), O—($C_1$-$C_6$ alkyldiyl), and O—($C_1$-$C_6$ fluoroalkyldiyl);
$R^1$ and $R^2$ are independently selected from H, F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$Cl, —CH$_2$F, —CHF$_2$, —CH$_2$NH$_2$, —CH$_2$NHSO$_2$CH$_3$, —CH$_2$NHCH$_3$, —CH$_2$N(CH$_3$)$_2$, —CF$_3$, —CH$_2$CF$_3$, —CH$_2$CHF$_2$, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CONHCH$_2$CH$_3$, —CONHCH(CH$_3$)$_2$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazine-1-yl, morpholinomethyl, morpholino-methanone, and morpholino;

R³ is selected from C₁-C₆ alkyl, C₁-C₆ fluoroalkyl, allyl, propargyl, C₃-C₆ cycloalkyl, phenyl, C₃-C₆ heterocyclyl, C₆-C₂₀ aryl or C₁-C₆ heteroaryl, —CO—(C₁-C₆ alkyl), —CO—(C₃-C₆ cycloalkyl), —S(O)₂—(C₁-C₆ alkyl), and —S(O)₂—(C₃-C₆ cycloalkyl), optionally substituted with one or more groups independently selected from F, Cl, Br, I, CN, OH, OCH₃, and SO₂CH₃;

R⁴ is independently selected from F, Cl, Br, I, —CN, —CH₃, —CH₂CH₃, —CH(CH₃)₂, —CH₂CH(CH₃)₂, —CH₂OH, —CH₂OCH₃, —CH₂CH₂OH, —C(CH₃)₂OH, —CH(OH)CH(CH₃)₂, —C(CH₃)₂CH₂OH, —CH₂CH₂SO₂CH₃, —CH₂OP(O)(OH)₂, —CH₂F, —CHF₂, —CH₂NH₂, —CH₂NHSO₂CH₃, —CH₂NHCH₃, —CH₂N(CH₃)₂, —CF₃, —CH₃CF₃, —CH₂CHF₂, —CH(CH₃)CN, —C(CH₃)₂CN, —CH₂CN, —CO₂H, —COCH₃, —CO₂CH₃, —CO₂C(CH₃)₃, —COCH(OH)CH₃, —CONH₂, —CONHCH₃, —CONHCH₂CH₃, —CONHCH(CH₃)₂, —CON(CH₃)₂, —C(CH₃)₂CONH₂, —NH₂, —NHCH₃, —N(CH₃)₂, —NHCOCH₃, —N(CH₃)COCH₃, —NHS(O)₂CH₃, —N(CH₃)C(CH₃)₂CONH₂, —N(CH₃)CH₂CH₂S(O)₂CH₃, —NO₂, =O, —OH, —OCH₃, —OCH₂CH₃, —OCH₂CH₂OCH₃, —OCH₂CH₂OH, —OCH₂CH₂N(CH₃)₂, —OP(O)(OH)₂, —S(O)₂N(CH₃)₂, —SCH₃, —S(O)₂CH₃, —S(O)₃H, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-ylmethanone, piperazine-1-yl, morpholinomethyl, morpholino-methanone, and morpholino; or two R⁴ groups on vicinal carbon atoms form a five- or six-membered, fused carbocyclyl, heterocyclyl, or heteroaryl ring;

R⁵ is selected from H, F, Cl, Br, I, —CN, —CH₃, —CH₂CH₃, —CH(CH₃)₂, —CH₂CH(CH₃)₂, —CH₂OH, —CH₂OCH₃, —CH₂CH₂OH, —CH(OH)₂OH, —CH(CH₃)₂, —C(CH₃)₂CH₂OH, —CH₂CH₂SO₂CH₃, —CH₂OP(O)(OH)₂, —CH₂F, —CHF₂, —CH₂NH₂, —CH₂NHSO₂CH₃, —CH₂NHCH₃, —CH₂N(CH₃)₂, —CF₃, —CH₂CF₃, —CH₂CHF₂, —CH(CH₃)CN, —C(CH₃)₂CN, —CH₂CN, —CO₂H, —COCH₃, —CO₂CH₃, —CO₂C(CH₃)₃, —COCH(OH)CH₃, —CONH₂, —CONHCH₃, —CONHCH₂CH₃, —CONHCH(CH₃)₂, —CON(CH₃)₂, —C(CH₃)₂CONH₂, —NH₂, —NHCH₃, —N(CH₃)₂, —NHCOCH₃, —N(CH₃)COCH₃, —NHS(O)₂CH₃, —N(CH₃)C(CH₃)₂CONH₂, —N(CH₃)CH₂CH₂S(O)₂CH₃, —NO₂, =O, —OCH₃, —OCH₂CH₃, —OCH₂CH₂OCH₃, —OCH₂CH₂OH, —OCH₂CH₂N(CH₃)₂, —OP(O)(OH)₂, —S(O)₂N(CH₃)₂, —SCH₃, —S(O)₂CH₃, —S(O)₃H, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-ylmethanone, piperazine-1-yl, morpholinomethyl, morpholino-methanone, and morpholino;

R⁶ is selected from H, F, and C₁-C₆ alkyl optionally substituted with one or more groups independently selected from F, Cl, Br, I, CN, OH, OCH₃, and SO₂CH₃;

R⁷ is independently selected from F, and C₁-C₆ alkyl optionally substituted with one or more groups independently selected from F, Cl, Br, I, CN, OH, OCH₃, and SO₂CH₃;

m is selected from 0, 1, 2, 3, and 4;
n is selected from 0, 1, 2, 3, and 4; and
p is 1 or 2;

where alkyldiyl, fluoroalkyldiyl, aryl, carbocyclyl, heterocyclyl, and heteroaryl are optionally substituted with one or more groups independently selected from F, Cl, Br, I, —CN, —CH₃, —CH₂CH₃, —CH(CH₃)₂, —CH₂CH(CH₃)₂, —CH₂OH, —CH₂OCH₃, —CH₂CH₂OH, —C(CH₃)₂OH, —CH(OH)CH(CH₃)₂, —C(CH₃)₂CH₂OH, —CH₂CH₂SO₂CH₃, —CH₂OP(O)(OH)₂, —CH₂F, —CHF₂, —CF₃, —CH₂CF₃, —CH₂CHF₂, —CH(CH₃)₂CN, —C(CH₃)₂CN, —CH₂CN, —CH₂NH₂, —CH₂NHSO₂CH₃, —CH₂NHCH₃, —CH₂N(CH₃)₂, —CO₂H, —COCH₃, —CO₂CH₃, —CO₂C(CH₃)₃, —COCH(OH)CH₃, —CONH₂, —CONHCH₃, —CON(CH₃)₂, —C(CH₃)₂CONH₂, —NH₂, —NHCH₃, —N(CH₃)₂, —NHCOCH₃, —N(CH₃)COCH₃, —NHS(O)₂CH₃, —N(CH₃)C(CH₃)₂CONH₂, —N(CH₃)CH₂CH₂S(O)₂CH₃, —NO₂, =O, —OH, —OCH₃, —OCH₂CH₃, —OCH₂CH₂OCH₃, —OCH₂CH₂OH, —OCH₂CH₂N(CH₃)₂, —OP(O)(OH)₂, —S(O)²N(CH₃)₂, —SCH₃, —S(O)₂CH₃, —S(O)₃H, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-ylmethanone, piperazine-1-yl, morpholinomethyl, morpholino-methanone, and morpholino.

Formula Ia-i compounds have the structures:

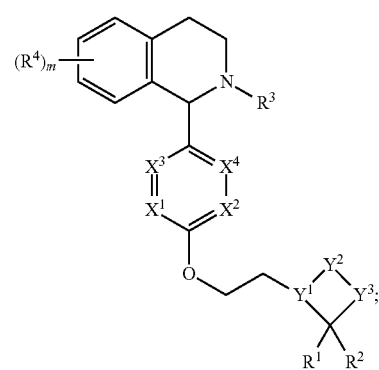

Ia

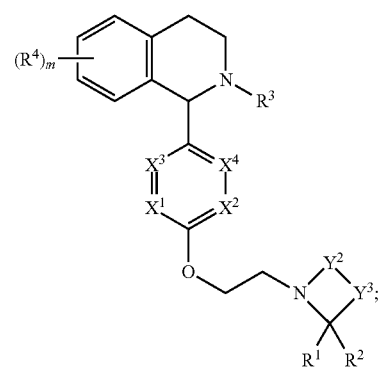

Ib

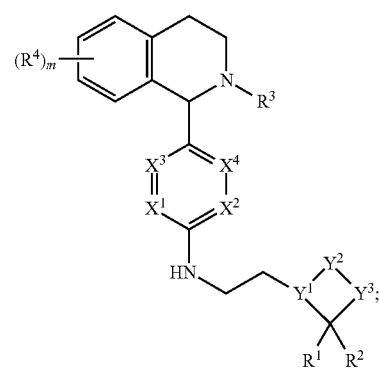

Ic

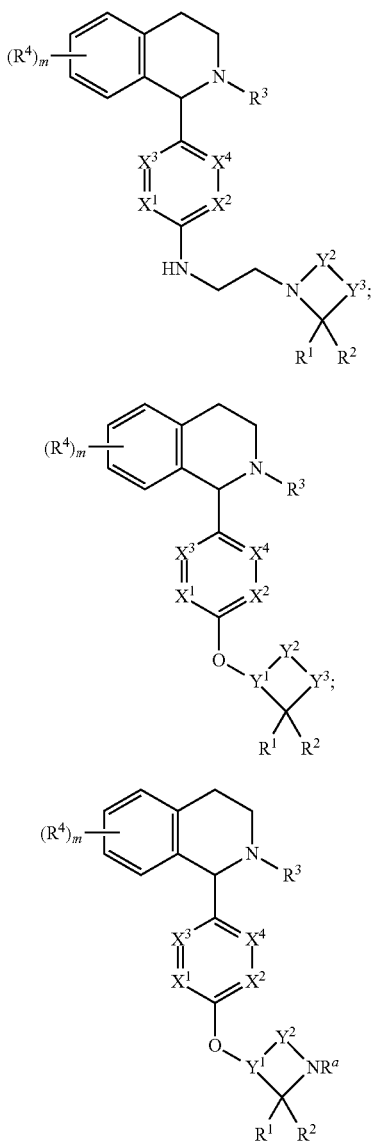

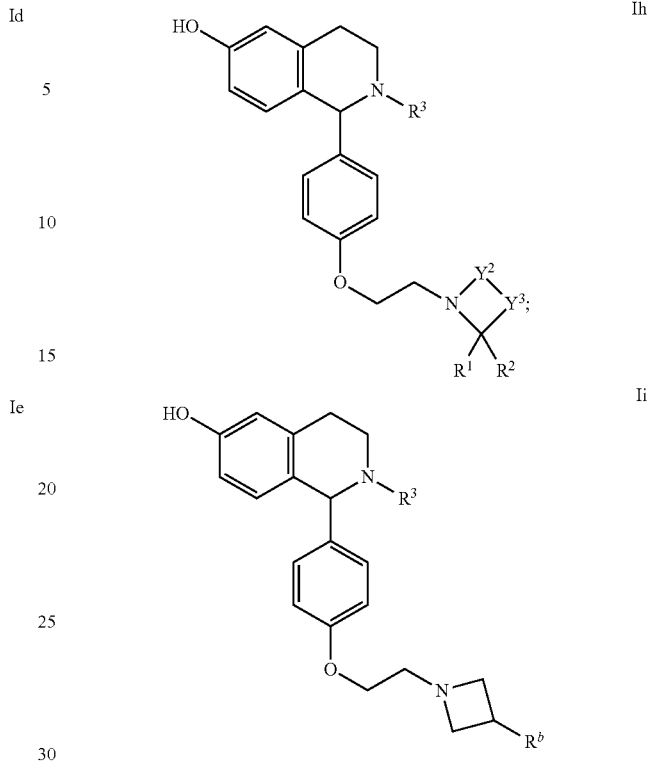

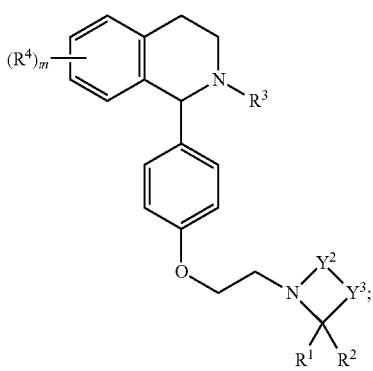

wherein R$^a$ is —CH$_2$Cl, —CH$_2$F, —CHF$_2$, —CF$_3$, —CH$_2$CH$_2$F, —CH$_2$CHF$_2$, —CH$_2$CF$_3$, or —CH$_2$CH$_2$CH$_2$F;

Exemplary embodiments of Formula I compounds include wherein R$^a$ is selected from —CH$_2$Cl, —CH$_2$F, —CHF$_2$, —CF$_3$, —CH$_2$CH$_2$F, —CH$_2$CHF$_2$, —CH$_2$CF$_3$, and —CH$_2$CH$_2$CH$_2$F.

Exemplary embodiments of Formula I compounds include wherein Y$^1$ is —C(R$^b$)— and Y$^3$ is —N(R$^a$)—.

Exemplary embodiments of Formula I compounds include wherein Y$^1$ is N and Y$^3$ is —C(R$^b$)$_2$—.

Exemplary embodiments of Formula I compounds include wherein Y$^2$ is —CH$_2$—.

Exemplary embodiments of Formula I compounds include wherein p is 1.

Exemplary embodiments of Formula I compounds include wherein p is 2.

Exemplary embodiments of Formula I compounds include wherein Y$^3$ is —N(R$^a$)— and R$^a$ is —CH$_2$Cl, —CH$_2$F, —CHF$_2$, —CF$_3$, —CH$_2$CH$_2$F, —CH$_2$CHF$_2$, or —CH$_2$CF$_3$.

Exemplary embodiments of Formula I compounds include wherein X$^1$, X$^2$, X$^3$, and X$^4$ are each CR$^5$ and R$^5$ is H or F.

Exemplary embodiments of Formula I compounds include wherein one of X$^1$, X$^2$, X$^3$, and X$^4$ is N.

Exemplary embodiments of Formula I compounds include wherein Z is O or O—(C$_1$-C$_6$ alkyldiyl).

Exemplary embodiments of Formula I compounds include wherein R$^1$ and R$^2$ are H.

Exemplary embodiments of Formula I compounds include wherein R$^3$ is C$_1$-C$_6$ fluoroalkyl.

Exemplary embodiments of Formula I compounds include wherein R$^3$ is C$_6$-C$_{20}$ aryl, and wherein R$^3$ is phenyl.

Exemplary embodiments of Formula I compounds include wherein R$^4$ is OH, and m is 1.

Exemplary embodiments of Formula I compounds include wherein two R$^4$ groups form a pyrazole ring.

Exemplary embodiments of Formula I compounds include wherein R$^6$ is H.

Biological Evaluation

Formula I compounds demonstrate surprising and unexpected cell-based potency and efficient ERa degradation. The relative efficacies of Formula I compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$". Determination of $IC_{50}$ values can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

Cell proliferation, cytotoxicity, and cell viability of the Formula I compounds can be measure by the CellTiter-Glo® Luminescent Cell Viability Assay (Promega Corp.). The CellTiter-Glo® Luminescent Cell Viability Assay is a homogeneous method of determining the number of viable cells in culture based on quantitation of the ATP present, an indicator of metabolically active cells. The CellTiter-Glo® Assay is designed for use with multiwell formats, making it ideal for automated high-throughput screening (HTS), cell proliferation and cytotoxicity assays. The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

Exemplary Formula I compounds in Tables 1a and 1b were made, characterized, and tested for binding to ERa (Estrogen Receptor alpha) and biological activity according to the assays, protocols, and procedures of Examples 901-907. ER-alpha MCF7 HCS $S_{inf}$(%) values in Tables 1a and 1b were measured by the Breast Cancer Cell ERa High Content Fluorescence Imaging Degradation Assay of Example 901. ER-alpha MCF7 HCS $EC_{50}$ (μM) values in Table 1 were measured by the in vitro cell proliferation assays described in Examples 902 and 903. The rat uterine wet weight assays of Examples 906 and 906 allow rapid determination of compound antagonist activity in an ER responsive tissue (immature rat uterus) while competing against the native ER ligand estradiol, i.e. antagonist mode (Ashby, J.; et al (1997) Regulatory toxicology and pharmacology: RTP, 25 (3):226-31).

Exemplary Formula I compounds in Tables 1a and 1b have the following structures, corresponding names (ChemBioDraw, Versions 11, 12, or 14, CambridgeSoft Corp., Cambridge Mass.), and biological activity. Where more than one name is associated with a Formula I compound or intermediate, the chemical structure shall define the compound. Assignment of configuration at chiral centers may be tentative. In some instances, the absolute stereochemistry of enantiomers has been assigned arbitrarily and will await determination by conventional techniques such as x-ray crystallography. The invention contemplates all stereoisomers, as racemic mixtures, stereoisomeric enriched mixtures, and separated enantiomers or diastereomers.

Exemplary Formula I compounds may be compared in Table 2 with lasofoxifene, (5R,6S)-6-phenyl-5-(4-(2-(pyrrolidin-1-yl)ethoxy)phenyl)-5,6,7,8-tetrahydronaphthalen-2-ol (FABLYN®, Pfizer, CAS Reg. 180916-16-9, Gennari, L. et al (2006) Expert Opin. Investig. Drugs 15 (9): 1091-103) in the MCF7 ERa degradation assay. The maximal degradation effect (S inf) of lasofoxifene is −73.5%, which is significantly lower than many of the Formula I compounds of Table 1. Another comparator ERa-selective tetrahydroisoquinoline compound, 2-phenyl-1-(4-(2-(piperidine-1-yl)ethoxy)phenyl)-1,2,3,4-tetrahydroisoquinolin-6-ol, CAS Reg. 573674-34-7 (racemic), 573674-59-6 (R isomer), 573674-60-9 (S isomer) (Compound 18a: Renaud et al (2003) Jour. Med. Chem. 46(14):2945-2957; Compound 60: Renaud et al (2005) Jour. Med. Chem. 48(2):364-379), showed only weak in vitro cellular proliferation inhibition (0.00174 μMol EC50) and weak SERD degradation effect −52.5 HCS S inf. The structural features of Formula I compounds provide surprising and unexpected properties of in vitro potency and ERa degradation.

TABLE 1a

Formula I compounds

| No. | Structure | IUPAC Name | ER-alpha (WT) MCF7 HCS (EC50) (μMol) | ERalpha (WT) MCF7 HCS (S inf) | Mass Spec. M + H/1 |
|---|---|---|---|---|---|
| 101 | 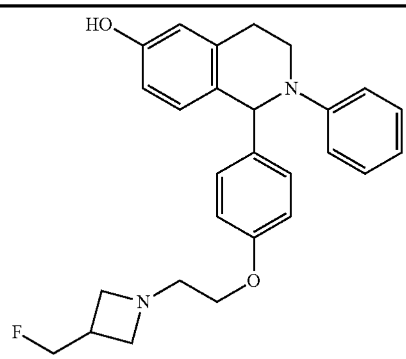 | 1-[4-[2-[3-(fluoromethyl)azetidin-1-yl]ethoxy]phenyl]-2-phenyl-3,4-dihydro-1H-isoquinolin-6-ol | 0.00021 | −99 | 433.1 |

TABLE 1a-continued

Formula I compounds

| No. | Structure | IUPAC Name | ER-alpha (WT) MCF7 HCS (EC50) (μMol) | ERalpha (WT) MCF7 HCS (S inf) | Mass Spec. M + H/1 |
|---|---|---|---|---|---|
| 102 | 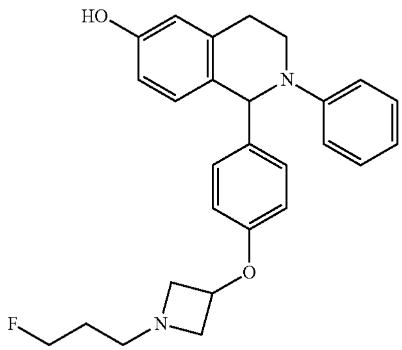 [SMILES: Oc1ccc2c(c1)CCN(c1ccccc1)C2c1ccc(OC2CN(CCCF)C2)cc1] | 1-[4-[1-(3-fluoropropyl)azetidin-3-yl]oxyphenyl]-2-phenyl-3,4-dihydro-1H-isoquinolin-6-ol | 0.00087 | −98 | 433.3 |
| 103 | 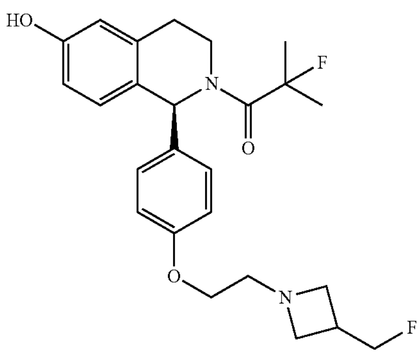 [SMILES: CC(C)(F)C(=O)N1CCc2cc(O)ccc2[C@@H]1c1ccc(OCCN2CC(CF)C2)cc1] | 2-fluoro-1-[(1S)-1-[4-[2-[3-(fluoromethyl)azetidin-1-yl]ethoxy]phenyl]-6-hydroxy-3,4-dihydro-1H-isoquinolin-2-yl]-2-methyl-propan-1-one | 0.10 | | 445.2 |
| 104 | 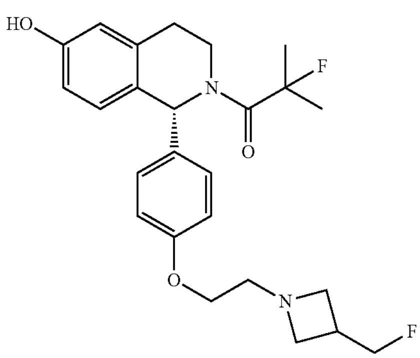 [SMILES: CC(C)(F)C(=O)N1CCc2cc(O)ccc2[C@H]1c1ccc(OCCN2CC(CF)C2)cc1] | 2-fluoro-1-[(1R)-1-[4-[2-[3-(fluoromethyl)azetidin-1-yl]ethoxy]phenyl]-6-hydroxy-3,4-dihydro-1H-isoquinolin-2-yl]-2-methyl-propan-1-one | 0.000741 | −90 | 445.2 |
| 105 | 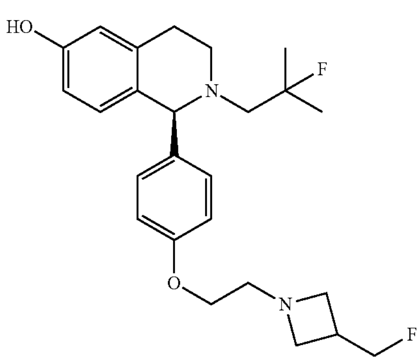 [SMILES: CC(C)(F)CN1CCc2cc(O)ccc2[C@@H]1c1ccc(OCCN2CC(CF)C2)cc1] | (S)-2-(2-fluoro-2-methylpropyl)-1-(4-(2-(3-(fluoromethyl)azetidin-1-yl)ethoxy)phenyl)-1,2,3,4-tetrahydroisoquinolin-6-ol | 0.000146 | −98 | 432.3 |

TABLE 1a-continued

Formula I compounds

| No. | Structure | IUPAC Name | ER-alpha (WT) MCF7 HCS (EC50) (μMol) | ERalpha (WT) MCF7 HCS (S inf) | Mass Spec. M + H/1 |
|---|---|---|---|---|---|
| 106 | 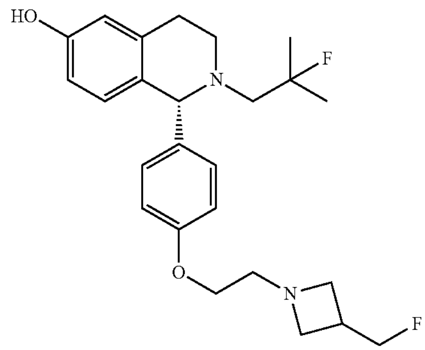 [SMILES: CC(C)(F)CN1CCc2cc(O)ccc2[C@H]1c1ccc(OCCN2CC(CF)C2)cc1] | (R)-2-(2-fluoro-2-methylpropyl)-1-(4-(2-(3-(fluoromethyl)azetidin-1-yl)ethoxy)phenyl)-1,2,3,4-tetrahydroisoquinolin-6-ol | 0.000042 | −101 | 432.2 |
| 107 | 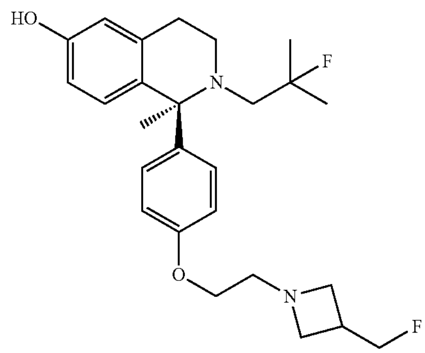 [SMILES: CC(C)(F)CN1CCc2cc(O)ccc2[C@]1(C)c1ccc(OCCN2CC(CF)C2)cc1] | (1S)-1-[4-[2-[3-(fluoromethyl)azetidin-1-yl]ethoxy]phenyl]-2-(2-fluoro-2-methyl-propyl)-1-methyl-3,4-dihydroisoquinolin-6-ol | 0.00322 | −97 | 445.3 |
| 108 | 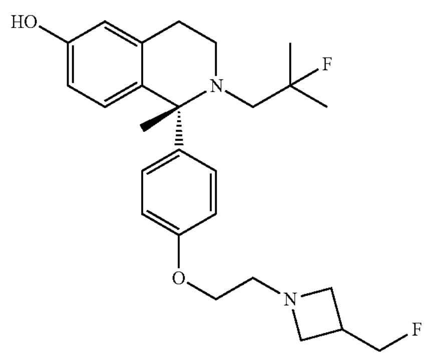 [SMILES: CC(C)(F)CN1CCc2cc(O)ccc2[C@@]1(C)c1ccc(OCCN2CC(CF)C2)cc1] | (1R)-1-[4-[2-[3-(fluoromethyl)azetidin-1-yl]ethoxy]phenyl]-2-(2-fluoro-2-methyl-propyl)-1-methyl-3,4-dihydroisoquinolin-6-ol | 0.0000344 | −98 | 445.3 |
| 109 | 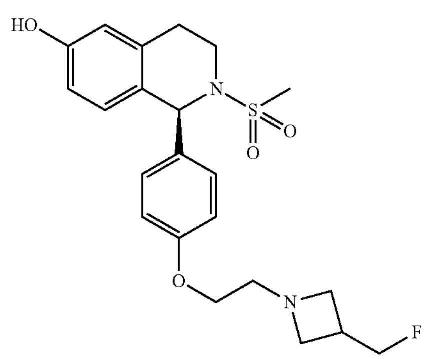 [SMILES: CS(=O)(=O)N1CCc2cc(O)ccc2[C@@H]1c1ccc(OCCN2CC(CF)C2)cc1] | (1S)-1-[4-[2-[3-(fluoromethyl)azetidin-1-yl]ethoxy]phenyl]-2-methylsulfonyl-3,4-dihydro-1H-isoquinolin-6-ol | 0.1 | | 435.2 |

TABLE 1a-continued

Formula I compounds

| No. | Structure | IUPAC Name | ER-alpha (WT) MCF7 HCS (EC50) (µMol) | ERalpha (WT) MCF7 HCS (S inf) | Mass Spec. M + H/1 |
|---|---|---|---|---|---|
| 110 | 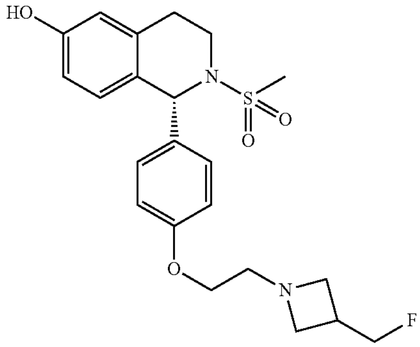 [SMILES: CS(=O)(=O)N1CCc2cc(O)ccc2[C@H]1c1ccc(OCCN2CC(CF)C2)cc1] | (1R)-1-[4-[2-[3-(fluoromethyl)azetidin-1-yl]ethoxy]phenyl]-2-methylsulfonyl-3,4-dihydro-1H-isoquinolin-6-ol | 0.00828 | −85 | 435.2 |
| 111 | 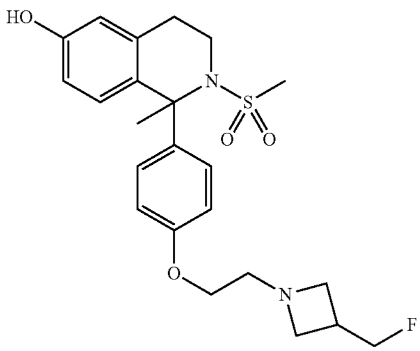 [SMILES: CC1(c2ccc(OCCN3CC(CF)C3)cc2)c2ccc(O)cc2CCN1S(C)(=O)=O] | 1-[4-[2-[3-(fluoromethyl)azetidin-1-yl]ethoxy]phenyl]-1-methyl-2-methylsulfonyl-3,4-dihydroisoquinolin-6-ol | 0.1 | | 449.2 |
| 112 | 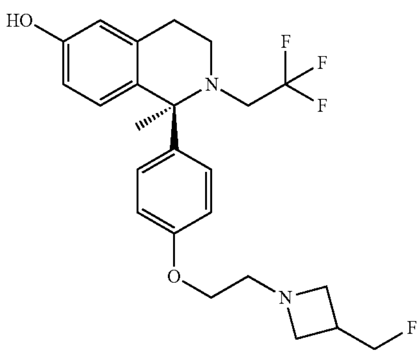 [SMILES: C[C@]1(c2ccc(OCCN3CC(CF)C3)cc2)c2ccc(O)cc2CCN1CC(F)(F)F] | (1S)-1-[4-[2-[3-(fluoromethyl)azetidin-1-yl]ethoxy]phenyl]-1-methyl-2-(2,2,2-trifluoroethyl)-3,4-dihydroisoquinolin-6-ol | 0.00441 | −97 | 453.2 |
| 113 | 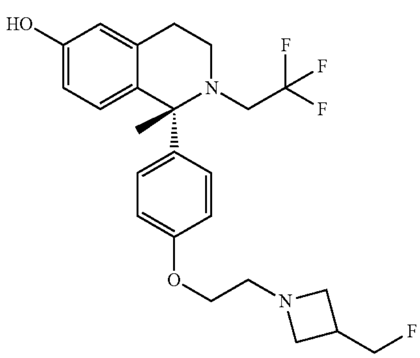 | (1R)-1-[4-[2-[3-(fluoromethyl)azetidin-1-yl]ethoxy]phenyl]-1-methyl-2-(2,2,2-trifluoroethyl)-3,4-dihydroisoquinolin-6-ol | 0.0000608 | −99 | 453.2 |

TABLE 1a-continued

Formula I compounds

| No. | Structure | IUPAC Name | ER-alpha (WT) MCF7 HCS (EC50) (µMol) | ERalpha (WT) MCF7 HCS (S inf) | Mass Spec. M + H/1 |
|---|---|---|---|---|---|
| 114 | 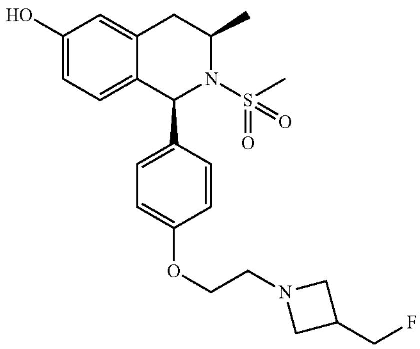 [SMILES: C[C@@H]1Cc2cc(O)ccc2[C@H](c2ccc(OCCN3CC(CF)C3)cc2)N1S(C)(=O)=O] | (1S,3R)-1-[4-[2-[3-(fluoromethyl)azetidin-1-yl]ethoxy]phenyl]-3-methyl-2-methylsulfonyl-3,4-dihydro-1H-isoquinolin-6-ol | 0.1 | | 449.2 |
| 115 | 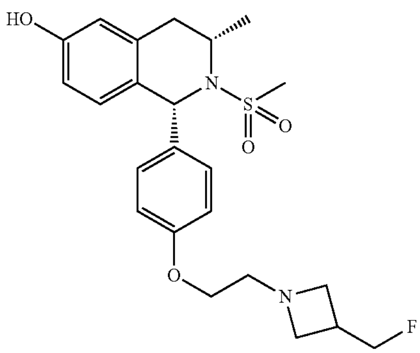 [SMILES: C[C@H]1Cc2cc(O)ccc2[C@@H](c2ccc(OCCN3CC(CF)C3)cc2)N1S(C)(=O)=O] | (1R,3S)-1-[4-[2-[3-(fluoromethyl)azetidin-1-yl]ethoxy]phenyl]-3-methyl-2-methylsulfonyl-3,4-dihydro-1H-isoquinolin-6-ol | 0.0614 | −53 | 449.2 |
| 116 | 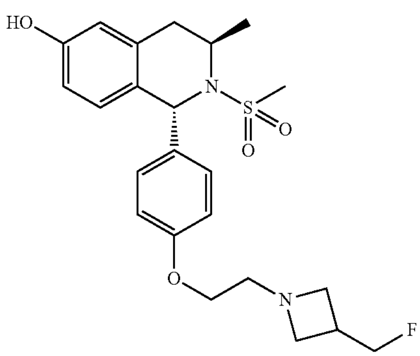 [SMILES: C[C@@H]1Cc2cc(O)ccc2[C@@H](c2ccc(OCCN3CC(CF)C3)cc2)N1S(C)(=O)=O] | (1R,3R)-1-[4-[2-[3-(fluoromethyl)azetidin-1-yl]ethoxy]phenyl]-3-methyl-2-methylsulfonyl-3,4-dihydro-1H-isoquinolin-6-ol | 0.00030 | −93 | 449.2 |
| 117 | 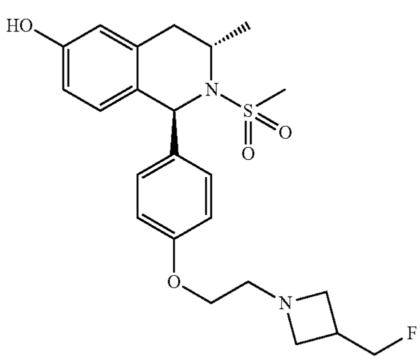 [SMILES: C[C@H]1Cc2cc(O)ccc2[C@H](c2ccc(OCCN3CC(CF)C3)cc2)N1S(C)(=O)=O] | (1S,3S)-1-[4-[2-[3-(fluoromethyl)azetidin-1-yl]ethoxy]phenyl]-3-methyl-2-methylsulfonyl-3,4-dihydro-1H-isoquinolin-6-ol | 0.1 | | 449.2 |

TABLE 1a-continued

Formula I compounds

| No. | Structure | IUPAC Name | ER-alpha (WT) MCF7 HCS (EC50) (μMol) | ERalpha (WT) MCF7 HCS (S inf) | Mass Spec. M + H/1 |
|---|---|---|---|---|---|
| 118 | 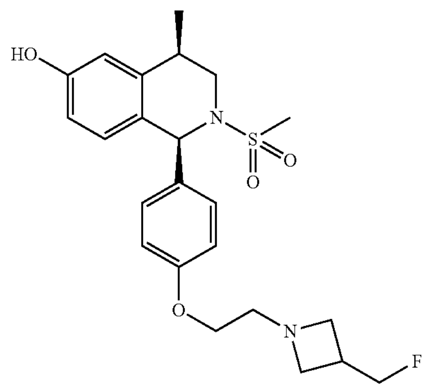 [SMILES: C[C@H]1CN(S(C)(=O)=O)[C@@H](c2ccc(OCCN3CC(CF)C3)cc2)c2ccc(O)cc21] | (1S,4R)-1-[4-[2-[3-(fluoromethyl)azetidin-1-yl]ethoxy]phenyl]-4-methyl-2-methylsulfonyl-3,4-dihydro-1H-isoquinolin-6-ol | 0.1 | | 449.2 |
| 119 | 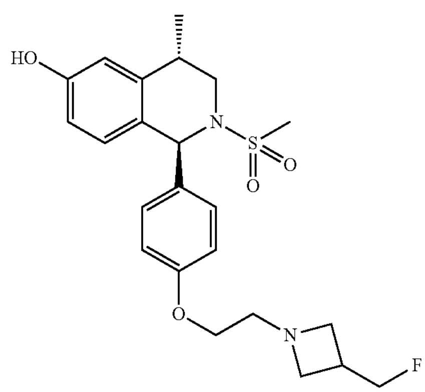 [SMILES: C[C@@H]1CN(S(C)(=O)=O)[C@@H](c2ccc(OCCN3CC(CF)C3)cc2)c2ccc(O)cc21] | (1S,4S)-1-[4-[2-[3-(fluoromethyl)azetidin-1-yl]ethoxy]phenyl]-4-methyl-2-methylsulfonyl-3,4-dihydro-1H-isoquinolin-6-ol | 0.1 | | 449.2 |
| 120 | 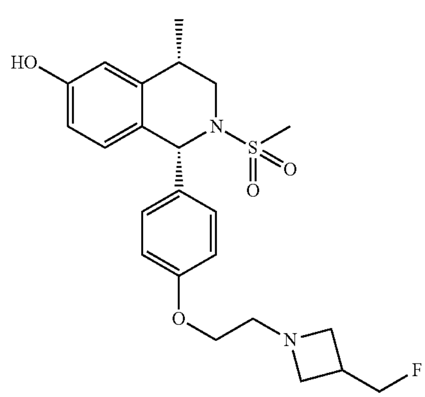 [SMILES: C[C@@H]1CN(S(C)(=O)=O)[C@H](c2ccc(OCCN3CC(CF)C3)cc2)c2ccc(O)cc21] | (1R,4S)-1-[4-[2-[3-(fluoromethyl)azetidin-1-yl]ethoxy]phenyl]-4-methyl-2-methylsulfonyl-3,4-dihydro-1H-isoquinolin-6-ol | 0.0259 | −60 | 449.2 |

TABLE 1a-continued

Formula I compounds

| No. | Structure | IUPAC Name | ER-alpha (WT) MCF7 HCS (EC50) (μMol) | ERalpha (WT) MCF7 HCS (S inf) | Mass Spec. M + H/1 |
|---|---|---|---|---|---|
| 121 | 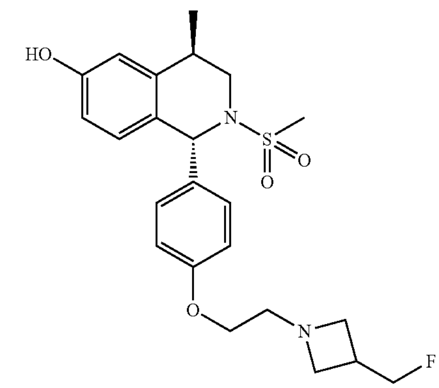 [SMILES: C[C@H]1CN(S(C)(=O)=O)[C@H](c2ccc(OCCN3CC(CF)C3)cc2)c2ccc(O)cc21] | (1R,4R)-1-[4-[2-[3-(fluoromethyl)azetidin-1-yl]ethoxy]phenyl]-4-methyl-2-methylsulfonyl-3,4-dihydro-1H-isoquinolin-6-ol | 0.0181 | −70 | 449.2 |
| 122 | 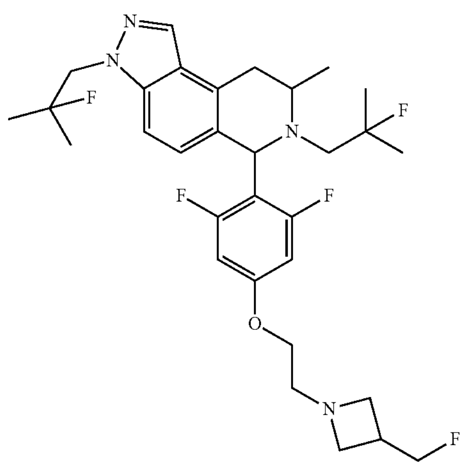 [SMILES: CC1Cc2c(ccc3c2cnn3CC(C)(C)F)C(c2c(F)cc(OCCN3CC(CF)C3)cc2F)N1CC(C)(C)F] | 6-(2,6-difluoro-4-(2-(3-(fluoromethyl)azetidin-1-yl)ethoxy)phenyl)-3,7-bis(2-fluoro-2-methylpropyl)-8-methyl-6,7,8,9-tetrahydro-3H-pyrazolo[4,3-f]isoquinoline | 0.0252 | −62 | 579.3 |
| 123 | 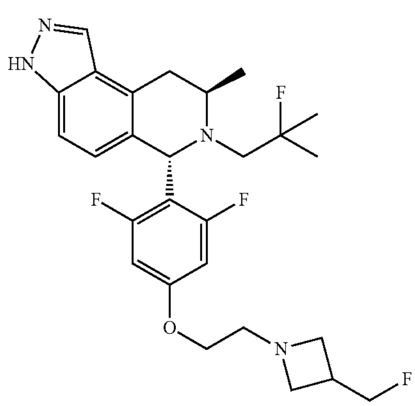 [SMILES: C[C@@H]1Cc2c(ccc3[nH]ncc23)[C@@H](c2c(F)cc(OCCN3CC(CF)C3)cc2F)N1CC(C)(C)F] | (6S,8R)-6-(2,6-difluoro-4-(2-(3-(fluoromethyl)azetidin-1-yl)ethoxy)phenyl)-7-(2-fluoro-2-methylpropyl)-8-methyl-6,7,8,9-tetrahydro-3H-pyrazolo[4,3-f]isoquinoline | 0.00006 | −98.8 | 505.2 |

TABLE 1a-continued

Formula I compounds

| No. | Structure | IUPAC Name | ER-alpha (WT) MCF7 HCS (EC50) (μMol) | ERalpha (WT) MCF7 HCS (S inf) | Mass Spec. M + H/1 |
|---|---|---|---|---|---|
| 124 | 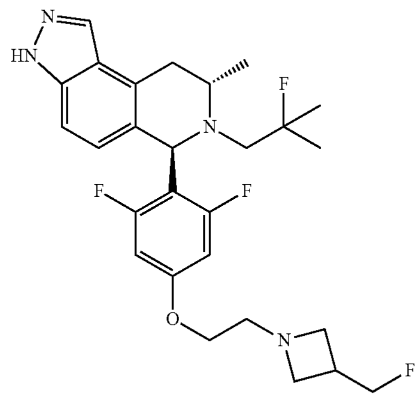 [SMILES: C[C@H]1Cc2c(ccc3[nH]ncc23)[C@H](c2c(F)cc(OCCN3CC(CF)C3)cc2F)N1CC(C)(C)F] | (6R,8S)-6-(2,6-difluoro-4-(2-(3-(fluoromethyl)azetidin-1-yl)ethoxy)phenyl)-7-(2-fluoro-2-methylpropyl)-8-methyl-6,7,8,9-tetrahydro-3H-pyrazolo[4,3-f]isoquinoline | 0.00323 | −90 | 505.2 |
| 125 | 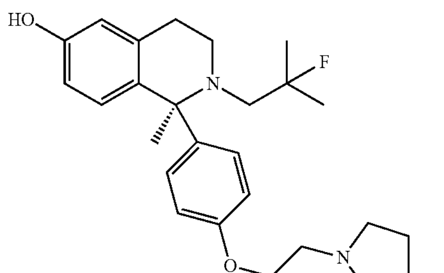 | (S)-2-(2-fluoro-2-methylpropyl)-1-methyl-1-(4-(2-((R)-3-methylpyrrolidin-1-yl)ethoxy)phenyl)-1,2,3,4-tetrahydroisoquinolin-6-ol | 0.0074 | −57 | 441.3 |
| 126 | 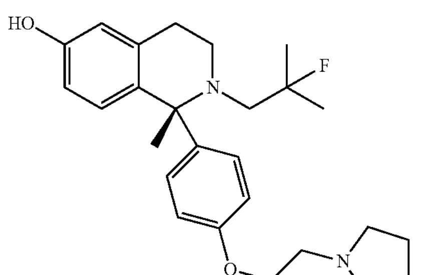 | (R)-2-(2-fluoro-2-methylpropyl)-1-methyl-1-(4-(2-((R)-3-methylpyrrolidin-1-yl)ethoxy)phenyl)-1,2,3,4-tetrahydroisoquinolin-6-ol | 0.00024 | −68 | 441.3 |
| 127 | 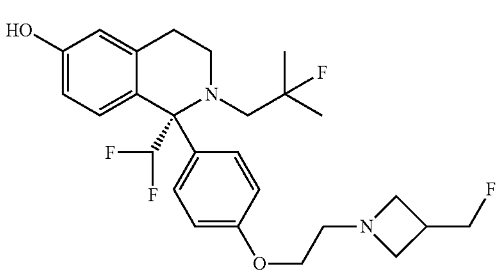 [SMILES: CC(C)(F)CN1CCc2cc(O)ccc2[C@@]1(c1ccc(OCCN2CC(CF)C2)cc1)C(F)F] | (S)-1-(difluoromethyl)-2-(2-fluoro-2-methylpropyl)-1-(4-(2-(3-(fluoromethyl)azetidin-1-yl)ethoxy)phenyl)-1,2,3,4-tetrahydroisoquinolin-6-ol | 0.022 | −85 | 481.3 |

TABLE 1a-continued

Formula I compounds

| No. | Structure | IUPAC Name | ER-alpha (WT) MCF7 HCS (EC50) (μMol) | ERalpha (WT) MCF7 HCS (S inf) | Mass Spec. M + H/1 |
|---|---|---|---|---|---|
| 128 | 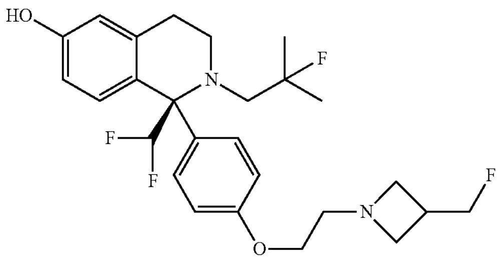 [SMILES: CC(C)(F)CN1CCc2cc(O)ccc2[C@]1(c1ccc(OCCN2CC(CF)C2)cc1)C(F)F] | (R)-1-(difluoromethyl)-2-(2-fluoro-2-methylpropyl)-1-(4-(2-(3-(fluoromethyl)azetidin-1-yl)ethoxy)phenyl)-1,2,3,4-tetrahydroisoquinolin-6-ol | 0.000075 | −95 | 481.3 |
| 129 | 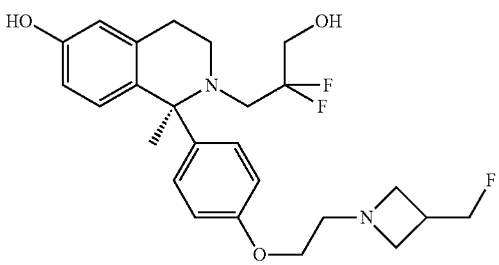 [SMILES: C[C@]1(c2ccc(OCCN3CC(CF)C3)cc2)c2ccc(O)cc2CCN1CC(F)(F)CO] | (S)-2-(2,2-difluoro-3-hydroxypropyl)-1-(4-(2-(3-(fluoromethyl)azetidin-1-yl)ethoxy)phenyl)-1-methyl-1,2,3,4-tetrahydroisoquinolin-6-ol | 0.0027 | −101 | 465.3 |
| 130 | 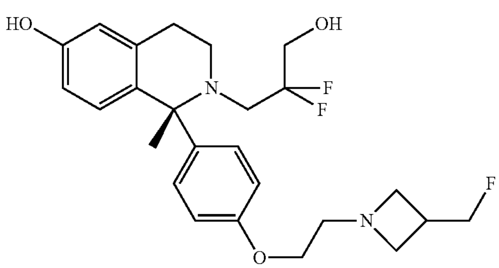 [SMILES: C[C@@]1(c2ccc(OCCN3CC(CF)C3)cc2)c2ccc(O)cc2CCN1CC(F)(F)CO] | (R)-2-(2,2-difluoro-3-hydroxypropyl)-1-(4-(2-(3-(fluoromethyl)azetidin-1-yl)ethoxy)phenyl)-1-methyl-1,2,3,4-tetrahydroisoquinolin-6-ol | 0.000042 | −101 | 465.3 |
| 131 | 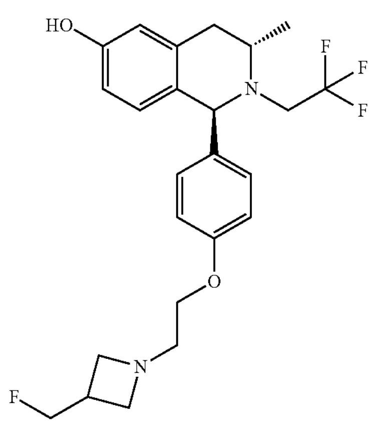 [SMILES: C[C@H]1Cc2cc(O)ccc2[C@H](c2ccc(OCCN3CC(CF)C3)cc2)N1CC(F)(F)F] | (1S,3S)-1-(4-(2-(3-(fluoromethyl)azetidin-1-yl)ethoxy)phenyl)-3-methyl-2-(2,2,2-trifluoroethyl)-1,2,3,4-tetrahydroisoquinolin-6-ol | 0.0014 | −96 | 453.1 |

TABLE 1a-continued

Formula I compounds

| No. | Structure | IUPAC Name | ER-alpha (WT) MCF7 HCS (EC50) (μMol) | ERalpha (WT) MCF7 HCS (S inf) | Mass Spec. M + H/1 |
|---|---|---|---|---|---|
| 132 | 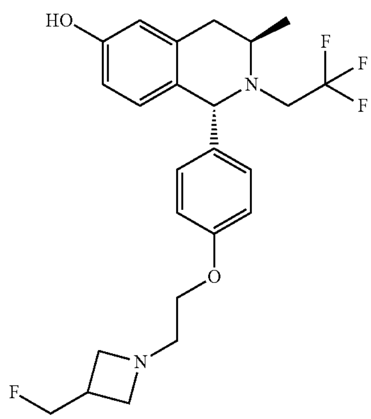 [SMILES: C[C@@H]1Cc2cc(O)ccc2[C@@H](c2ccc(OCCN3CC(CF)C3)cc2)N1CC(F)(F)F] | (1R,3R)-1-(4-(2-(3-(fluoromethyl)azetidin-1-yl)ethoxy)phenyl)-3-methyl-2-(2,2,2-trifluoroethyl)-1,2,3,4-tetrahydroisoquinolin-6-ol | 0.000011 | −97 | 453.1 |
| 133 | 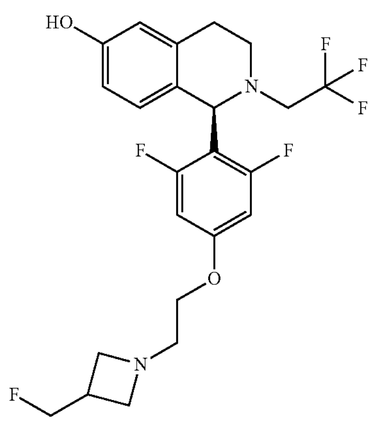 [SMILES: Oc1ccc2c(c1)CCN(CC(F)(F)F)[C@H]2c1c(F)cc(OCCN2CC(CF)C2)cc1F] | (1R)-1-[2,6-difluoro-4-[2-[3-(fluoromethyl)azetidin-1-yl]ethoxy]phenyl]-2-(2,2,2-trifluoroethyl)-3,4-dihydro-1H-isoquinolin-6-ol | 0.017 | −90 | 475.1 |
| 134 | 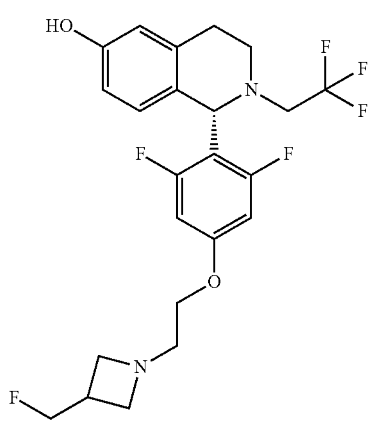 [SMILES: Oc1ccc2c(c1)CCN(CC(F)(F)F)[C@@H]2c1c(F)cc(OCCN2CC(CF)C2)cc1F] | (1S)-1-[2,6-difluoro-4-[2-[3-(fluoromethyl)azetidin-1-yl]ethoxy]phenyl]-2-(2,2,2-trifluoroethyl)-3,4-dihydro-1H-isoquinolin-6-ol | 0.000013 | −98 | 475.1 |

TABLE 1a-continued

Formula I compounds

| No. | Structure | IUPAC Name | ER-alpha (WT) MCF7 HCS (EC50) (μMol) | ERalpha (WT) MCF7 HCS (S inf) | Mass Spec. M + H/1 |
|---|---|---|---|---|---|
| 135 | 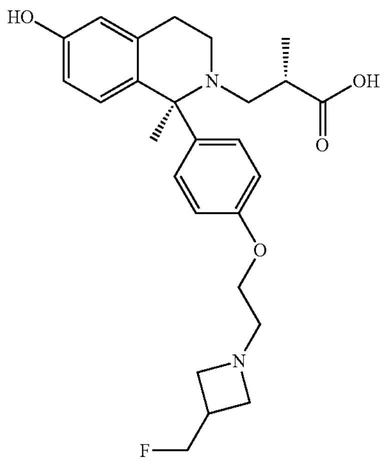 [SMILES: C[C@@H](CN1CCc2cc(O)ccc2[C@]1(C)c1ccc(OCCN2CC(CF)C2)cc1)C(=O)O] | (S)-3-((S)-1-(4-(2-(3-(fluoromethyl)azetidin-1-yl)ethoxy)phenyl)-6-hydroxy-1-methyl-3,4-dihydroisoquinolin-2(1H)-yl)-2-methylpropanoic acid | 0.1 | | 457.4 |
| 136 | 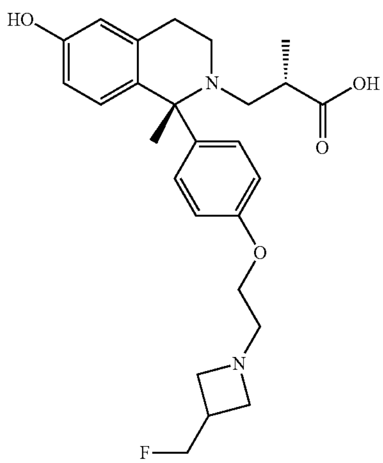 [SMILES: C[C@@H](CN1CCc2cc(O)ccc2[C@@]1(C)c1ccc(OCCN2CC(CF)C2)cc1)C(=O)O] | (S)-3-((R)-1-(4-(2-(3-(fluoromethyl)azetidin-1-yl)ethoxy)phenyl)-6-hydroxy-1-methyl-3,4-dihydroisoquinolin-2(1H)-yl)-2-methylpropanoic acid | 0.1 | | 457.4 |
| 137 | 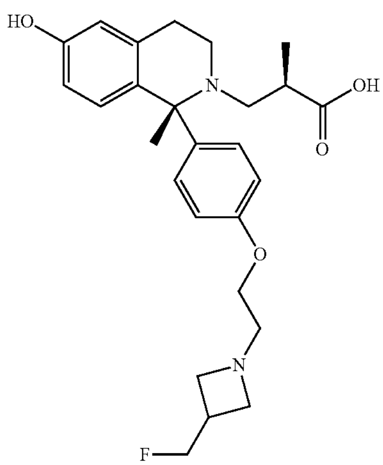 [SMILES: C[C@H](CN1CCc2cc(O)ccc2[C@@]1(C)c1ccc(OCCN2CC(CF)C2)cc1)C(=O)O] | (R)-3-((R)-1-(4-(2-(3-(fluoromethyl)azetidin-1-yl)ethoxy)phenyl)-6-hydroxy-1-methyl-3,4-dihydroisoquinolin-2(1H)-yl)-2-methylpropanoic acid | 0.040 | −45 | 457.4 |

TABLE 1a-continued

Formula I compounds

| No. | Structure | IUPAC Name | ER-alpha (WT) MCF7 HCS (EC50) (μMol) | ERalpha (WT) MCF7 HCS (S inf) | Mass Spec. M + H/1 |
|---|---|---|---|---|---|
| 138 | 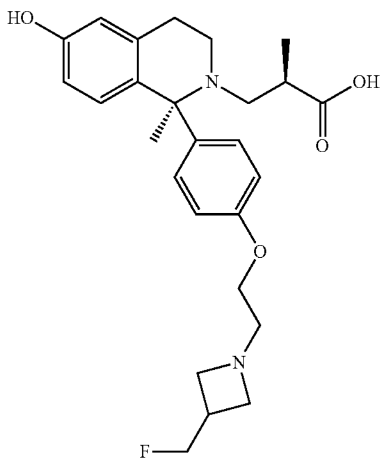 [SMILES: C[C@H](CN1CCc2cc(O)ccc2[C@]1(C)c1ccc(OCCN2CC(CF)C2)cc1)C(=O)O] | (R)-3-((S)-1-(4-(2-(3-(fluoromethyl)azetidin-1-yl)ethoxy)phenyl)-6-hydroxy-1-methyl-3,4-dihydroisoquinolin-2(1H)-yl)-2-methylpropanoic acid | 0.1 | | 457.4 |
| 139 | 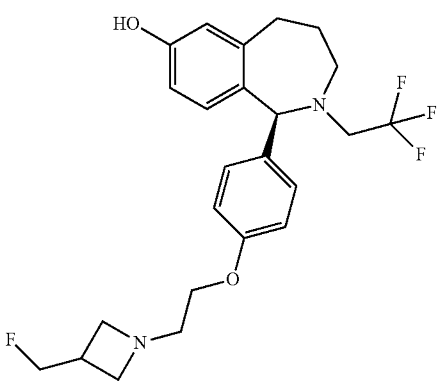 [SMILES: Oc1ccc2c(c1)CCCN(CC(F)(F)F)[C@H]2c1ccc(OCCN2CC(CF)C2)cc1] | (S)-1-(4-(2-(3-(fluoromethyl)azetidin-1-yl)ethoxy)phenyl)-2-(2,2,2-trifluoroethyl)-2,3,4,5-tetrahydro-1H-benzo[c]azepin-7-ol | 0.000101 | −95.4 | 453.2 |
| 140 | 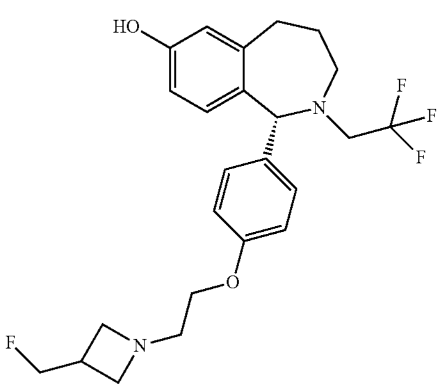 | (R)-1-(4-(2-(3-(fluoromethyl)azetidin-1-yl)ethoxy)phenyl)-2-(2,2,2-trifluoroethyl)-2,3,4,5-tetrahydro-1H-benzo[c]azepin-7-ol | 0.00005 | −96.6 | 453.2 |

TABLE 1a-continued

Formula I compounds

| No. | Structure | IUPAC Name | ER-alpha (WT) MCF7 HCS (EC50) (μMol) | ERalpha (WT) MCF7 HCS (S inf) | Mass Spec. M + H/1 |
|---|---|---|---|---|---|
| 141 | 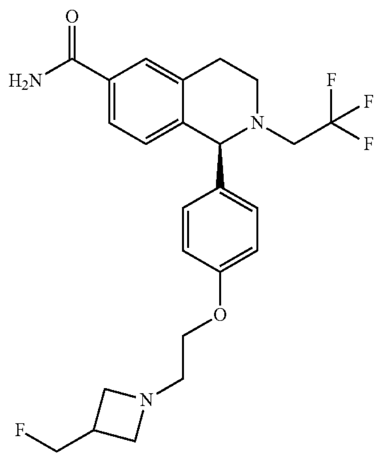 [SMILES: NC(=O)c1ccc2c(c1)CCN(CC(F)(F)F)[C@H]2c1ccc(OCCN2CC(CF)C2)cc1] | (1S)-1-[4-[2-[3-(fluoromethyl)azetidin-1-yl]ethoxy]phenyl]-2-(2,2,2-trifluoroethyl)-3,4-dihydro-1H-isoquinoline-6-carboxamide | 0.1 | | 466.2 |
| 142 | 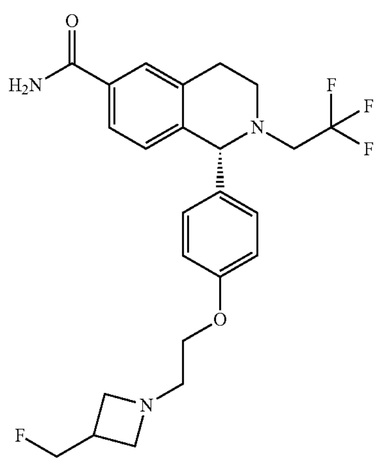 [SMILES: NC(=O)c1ccc2c(c1)CCN(CC(F)(F)F)[C@@H]2c1ccc(OCCN2CC(CF)C2)cc1] | (1R)-1-[4-[2-[3-(fluoromethyl)azetidin-1-yl]ethoxy]phenyl]-2-(2,2,2-trifluoroethyl)-3,4-dihydro-1H-isoquinoline-6-carboxamide | 0.029 | −79 | 466.2 |
| 143 | 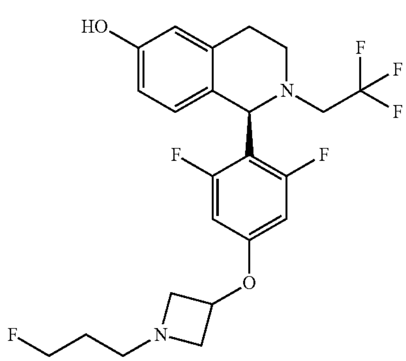 [SMILES: Oc1ccc2c(c1)CCN(CC(F)(F)F)[C@H]2c1c(F)cc(OC2CN(CCCF)C2)cc1F] | (1R)-1-[2,6-difluoro-4-[1-(3-fluoropropyl)azetidin-3-yl]oxy-phenyl]-2-(2,2,2-trifluoroethyl)-3,4-dihydro-1H-isoquinolin-6-ol | 0.022 | −100 | 475.3 |

TABLE 1a-continued

Formula I compounds

| No. | Structure | IUPAC Name | ER-alpha (WT) MCF7 HCS (EC50) (μMol) | ERalpha (WT) MCF7 HCS (S inf) | Mass Spec. M + H/1 |
|---|---|---|---|---|---|
| 144 | 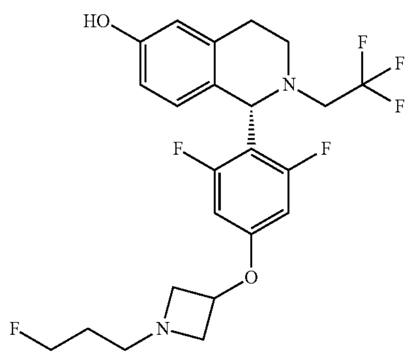 | (1S)-1-[2,6-difluoro-4-[1-(3-fluoropropyl)azetidin-3-yl]oxy-phenyl]-2-(2,2,2-trifluoroethyl)-3,4-dihydro-1H-isoquinolin-6-ol | 0.000041 | −102 | 475.3 |
| 145 | 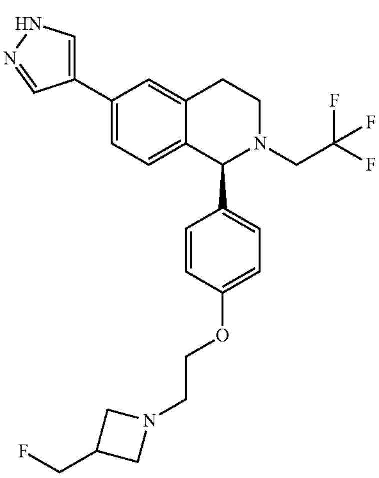 [SMILES: FCC1CN(CCOc2ccc([C@H]3c4ccc(-c5cn[nH]c5)cc4CCN3CC(F)(F)F)cc2)C1] | (1S)-1-[4-[2-[3-(fluoromethyl)azetidin-1-yl]ethoxy]phenyl]-6-(1H-pyrazol-4-yl)-2-(2,2,2-trifluoroethyl)-3,4-dihydro-1H-isoquinoline | 0.1 | −100 | 489.2 |
| 146 | 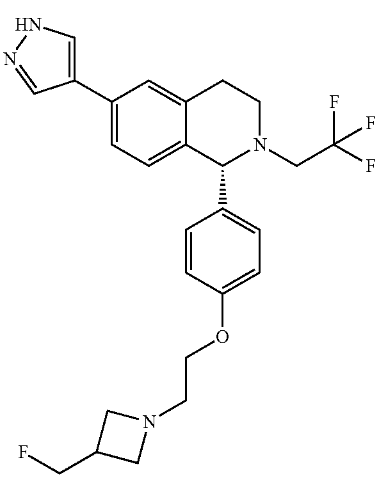 [SMILES: FCC1CN(CCOc2ccc([C@@H]3c4ccc(-c5cn[nH]c5)cc4CCN3CC(F)(F)F)cc2)C1] | (1R)-1-[4-[2-[3-(fluoromethyl)azetidin-1-yl]ethoxy]phenyl]-6-(1H-pyrazol-4-yl)-2-(2,2,2-trifluoroethyl)-3,4-dihydro-1H-isoquinoline | 0.00056 | −95 | 489.2 |

TABLE 1a-continued

Formula I compounds

| No. | Structure | IUPAC Name | ER-alpha (WT) MCF7 HCS (EC50) (µMol) | ERalpha (WT) MCF7 HCS (S inf) | Mass Spec. M + H/1 |
|---|---|---|---|---|---|
| 147 | 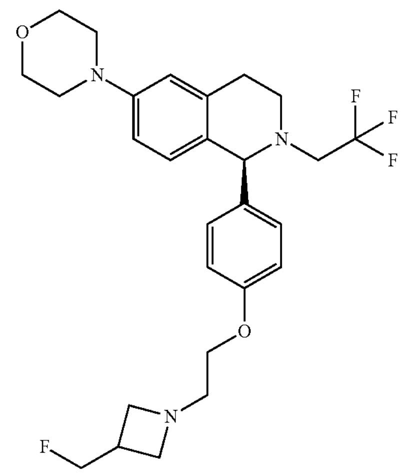 [SMILES: FCC1CN(CCOc2ccc([C@H]3c4ccc(N5CCOCC5)cc4CCN3CC(F)(F)F)cc2)C1] | 4-[(1S)-1-[4-[2-[3-(fluoromethyl)azetidin-1-yl]ethoxy]phenyl]-2-(2,2,2-trifluoroethyl)-3,4-dihydro-1H-isoquinolin-6-yl]morpholine | 0.1 | | 508.3 |
| 148 | 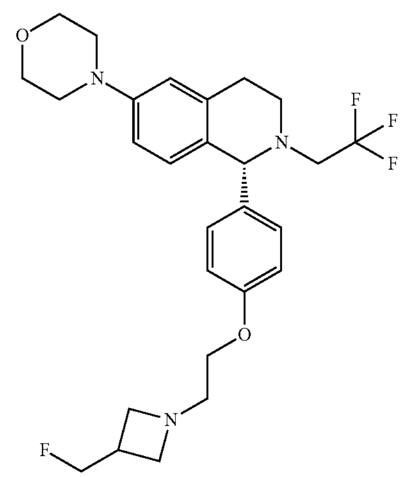 [SMILES: FCC1CN(CCOc2ccc([C@@H]3c4ccc(N5CCOCC5)cc4CCN3CC(F)(F)F)cc2)C1] | 4-[(1R)-1-[4-[2-[3-(fluoromethyl)azetidin-1-yl]ethoxy]phenyl]-2-(2,2,2-trifluoroethyl)-3,4-dihydro-1H-isoquinolin-6-yl]morpholine | 0.012 | −89 | 508.2 |
| 149 | 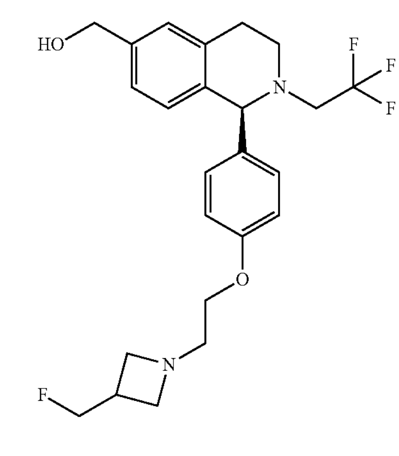 [SMILES: OCc1ccc2c(c1)CCN(CC(F)(F)F)[C@H]2c1ccc(OCCN2CC(CF)C2)cc1] | [(1S)-1-[4-[2-[3-(fluoromethyl)azetidin-1-yl]ethoxy]phenyl]-2-(2,2,2-trifluoroethyl)-3,4-dihydro-1H-isoquinolin-6-yl]methanol | 0.10 | −100 | 453.2 |

TABLE 1a-continued

Formula I compounds

| No. | Structure | IUPAC Name | ER-alpha (WT) MCF7 HCS (EC50) (μMol) | ERalpha (WT) MCF7 HCS (S inf) | Mass Spec. M + H/1 |
|---|---|---|---|---|---|
| 150 | 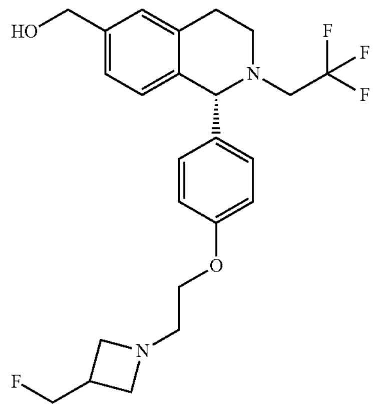 [SMILES: OCc1ccc2c(c1)CCN(CC(F)(F)F)[C@@H]2c1ccc(OCCN2CC(CF)C2)cc1] | [(1R)-1-[4-[2-[3-(fluoromethyl)azetidin-1-yl]ethoxy]phenyl]-2-(2,2,2-trifluoroethyl)-3,4-dihydro-1H-isoquinolin-6-yl]methanol | 0.0017 | −100 | 453.2 |
| 151 | 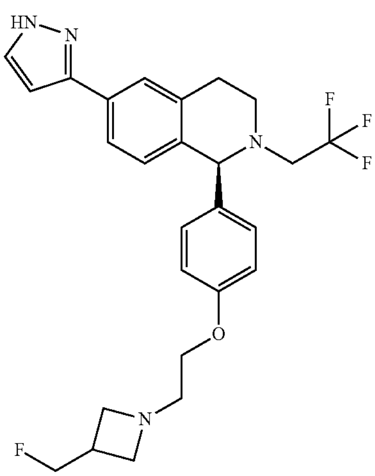 [SMILES: FCC1CN(CCOc2ccc([C@H]3c4ccc(-c5cc[nH]n5)cc4CCN3CC(F)(F)F)cc2)C1] | (1S)-1-[4-[2-[3-(fluoromethyl)azetidin-1-yl]ethoxy]phenyl]-6-(1H-pyrazol-3-yl)-2-(2,2,2-trifluoroethyl)-3,4-dihydro-1H-isoquinoline | 0.1 | | 489.2 |
| 152 | 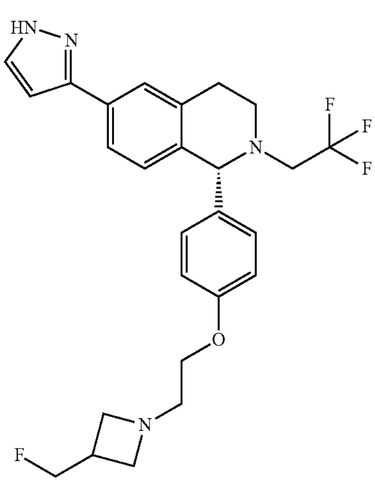 [SMILES: FCC1CN(CCOc2ccc([C@@H]3c4ccc(-c5cc[nH]n5)cc4CCN3CC(F)(F)F)cc2)C1] | (1R)-1-[4-[2-[3-(fluoromethyl)azetidin-1-yl]ethoxy]phenyl]-6-(1H-pyrazol-3-yl)-2-(2,2,2-trifluoroethyl)-3,4-dihydro-1H-isoquinoline | 0.017 | −91 | 489.2 |

TABLE 1a-continued

Formula I compounds

| No. | Structure | IUPAC Name | ER-alpha (WT) MCF7 HCS (EC50) (μMol) | ERalpha (WT) MCF7 HCS (S inf) | Mass Spec. M + H/1 |
|---|---|---|---|---|---|
| 153 | 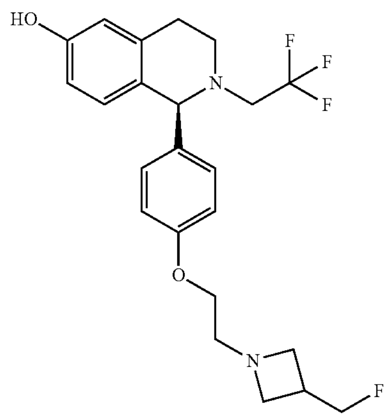 [SMILES: Oc1ccc2c(c1)CCN(CC(F)(F)F)[C@H]2c1ccc(OCCN2CC(CF)C2)cc1] | (S)-1-(4-(2-(3-(fluoromethyl)azetidin-1-yl)ethoxy)phenyl)-2-(2,2,2-trifluoroethyl)-1,2,3,4-tetrahydroisoquinolin-6-ol | 0.00054 | −99 | 439.2 |
| 154 | 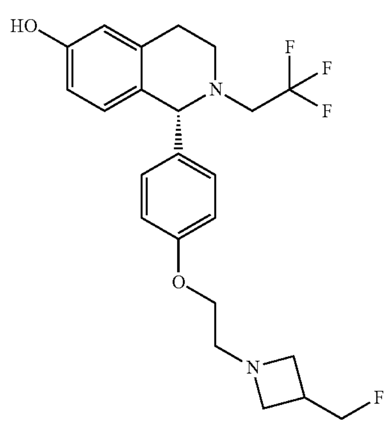 [SMILES: Oc1ccc2c(c1)CCN(CC(F)(F)F)[C@@H]2c1ccc(OCCN2CC(CF)C2)cc1] | (R)-1-(4-(2-(3-(fluoromethyl)azetidin-1-yl)ethoxy)phenyl)-2-(2,2,2-trifluoroethyl)-1,2,3,4-tetrahydroisoquinolin-6-ol | 0.000024 | −99 | 439.2 |

TABLE 1b

| No. | Structure | IUPAC Name | ER-alpha (WT) MCF7 HCS (EC50) (μMol) | ERalpha (WT) MCF7 HCS (S inf) | Mass Spec. M + H/1 |
|---|---|---|---|---|---|
| 155 | 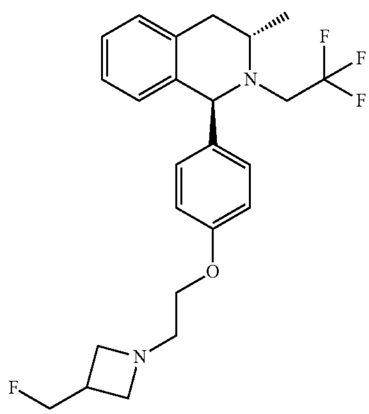 [SMILES: C[C@H]1Cc2ccccc2[C@H](c2ccc(OCCN3CC(CF)C3)cc2)N1CC(F)(F)F] | (1S,3S)-1-(4-(2-(3-(Fluoromethyl)azetidin-1-yl)ethoxy)phenyl)-3-methyl-2-(2,2,2-trifluoroethyl)-1,2,3,4-tetrahydroisoquinoline | 0.031 | −70 | 437.1 |
| 156 | 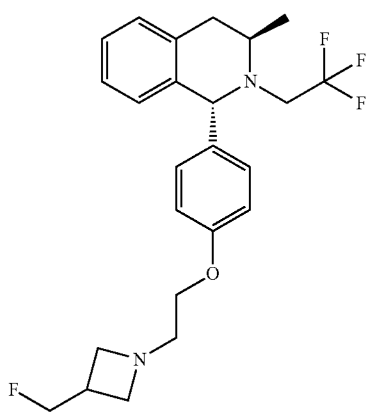 [SMILES: C[C@@H]1Cc2ccccc2[C@@H](c2ccc(OCCN3CC(CF)C3)cc2)N1CC(F)(F)F] | (1R,3R)-1-(4-(2-(3-(Fluoromethyl)azetidin-1-yl)ethoxy)phenyl)-3-methyl-2-(2,2,2-trifluoroethyl)-1,2,3,4-tetrahydroisoquinoline | 0.00085 | −97 | 437.1 |
| 157 | 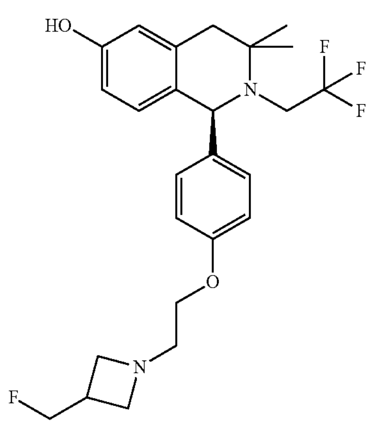 [SMILES: CC1(C)Cc2cc(O)ccc2[C@H](c2ccc(OCCN3CC(CF)C3)cc2)N1CC(F)(F)F] | (S)-1-(4-(2-(3-(Fluoromethyl)azetidin-1-yl)ethoxy)phenyl)-3,3-dimethyl-2-(2,2,2-trifluoroethyl)-1,2,3,4-tetrahydroisoquinolin-6-ol | 0.00048 | −98 | 467.1 |

TABLE 1b-continued

Formula I compounds

| No. | Structure | IUPAC Name | ER-alpha (WT) MCF7 HCS (EC50) (μMol) | ERalpha (WT) MCF7 HCS (S inf) | Mass Spec. M + H/1 |
|---|---|---|---|---|---|
| 158 | 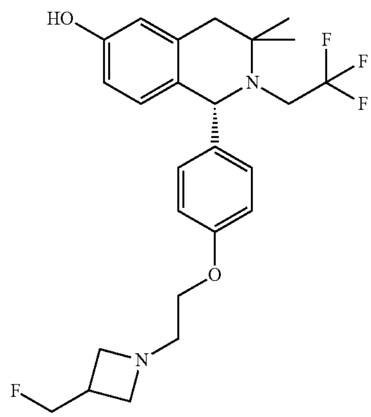 [SMILES: CC1(C)Cc2cc(O)ccc2[C@@H](c2ccc(OCCN3CC(CF)C3)cc2)N1CC(F)(F)F] | (R)-1-(4-(2-(3-(Fluoromethyl)azetidin-1-yl)ethoxy)phenyl)-3,3-dimethyl-2-(2,2,2-trifluoroethyl)-1,2,3,4-tetrahydroisoquinolin-6-ol | 0.000042 | −96 | 467.2 |
| 159 | 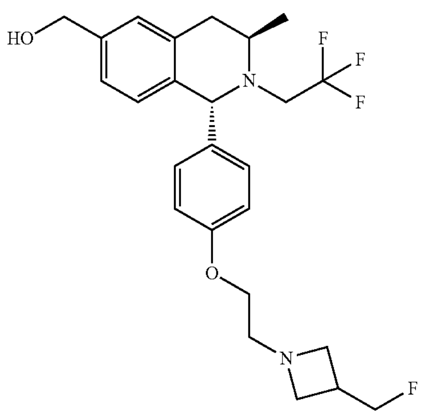 [SMILES: C[C@@H]1Cc2cc(CO)ccc2[C@@H](c2ccc(OCCN3CC(CF)C3)cc2)N1CC(F)(F)F] | ((1R,3R)-1-(4-(2-(3-(Fluoromethyl)azetidin-1-yl)ethoxy)phenyl)-3-methyl-2-(2,2,2-trifluoroethyl)-1,2,3,4-tetrahydroisoquinolin-6-yl)methanol | 0.000043 | −99 | 467.2 |
| 160 | 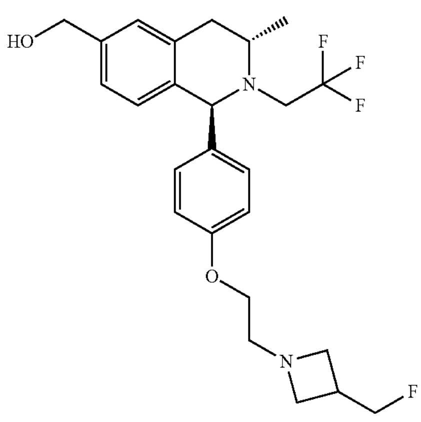 [SMILES: C[C@H]1Cc2cc(CO)ccc2[C@H](c2ccc(OCCN3CC(CF)C3)cc2)N1CC(F)(F)F] | ((1S,3S)-1-(4-(2-(3-(Fluoromethyl)azetidin-1-yl)ethoxy)phenyl)-3-methyl-2-(2,2,2-trifluoroethyl)-1,2,3,4-tetrahydroisoquinolin-6-yl)methanol | 0.019 | −88 | 467.2 |

TABLE 1b-continued

Formula I compounds

| No. | Structure | IUPAC Name | ER-alpha (WT) MCF7 HCS (EC50) (μMol) | ERalpha (WT) MCF7 HCS (S inf) | Mass Spec. M + H/1 |
|---|---|---|---|---|---|
| 161 | 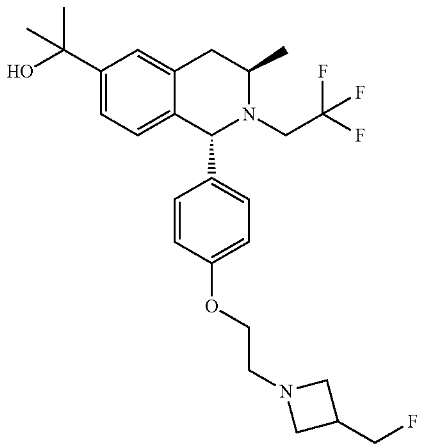 [SMILES: C[C@@H]1Cc2cc(C(C)(C)O)ccc2[C@@H](c2ccc(OCCN3CC(CF)C3)cc2)N1CC(F)(F)F] | 2-((1R,3R)-1-(4-(2-(3-(Fluoromethyl)azetidin-1-yl)ethoxy)phenyl)-3-methyl-2-(2,2,2-trifluoroethyl)-1,2,3,4-tetrahydroisoquinolin-6-yl)propan-2-ol | 0.011 | −82 | 495.1 |
| 162 | 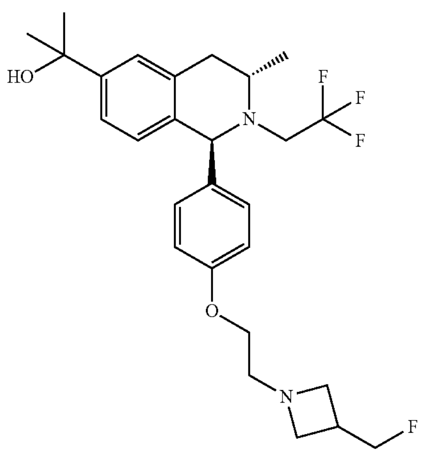 [SMILES: C[C@H]1Cc2cc(C(C)(C)O)ccc2[C@H](c2ccc(OCCN3CC(CF)C3)cc2)N1CC(F)(F)F] | 2-((1S,3S)-1-(4-(2-(3-(Fluoromethyl)azetidin-1-yl)ethoxy)phenyl)-3-methyl-2-(2,2,2-trifluoroethyl)-1,2,3,4-tetrahydroisoquinolin-6-yl)propan-2-ol | 0.28 | ND | 495.1 |
| 163 | 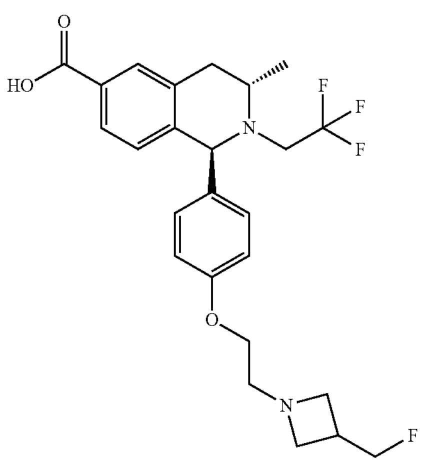 [SMILES: C[C@H]1Cc2cc(C(=O)O)ccc2[C@H](c2ccc(OCCN3CC(CF)C3)cc2)N1CC(F)(F)F] | (1S,3S)-1-(4-(2-(3-(Fluoromethyl)azetidin-1-yl)ethoxy)phenyl)-3-methyl-2-(2,2,2-trifluoroethyl)-1,2,3,4-tetrahydroisoquinoline-6-carboxylic acid | 0.011 | −92 | 481.0 |

TABLE 1b-continued

Formula I compounds

| No. | Structure | IUPAC Name | ER-alpha (WT) MCF7 HCS (EC50) (µMol) | ERalpha (WT) MCF7 HCS (S inf) | Mass Spec. M + H/1 |
|---|---|---|---|---|---|
| 164 | 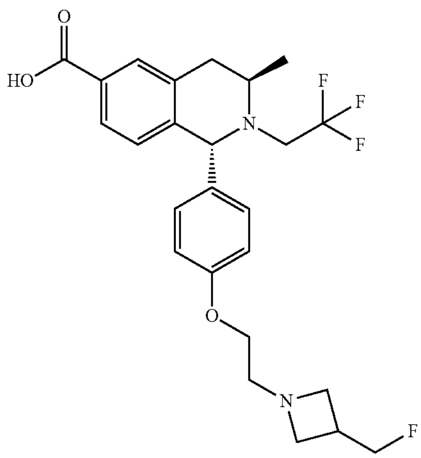 [SMILES: C[C@@H]1Cc2cc(C(=O)O)ccc2[C@@H](c2ccc(OCCN3CC(CF)C3)cc2)N1CC(F)(F)F] | (1R,3R)-1-(4-(2-(3-(Fluoromethyl)azetidin-1-yl)ethoxy)phenyl)-3-methyl-2-(2,2,2-trifluoroethyl)-1,2,3,4-tetrahydroisoquinoline-6-carboxylic acid | 0.0013 | −100 | 481.0 |
| 165 | 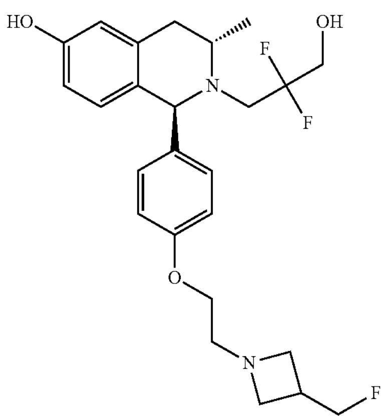 [SMILES: C[C@H]1Cc2cc(O)ccc2[C@H](c2ccc(OCCN3CC(CF)C3)cc2)N1CC(F)(F)CO] | (1S,3S)-2-(2,2-Difluoro-3-hydroxypropyl)-1-(4-(2-(3-(fluoromethyl)azetidin-1-yl)ethoxy)phenyl)-3-methyl-1,2,3,4-tetrahydroisoquinolin-6-ol | 0.00096 | −101 | 465.2 |
| 166 | 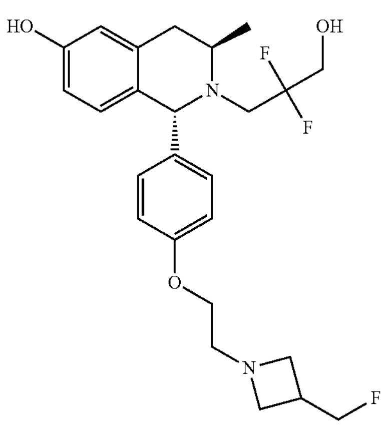 [SMILES: C[C@@H]1Cc2cc(O)ccc2[C@@H](c2ccc(OCCN3CC(CF)C3)cc2)N1CC(F)(F)CO] | (1R,3R)-2-(2,2-Difluoro-3-hydroxypropyl)-1-(4-(2-(3-(fluoromethyl)azetidin-1-yl)ethoxy)phenyl)-3-methyl-1,2,3,4-tetrahydroisoquinolin-6-ol | 0.000066 | −105 | 465.2 |

TABLE 1b-continued

Formula I compounds

| No. | Structure | IUPAC Name | ER-alpha (WT) MCF7 HCS (EC50) (µMol) | ERalpha (WT) MCF7 HCS (S inf) | Mass Spec. M + H/1 |
|---|---|---|---|---|---|
| 167 | 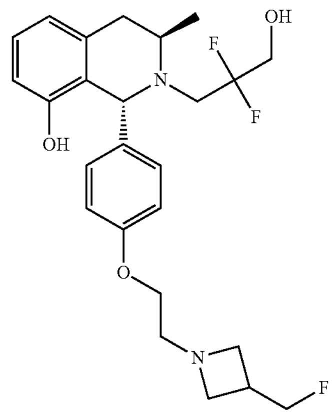 [SMILES: C[C@@H]1Cc2cccc(O)c2[C@@H](c2ccc(OCCN3CC(CF)C3)cc2)N1CC(F)(F)CO] | (1R,3R)-2-(2,2-Difluoro-3-hydroxypropyl)-1-(4-(2-(3-(fluoromethyl)azetidin-1-yl)ethoxy)phenyl)-3-methyl-1,2,3,4-tetrahydroisoquinolin-6-ol | 0.022 | −82 | 465.2 |
| 168 | 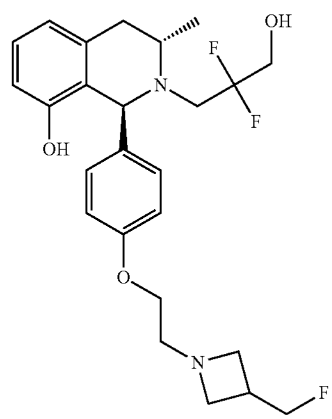 [SMILES: C[C@H]1Cc2cccc(O)c2[C@H](c2ccc(OCCN3CC(CF)C3)cc2)N1CC(F)(F)CO] | (1S,3S)-2-(2,2-Difluoro-3-hydroxypropyl)-1-(4-(2-(3-(fluoromethyl)azetidin-1-yl)ethoxy)phenyl)-3-methyl-1,2,3,4-tetrahydroisoquinolin-8-ol | 0.51 | ND | 465.2 |
| 169 | 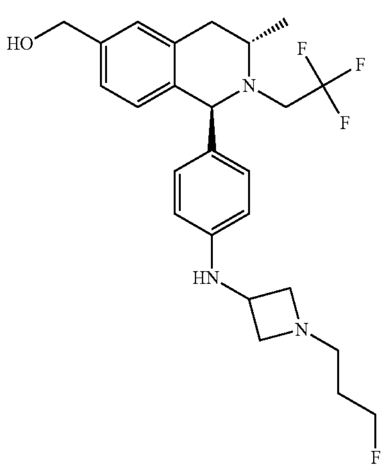 [SMILES: C[C@H]1Cc2cc(CO)ccc2[C@H](c2ccc(NC3CN(CCCF)C3)cc2)N1CC(F)(F)F] | ((1S,3S)-1-(4-((1-(3-Fluoropropyl)azetidin-3-yl)amino)phenyl)-3-methyl-2-(2,2,2-trifluoroethyl)-1,2,3,4-tetrahydroisoquinolin-6-yl)methanol | 0.037 | −60 | 466.1 |

TABLE 1b-continued

Formula I compounds

| No. | Structure | IUPAC Name | ER-alpha (WT) MCF7 HCS (EC50) (μMol) | ERalpha (WT) MCF7 HCS (S inf) | Mass Spec. M + H/1 |
|---|---|---|---|---|---|
| 170 | 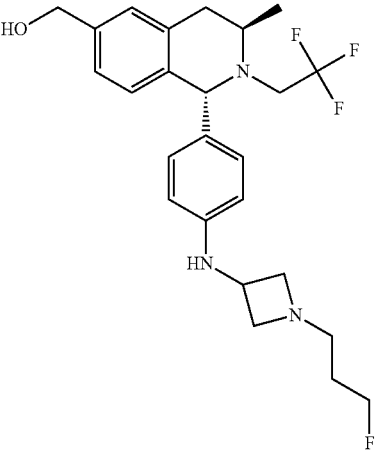 [SMILES: C[C@@H]1Cc2cc(CO)ccc2[C@@H](c2ccc(NC3CN(CCCF)C3)cc2)N1CC(F)(F)F] | ((1R,3R)-1-(4-((1-(3-Fluoropropyl)azetidin-3-yl)amino)phenyl)-3-methyl-2-(2,2,2-trifluoroethyl)-1,2,3,4-tetrahydroisoquinolin-6-yl)methanol | 0.000088 | −100 | 466.1 |
| 171 | 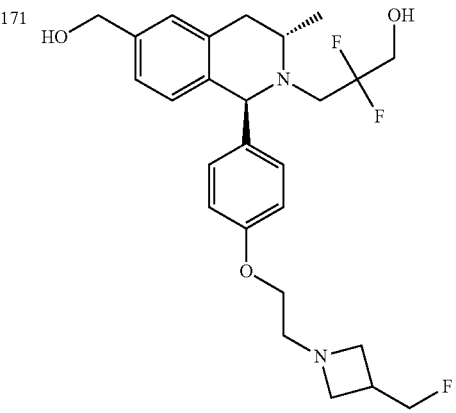 | 2,2-Difluoro-3-((1S,3S)-1-(4-(2-(3-(fluoromethyl)azetidin-1-yl)ethoxy)phenyl)-6-(hydroxymethyl)-3-methyl-3,4-dihydroisoquinolin-2(1H)-yl)propan-1-ol | 0.023 | −63 | 479.2 |
| 172 | 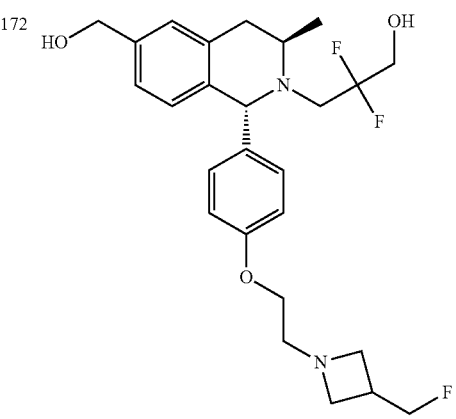 | 2,2-Difluoro-3-((1R,3R)-1-(4-(2-(3-(fluoromethyl)azetidin-1-yl)ethoxy)phenyl)-6-(hydroxymethyl)-3-methyl-3,4-dihydroisoquinolin-2(1H)-yl)propan-1-ol | 0.00014 | −99 | 479.2 |

TABLE 1b-continued

Formula I compounds

| No. | Structure | IUPAC Name | ER-alpha (WT) MCF7 HCS (EC50) (µMol) | ERalpha (WT) MCF7 HCS (S inf) | Mass Spec. M + H/1 |
|---|---|---|---|---|---|
| 173 | 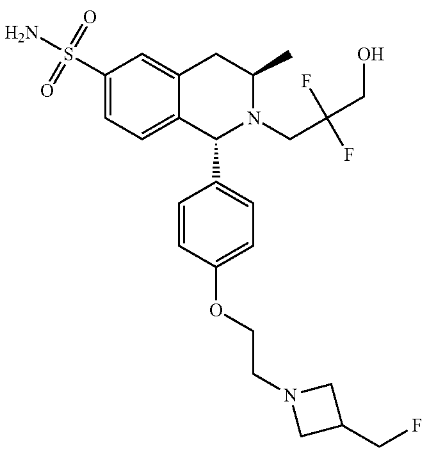 [SMILES: C[C@@H]1Cc2cc(S(N)(=O)=O)ccc2[C@@H](c2ccc(OCCN3CC(CF)C3)cc2)N1CC(F)(F)CO] | (1R,3R)-2-(2,2-Difluoro-3-hydroxypropyl)-1-(4-(2-(3-(fluoromethyl)azetidin-1-yl)ethoxy)phenyl)-3-methyl-1,2,3,4-tetrahydroisoquinoline-6-sulfonamide | 0.0029 | −98 | 528.1 |
| 174 | 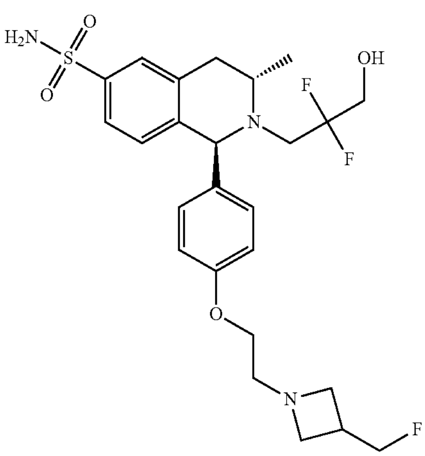 [SMILES: C[C@H]1Cc2cc(S(N)(=O)=O)ccc2[C@H](c2ccc(OCCN3CC(CF)C3)cc2)N1CC(F)(F)CO] | (1S,3S)-2-(2,2-Difluoro-3-hydroxypropyl)-1-(4-(2-(3-(fluoromethyl)azetidin-1-yl)ethoxy)phenyl)-3-methyl-1,2,3,4-tetrahydroisoquinoline-6-sulfonamide | 0.063 | −50 | 528.1 |
| 175 | 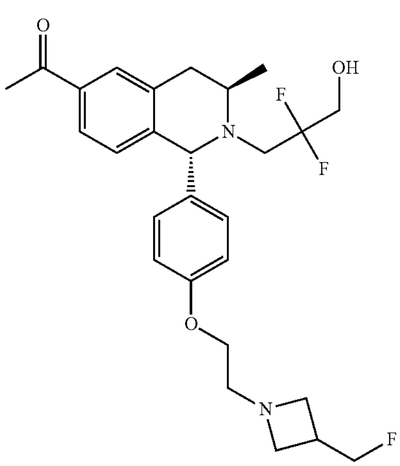 [SMILES: CC(=O)c1ccc2c(c1)C[C@@H](C)N(CC(F)(F)CO)[C@@H]2c1ccc(OCCN2CC(CF)C2)cc1] | 1-((1R,3R)-2-(2,2-Difluoro-3-hydroxypropyl)-1-(4-(2-(3-(fluoromethyl)azetidin-1-yl)ethoxy)phenyl)-3-methyl-1,2,3,4-tetrahydroisoquinolin-6-yl)ethanone | 0.000168 | −97 | 491.2 |

TABLE 1b-continued

Formula I compounds

| No. | Structure | IUPAC Name | ER-alpha (WT) MCF7 HCS (EC50) (μMol) | ERalpha (WT) MCF7 HCS (S inf) | Mass Spec. M + H/1 |
| --- | --- | --- | --- | --- | --- |
| 176 | 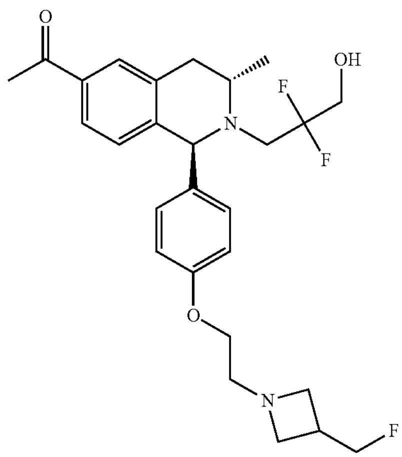 [SMILES: CC(=O)c1ccc2c(c1)C[C@H](C)N(CC(F)(F)CO)[C@H]2c1ccc(OCCN2CC(CF)C2)cc1] | 1-((1S,3S)-2-(2,2-Difluoro-3-hydroxypropyl)-1-(4-(2-(3-(fluoromethyl)azetidin-1-yl)ethoxy)phenyl)-3-methyl-1,2,3,4-tetrahydroisoquinolin-6-yl)ethanone | >0.1 | | 491.2 |
| 177 | 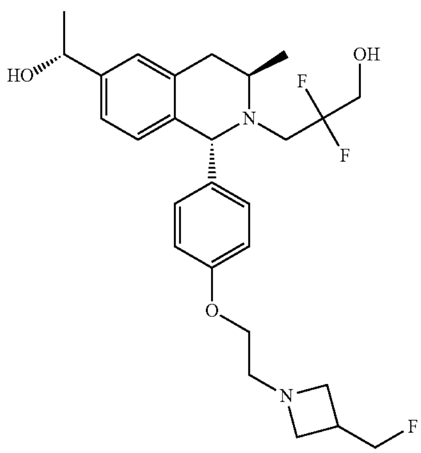 [SMILES: C[C@@H]1Cc2cc([C@@H](C)O)ccc2[C@@H](c2ccc(OCCN3CC(CF)C3)cc2)N1CC(F)(F)CO] | 2,2-Difluoro-3-((1R,3R)-1-(4-(2-(3-(Fluoromethyl)azetidin-1-yl)ethoxy)phenyl)-6-((R)-1-hydroxyethyl)-3-methyl-3,4-dihydroisoquinolin-2(1H)-yl)propan-1-ol | | | 493.1 |
| 178 | 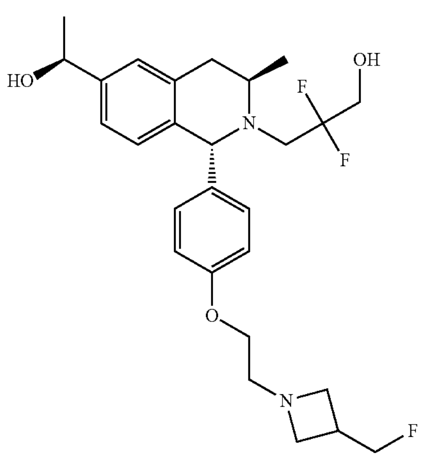 [SMILES: C[C@H](O)c1ccc2c(c1)C[C@@H](C)N(CC(F)(F)CO)[C@@H]2c1ccc(OCCN2CC(CF)C2)cc1] | 2,2-Difluoro-3-((1R,3R)-1-(4-(2-(3-(Fluoromethyl)azetidin-1-yl)ethoxy)phenyl)-6-((S)-1-hydroxyethyl)-3-methyl-3,4-dihydroisoquinolin-2(1H)-yl)propan-1-ol | >0.1 | | 493.1 |

TABLE 1b-continued

Formula I compounds

| No. | Structure | IUPAC Name | ER-alpha (WT) MCF7 HCS (EC50) (μMol) | ERalpha (WT) MCF7 HCS (S inf) | Mass Spec. M + H/1 |
|---|---|---|---|---|---|
| 179 | 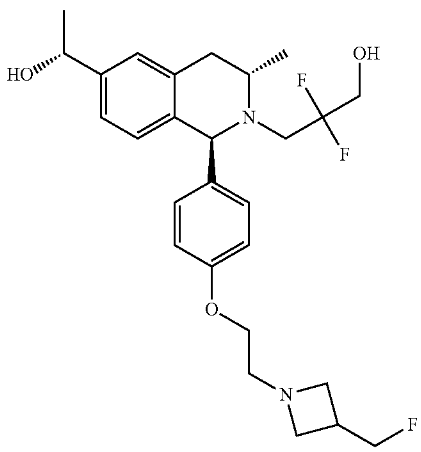 [SMILES: C[C@@H](O)c1ccc2c(c1)C[C@H](C)N(CC(F)(F)CO)[C@H]2c1ccc(OCCN2CC(CF)C2)cc1] | 2,2-Difluoro-3-((1S,3S)-1-(4-(2-(3-(Fluoromethyl)azetidin-1-yl)ethoxy)phenyl)-6-((R)-1-hydroxyethyl)-3-methyl-3,4-dihydroisoquinolin-2(1H)-yl)propan-1-ol | | | 493.1 |
| 180 | 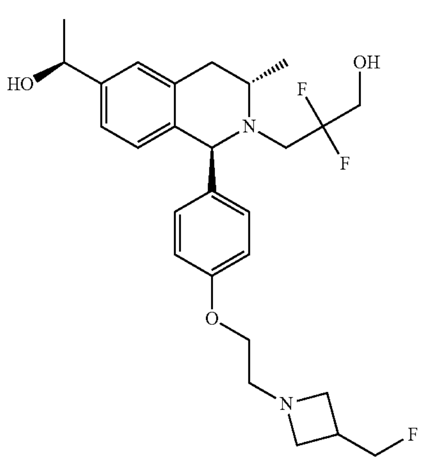 [SMILES: C[C@H](O)c1ccc2c(c1)C[C@H](C)N(CC(F)(F)CO)[C@H]2c1ccc(OCCN2CC(CF)C2)cc1] | 2,2-Difluoro-3-((1S,3S)-1-(4-(2-(3-(Fluoromethyl)azetidin-1-yl)ethoxy)phenyl)-6-((S)-1-hydroxyethyl)-3-methyl-3,4-dihydroisoquinolin-2(1H)-yl)propan-1-ol | | | 493.1 |

TABLE 2

Comparator compounds

| comparator compound | Structure | IUPAC Name | ER-alpha (WT) MCF7 HCS (EC50) (µMol) | ERalpha (WT) MCF7 HCS (S inf) | Mass Spec. M + H/1 |
|---|---|---|---|---|---|
| lasofoxifene | 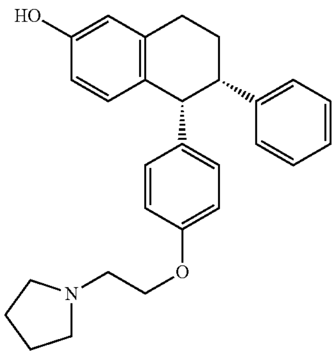 [SMILES: Oc1ccc2c(c1)CC[C@H](c1ccccc1)[C@@H]2c1ccc(OCCN2CCCC2)cc1] | (5R,6S)-6-phenyl-5-(4-(2-(pyrrolidin-1-yl)ethoxy)phenyl)-5,6,7,8-tetrahydronaphthalen-2-ol | 0.0000544 | −73.5 | 414.24 |
| Compound 18a: Renaud et al (2003) Jour. Med. Chem. 46(14): 2945-2957; Compound 60: Renaud et al (2005) Jour. Med. Chem. 48(2): 364-379 | 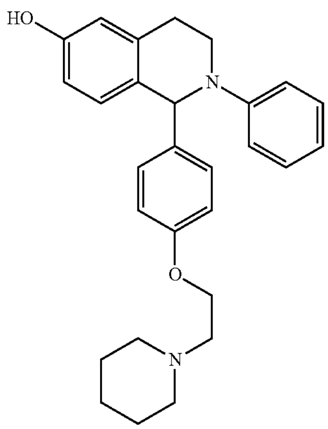 [SMILES: Oc1ccc2c(c1)CCN(c1ccccc1)C2c1ccc(OCCN2CCCCC2)cc1] | 2-phenyl-1-(4-(2-(piperidin-1-yl)ethoxy)phenyl)-1,2,3,4-tetrahydroisoquinolin-6-ol | 0.00174 | −52.5 | 429.4 |

Administration of Formula I Compounds

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Formula I compounds of the present invention are useful for treating a human or animal patient suffering from a disease or disorder arising from abnormal cell growth, function or behavior associated with USP7 such as an immune disorder, cardiovascular disease, viral infection, inflammation, a metabolism/endocrine disorder or a neurological disorder, may thus be treated by a method comprising the administration thereto of a compound of the present invention as defined above. A human or animal patient suffering from cancer may also be treated by a method comprising the administration thereto of a compound of the present invention as defined above. The condition of the patient may thereby be improved or ameliorated.

Methods of the invention also include treating cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic myelogenous leukemia, lymphocytic leukemia, chronic lymphoid leukemia (CLL), myeloid leukemia, oral cavity and pharynx, non-Hodgkin lymphoma, melanoma, and villous colon adenoma.

Pharmaceutical Formulations

In order to use a compound of this invention for the therapeutic treatment of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of Formula I may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs. The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with additional therapeutic agents for the treatment of a disease or disorder described herein, such as inflammation or a hyperproliferative disorder (e.g., cancer). In certain embodiments, a compound of Formula I is combined in a pharmaceutical combination formulation, or dosing regimen as combination therapy, with an additional, second therapeutic compound that has anti-inflammatory or anti-hyperproliferative properties or that is useful for treating an inflammation, immune-response disorder, or hyperproliferative disorder (e.g., cancer). The additional therapeutic may be a Bcl-2 inhibitor, a JAK inhibitor, a PI3K inhibitor, an mTOR inhibitor, an anti-inflammatory agent, an immunomodulatory agent, chemotherapeutic agent, an apoptosis-enhancer, a neurotropic factor, an agent for treating cardiovascular disease, an agent for treating liver disease, an anti-viral agent, an agent for treating blood disorders, an agent for treating diabetes, and an agent for treating immunodeficiency disorders. The second therapeutic agent may be an NSAID anti-inflammatory agent. The second therapeutic agent may be a chemotherapeutic agent. The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, or a stereoisomer, tautomer, solvate, metabolite, or pharmaceutically acceptable salt or prodrug thereof, in combination with a therapeutic agent such as an NSAID.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound of Formula I, or a stereoisomer, tautomer, solvate, metabolite, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula I, or a stereoisomer, tautomer, solvate, metabolite, or pharmaceutically acceptable salt or prodrug thereof, and the use of at least one other cancer treatment method. The amounts of the compound(s) of Formula I and the other pharmaceutically active therapeutic agent(s) and the relative timings of administration will be selected in order to achieve the desired combined therapeutic effect.

Metabolites of Compounds of Formula I

Also falling within the scope of this invention are the in vivo metabolic products of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. In one embodiment, the kit comprises a container comprising a compound of Formula I, or a stereoisomer, tautomer, solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I Compounds

Compounds of Formula I may be synthesized by synthetic routes that include processes analogous to those well-known in the chemical arts, particularly in light of the description contained herein, and those for tetrahydronaphthalene compounds described in Bencze, W. L. et al (1967) J. Med. Chem. 10:138-144; Lednicer, D. et al (1969) J. Med. Chem. 12:881-885; Prakash, C. et al (2008) 36:1218-1226; Rosati, R. L, et al (1998) J. Med. Chem. 41:2928-2931; WO 1996/021656, and other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

Synthetic chemistry transformations and protecting group methodologies (protection and deprotection) useful in synthesizing Formula I compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

The Examples provide exemplary methods for preparing Formula I compounds. Those skilled in the art will appreciate that other synthetic routes may be used to synthesize the Formula I compounds. Although specific starting materials and reagents are depicted and discussed in the Figures and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

In the methods of preparing Formula I compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 1996/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Formula I compounds can be prepared by the General Procedures of Schemes 1-6.

Scheme 1

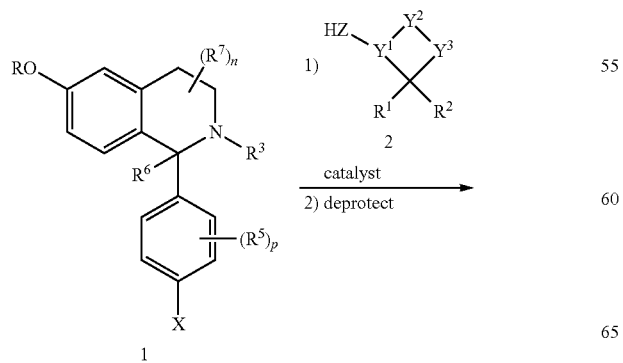

R = protecting group
$R^3$ = aryl or heteroaryl
X = I, Br, OTf

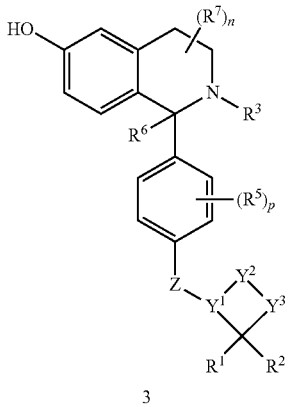

A general synthesis of compound 3, in which $R^3$ is an optionally substituted aryl or heteroaryl group, is shown in Scheme 1. A transition metal-catalyzed coupling reaction of compound 1 with an amine or alcohol 2, followed by deprotection of the protected phenol group, lead to compound 3.

Scheme 2

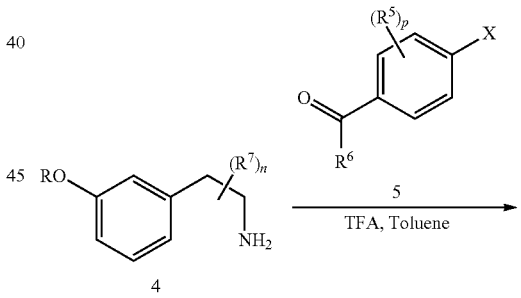

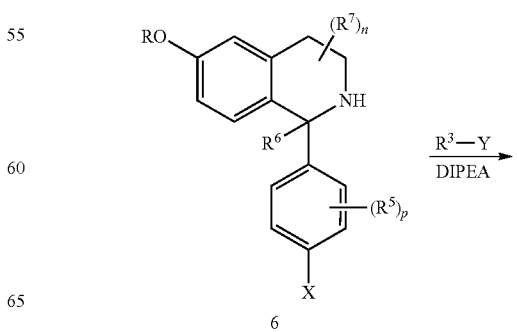

89
-continued

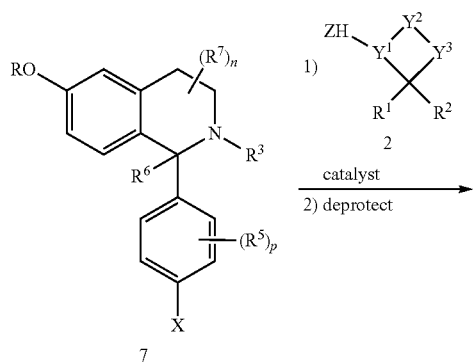

7

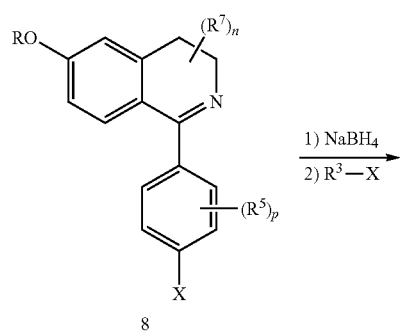

8

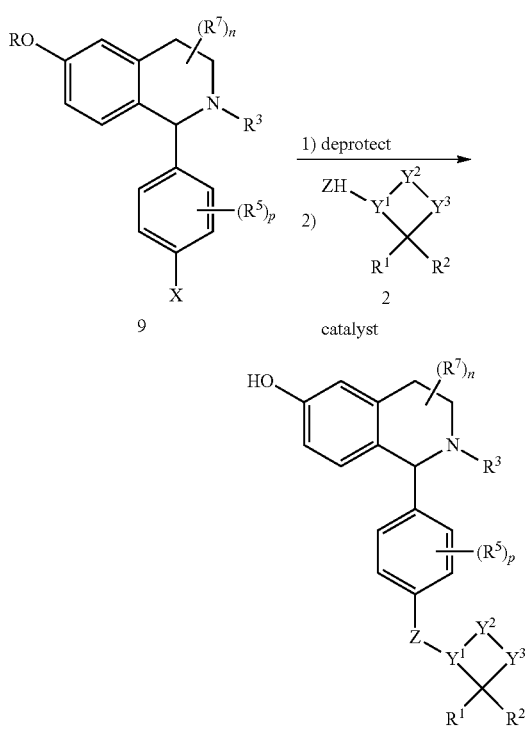

R = protecting group
X = I or Br
Y is a leaving group such as OTf, I, Br, etc.

When R³ is an alkyl or cycloalkyl or heterocycle, the synthesis of compound 3 is shown in Scheme 2. A Pictet-Spengler cyclization of amine 4 with an aldehyde or ketone 5 leads to intermediate 6. Alkylation of 6 produces intermediate 7. A transition metal-catalyzed coupling reaction of 7 with an amine or alcohol 2, followed by deprotection of the protected phenol group, leads to compound 3.

Scheme 3

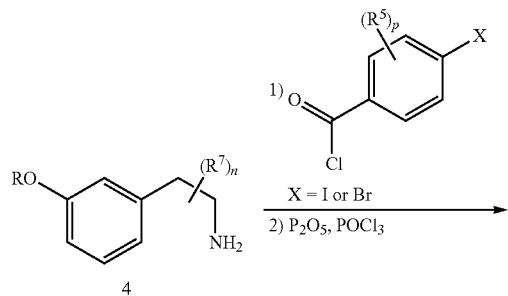

90
-continued

R = protecting group
X is a leaving group such as OTf, I, Br, etc

Alternatively, compound 3 can also be prepared as shown in Scheme 3. Amide coupling reaction of amine 4 with an acid chloride, followed by treatment with $P_2O_5/POCl_3$, gives imine 8. Reduction with sodium borohydride, followed by alkylation produces intermediate 9. Deprotection of the protected phenol group, followed by a transition metal-catalyzed coupling reaction with an amine or alcohol 2, leads to compound 3.

Scheme 4

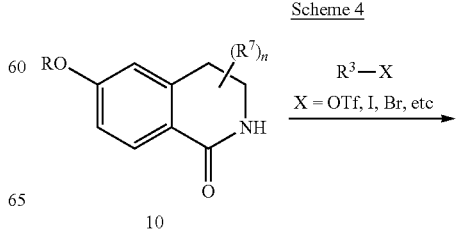

-continued

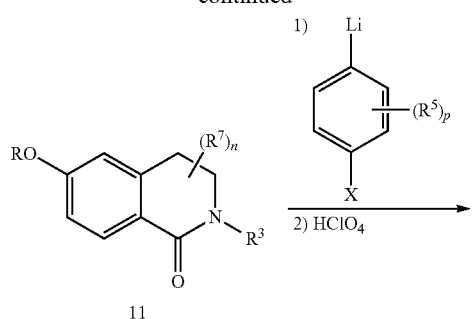

11

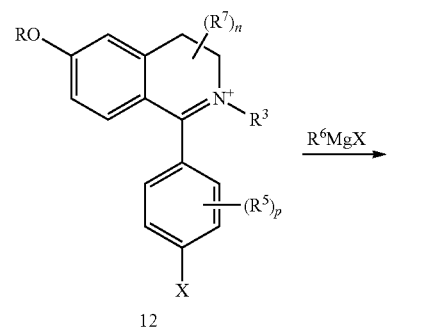

12

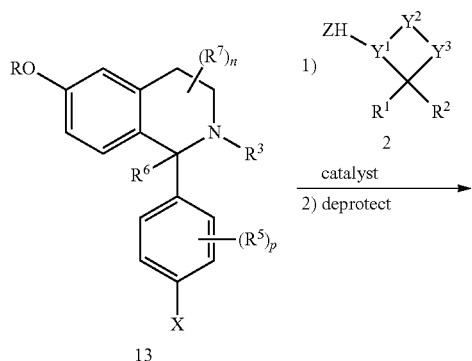

13

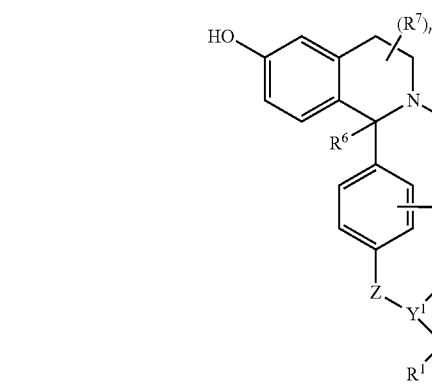

3

R = protecting group

Alternatively, compound 3 can also be prepared as shown in Scheme 4. Alkylation of lactam 10 produces intermediate 11. Addition of aryl lithium, followed by treatment with acid, gives iminium intermediate 12. Grignard addition leads to intermediate 13. A transition metal-catalyzed coupling reaction of 13 with an amine or alcohol 2, followed by deprotection of the protected phenol group, leads to compound 3.

Scheme 5

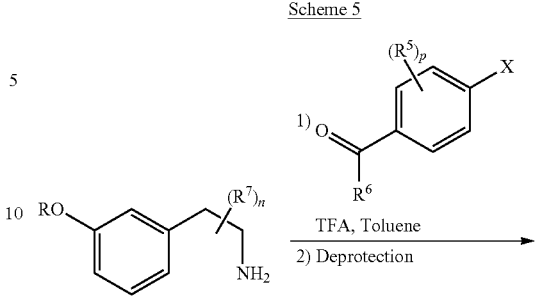

4

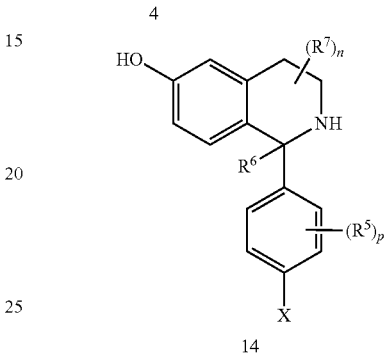

14

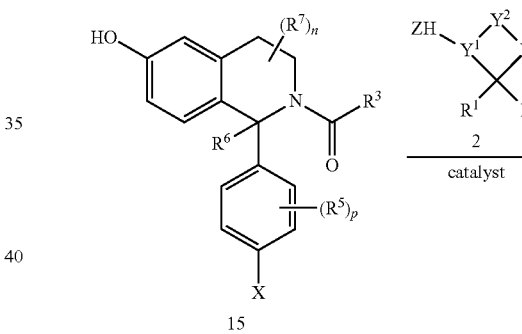

15

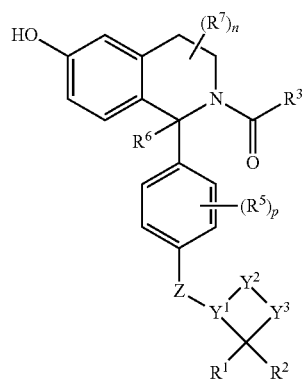

16

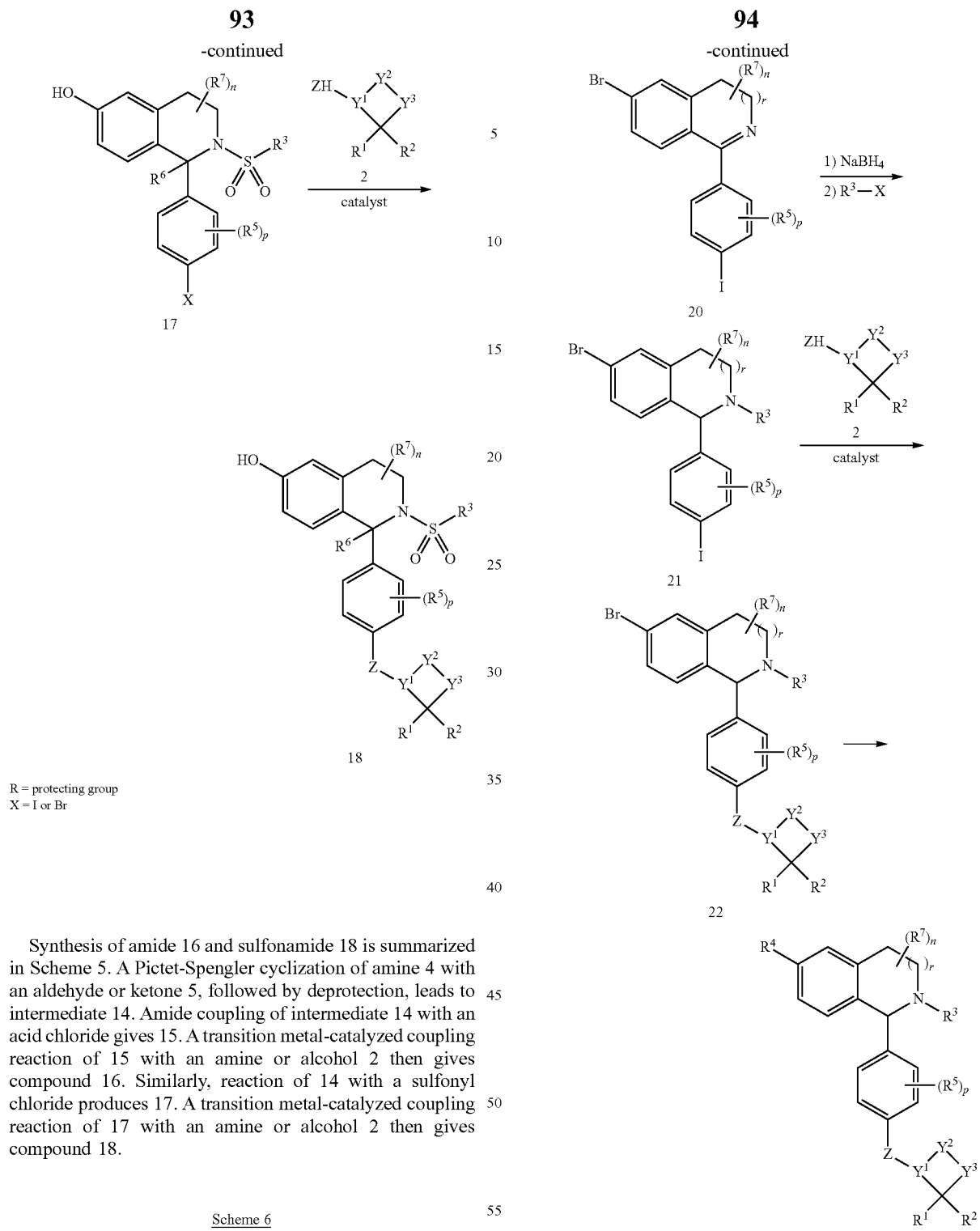

R = protecting group
X = I or Br

Synthesis of amide 16 and sulfonamide 18 is summarized in Scheme 5. A Pictet-Spengler cyclization of amine 4 with an aldehyde or ketone 5, followed by deprotection, leads to intermediate 14. Amide coupling of intermediate 14 with an acid chloride gives 15. A transition metal-catalyzed coupling reaction of 15 with an amine or alcohol 2 then gives compound 16. Similarly, reaction of 14 with a sulfonyl chloride produces 17. A transition metal-catalyzed coupling reaction of 17 with an amine or alcohol 2 then gives compound 18.

Scheme 6

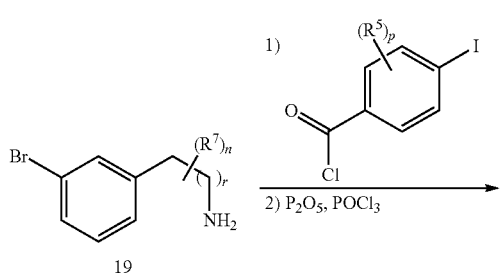

X is a leaving group such as OTf, I, Br, etc

General synthesis of compound 23 is shown in Scheme 6. Amide formation of compound 19 with an acid chloride, followed by treatment with $P_2O_5/POCl_3$, gives imine 20. Reduction with sodium borohydride, followed by alkylation, produces intermediate 21. A selective transition metal-catalyzed coupling reaction of the iodide in 21 with an amine or alcohol 2 then gives compound 22. The bromide in compound 22 can be further transformed to compound 23, through a variety of transition metal-catalyzed coupling reactions, such as Suzuki-coupling reaction, or a Buchwald-coupling reaction, or a Pd-mediated carbonylation reaction, etc.

EXAMPLES

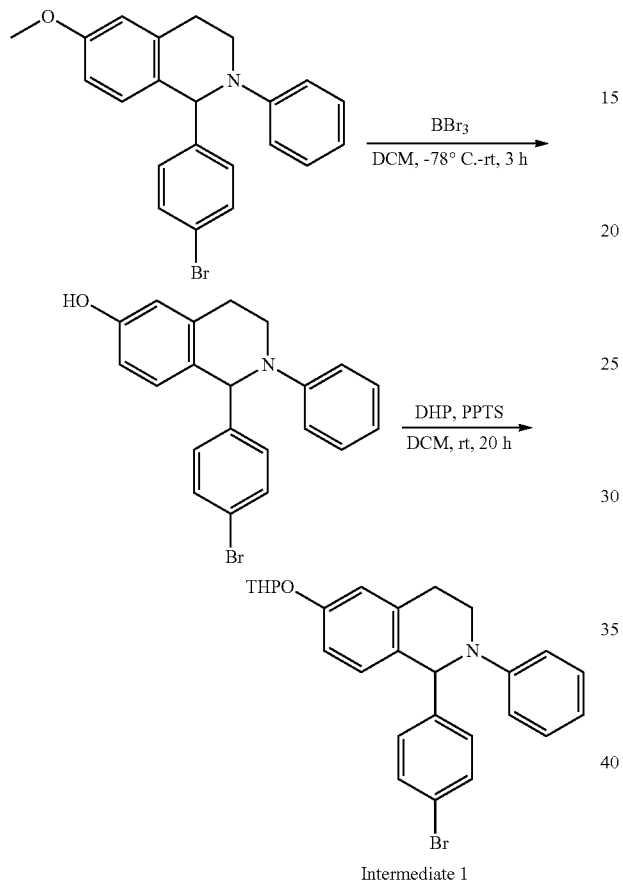

Intermediate 1

Intermediate 1: 1-(4-Bromophenyl)-2-phenyl-6-((tetrahydro-2H-pyran-2-yl)oxy)-1,2,3,4-tetrahydroisoquinoline

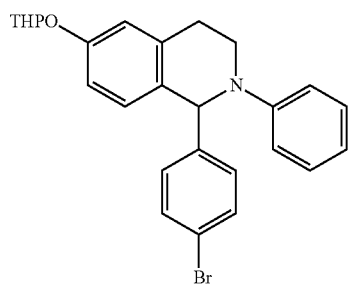

Step 1 1-(4-Bromophenyl)-2-phenyl-1,2,3,4-tetrahydroisoquinolin-6-ol

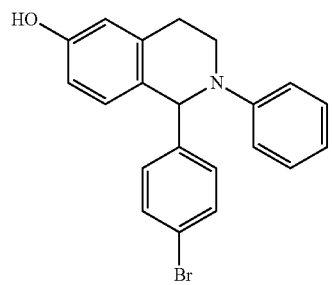 [SMILES: Oc1ccc2c(c1)CCN(c1ccccc1)C2c1ccc(Br)cc1]

To a solution of tribromoborane (0.76 mL, 0.76 mmol) in dichloromethane (3 mL) was added 1-(4-bromophenyl)-6-methoxy-2-phenyl-3,4-dihydro-1H-isoquinoline (200 mg, 0.51 mmol) at −78° C. dropwise. The reaction mixture was gradually warmed to 25° C. and stirred at 25° C. for 3 hours. To the reaction mixture was added sat. aq. NaHCO$_3$ (5 mL) and the mixture was extracted with DCM (10 mL×2) and the combined organic layers were washed with water (10 mL). The organic layer was dried over anhydrous Na$_2$SO$_4$ and was concentrated to afford the title compound as a light yellow oil (192 mg, 99%). $^1$H NMR (400 MHz, CDCl$_3$): δ 7.28 (d, J=8.4 Hz, 2H), 7.18-7.14 (m, 2H), 7.03-7.01 (m, 3H), 6.76-6.70 (m, 3H), 6.63-6.59 (m, 2H), 5.63 (s, 1H), 4.70 (s, 1H), 3.58-3.39 (m, 2H), 2.82-2.74 (m, 2H).

Step 2 1-(4-Bromophenyl)-2-phenyl-6-((tetrahydro-2H-pyran-2-yl)oxy)-1,2,3,4-tetrahydroisoquinoline

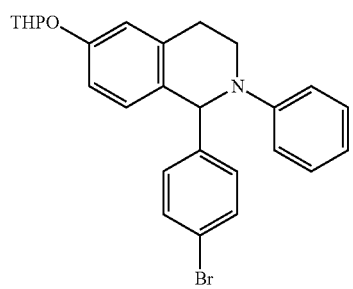

To a solution of pyridinium p-toluenesulfonate (316 mg, 1.27 mmol) in THF (5 mL) was added 1-(4-bromophenyl)-2-phenyl-3,4-dihydro-1H-isoquinolin-6-ol (From step 1, 482 mg, 1.27 mmol) and 3,4-dihydro-2H-pyran (0.53 g, 6.34 mmol). The reaction mixture was stirred at 85° C. for 16 hours. The reaction mixture was then concentrated and the residue was purified by chromatography on silica gel (0-10% EtOAc in petroleum ether) to afford the title compound as a light yellow solid (270 mg, 46%). $^1$H NMR (400 MHz, CDCl$_3$): δ 7.27 (d, J=8.4 Hz, 2H), 7.17-7.13 (m, 2H), 7.08-7.02 (m, 3H), 6.85-6.80 (m, 2H), 6.74 (d, J=8.4 Hz, 2H), 6.71-6.67 (m, 1H), 5.63 (s, 1H), 5.33-5.30 (m, 1H), 3.90-3.78 (m, 2H), 3.65-3.32 (m, 2H), 2.87-2.75 (m, 2H), 1.85-1.49 (m, 6H).

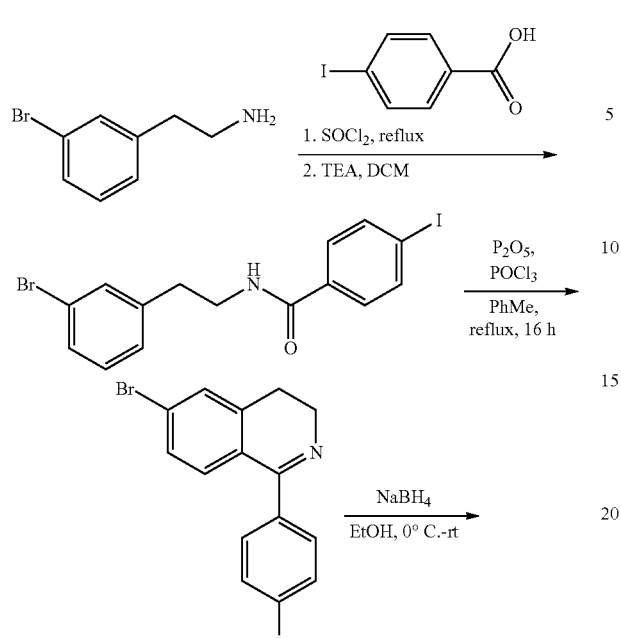

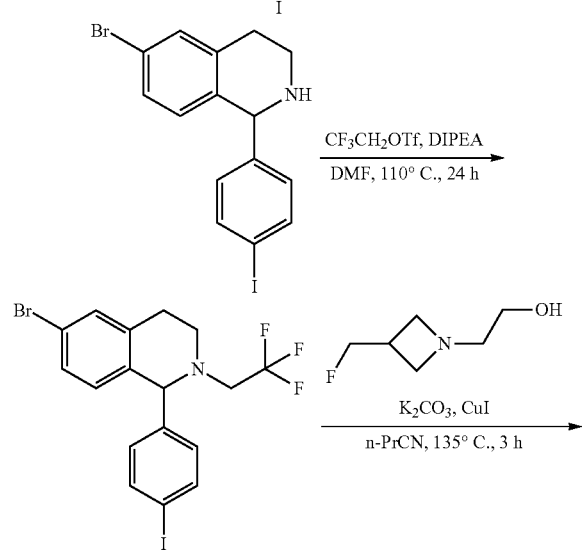

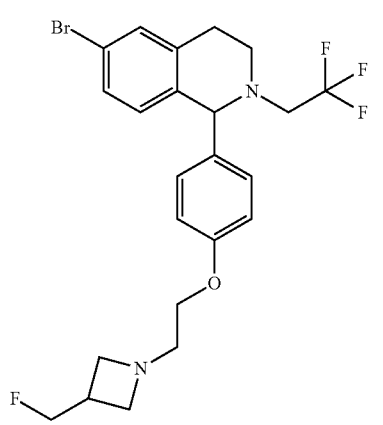

Intermediate 2

Intermediate 2: 6-Bromo-1-(4-(2-(3-(fluoromethyl) azetidin-1-yl)ethoxy)phenyl)-2-(2,2,2-trifluoro-ethyl)-1,2,3,4-tetrahydroisoquinoline

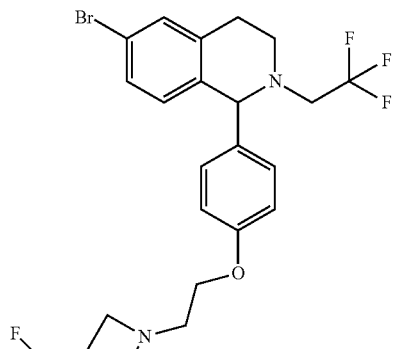

Step 1 N-[2-(3-Bromophenyl)ethyl]-4-iodo-benzamide

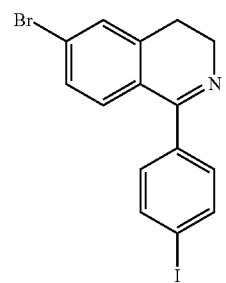 [SMILES: Brc1ccc2c(c1)CCN=C2c1ccc(I)cc1]

A mixture of 4-iodobenzoic acid (10.0 g, 40.32 mmol) in thionyl chloride (40 mL, 40.32 mmol) was stirred at 80° C. for 16 hours. The reaction mixture was concentrated to give 4-iodobenzoyl chloride (10.7 g, 99%) as a white solid. To a solution of 2-(3-bromophenyl)ethylamine (6.0 g, 29.99 mmol) and triethylamine (20 mL, 149.94 mmol) in dichloromethane (100 mL) at 0° C. was added 4-iodobenzoyl chloride prepared above (9.6 g, 35.99 mmol) portionwise. The resulting mixture was stirred at 25° C. for 4 hours and was then diluted with DCM (500 mL). Water (100 mL) was added to the reaction mixture and two layers were separated. The organic layer was dried over anhydrous sodium sulfate, and was concentrated to give the title compound as a white solid (12 g, 93%). $^1$H NMR (400 MHz, CDCl$_3$) δ 7.75 (d, J=8.4 Hz, 2H), 7.42-7.36 (m, 3H), 6.15 (s, 1H), 3.69-3.64 (m, 2H), 2.91-2.87 (m, 2H).

Step 2
6-Bromo-1-(4-iodophenyl)-3,4-dihydroisoquinoline

To a mixture of N-[2-(3-bromophenyl)ethyl]-4-iodo-benzamide (From step 1, 4.73 g, 11 mmol), phosphoruspentoxide (10.7 g, 75.5 mmol) in anhydrous toluene (60 mL) was added phosphorus oxychloride (113 mL, 1223.7 mmol) slowly. The reaction mixture was stirred at 110° C. for 16 hours. The reaction mixture was then poured onto ice-water (100 mL) The pH value of solution was adjusted to 9 with 15% aq. NaOH solution, The mixture was extracted with EtOAc (300 mL×3) and the combined organic layers were dried over anhydrous $Na_2SO_4$, filtered and concentrated to give the title compound (6 g, 96%). $^1$H NMR (400 MHz, $CDCl_3$) δ 7.78 (d, J=8.0 Hz, 2H), 7.44-7.38 (m, 2H), 7.32 (d, J=8.0 Hz, 2H), 7.09 (d, J=8.0 Hz, 1H), 3.84-3.81 (m, 2H), 2.78 (t, J=7.2 Hz, 2H).

Step 3 6-Bromo-1-(4-iodophenyl)-1,2,3,4-tetrahydroisoquinoline

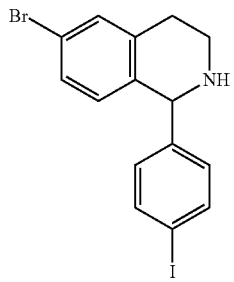 [SMILES: Brc1ccc2c(c1)CCNC2c1ccc(I)cc1]

To a solution of 6-bromo-1-(4-iodophenyl)-3,4-dihydroisoquinoline (From step 2, 31.0 g, 75.2 mmol) in ethanol (400 mL) at 0° C. was added sodium borohydride (8.54 g, 225.7 mmol). The resulting mixture was stirred at 15° C. for 16 hours. Solvent was evaporated, and the residue was dissolved in DCM (500 mL). The solution was washed with water (100 mL), dried over anhydrous sodium sulfate, and concentrated to give the title compound as a white solid (30 g, 96%). $^1$H NMR (400 MHz, $CDCl_3$) δ 7.66 (d, J=8.0 Hz, 2H), 7.31 (s, 1H), 7.17 (d, J=8.0 Hz, 1H), 7.01 (d, J=8.4 Hz, 2H), 6.59 (d, J=8.0 Hz, 1H), 4.98 (s, 1H), 3.26-3.20 (m, 1H), 3.10-2.98 (m, 2H), 2.84-2.77 (m, 1H), 1.83 (s, 1H).

Step 4 6-Bromo-1-(4-iodophenyl)-2-(2,2,2-trifluoroethyl)-3,4-dihydro-1H-isoquinoline

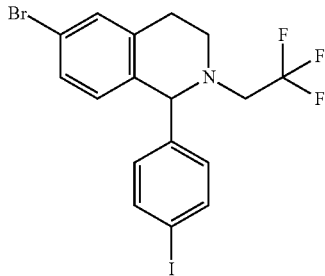 [SMILES: FC(F)(F)CN1CCc2cc(Br)ccc2C1c1ccc(I)cc1]

To a solution of 6-bromo-1-(4-iodophenyl)-1,2,3,4-tetrahydroisoquinoline (From step 3, 30.0 g, 72.4 mmol) in DMF (200 mL) was added 2,2,2-trifluoroethyltrifluoromethanesulfonate (84 g, 362 mmol) and N,N-diisopropylethylamine (103 mL, 579 mmol). The resulting mixture was stirred at 90° C. for 16 hours and was then cooled to room temperature. Solvent was removed and the residue was purified by flash chromatography on silica gel (0-5% EtOAc in petroleum ether) to give the title compound (26 g, 72%) as a brown oil. $^1$H NMR (400 MHz, $CDCl_3$) δ 7.66 (d, J=8.4 Hz, 2H), 7.30 (s, 1H), 7.16 (d, J=8.4 Hz, 1H), 7.02 (d, J=8.4 Hz, 2H), 6.56 (d, J=8.4 Hz, 1H), 4.76 (s, 1H), 3.31-3.26 (m, 1H), 3.12-3.01 (m, 4H), 2.98-2.79 (m, 2H).

Step 5 6-Bromo-1-[4-[2-[3-(fluoromethyl)azetidin-1-yl]ethoxy]phenyl]-2-(2,2,2-trifluoroethyl)-3,4-dihydro-1H-isoquinoline

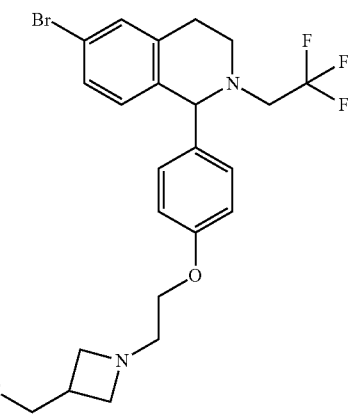

A mixture of 2-[3-(fluoromethyl)azetidin-1-yl]ethanol (10 g, 80 mmol), 6-bromo-1-(4-iodophenyl)-2-(2,2,2-trifluoroethyl)-3,4-dihydro-1H-isoquinoline (From step 4, 8.0 g, 16 mmol), CuI (3 g, 16 mmol) and $K_2CO_3$ (6 g, 48 mmol) in n-PrCN (80 mL) was stirred at 135° C. for 3 hours under $N_2$ atmosphere. The reaction mixture was filtered and the filtrate was concentrated to dryness. The residue was purified by flash column chromatography (0-50% EtOAc in DCM) to give the title compound (3.8 g, 47%) as a brown oil. $^1$H NMR (400 MHz, $CDCl_3$) δ 7.28 (s, 1H), 7.13 (d, J=8.0 Hz, 3H), 6.83 (d, J=8.0 Hz, 2H), 6.57 (d, J=8.4 Hz, 1H), 4.73 (s, 1H), 4.58-4.45 (m, 2H), 3.98 (t, J=5.2 Hz, 2H), 3.59-3.56 (m, 2H), 3.30-3.19 (m, 3H), 3.10-3.01 (m, 3H), 2.94-2.79 (m, 5H).

Example 101 1-(4-(2-(3-(Fluoromethyl)azetidin-1-yl)ethoxy)phenyl)-2-phenyl-1,2,3,4-tetrahydroisoquinolin-6-ol 101

Step 1: 1-(4-(2-(3-(Fluoromethyl)azetidin-1-yl)ethoxy)phenyl)-2-phenyl-6-((tetrahydro-2H-pyran-2-yl)oxy)-1,2,3,4-tetrahydroisoquinoline

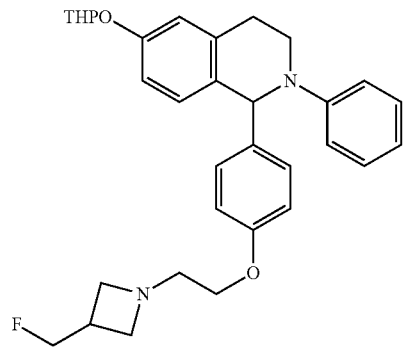

To a solution of 1-(4-bromophenyl)-2-phenyl-6-tetrahydropyran-2-yloxy-3,4-dihydro-1H-isoquinoline (Intermediate 1, 370.0 mg, 0.80 mmol) in n-PrCN (2.0 mL, 0.80 mmol) was added 2-[3-(fluoromethyl)azetidin-1-yl]ethanol (318 mg, 2.39 mmol),

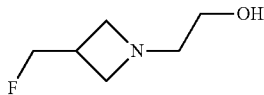

CuI (455 mg, 2.39 mmol) and K$_2$CO$_3$ (330 mg, 2.39 mmol). The solution was purged with N$_2$ for 5 minutes and was stirred at 135° C. for 16 hours. The reaction mixture was concentrated to dryness. The residue was purified by column chromatography on silica gel (0-5% MeOH in DCM) to afford the title compound as a light yellow oil (140 mg, 34%); LCMS: 517.3 [M+H]$^+$.

Step 2

A mixture of 1-[4-[2-[3-(Fluoromethyl)azetidin-1-yl]ethoxy]phenyl]-2-phenyl-6-tetrahydropyran-2-yloxy-3,4-dihydro-1H-isoquinoline (From step 1, 140 mg, 0.27 mmol) in acetic acid (8 mL) and water (4 mL) was stirred at 18° C. for 16 hours. The reaction mixture was concentrated to dryness and the residue was taken up in EtOAc (20 mL×2) and saturated NaHCO$_3$ (20 mL) solution. The organic layer was then separated and dried over anhydrous Na$_2$SO$_4$ before concentration to dryness. The residue was purified by column chromatography on silica gel (0-7% MeOH in DCM) to afford 101 (80 mg, 68%) as a yellow oil. $^1$H NMR (400 MHz, CDCl$_3$) δ 7.25-7.21 (m, 2H), 7.05 (d, J=8.4 Hz, 2H), 6.98 (d, J=8.0 Hz, 1H), 6.86 (d, J=8.0 Hz, 2H), 6.75 (t, J=7.2 Hz, 1H), 6.69 (d, J=8.0 Hz, 2H), 6.64 (d, J=8.0 Hz, 1H), 6.59 (s, 1H), 5.71 (s, 1H), 4.60-4.41 (m, 2H), 3.93 (t, J=4.8 Hz, 2H), 3.65-3.50 (m, 3H), 3.48-3.38 (m, 1H), 3.26 (t, J=7.2 Hz, 2H), 3.00-2.75 (m, 4H), 2.63-2.59 (m, 1H); LCMS: 433.1 [M+H]$^+$.

Example 102 1-[4-[1-(3-Fluoropropyl)azetidin-3-yl]oxyphenyl]-2-phenyl-3,4-dihydro-1H-isoquinolin-6-ol 102

Step 1: 4-(2-Phenyl-6-tetrahydropyran-2-yloxy-3,4-dihydro-1H-isoquinolin-1-yl)phenol

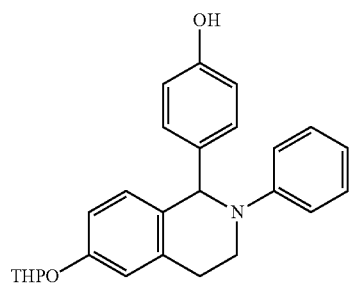

To a mixture of 1-(4-bromophenyl)-2-phenyl-6-tetrahydropyran-2-yloxy-3,4-dihydro-1H-isoquinoline (Intermediate 1, 300 mg, 0.65 mmol) in 1,4-dioxane (5 mL) and water (3 mL) was added Pd$_2$(dba)$_3$ (591 mg, 0.65 mmol), KOH (36 mg, 0.65 mmol) and t-BuXphos (274 mg, 0.65 mmol). The reaction solution was purged with N$_2$ for 5 minutes and was stirred at 90° C. for 16 hours. The solution was concentrated to dryness. The residue was purified by column chromatography on silica gel (0-30% EtOAc in petroleum ether) to give the title compound as a light yellow oil (170 mg, 66%). $^1$H NMR (400 MHz, CDCl$_3$): δ 7.25-7.21 (m, 2H), 7.15-7.13 (m, 1H), 7.08-7.06 (m, 2H), 6.95-6.84 (m, 4H), 6.76-6.72 (m, 1H), 6.67 (d, J=8.8 Hz, 2H), 5.73 (s, 1H), 5.41-5.40 (m, 1H), 3.95-3.90 (m, 1H), 3.65-3.60 (m, 2H), 3.51-3.45 (m, 1H), 2.95-2.80 (m, 1H), 2.03-1.98 (m, 1H), 1.87-1.85 (m, 2H), 1.71-1.65 (m, 3H); LCMS: 402.0 [M+H]$^+$.

Step 2: tert-Butyl 3-[4-(2-phenyl-6-tetrahydropyran-2-yloxy-3,4-dihydro-1H-isoquinolin-1-yl)phenoxy]azetidine-1-carboxylate

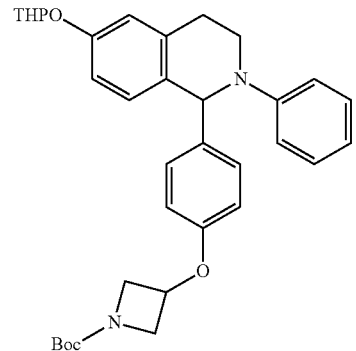

To a mixture of 4-(2-phenyl-6-tetrahydropyran-2-yloxy-3,4-dihydro-1H-isoquinolin-1-yl)phenol (From step 1, 130 mg, 0.32 mmol) in DMF (3 mL) was added 1-Boc-3-iodoazetidine (137 mg, 0.49 mmol) and Cs$_2$CO$_3$ (106 mg, 0.32 mmol). The reaction mixture was stirred at 80° C. for 16 hours. The solution was concentrated to dryness. The residue was purified by column chromatography on silica gel (0-20% EtOAc in petroleum ether) to afford the title compound as a light yellow oil (90 mg, 50%). LCMS: 557.1 [M+H]$^+$.

Step 3: 1-[4-(Azetidin-3-yloxy)phenyl]-2-phenyl-3,4-dihydro-1H-isoquinolin-6-ol

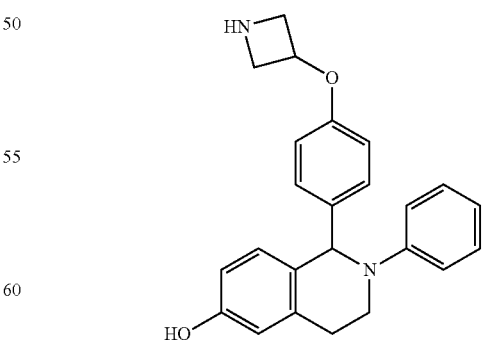

To a mixture of tert-butyl 3-[4-(2-phenyl-6-tetrahydropyran-2-yloxy-3,4-dihydro-1H-isoquinolin-1-yl)phenoxy]azetidine-1-carboxylate (From step 2, 130 mg, 0.23 mmol) in dichloromethane (2 mL) was added 2,2,2-trifluoroacetic acid (0.20 mL) at 0° C. The reaction was warmed to 25° C. and stirred for further 3 hours. To the reaction mixture was added saturated aqueous NaHCO$_3$ (10 mL). The mixture was extracted with DCM (10 mL×2). The combined organic layers were dried over anhydrous Na$_2$SO$_4$ and were concentrated to afford the title compound as a yellow oil (86 mg, 99%). The crude compound was used for the next step directly. LCMS: 373.0 [M+H]$^+$.

Step 4

To a solution of 1-[4-(azetidin-3-yloxy)phenyl]-2-phenyl-3,4-dihydro-1H-isoquinolin-6-ol (From step 3, 86 mg, 0.23 mmol) in DMF (5 mL) was added 1-bromo-3-fluoropropane (33 mg, 0.23 mmol) and DIEA (0.08 mL, 0.46 mmol). The reaction mixture was stirred at 25° C. for 6 hours. The reaction mixture was concentrated and the residue was purified by chromatography on silica (0-5% MeOH in DCM) to afford 102 as a light yellow solid (29 mg, 29%). $^1$H NMR (400 MHz, CDCl$_3$) δ 7.23 (t, J=8.0 Hz, 2H), 7.11-7.09 (m, 3H), 6.84 (d, J=8.0 Hz, 2H), 6.76 (t, J=7.2 Hz, 1H), 6.71-6.60 (m, 4H), 5.72 (s, 1H), 4.78-4.70 (m, 1H), 4.58-4.40 (m, 2H), 3.89-3.83 (m, 2H), 3.66-3.60 (m, 1H), 3.50-3.44 (m, 1H), 3.15-3.07 (m, 2H), 2.92-2.77 (m, 2H), 2.68 (t, J=6.8 Hz, 2H), 1.83-1.76 (m, 2H). LCMS: 433.0 [M+H]$^+$.

Examples 103 and 104 2-fluoro-1-[(1S)-1-[4-[2-[3-(fluoromethyl)azetidin-1-yl]ethoxy]phenyl]-6-hydroxy-3,4-dihydro-1H-isoquinolin-2-yl]-2-methyl-propan-1-one 103 and 2-fluoro-1-[(1R)-1-[4-[2-[3-(fluoromethyl)azetidin-1-yl]ethoxy]phenyl]-6-hydroxy-3,4-dihydro-1H-isoquinolin-2-yl]-2-methyl-propan-1-one 104

Step 1: 1-(4-iodophenyl)-6-methoxy-1,2,3,4-tetrahydroisoquinoline

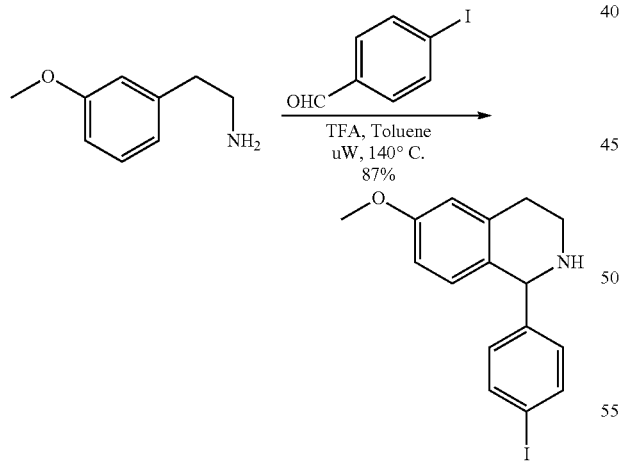

A mixture of 2-(3-methoxyphenyl)ethanamine (300 mg, 1.984 mmol) and 4-iodobenzaldehyde (483 mg, 2.08 mmol) in toluene (4 mL) and TFA (1.5 mL) in a sealed microwave tube was heated at 140° C. in a microwave for 30 min. The mixture was concentrated. The residue was dissolved in EtOAc, washed with sat. NaHCO$_3$ (2×). The organic was dried (Na$_2$SO$_4$), filtered and concentrated. The crude product was purified by silica flash chromatography (0-10% MeOH/DCM) to give the title compound (630 mg, 87% yield) as a white solid. $^1$H NMR (400 MHz, Chloroform-d) δ 7.66-7.60 (m, 2H), 7.05-6.99 (m, 2H), 6.68-6.64 (m, 1H), 6.63-6.60 (m, 2H), 4.98 (s, 1H), 3.77 (s, 3H), 3.25-3.17 (m, 1H), 3.11-2.92 (m, 2H), 2.81-2.73 (m, 1H). LCMS (ESI) m/z 366 [M+H$^+$].

Step 2: 1-(4-iodophenyl)-1,2,3,4-tetrahydroisoquinolin-6-ol

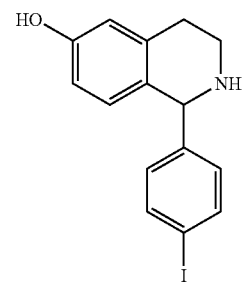 [SMILES: Oc1ccc2c(c1)CCNC2c1ccc(I)cc1]

To a solution of 1-(4-iodophenyl)-6-methoxy-1,2,3,4-tetrahydroisoquinoline (623 mg, 1.706 mmol) in DCM (11.4 mL) at −78° C. was added BBr$_3$ (1 mol/L) in DCM (3.4 mL) dropwise. The mix was warmed to 0° C. and stirred for 1 h. The mixture was then stirred at rt for 1 h. The mixture was re-cooled to −78° C., quenched with MeOH (5 mL), warmed up to room temperature and concentrated to a solid which was triturated with DCM to give 645 mg of an off-white solid. The crude product was purified by silica flash chromatography (0-10% MeOH/DCM) to give the title compound (490 mg, 81.8% yield) as an off-white solid. $^1$H NMR (400 MHz, DMSO-d6) δ 9.57 (s, 1H), 9.02 (s, 1H), 7.90-7.79 (m, 2H), 7.22-7.11 (m, 2H), 6.67 (d, J=2.5 Hz, 1H), 6.61 (dd, J=8.5, 2.5 Hz, 1H), 6.53 (dd, J=8.5, 0.8 Hz, 1H), 5.64 (d, J=4.5 Hz, 1H), 3.42-3.28 (m, 2H), 3.16-3.06 (m, 1H), 2.98 (dt, J=17.3, 5.7 Hz, 1H). LCMS (ESI) m/z 352 [M+H$^+$].

Step 3: 2-fluoro-1-(6-hydroxy-1-(4-iodophenyl)-3,4-dihydroisoquinolin-2(1H)-yl)-2-methylpropan-1-one

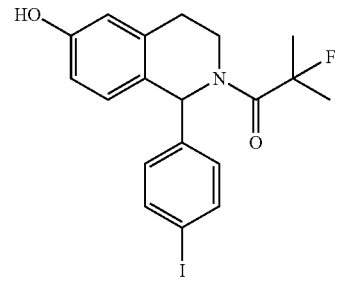 [SMILES: CC(C)(F)C(=O)N1CCc2cc(O)ccc2C1c1ccc(I)cc1]

To a solution of 1-(4-iodophenyl)-1,2,3,4-tetrahydroisoquinolin-6-ol (195 mg, 0.555 mmol) in DMF (2.2 mL) was added DIPEA (108 mg, 0.833 mmol) followed by 2-fluoro-2-methyl-propanoyl chloride (1 M in CHCl$_3$) (0.666 mL, 0.666 mmol) dropwise. The mixture was stirred at room temperature for 20 min. The reaction was quenched with sat. NaHCO$_3$, extracted with EtOAc (2×). The combined organics were dried (Na$_2$SO$_4$), filtered and concentrated. The crude product was purified by silica flash chromatography (0-50% iPrOAc/heptane) to give the title compound (210 mg, 86.1% yield). LCMS (ESI) m/z 440 [M+H⁺].

Step 4

The mixture of 2-fluoro-1-[6-hydroxy-1-(4-iodophenyl)-3,4-dihydro-1H-isoquinolin-2-yl]-2-methyl-propan-1-one (157 mg, 0.357 mmol), 2-[3-(fluoromethyl)azetidin-1-yl]ethanol (190 mg, 1.43 mmol), CuI (27 mg, 0.143 mmol) and K₂CO₃ (148 mg, 1.072 mmol) in butyronitrile (2.4 mL) in a microwave vial was purged with N₂ for 5 min, and then sealed and heated at 135° C. for 15 h. The mixture was filtered through celite, concentrated. The crude product was purified by chiral SFC (Chiralpak AD 150×21.1 mm, 5 μm; 20% MeOH w/0.1% NH₄OH) to give 103 (60 mg, 38% yield) 104 (64 mg, 40% yield) as off-white solids.

103 1$^{st}$ peak: ¹H NMR (400 MHz, DMSO-d₆) δ 9.35 (s, 1H), 6.99 (d, J=8.7 Hz, 2H), 6.90-6.77 (m, 3H), 6.63-6.53 (m, 3H), 4.49 (dd, J=47.6, 6.2 Hz, 2H), 4.22-4.07 (m, 1H), 3.86 (t, J=5.5 Hz, 2H), 3.28-3.17 (m, 3H), 3.07-2.92 (m, 2H), 2.92-2.79 (m, 1H), 2.79-2.58 (m, 4H), 1.56 (dd, J=21.9, 11.8 Hz, 6H).

104 2$^{nd}$ peak: ¹H NMR (400 MHz, DMSO-d6) δ 9.34 (s, 1H), 6.99 (d, J=8.3 Hz, 2H), 6.91-6.77 (m, 3H), 6.63-6.50 (m, 3H), 4.49 (dd, J=47.6, 6.1 Hz, 2H), 4.22-4.07 (m, 1H), 3.86 (s, 2H), 3.30-3.14 (m, 2H), 3.09-2.91 (m, 4H), 2.95-2.79 (m, 1H), 2.80-2.59 (m, 3H), 1.72-1.39 (m, 6H). LCMS (ESI) m/z 445 [M+H⁺].

Example 107 and 108 (1S)-1-[4-[2-[3-(fluoromethyl)azetidin-1-yl]ethoxy]phenyl]-2-(2-fluoro-2-methyl-propyl)-1-methyl-3,4-dihydroisoquinolin-6-ol 107 and (1R)-1-[4-[2-[3-(fluoromethyl)azetidin-1-yl]ethoxy]phenyl]-2-(2-fluoro-2-methyl-propyl)-1-methyl-3,4-dihydroisoquinolin-6-ol 108

Step 1: 1-(4-iodophenyl)-6-methoxy-1-methyl-3,4-dihydroisoquinoline-2(1H)-carbaldehyde

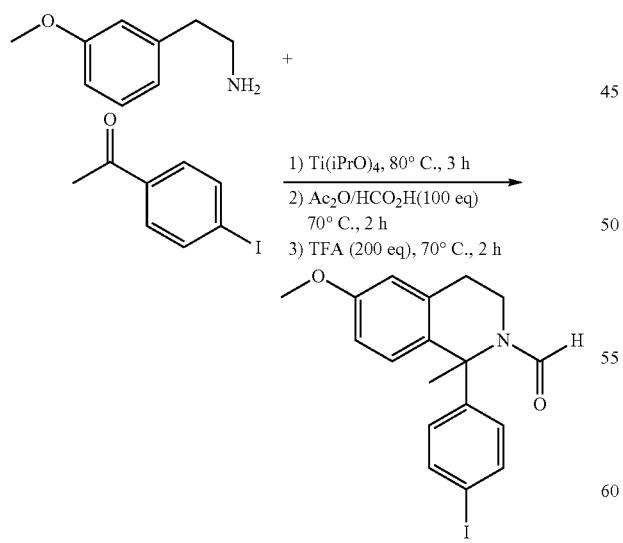

A mixture of 2-(3-methoxyphenyl)ethanamine (516 mg, 3.41 mmol) and 1-(4-iodophenyl)ethanone (700 mg, 2.84 mmol) in Ti(iPrO)₄ (1.26 mL) was heated at 80° C. for 3 h. A solution of acetic-formic anhydride (prepared from formic acid (13 1 g, 284.5 mmol,) and acetic anhydride (29.05 g, 284.5 mmol) was added at 0° C. and heated at 70° C. for 2 h. To this reaction mixture was added TFA (64.88 g, 569 mmol) at 0° C. The mixture was then heated at 70° C. for 1.5 h. The mixture was then concentrated. The residue was dissolved in EtOAc, washed with brine/sat. NaHCO₃ (1:1) twice. The aqueous layer was back-extracted with EtOAc once. The combined organics were dried (Na₂SO4), filtered and concentrated. The crude product was purified by silica flash chromatography (0-60% iPrOAc/heptane) to give the title compound (950 mg, 82% yield) as a yellow solid. ¹H NMR (400 MHz, Chloroform-d) 8.15 (s, 1H), 7.67 7.54 (m, 2H), 7.12 6.95 (m, 2H), 6.79 6.62 (m, 3H), 4.10 3.98 (m, 1H), 3.77 (s, 3H), 3.73 3.61 (m, 1H), 2.93 2.84 (m, 2H), 1.98 (s, 3H). LCMS (ESI) m/z 408 [M+H⁺].

Step 2: 1-(4-iodophenyl)-6-methoxy-1-methyl-1,2,3,4-tetrahydroisoquinoline

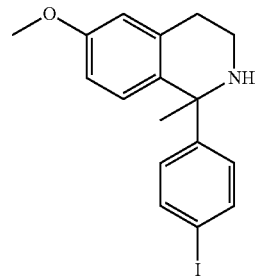 [SMILES: COc1ccc2c(c1)CCNC2(C)c1ccc(I)cc1]

The mixture solution of 1-(4-iodophenyl)-6-methoxy-1-methyl-3,4-dihydroisoquinoline-2-carbaldehyde (950 mg, 2.33 mmol) in EtOH (80 mL) and NaOH (20% in water, (78.7 mL) was heated at reflux for 43 h. The mixture was cooled to room temperature, layers were separated, the aqueous layer was extracted with EtOAc (2×). The combined organics were concentrated. The residue was partitioned between DCM and water. The layers were separated, the aqueous layer was extracted with DCM (2×). The combined organics were dried (Na₂SO₄), filtered and concentrated. The crude product was purified by silica flash chromatography (0-5% MeOH/DCM) to give the title compound (635 mg, 71.8% yield) as a yellow oil. LCMS (ESI) m/z 380 [M+H⁺].

Step 3: 1-(4-iodophenyl)-1-methyl-1,2,3,4-tetrahydroisoquinolin-6-ol

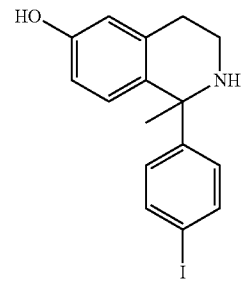 [SMILES: CC1(c2ccc(I)cc2)NCCc2cc(O)ccc21]

To a solution of 1-(4-iodophenyl)-6-methoxy-1-methyl-3,4-dihydro-2H-isoquinoline (586 mg, 1.545 mmol) in DCM (10.30 mL) at −78° C. was added BBr₃ in DCM (1 M, 4.64 mL) dropwise. The mixture was warmed to 0° C. and stirred for 2 h. The mixture was re-cooled to −78° C., quenched with MeOH (5 mL), warmed up to room temperature and concentrated to a solid which was triturated with DCM to give a brown solid. The crude solid was purified by silica flash chromatography (0-10% MeOH/DCM) to give the title compound (476 mg, 84.3% yield) as a yellow solid. LCMS (ESI) m/z 366 [M+H⁺].

Step 4: 6-((tert-butyldimethylsilyl)oxy)-1-(4-iodo-phenyl)-1-methyl-1,2,3,4-tetrahydroisoquinoline

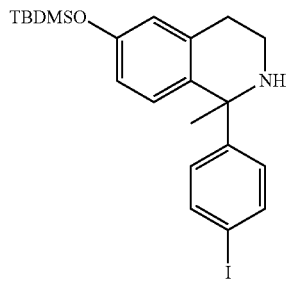

To a solution of 1-(4-iodophenyl)-1-methyl-3,4-dihydro-2H-isoquinolin-6-ol (476 mg, 1.30 mmol) and imidazole (266 mg, 3.91 mmol) in DMF (6.5 mL) was added tert-butyldimethylsilyl chloride, TBDMS-Cl (354 mg, 2.35 mmol) dropwise. The mixture was stirred at room temperature for 2 h. The mix was diluted with EtOAc, washed with sat. NaHCO₃. The aqueous layer was extracted with EtOAc one more time. The combined organics were dried (Na₂SO₄), filtered and concentrated. The crude product was purified by silica flash chromatography (0-50% iPrOAc/heptane) to give the title compound (492 mg, 78.7% yield) as a pale yellow oil. LCMS m/z 480 [M+H⁺].

Step 5: 6-((tert-butyldimethylsilyl)oxy)-2-(2-fluoro-2-methylpropyl)-1-(4-iodophenyl)-1-methyl-1,2,3,4-tetrahydroisoquinoline

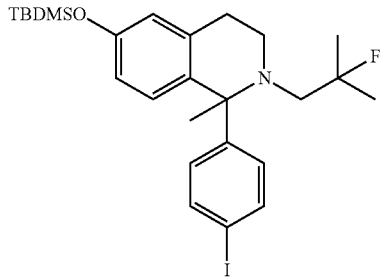 [SMILES: CC(C)(F)CN1CCc2cc(O[Si](C)(C)C(C)(C)C)ccc2C1(C)c1ccc(I)cc1]

The mixture of tert-butyl-[[1-(4-iodophenyl)-1-methyl-3,4-dihydro-2H-isoquinolin-6-yl]oxy]-dimethyl-silane (357 mg, 0.745 mmol), (2-fluoro-2-methyl-propyl) trifluoromethanesulfonate (1.23 g, 5.47 mmol) and DIPEA (707 mg, 5.47 mmol) in 1,4-dioxane (5 mL) was heated at 100° C. for 23 h. The mixture was diluted with EtOAc, washed with sat. NaHCO₃. The aqueous layer was extracted with EtOAc. The combined organics were dried (Na₂SO₄), filtered and concentrated. The crude product was purified by silica flash chromatography (0-10% iPrOAc/heptane) to give the title compound (280 mg, 67.9% yield) as a colorless oil. ¹H NMR (400 MHz, Chloroform-d) 7.60 7.52 (m, 2H), 7.20 7.12 (m, 2H), 6.54 (d, J=2.5 Hz, 1H), 6.49 6.43 (m, 1H), 6.40 (d, J=8.6 Hz, 1H), 3.29 (dddd, J=12.1, 5.6, 3.0, 1.8 Hz, 1H), 3.17 3.06 (m, 1H), 2.93 (ddd, J=12.0, 10.8, 3.4 Hz, 1H), 2.69 (dt, J=15.9, 3.2 Hz, 1H), 2.57 (t, J=13.9 Hz, 1H), 2.21 (dd, J=32.8, 14.3 Hz, 1H), 1.63 (s, 3H), 1.13 (dd, J=21.7, 11.4 Hz, 6H), 0.97 (s, 9H), 0.18 (s, 6H). LCMS (ESI) m/z 554 [M+H⁺].

Step 6: 6-((tert-butyldimethyl silyl)oxy)-2-(2-fluoro-2-methylpropyl)-1-(4-(2-(3-(fluoromethyl)azetidin-1-yl)ethoxy)phenyl)-1-methyl-1,2,3,4-tetrahydroiso-quinoline

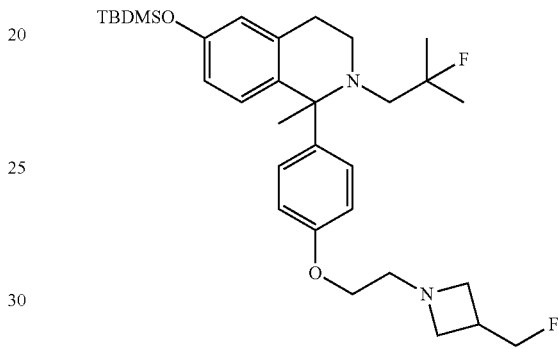

The mixture of 6-((tert-butyldimethylsilyl)oxy)-2-(2-fluoro-2-methylpropyl)-1-(4-iodophenyl)-1-methyl-1,2,3,4-tetrahydroisoquinoline (278 mg, 0. mmol), 2-[3-(fluoromethyl)azetidin-1-yl]ethanol (200 mg, 1.51 mmol), CuI (38 mg, 0.201 mmol) and K₂CO₃ (208 mg, 1.51 mmol) in butyronitrile (3.35 mL) in a microwave vial was purged with N₂ for 5 min, and then sealed and heated at 135° C. for 17 h. The mixture was filtered through celite, washed with EtOAc, concentrated. The crude product was used without purification. LCMS (ESI) m/z 559 [M+H⁺].

Step 7

To a solution of 6-((tert-butyldimethylsilyl)oxy)-2-(2-fluoro-2-methylpropyl)-1-(4-(2-(3-(fluoromethyl)azetidin-1-yl)ethoxy)phenyl)-1-methyl-1,2,3,4-tetrahydroisoquino-line (281 mg, 0.502 mmol) in THF (2.01 mL) was added TBAF in THF (1 M, 0.502 mL). The mixture was stirred at room temperature for 2.5 h. The mixture was diluted with EtOAc and brine. The layers were separated. The aqueous layer was extracted with EtOAc (2×). The combined organics were dried (Na₂SO₄), filtered and concentrated. The crude prod was purified by chiral SFC (Chiralpak ID 150× 21.1 mm, 5 um; 35% MeOH w/0.1% NH₄OH) to give 107 (44.7 mg, 20% yield) and 108 (43.4 mg, 19.4% yield) as off-white solids. LCMS (ESI) m/z 559 [M+H⁺].

107 1ˢᵗ peak: ¹H NMR (400 MHz, DMSO-d6) 9.07 (s, 1H), 7.26-7.17 (m, 2H), 6.80-6.72 (m, 2H), 6.43 (d, J=2.4 Hz, 1H), 6.40-6.35 (m, 1H), 6.34 (d, J=8.6 Hz, 1H), 4.56 (d, J=6.3 Hz, 1H), 4.44 (d, J=6.3 Hz, 1H), 3.86 (t, J=5.6 Hz, 2H), 3.30-3.21 (m, 2H), 3.15-3.03 (m, 1H), 3.02-2.90 (m, 3H), 2.89-2.79 (m, 1H), 2.77-2.66 (m, 3H), 2.63 (dt, J=15.6, 3.3 Hz, 1H), 2.18 (dd, J=31.2, 14.4 Hz, 1H), 1.55 (s, 3H), 1.07 (dd, J=21.7, 12.4 Hz, 6H).

108 2$^{nd}$ peak: $^1$H NMR (400 MHz, DMSO-d6) 9.05 (s, 1H), 7.26-7.17 (m, 2H), 6.79-6.70 (m, 2H), 6.42 (d, J=2.4 Hz, 1H), 6.37 (dd, J=8.6, 2.4 Hz, 1H), 6.33 (d, J=8.5 Hz, 1H), 4.55 (d, J=6.2 Hz, 1H), 4.44 (d, J=6.2 Hz, 1H), 3.86 (t, J=5.6 Hz, 2H), 3.14 3.04 (m, 1H), 3.03-2.90 (m, 3H), 2.89-2.80 (m, 1H), 2.79-2.66 (m, 3H), 2.62 (dt, J=15.5, 3.3 Hz, 1H), 2.18 (dd, J=31.2, 14.4 Hz, 1H), 1.55 (s, 3H), 1.07 (dd, J=21.7, 12.4 Hz, 6H).

Examples 109 and 110 (1S)-1-[4-[2-[3-(fluoromethyl)azetidin-1-yl]ethoxy]phenyl]-2-methylsulfonyl-3,4-dihydro-1H-isoquinolin-6-ol 109 and (1R)-1-[4-[2-[3-(fluoromethyl)azetidin-1-yl]ethoxy]phenyl]-2-methylsulfonyl-3,4-dihydro-1H-isoquinolin-6-ol 110

Step 1: 1-(4-iodophenyl)-6-methoxy-2-(methylsulfonyl)-1,2,3,4-tetrahydroisoquinoline

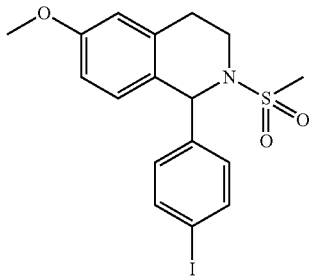 [SMILES: COc1ccc2c(c1)CCN(S(C)(=O)=O)C2c1ccc(I)cc1]

To a solution of 1-(4-iodophenyl)-6-methoxy-1,2,3,4-tetrahydroisoquinoline (119 mg, 0.326 mmol) and DIPEA (93 mg, 0.717 mmol) in DCM (2.2 mL) was added methanesulfonyl chloride (75 mg, 0.652 mmol) dropwise. The mixture was stirred at room temperature for 30 min. The reaction was quenched with sat. NaHCO$_3$, extracted with DCM (3×). The combined organics were dried (Na$_2$SO$_4$), filtered and concentrated. The crude product was purified by silica flash chromatography (0-50% iPrOAc/heptane) to give the title compound (140 mg, 96.9% yield) as an off-white solid. $^1$H NMR (400 MHz, Chloroform-d) δ 7.69-7.58 (m, 2H), 7.04-6.96 (m, 2H), 6.91 (d, J=8.4 Hz, 1H), 6.80-6.70 (m, 2H), 5.95 (s, 1H), 3.84-3.78 (m, 3H), 3.81 (s, 3H), 3.33-3.20 (m, 1H), 3.14-3.00 (m, 1H), 2.81-2.72 (m, 1H), 2.63 (s, 3H). LCMS (ESI) m/z 444 [M+H$^+$].

Step 2: 1-(4-iodophenyl)-2-(methylsulfonyl)-1,2,3,4-tetrahydroisoquinolin-6-ol

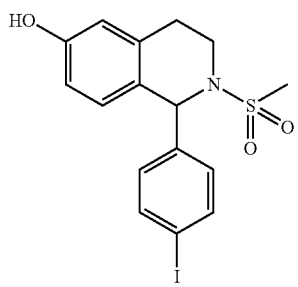 [SMILES: CS(=O)(=O)N1CCc2cc(O)ccc2C1c1ccc(I)cc1]

To a solution of 1-(4-iodophenyl)-6-methoxy-2-methylsulfonyl-3,4-dihydro-1H-isoquinoline (138 mg, 0.3113 mmol) in DCM (2 mL) at −78° C. was added BBr$_3$ (1 mol/L) in DCM (0.623 mL). The mixture was then stirred at 0° C. for 1 h. The mixture was re-cooled to −78° C. and quenched with MeOH. The mixture was concentrated. The crude product was purified by silica flash chromatography (0-60% iPrOAc/heptane) to give the title compound (130 mg, 97.3% yield) as a white solid. $^1$H NMR (400 MHz, Chloroform-d) δ 7.69-7.57 (m, 2H), 7.04-6.94 (m, 2H), 6.90-6.81 (m, 1H), 6.73-6.64 (m, 2H), 5.95 (d, J=1.2 Hz, 1H), 4.74 (s, 1H), 3.86-3.73 (m, 1H), 3.36-3.19 (m, 1H), 3.13-2.94 (m, 1H), 2.79-2.69 (m, 1H), 2.64 (s, 3H). LCMS (ESI) m/z 430 [M+H$^+$].

Step 3

A mixture of 1-(4-iodophenyl)-2-methylsulfonyl-3,4-dihydro-1H-isoquinolin-6-ol (130 mg, 0.303 mmol), 2-[3-(fluoromethyl)azetidin-1-yl]ethanol (161 mg, 1.21 mmol), CuI (0.1211 mmol, 23 mg) and K$_2$CO$_3$ (125 mg, 0.908 mmol) in butyronitrile (2 mL) in a microwave vial was purged with N$_2$ for 5 min, and then sealed and heated at 135° C. for 17 h. The mixture was filtered through celite and concentrated. The crude product was purified by chiral SFC (Chiralpak AD (250×30.0 mm, 5 um; 15% MeOH w/0.1% NH$_4$OH) to give 109 (0.04281 mmol, 14.14% Yield, 18.6 mg) and 110 (14.36% Yield, 18.9 mg) as yellow solids.

109 1st peak: 1H NMR (400 MHz, DMSO-d6) δ 9.37 (s, 1H), 7.10-7.00 (m, 2H), 6.91-6.79 (m, 3H), 6.64-6.55 (m, 2H), 5.81 (s, 1H), 4.49 (dd, J=47.6, 6.2 Hz, 2H), 3.87 (t, J=5.6 Hz, 2H), 3.67-3.55 (m, 1H), 3.30-3.26 (m, 2H), 3.22-3.12 (m, 1H), 3.01-2.96 (m, 2H), 2.96-2.86 (m, 1H), 2.78-2.61 (m, 7H).

110 2$^{nd}$ peak: 1H NMR (400 MHz, DMSO-d6) δ 9.36 (s, 1H), 7.11-6.99 (m, 2H), 6.91-6.78 (m, 3H), 6.64-6.54 (m, 2H), 5.81 (s, 1H), 4.49 (dd, J=47.6, 6.2 Hz, 2H), 3.87 (t, J=5.6 Hz, 2H), 3.68-3.53 (m, 1H), 3.31-3.23 (m, 2H), 3.22-3.11 (m, 1H), 3.02-2.96 (m, 2H), 2.96-2.87 (m, 1H), 2.81-2.61 (m, 7H). LCMS (ESI) m/z 435 [M+H+].

Examples 118, 119, 120, 121 (1S,4R)-1-[4-[2-[3-(fluoromethyl)azetidin-1-yl]ethoxy]phenyl]-4-methyl-2-methylsulfonyl-3,4-dihydro-1H-isoquinolin-6-ol 118, (1S,4S)-1-[4-[2-[3-(fluoromethyl)azetidin-1-yl]ethoxy]phenyl]-4-methyl-2-methylsulfonyl-3,4-dihydro-1H-isoquinolin-6-ol 119, (1R,4S)-1-[4-[2-[3-(fluoromethyl)azetidin-1-yl]ethoxy]phenyl]-4-methyl-2-methylsulfonyl-3,4-dihydro-1H-isoquinolin-6-ol 120, and (1R,4R)-1-[4-[2-[3-(fluoromethyl)azetidin-1-yl]ethoxy]phenyl]-4-methyl-2-methylsulfonyl-3,4-dihydro-1H-isoquinolin-6-ol 121

Step 1: 1-methoxy-3-(1-nitropropan-2-yl)benzene

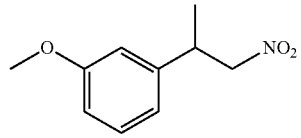

To a solution of methyllithium/lithium bromide, MeLi LiBr complex in Et$_2$O (1.5 M, 20.4 mL) at 0° C. was added cuprous iodide CuI (31.36 mmol, 5973 mg) followed by 1-methoxy-3-[(E)-2-nitrovinyl]benzene (4.225 g, 23.6 mmol) in THF (20 mL) dropwise. The mixture was stirred at 0° C. for 3 h, poured into NH₄OH (saturated with NH₄Cl) (300 mL), and extracted with Et₂O (2×). The combined organics were dried (Na₂SO₄), filtered and concentrated. The crude product was purified by silica flash chromatography (0-15% iPrOAc/heptaneiPrOAc/hepatane) to give the title compound (964 mg, 21% yield) as a colorless oil. ¹H NMR (400 MHz, Chloroform-d) δ 7.29-7.23 (m, 1H), 6.92-6.67 (m, 3H), 4.63-4.37 (m, 2H), 3.68-3.51 (m, 1H), 1.37 (d, J=7.0 Hz, 3H).

Step 2: 2-(3-methoxyphenyl)propan-1-amine

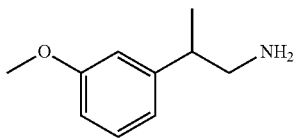

To a solution of 1-methoxy-3-(1-methyl-2-nitro-ethyl) benzene (6.634 mmol, 1295 mg) in MeOH (26.5 mL) was added 10% Pd/C (494 mg), followed by ammonium formate (2.09 g, 33.2 mmol). The mixture was stirred at room temperature for 4 h. The mix was filtered and concentrated. The residue was suspended in water with 1 mL of 25% NaOH and chloroform. The layers were separated. The aqueous layer was saturated with NaCl, extracted with CHCl₃/iPrOH(3/1) twice. The combined organics were dried (Na₂SO₄), filtered and concentrated to give the title compound (850 mg, 77.6% yield) as colorless oil. ¹H NMR (400 MHz, Chloroform-d) δ 7.26-7.18 (m, 1H), 6.84-6.79 (m, 1H), 6.79-6.71 (m, 2H), 3.81 (d, J=0.5 Hz, 3H), 2.84 (d, J=6.9 Hz, 2H), 2.72 (h, J=6.9 Hz, 1H), 1.25 (dd, J=6.9, 0.5 Hz, 3H). LCMS (ESI) m/z 166 [M+H⁺].

Step 3: 1-(4-iodophenyl)-6-methoxy-4-methyl-1,2,3,4-tetrahydroisoquinoline

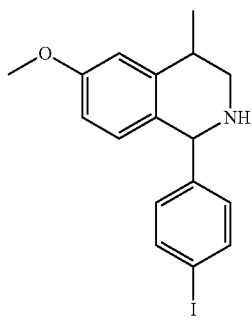 [SMILES: COc1ccc2c(c1)C(C)CNC2c1ccc(I)cc1]

The mixture of 2-(3-methoxyphenyl)propan-1-amine (535 mg, 3.24 mmol) and 4-iodobenzaldehyde (751 mg, 3.24 mmol) in toluene (6.5 mL) and TFA (4.9 mL) in a sealed microwave tube was heated at 150° C. in a microwave for 2 h. The mixture was concentrated. The residue was dissolved in EtOAc and washed with sat. NaHCO₃. The aqueous layer was extracted with EtOAc (2×). The combined organics were dried (Na₂SO₄), filtered and concentrated. The crude product was purified by silica flash chromatography (0-10% MeOH/DCM) to give the title compound (1.087 g, 88.5% yield) as an off-white solid. ¹H NMR (400 MHz, Chloroform-d) δ 7.73-7.55 (m, 2H), 7.06-6.96 (m, 2H), 6.86-6.79 (m, 1H), 6.63-6.57 (m, 2H), 4.99 (s, 0.84H), 4.96 (s, 0.23H), 3.79 (d, J=0.9 Hz, 3H), 3.25 (dd, J=12.1, 5.3 Hz, 1H), 3.10-2.97 (m, 1H), 2.73 (dd, J=12.1, 8.1 Hz, 1H), 1.42 (d, J=6.7 Hz, 0.6H), 1.31 (d, J=6.9 Hz, 2.6H). LCMS (ESI) m/z 380 [M+H⁺].

Step 4: 1-(4-iodophenyl)-6-methoxy-4-methyl-2-(methylsulfonyl)-1,2,3,4-tetrahydroisoquinoline

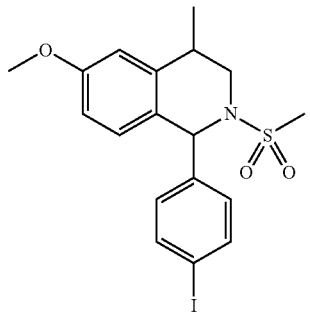

To a solution of 1-(4-iodophenyl)-6-methoxy-4-methyl-1,2,3,4-tetrahydroisoquinoline (500 mg, 1.32 mmol) and DIPEA (341 mg, 2.64 mmol) in DCM (8.8 mL) was added methanesulfonyl chloride (272 mg, 2.37 mmol) dropwise. The mixture was stirred at room temperature for 20 min. The reaction was quenched with sat. NaHCO₃, extracted with DCM (3×). The combined organics were dried (Na₂SO₄), filtered and concentrated. The crude product was purified by silica flash chromatography (0-50% iPrOAc/heptane) to give the title compound (580 mg, 96.2% yield) as an off-white solid. LCMS (ESI) m/z 458 [M+H⁺].

Step 5: 1-(4-iodophenyl)-4-methyl-2-(methylsulfonyl)-1,2,3,4-tetrahydroisoquinolin-6-ol

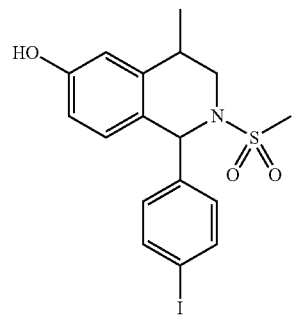 [SMILES: CC1CN(S(C)(=O)=O)C(c2ccc(I)cc2)c2ccc(O)cc21]

To a solution of 1-(4-iodophenyl)-6-methoxy-4-methyl-2-methylsulfonyl-3,4-dihydro-1H-isoquinoline (580 mg, 1.27 mmol) in DCM (8.455 mL) at −78° C. was added BBr₃ in DCM (1 M, 2.54 mL). The mixture was then stirred at 0° C. for 3 h. The mixture was re-cooled to −78° C., quenched with MeOH, concentrated. The crude product was purified by silica flash chromatography (0-5% MeOH/DCM) to give the title compound (555 mg, 98.7% yield) as white foam. LCMS (ESI) m/z 444 [M+H⁺].

Step 6

The mixture of 1-(4-iodophenyl)-4-methyl-2-methylsulfonyl-3,4-dihydro-1H-isoquinolin-6-ol (555 mg, 1.252 mmol), 2-[3-(fluoromethyl)azetidin-1-yl]ethanol (834 mg, 6.26 mmol), CuI (95 mg, 0.501 mmol) and K₂CO₃ (519 mg, 3.76 mmol) in butyronitrile (8.35 mL) in a microwave vial was purged with N₂ for 5 min, and then sealed and heated at 135° C. for 24 h. The mixture was filtered through celite, concentrated. The crude product was purified by chiral SFC (Chiralpak ID 150×21.1 mm, 5 μm; 40% MeOH w/0.1% NH₄OH) to give separated 118, 119, 120, and 121 as yellow solids. LCMS (ESI) m/z 449 [M+H⁺].

118 1ˢᵗ peak: (1S,4R)-1-[4-[2-[3-(fluoromethyl)azetidin-1-yl]ethoxy]phenyl]-4-methyl-2-methylsulfonyl-3,4-dihydro-1H-isoquinolin-6-ol (53 mg, 9.4% yield). ¹H NMR (400 MHz, DMSO-d6) δ 9.34 (s, 1H), 7.18-7.03 (m, 2H), 6.91-6.82 (m, 2H), 6.78 (d, J=8.4 Hz, 1H), 6.63 (d, J=2.5 Hz, 1H), 6.57 (dd, J=8.3, 2.5 Hz, 1H), 5.78 (s, 1H), 4.49 (dd, J=47.6, 6.3 Hz, 2H), 3.88 (t, J=5.6 Hz, 2H), 3.50-3.42 (m, 1H), 3.29-3.20 (m, 3H), 2.98 (t, J=6.4 Hz, 2H), 2.94-2.86 (m, 1H), 2.76-2.65 (m, 3H), 2.46 (s, 3H), 1.23 (d, J=6.9 Hz, 3H).

119 2ⁿᵈ peak: (1S,4S)-1-[4-[2-[3-(fluoromethyl)azetidin-1-yl]ethoxy]phenyl]-4-methyl-2-methylsulfonyl-3,4-dihydro-1H-isoquinolin-6-ol (55 mg, 9.8% yield., ¹H NMR (400 MHz, DMSO-d6) δ 9.37 (s, 1H), 7.08-6.98 (m, 2H), 6.91-6.82 (m, 2H), 6.82-6.74 (m, 2H), 6.59 (dd, J=8.3, 2.5 Hz, 1H), 5.82 (s, 1H), 4.49 (dd, J=47.6, 6.3 Hz, 2H), 3.88 (t, J=5.6 Hz, 2H), 3.71-3.60 (m, 1H), 3.29-3.26 (m, 2H), 3.13-3.03 (m, 1H), 3.02-2.94 (m, 2H), 2.77-2.64 (m, 7H), 1.21 (d, J=6.7 Hz, 3H).

120 3ʳᵈ peak: (1R,4S)-1-[4-[2-[3-(fluoromethyl)azetidin-1-yl]ethoxy]phenyl]-4-methyl-2-methylsulfonyl-3,4-dihydro-1H-isoquinolin-6-ol (71 mg, 10.9% yield). ¹H NMR (400 MHz, DMSO-d6) δ 8.18 (s, 1H), 7.15-6.95 (m, 2H), 6.91-6.83 (m, 2H), 6.81-6.74 (m, 2H), 6.63-6.54 (m, 1H), 5.82 (s, 1H), 4.50 (dd, J=47.6, 6.2 Hz, 2H), 3.88 (t, J=5.6 Hz, 2H), 3.73-3.05 (m, 4H), 3.00 (t, J=6.6 Hz, 2H), 2.76-2.68 (m, 4H), 2.67 (s, 3H), 1.21 (d, J=6.7 Hz, 3H).

121 4ᵗʰ peak: (1R,4R)-1-[4-[2-[3-(fluoromethyl)azetidin-1-yl]ethoxy]phenyl]-4-methyl-2-methylsulfonyl-3,4-dihydro-1H-isoquinolin-6-ol (58 mg, 10.3% yield). ¹H NMR (400 MHz, DMSO-d6) δ 9.34 (s, 1H), 7.16-7.07 (m, 2H), 6.90-6.83 (m, 2H), 6.78 (d, J=8.4 Hz, 1H), 6.63 (d, J=2.5 Hz, 1H), 6.57 (dd, J=8.3, 2.5 Hz, 1H), 5.78 (s, 1H), 4.49 (dd, J=47.6, 6.2 Hz, 2H), 3.88 (t, J=5.5 Hz, 2H), 3.46 (dd, J=12.4, 4.1 Hz, 1H), 3.30-3.16 (m, 3H), 2.98 (t, J=6.6 Hz, 2H), 2.95-2.85 (m, 1H), 2.77-2.62 (m, 3H), 2.46 (s, 3H), 1.23 (d, J=6.9 Hz, 3H).

Examples 123 and 124 (6S,8R)-6-(2,6-difluoro-4-(2-(3-(fluoromethyl)azetidin-1-yl)ethoxy)phenyl)-7-(2-fluoro-2-methylpropyl)-8-methyl-6,7,8,9-tetrahydro-3H-pyrazolo[4,3-f]isoquinoline 123 and (6R,8S)-6-(2,6-difluoro-4-(2-(3-(fluoromethyl)azetidin-1-yl)ethoxy)phenyl)-7-(2-fluoro-2-methylpropyl)-8-methyl-6,7,8,9-tetrahydro-3H-pyrazolo[4,3-f]isoquinoline 124

Step 1: 1-(1H-indazol-4-yl)propan-2-amine

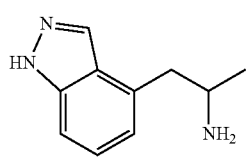

A mixture of 1H-indazole-4-carbaldehyde (2.07 g, 14.2 mmol)

and ammonium acetate (983 mg, 12.7 mmol) in nitroethane (20 mL) was heated at 100° C. for 3 h. The reaction mixture was cooled, diluted with isopropyl acetate, washed with water, brine, dried over sodium sulfate and was concentrated. The residue was purified by flash chromatography (silica gel 20-100% iPrOAc/heptane) to obtain 4-[2-nitroprop-1-enyl]-1H-indazole as a yellow solid (1.38 g).

The above solid (1.30 g, 6.4 mmol) was dissolved in dry THF (75 mL) and was cooled in ice-bath. To this solution was added lithium aluminum hydride LiAlH₄ (26 mL, 1M) using a syringe. The resulting heterogeneous mixture was heated at reflux for 2 h and was then cooled in ice-bath and was quenched with a few ice cubes followed by 2N NaOH (5 mL). The solids were removed by filtration through celite and washed well with isopropyl acetate. The filtrate was dried over sodium sulfate and concentrated. The residue was purified by flash chromatography (silica gel 0-5% ammonia in MeOH/DCM) to obtain 1-(1H-indazol-4-yl)propan-2-amine (750 mg, 67%): MS=176 (M+H).

Step 2: 6-(2,6-difluoro-4-iodophenyl)-8-methyl-6,7,8,9-tetrahydro-3H-pyrazolo[4,3-f]isoquinoline

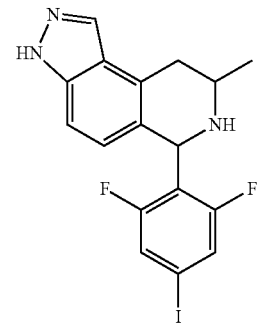 [SMILES: CC1Cc2c(ccc3[nH]ncc23)C(c2c(F)cc(I)cc2F)N1]

A mixture of 1-(1H-indazol-4-yl)propan-2-amine (320 mg, 1.8 mmol), (2,6-difluoro-4-iodobenzaldehyde (500 mg, 1.82 mmol) and TFA (1.1 mL) in DCE (5 mL) was heated at 155° C. for 55 min in a microwave reactor. The reaction mixture was cooled and concentrated. The residue was dissolved in isopropyl acetate and washed with sodium bicarbonate, brine, dried over sodium sulfate and was concentrated. The yellow solid was collected by filtration to obtain 6-(2,6-difluoro-4-iodophenyl)-8-methyl-6,7,8,9-tetrahydro-3H-pyrazolo[4,3-f]isoquinoline (300 mg, 41%): $^1$H NMR (400 MHz, DMSO-d6) δ 13.22 (s, 1H), 10.06 (s, 1H), 8.81 (s, 1H), 8.19 (s, 1H), 7.78 (d, J=8.7 Hz, 2H), 7.37 (d, J=8.7 Hz, 1H), 6.71 (d, J=8.7 Hz, 1H), 6.22 (d, J=9.7 Hz, 1H), 4.00 (d, J=12.2 Hz, 1H), 3.45 (d, J=18.3 Hz, 1H), 3.14 (t, J=15.1 Hz, 1H), 1.50 (d, J=6.3 Hz, 3H); MS: 426.0 (M+H);

Step 3: 6-(2,6-difluoro-4-iodophenyl)-8-methyl-3-(tetrahydro-2H-pyran-2-yl)-6,7,8,9-tetrahydro-3H-pyrazolo[4,3-f]isoquinoline

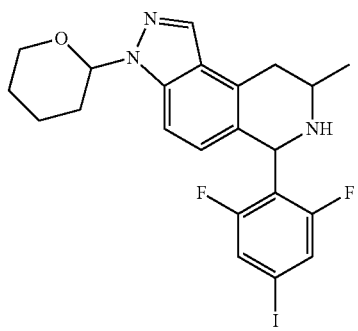 [SMILES: CC1Cc2c(ccc3c2cnn3C2CCCCO2)C(c2c(F)cc(I)cc2F)N1]

To a suspension of 6-(2,6-difluoro-4-iodophenyl)-8-methyl-6,7,8,9-tetrahydro-3H-pyrazolo[4,3-f]isoquinoline (800 mg, 1.88 mmol) in DCM (10 mL) were added dihydropyran (8.0 mL, 87 mmol) and PPTS (710 mg, 2.82 mmol) and the mixture was stirred at ambient temperature for 20 h. The clear solution was diluted with DCM and was washed with sodium bicarbonate solution followed by water, brine, dried over sodium sulfate and was concentrated. The residue was purified by flash chromatography (silica gel, 0-5% MeOH/DCM) to obtain (850 mg) of yellow gum: MS: 510.1 (M+H)

Step 4: 6-(2,6-Difluoro-4-iodophenyl)-7-(2-fluoro-2-methylpropyl)-8-methyl-3-(tetrahydro-2H-pyran-2-yl)-6,7,8,9-tetrahydro-3H-pyrazolo[4,3-f]isoquinoline

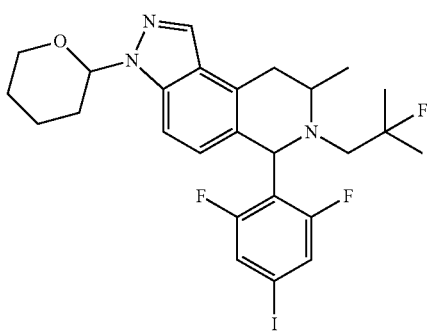 [SMILES: CC1Cc2c(ccc3c2cnn3C2CCCCO2)C(c2c(F)cc(I)cc2F)N1CC(C)(C)F]

The above residue was dissolved in DCE (10 mL) and 2-fluoro-2-methylpropyl trifluoromethanesulfonate (530 mg, 0.9 mmol) and potassium carbonate (460 mg, 3.3 mmol) were added and the resulting mixture was heater at 90° C. for 10 days. The reaction mixture was cooled and was filtered through celite. The filtrate was diluted with isopropyl acetate, washed with water, brine, dried over sodium sulfate and was concentrated. The residue was purified by column chromatography (silica gel, 0-100% iPrOAc/heptane) to obtain the title compound (530 mg, 54%): MS: 584.1 (M+H).

Step 5: 6-(2,6-difluoro-4-(2-(3-(fluoromethyl)azetidin-1-yl)ethoxy)phenyl)-7-(2-fluoro-2-methylpropyl)-8-methyl-3-(tetrahydro-2H-pyran-2-yl)-6,7,8,9-tetrahydro-3H-pyrazolo[4,3-f]isoquinoline

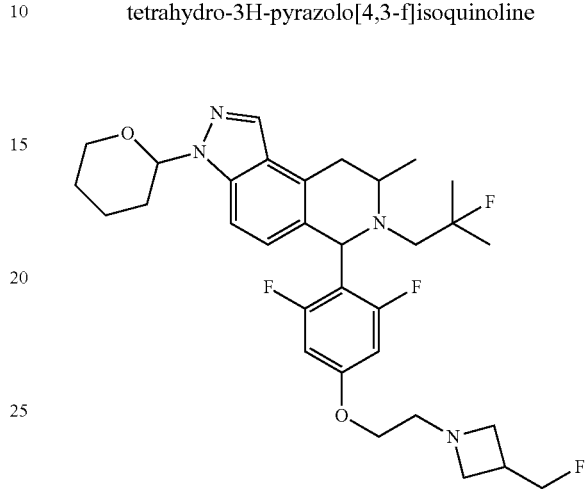

A mixture of 6-(2,6-difluoro-4-iodophenyl)-7-(2-fluoro-2-methylpropyl)-8-methyl-3-(tetrahydro-2H-pyran-2-yl)-6,7,8,9-tetrahydro-3H-pyrazolo[4,3-f]isoquinoline (300 mg, 0.51 mmol), 2-[3-(fluoromethyl)azetidin-1-yl]ethanol (103 mg, 0.77 mmol), cuprous iodide (29 mg, 0.15 mmol) in butyronitrile (2 mL) was degassed by purging/evacuation with nitrogen three times. The resulting mixture was heated at 140° C. in a sealed flask for 20 h. The reaction mixture was cooled, diluted with isopropyl acetate and was filtered through celite. The filtrate was washed with water, brine, dried over sodium sulfate and was concentrated. The residue was purified by column chromatograph (silica gel, 0-5% MeOH/DCM) to obtain the desired coupled product (130 mg, 43%): MS: 589.3 (M+H).

Step 6

The above material was dissolved in methanol (2 mL) and aqueous HCl (1 mL, 1M) was added and stirred at ambient temperature for 20 h. The reaction mixture was basified with 1N NaOH (1 mL) and concentrated. Chiral separation with chiral superfluid chromatography (Column: AD, mobile phase: IPA w/0.1% NH$_4$OH) afforded two enantiomers 123 and 124: RT 1.48 min and 1.71 min.

123 (6S,8R)-6-(2,6-difluoro-4-(2-(3-(fluoromethyl)azetidin-1-yl)ethoxy)phenyl)-7-(2-fluoro-2-methylpropyl)-8-methyl-6,7,8,9-tetrahydro-3H-pyrazolo[4,3-f]isoquinoline (35 mg): 1H NMR (400 MHz, DMSO-d6) δ 8.10 (d, J=1.0 Hz, 1H), 7.21 (dd, J=8.7, 1.0 Hz, 1H), 6.70-6.56 (m, 3H), 5.16 (s, 1H), 4.50 (dd, J=47.6, 6.2 Hz, 2H), 3.93 (t, J=5.4 Hz, 2H), 3.30-3.20 (m, 2H), 3.16-2.89 (m, 6H), 2.81-2.54 (m, 4H), 1.18-1.07 (m, 6H), 0.98 (d, J=21.6 Hz, 3H); MS=505.2 (M+H). RT=1.48 min.

124 (6R,8S)-6-(2,6-difluoro-4-(2-(3-(fluoromethyl)azetidin-1-yl)ethoxy)phenyl)-7-(2-fluoro-2-methylpropyl)-8-methyl-6,7,8,9-tetrahydro-3H-pyrazolo[4,3-f]isoquinoline (40 mg): 1H NMR (400 MHz, DMSO-d6) δ 8.10 (d, J=1.0 Hz, 1H), 7.21 (d, J=8.7 Hz, 1H), 6.69-6.58 (m, 3H), 5.16 (s, 1H), 4.50 (dd, J=47.6, 6.2 Hz, 2H), 3.93 (t, J=5.4 Hz, 2H), 3.51-3.33 (m, 2H), 3.23-2.86 (m, 5H), 2.77-2.52 (m, 5H), 1.19-1.04 (m, 6H), 0.98 (d, J=21.6 Hz, 3H). MS=505.2, RT: 1.71 min.

Examples 127 and 128 (S)-1-(difluoromethyl)-2-(2-fluoro-2-methylpropyl)-1-(4-(2-(3-(fluoromethyl)azetidin-1-yl)ethoxy)phenyl)-1,2,3,4-tetrahydroisoquinolin-6-ol 127 and (R)-1-(difluoromethyl)-2-(2-fluoro-2-methylpropyl)-1-(4-(2-(3-(fluoromethyl)azetidin-1-yl)ethoxy)phenyl)-1,2,3,4-tetrahydroisoquinolin-6-ol 128

Step 1: 6-(Benzyloxy)-3,4-dihydroisoquinolin-1(2H)-one

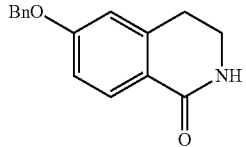 [SMILES: O=C1NCCc2cc(OCc3ccccc3)ccc21]

To a solution of 6-hydroxy-3,4-dihydro-2H-isoquinolin-1-one (200 mg, 1.23 mmol) in DMF (2 mL) was added benzyl bromide (0.13 mL, 1.1 mmol) dropwise. The mixture was stirred at 25° C. for 12 hours. The mixture was diluted with EtOAc (20 mL), washed with sat. NaHCO$_3$ (10 mL) solution. The aqueous phase was extracted with EtOAc one more time. The combined organic layers were dried over anhydrous Na$_2$SO$_4$, filtered and concentrated. The crude product was purified by silica flash chromatography (0-30% EtOAc in petroleum ether) to afford the title compound as a white solid (300 mg, 97%). $^1$H NMR (400 MHz, CDCl$_3$) δ 8.00-8.03 (m, 1H), 7.72-7.28 (m, 5H), 6.95 (d, J=8.8 Hz, 1H), 6.79 (d, J=2.4 Hz, 1H), 6.02 (s, 1H), 3.57-3.53 (m, 2H), 3.00-2.96 (m, 2H).

Step 2: 6-(Benzyloxy)-2-(2-fluoro-2-methylpropyl)-3,4-dihydroisoquinolin-1(2H)-one

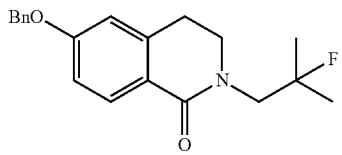 [SMILES: CC(C)(F)CN1CCc2cc(OCc3ccccc3)ccc2C1=O]

To a solution of 6-benzyloxy-3,4-dihydro-2H-isoquinolin-1-one (From step 1, 300 mg, 1.18 mmol) in DMF (3 mL) was added NaH (95 mg, 2.37 mmol) at 0° C. The mixture was stirred at 0° C. for 30 minutes. (2-Fluoro-2-methylpropyl) trifluoromethanesulfonate (319 mg, 1.42 mmol) in DMF (1 mL) was added to the above solution dropwise. The reaction mixture was stirred at 25° C. for 1 hour. Saturated NH$_4$Cl solution (2 mL) was added to the reaction mixture and the mixture was diluted with EtOAc (20 mL) and washed with water (10 mL). The organic layer was dried over anhydrous Na$_2$SO$_4$ before concentration to dryness. The crude was purified by silica gel flash chromatography (0-30% EtOAc in petroleum ether) to afford the title compound as a white solid (200 mg, 52%). $^1$H NMR (400 MHz, CDCl$_3$) δ 8.02 (d, J=8.8 Hz, 1H), 7.50-7.31 (m, 5H), 6.95 (dd, J=8.8, 2.4 Hz, 1H), 6.77 (d, J=2.0 Hz, 1H), 5.12 (s, 2H), 3.77 (d, J=23.6 Hz, 2H), 3.69 (t, J=6.8 Hz, 2H), 2.96 (t, J=6.4 Hz, 2H), 1.44 (d, J=21.6 Hz, 6H); LCMS: 327.9 [M+H]$^+$.

Step 3: 6-(Benzyloxy)-1-(4-bromophenyl)-2-(2-fluoro-2-methylpropyl)-3,4-dihydroisoquinolin-2-ium

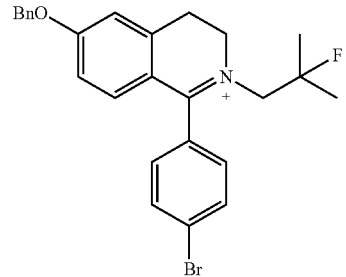

To a solution of 1-bromo-4-iodobenzene (3.89 g, 13.75 mmol) in hexane (40 mL) was added n-BuLi (5.5 mL, 13.75 mmol) (2.5 M in hexane) at 25° C., a white precipitate formed immediately. The reaction mixture was stirred at 25° C. for 1 hour and was then cooled to −78° C. and a solution of 6-benzyloxy-2-(2-fluoro-2-methylpropyl)-3,4-dihydroisoquinolin-1-one (From step 2, 1.5 g, 4.58 mmol) in THF (30 mL) was added. The reaction mixture was stirred at −78° C. for 1 hour. Water was added to the reaction mixture and the mixture was diluted with EtOAc (60 mL) and warmed to 25° C. HClO$_4$ (2.96 g, 20.62 mmol) was added and the reaction mixture was stirred for 30 minutes at 25° C. The reaction mixture was diluted with water (100 mL) and extracted with EtOAc (100 mL×2). The organic layers were combined, washed with brine (150 mL), dried over anhydrous Na$_2$SO$_4$, filtered, concentrated to afford the title compound as a yellow oil which was used directly in the next step (2.14 g, 99%). LCMS: 466.2 [M$^+$].

Step 4: Ethyl 2-(6-(benzyloxy)-1-(4-bromophenyl)-2-(2-fluoro-2-methylpropyl)-1,2,3,4-tetrahydroisoquinolin-1-yl)-2,2-difluoroacetate

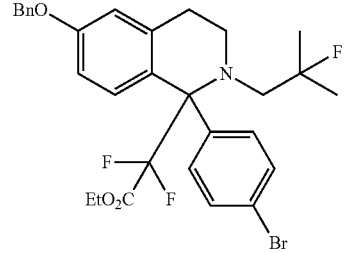 [SMILES: CC(C)(F)CN1CCc2cc(OCc3ccccc3)ccc2C1(c1ccc(Br)cc1)C(F)(F)C(=O)O]

To a mixture of 6-benzyloxy-1-(4-bromophenyl)-2-(2-fluoro-2-methyl-propyl)-3,4-dihydroiso quinolin-2-ium (From step 2, 2.14 g, 4.58 mmol) in DMF (40 mL) was added KF (798 mg, 13.74 mmol). A solution of ethyl difluoro(trimethylsilyl)acetate (1.8 g, 9.16 mmol) in DMF (10 mL) was then added dropwise and the reaction mixture was stirred at 25° C. for 16 hours. Saturated aqueous NaHCO$_3$ solution (150 mL) was added to the reaction mixture and the mixture was extracted with DCM (150 mL×2). The combined organic layers were dried over anhydrous Na₂SO₄, filtered and concentrated. The residue was purified by column chromatography (0-5% EtOAc in petroleum ether) to afford the title compound as a colorless oil (1.65 g, 61%). LCMS: 590.2 [M+H⁺].

Step 5: 2-(6-(Benzyloxy)-1-(4-bromophenyl)-2-(2-fluoro-2-methylpropyl)-1,2,3,4-tetrahydroisoquinolin-1-yl)-2,2-difluoroacetic acid

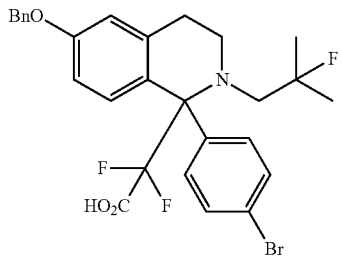

To a mixture of ethyl 2-(6-(benzyloxy)-1-(4-bromophenyl)-2-(2-fluoro-2-methylpropyl)-1,2,3,4-tetrahydroisoquinolin-1-yl)-2,2-difluoroacetate (From step 3, 1.55 g, 2.63 mmol) in 1,4-dioxane (15 mL) was added 1M LiOH.H₂O (7.88 mL, 7.88 mmol). The reaction mixture was stirred at 25° C. for 16 hours. The reaction mixture was acidified to pH=1 with 1M HCl and the mixture was extracted with DCM (50 mL×3). The combined organic layers were dried over anhydrous Na₂SO₄, filtered, and concentrated to afford the title compound (1.45 g, 98%) as a white solid which was used in the next step directly. LCMS: 562.2 [M+H⁺].

Step 6: 6-(Benzyloxy)-1-(4-bromophenyl)-1-(difluoromethyl)-2-(2-fluoro-2-methylpropyl)-1,2,3,4-tetrahydroisoquinoline

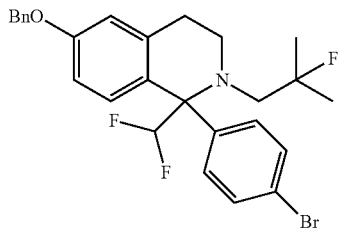 [SMILES: CC(C)(F)CN1CCc2cc(OCc3ccccc3)ccc2C1(c1ccc(Br)cc1)C(F)F]

To a mixture of 2-(6-(benzyloxy)-1-(4-bromophenyl)-2-(2-fluoro-2-methylpropyl)-1,2,3,4-tetrahydroisoquinolin-1-yl)-2,2-difluoroacetic acid (From step 4, 1.55 g, 2.76 mmol) and CsF (2.09 g, 13.78 mmol) in 1-methyl-2-pyrrolidinone (45 mL) was stirred at 190° C. for 28 hours under N₂ atmosphere. After cooling to 25° C., the reaction mixture was diluted with EtOAc (300 mL), washed with water (150 mL×3) and brine (150 mL), dried over Na₂SO₄, filtered and concentrated. The residue was purified by column chromatography (0-5% EtOAc in petroleum ether) and prep-TLC (10% EtOAc in petroleum ether) to afford the title compound as a colorless oil (610 mg, 43%). ¹H NMR (400 MHz, CDCl₃) δ 7.44-7.32 (m, 7H), 7.27-7.25 (m, 2H), 6.78 (d, J=1.6 Hz, 1H), 6.68-6.38 (m, 2H), 6.24 (t, J=54.8 Hz, 1H), 5.03 (s, 2H), 3.44-3.32 (m, 1H), 3.30-3.17 (m, 1H), 3.07-2.88 (m, 2H), 2.83-2.70 (m, 1H), 2.54-2.39 (m, 1H), 1.28-1.11 (m, 6H). LCMS: 518.2 [+H⁻].

Step 7: 6-(Benzyloxy)-1-(difluoromethyl)-2-(2-fluoro-2-methylpropyl)-1-(4-(2-(3-(fluoromethyl)azetidin-1-yl)ethoxy)phenyl)-1,2,3,4-tetrahydroisoquinoline

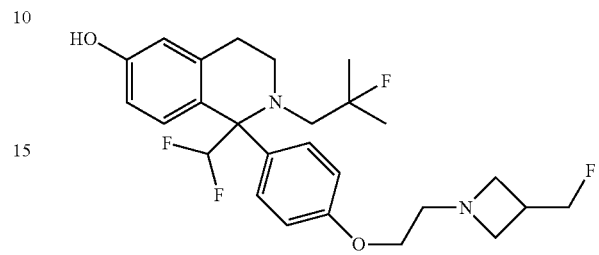

A mixture of 6-(benzyloxy)-1-(4-bromophenyl)-1-(difluoromethyl)-2-(2-fluoro-2-methylpropyl)-1,2,3,4-tetrahydroisoquinoline (From step 5, 500 mg, 0.96 mmol), CuI (367 mg, 1.93 mmol), 2-[3-(fluoromethyl)azetidin-1-yl]ethanol (385 mg, 2.89 mmol) and K₂CO₃ (667 mg, 4.82 mmol) in butyronitrile (7 mL) was stirred at 135° C. for 16 hours under N₂ atmosphere. After being cooled to 25° C., the mixture was filtered and the filtrate was concentrated to dryness. The residue was purified by column chromatography (0-80% EtOAc in DCM) to afford the title compound as a yellow oil (450 mg, 82%). LCMS: 571.4[M+H⁺].

Step 8: 1-(Difluoromethyl)-2-(2-fluoro-2-methylpropyl)-1-(4-(2-(3-(fluoromethyl)azetidin-1-yl)ethoxy)phenyl)-1,2,3,4-tetrahydroisoquinolin-6-ol

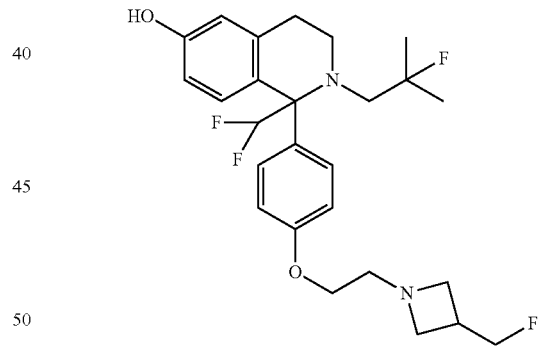

To a solution of 6-(benzyloxy)-1-(difluoromethyl)-2-(2-fluoro-2-methylpropyl)-1-(4-(2-(3-(fluoromethyl)azetidin-1-yl)ethoxy)phenyl)-1,2,3,4-tetrahydroisoquinoline (From step 6, 350 mg, 0.61 mmol) in THF (5 mL) and MeOH (5 mL) was added 10% Pd(OH)₂ (861 mg, 0.61 mmol) on carbon. The mixture was stirred under H₂ (15 psi) at 20° C. for 15 hours. The mixture was filtered and the filtrate was concentrated. The residue was purified by prep-TLC (7% MeOH in DCM) to afford the title compound as a white solid (100 mg, 34%). LCMS: 481.3 [M+H⁺].

Step 9

1-(Difluoromethyl)-1-[4-[2-[3-(fluoromethyl)azetidin-1-yl]ethoxy]phenyl]-2-(2-fluoro-2-methyl-propyl)-3,4-dihydroisoquinolin-6-ol (100.0 mg, 0.21 mmol) was separated by chiral SFC (Chiralpak AS 250 mm*30 mm, 5 um, Supercritical CO$_2$/IPA+0.05% DEA=85/15; 60 mL/min) to give 127 (7.7 mg, 7.7%) (peak 1, Rt=3.249 min) and 128 (11.4 mg, 11%) (peak 2, Rt=3.379 min) both as white solid.

127: $^1$H NMR (400 MHz, CDCl$_3$) δ 7.21 (d, J=8.4 Hz, 2H), 6.67 (d, J=9.2 Hz, 2H), 6.62 (d, J=2.0 Hz, 1H), 6.54-6.49 (m, 1H), 6.47-6.42 (m, 1H), 6.24 (t, J=54.8 Hz, 1H), 4.51 (dd, J=47.2, 5.2 Hz, 2H), 4.02-3.88 (m, 2H), 3.61-3.50 (m, 2H), 3.41-3.30 (m, 1H), 3.27-3.15 (m, 3H), 3.02-2.83 (m, 5H), 2.80-2.68 (m, 1H), 2.52-2.40 (m, 1H), 1.25-1.06 (m, 6H); LCMS 481.3 [M+H$^+$].

128: $^1$H NMR (400 MHz, CDCl$_3$) δ 7.21 (d, J=8.4 Hz, 2H), 6.66 (d, J=8.8 Hz, 2H), 6.62 (d, J=2.0 Hz, 1H), 6.53-6.48 (m, 1H), 6.47-6.41 (m, 1H), 6.24 (t, J=54.8 Hz, 1H), 4.51 (dd, J=47.2, 5.2 Hz, 2H), 4.03-3.89 (m, 2H), 3.62-3.51 (m, 2H), 3.40-3.31 (m, 1H), 3.27-3.16 (m, 3H), 3.02-2.81 (m, 5H), 2.81-2.68 (m, 1H), 2.53-2.40 (m, 1H), 1.25-1.08 (m, 6H); LCMS 481.3 [M+H$^+$].

Examples 131 and 132 (1S,3S)-1-(4-(2-(3-(Fluoromethyl)azetidin-1-yl)ethoxy)phenyl)-3-methyl-2-(2,2,2-trifluoroethyl)-1,2,3,4-tetrahydroisoquinolin-6-ol 131 and (1R,3R)-1-(4-(2-(3-(fluoromethyl)azetidin-1-yl)ethoxy)phenyl)-3-methyl-2-(2,2,2-trifluoroethyl)-1,2,3,4-tetrahydroisoquinolin-6-ol 132

Step 1: 3-(2-Nitroprop-1-en-1-yl)phenol

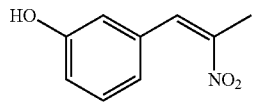

To a solution of 3-hydroxybenzaldehyde (20.0 g, 163.77 mmol) in acetic acid (40 mL) was added nitroethane (32.0 g, 426.27 mmol) and ammonium acetate (8.0 g, 103.79 mmol). The resulting mixture was stirred at 80° C. for 6 hours. The reaction mixture was poured into 400 mL of water and the precipitate was collected by filtration to afford the title compound as a yellow solid (25 g, 85%). $^1$H NMR (400 MHz, CDCl$_3$) δ 8.02 (s, 1H), 7.34-7.30 (m, 1H), 6.99 (d, J=8.0 Hz, 1H), 6.94-6.86 (m, 2H), 2.44 (s, 3H).

Step 2: 3-(2-Aminopropyl)phenol

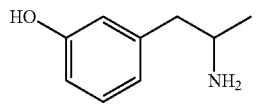

To a solution of lithium aluminum hydride (6.35 g, 167.44 mmol) in THF (100 mL) was added 3-[2-nitroprop-1-enyl]phenol (From step 1, 10.0 g, 55.81 mmol) in THF (50 mL) at 0~10° C. The reaction mixture was refluxed at 80° C. for 2 hours. To the reaction mixture was added sequentially water (13 mL), 15% NaOH solution (13 mL) and water (13 mL). The mixture was dried over anhydrous MgSO$_4$, filtered and the filtrate was evaporated to dryness. The residual was treated with DCM (30 mL) and petroleum ether (30 mL). The product precipitated while concentrated to remove the solvent. The product was suspended in petroleum ether (40 mL), filtered and concentrated to give the title compound as a light yellow solid (6.0 g, 71%). $^1$H NMR (400 MHz, CD$_3$OD) δ 7.12-7.05 (m, 1H), 6.66-6.60 (m, 3H), 3.15-3.02 (m, 1H), 2.63-2.44 (m, 2H), 1.07 (d, J=6.4 Hz, 3H).

Step 3: 3-(2-((2,2,2-Trifluoroethyl)amino)propyl)phenol

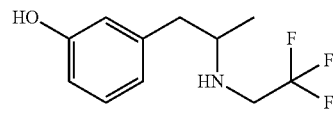 [SMILES: CC(Cc1cccc(O)c1)NCC(F)(F)F]

To a solution of 3-(2-aminopropyl)phenol (From step 2, 6.00 g, 39.68 mmol) and N,N-diisopropylethylamine (15.38 g, 119.04 mmol) in N,N-dimethylformamide (20 mL) was added 2,2,2-trifluoroethyltrifluoromethane sulfonate (11.05 g, 47.62 mmol). The resulting mixture was stirred at 15° C. for 15 hours. The reaction mixture was concentrated and purified by column (0-10% EtOAc in petroleum ether) to give the title compound (7.0 g, 76%) as a light yellow oil. $^1$H NMR (400 MHz, CDCl$_3$) δ 7.20-7.16 (m, 1H), 6.78-6.62 (m, 3H), 3.19-3.16 (m, 2H), 3.10-3.01 (m, 1H), 2.70-2.62 (m, 2H), 1.10 (d, J=6.4 Hz, 3H).

Step 4: rac-1-(4-Iodophenyl)-3-methyl-2-(2,2,2-trifluoroethyl)-1,2,3,4-tetrahydroisoquinolin-6-ol

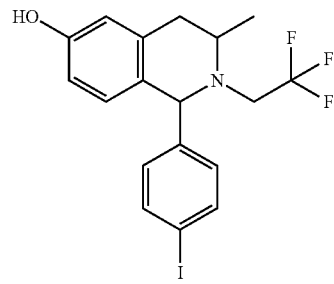 [SMILES: CC1Cc2cc(O)ccc2C(c2ccc(I)cc2)N1CC(F)(F)F]

A reaction mixture of 4-iodobenzaldehyde (6.0 g, 25.73 mmol) 3-[2-(2,2,2-trifluoroethylamino)propyl]phenol (From step 3, 6.0 g, 25.73 mmol) and acetic acid (3.1 g, 51.45 mmol) in toluene (60 mL) was heated at 80° C. for 16 hours. The reaction mixture was concentrated and purified by column (0-5% EtOAc in petroleum ether) to give the title compound as a light yellow oil (2.5 g, 22%). $^1$H NMR (400 MHz, CDCl$_3$) δ 7.59 (d, J=8.4 Hz, 2H), 6.98 (d, J=8.4 Hz, 2H), 6.78 (d, J=8.4 Hz, 1H), 6.66-6.59 (m, 2H), 4.85 (s, 1H), 3.25-3.09 (m, 2H), 2.98-2.82 (m, 1H), 2.77-2.74 (m, 1H), 2.54-2.49 (m, 1H), 1.04 (d, J=6.8 Hz, 3H).

Step 5: rac-1-(4-(2-(3-(Fluoromethyl)azetidin-1-yl)ethoxy)phenyl)-3-methyl-2-(2,2,2-trifluoroethyl)-1,2,3,4-tetrahydroisoquinolin-6-ol

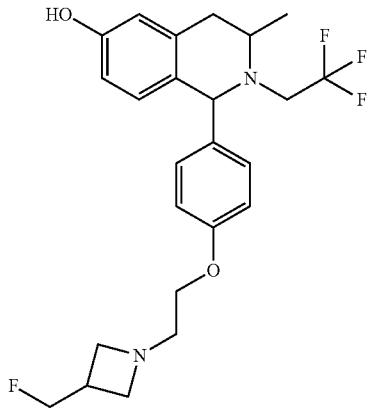 [SMILES: CC1Cc2cc(O)ccc2C(c2ccc(OCCN3CC(CF)C3)cc2)N1CC(F)(F)F]

A mixture of rac-1-(4-Iodophenyl)-3-methyl-2-(2,2,2-trifluoroethyl)-1,2,3,4-tetrahydroisoquinolin-6-ol (From step 4, 1.0 g, 2.24 mmol), 2-[3-(fluoromethyl)azetidin-1-yl]ethanol (893 mg, 6.71 mmol), CuI (426 mg, 2.24 mmol), and $K_2CO_3$ (927 mg, 6.71 mmol) in butyronitrile (10 mL) was heated at 135° C. under $N_2$ for 3 hours. After cooling, the reaction mixture was filtered and the filtrate was concentrated and purified by column (0-50% EtOAc in DCM) to afford a crude compound which was further purified by prep-HPLC (Gemini 150*25 5u, water (0.05% ammonia hydroxide v/v)-ACN, 47%-77%) to afford the title compound as a light yellow solid (450 mg, trans/cis=10:1, 45%).

Step 6 rac-1-(4-(2-(3-(Fluoromethyl)azetidin-1-yl)ethoxy)phenyl)-3-methyl-2-(2,2,2-trifluoroethyl)-1,2,3,4-tetrahydroisoquinolin-6-ol (From step 5, 450 mg, 0.99 mmol) (trans: cis=10:1) was separated by SFC (OD, Base (0.1% $NH_4OH$)-IPA, 30%) to afford a crude product (first peak on SFC, 280 mg containing cis by product) and pure 132 as light yellow solid (second peak on SFC, 169 mg, 38%).

The prior crude product (first peak 280 mg, containing cis by-product) was further purified by SFC (AD, Base (0.1% $NH_4OH$)-IPA, 35%) to afford 131 as a light yellow solid (168 mg, 37%).

131: (1S,3S)-1-(4-(2-(3-(Fluoromethyl)azetidin-1-yl)ethoxy)phenyl)-3-methyl-2-(2,2,2-trifluoroethyl)-1,2,3,4-tetrahydroisoquinolin-6-ol: $^1$H NMR (400 MHz, $CD_3OD$) δ 7.08 (d, J=8.4 Hz, 1H), 6.79 (d, J=8.4 Hz, 1H), 6.67 (d, J=8.4 Hz, 1H), 6.59-6.47 (m, 2H), 4.81 (s, 1H), 4.54-4.36 (m, 2H), 3.96 (t, J=5.2 Hz, 2H), 3.51 (t, J=7.6 Hz, 2H), 3.29-3.14 (m, 4H), 2.96-2.72 (m, 5H), 2.54-2.51 (m, 1H, 1.02 (d, J=6.8 Hz, 3H); LCMS: 453.1 [M+H]$^+$.

132: (1R,3R)-1-(4-(2-(3-(Fluoromethyl)azetidin-1-yl)ethoxy)phenyl)-3-methyl-2-(2,2,2-trifluoroethyl)-1,2,3,4-tetrahydroisoquinolin-6-ol: $^1$H NMR (400 MHz, $CD_3OD$) δ 7.09 (d, J=8.4 Hz, 2H), 6.80 (d, J=8.4 Hz, 1H), 6.68 (d, J=8.4 Hz, 1H), 6.59-6.51 (m, 2H), 4.82 (s, 1H), 4.55-4.37 (m, 2H), 3.97 (t, J=5.2 Hz, 2H), 3.52 (t, J=7.6 Hz, 2H), 3.29-3.16 (m, 4H), 2.97-2.73 (m, 5H), 2.54-2.51 (m, 1H), 1.02 (d, J=6.8 Hz, 3H); LCMS: 453.1[M+H]$^+$.

Examples 139 and 140 (S)-1-(4-(2-(3-(Fluoromethyl)azetidin-1-yl)ethoxy)phenyl)-2-(2,2,2-trifluoroethyl)-2,3,4,5-tetrahydro-1H-benzo[c]azepin-7-ol 139 and (R)-1-(4-(2-(3-(Fluoromethyl)azetidin-1-yl)ethoxy)phenyl)-2-(2,2,2-trifluoroethyl)-2,3,4,5-tetrahydro-1H-benzo[c]azepin-7-ol 140

Step 1: 4-Iodobenzoyl chloride

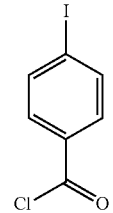

To a mixture of 4-iodobenzoic acid (10.0 g, 40.32 mmol) in $SOCl_2$ (40.0 mL, 550.73 mmol) was stirred at 80° C. for 15 hours under $N_2$ atmosphere. The reaction mixture was concentrated to afford the title compound as white solid (10.5 g, 98%). The crude product was used for the next step directly.

Step 2: 4-Iodo-N-(3-(3-methoxyphenyl)propyl)benzamide

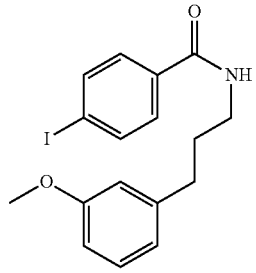 [SMILES: COc1cccc(CCCNC(=O)c2ccc(I)cc2)c1]

To a solution of 3-(3-methoxyphenyl)propan-1-amine (1.0 g, 6.05 mmol) and TEA (2.53 mL, 18.16 mmol) in dichloromethane (30 mL) was added 4-iodobenzoyl chloride (From step 1, 1.77 g, 6.66 mmol) under $N_2$ atmosphere. The resulting mixture was stirred at 20° C. for 1 hour. The reaction mixture was diluted with DCM (200 mL), washed with water (150 mL) and brine (150 mL). The organic layer was dried over anhydrous $Na_2SO_4$, filtered and concentrated to afford the title compound as a white solid (2.3 g, 96%). $^1$H NMR (400 MHz, $CDCl_3$) δ 7.75 (d, J=8.0 Hz, 2H), 7.37 (d, J=8.0 Hz, 2H), 7.25-7.18 (m, 1H), 6.86-6.72 (m, 3H), 6.04 (s, 1H), 3.79 (s, 3H), 3.54-3.45 (m, 2H), 2.75-2.68 (m, 2H), 2.00-1.92 (m, 2H).

Step 3: 1-(4-Iodophenyl)-7-methoxy-4,5-dihydro-3H-benzo[c]azepine

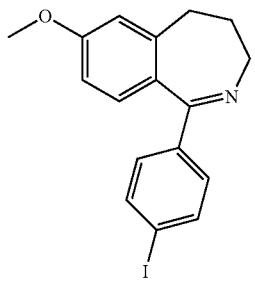 [SMILES: COc1ccc2c(c1)CCCN=C2c1ccc(I)cc1]

To a stirred solution of 4-iodo-N-[3-(3-methoxyphenyl)propyl]benzamide (From step 2, 1.8 g, 4.55 mmol) and P$_2$O$_5$ (3232 mg, 22.77 mmol) in toluene (30 mL) was added POCl$_3$ 2.12 mL, 22.77 mmol). The mixture was stirred at 110° C. for 15 hours. After being cooled to 20° C., the mixture was concentrated to dryness. The residue was poured into 15% aq. NaOH (100 mL). The mixture was stirred at 20° C. for 1 hour. The emulsified solution was extracted with DCM (100 mL×2). The combined organic layers were washed with brine (100 mL), dried over anhydrous Na$_2$SO$_4$, filtered and concentrated to dryness. The residue was purified by column chromatography (0-15% EtOAc in petroleum ether) to afford the title compound as a yellow oil (1.2 g, 70%). $^1$H NMR (400 MHz, CDCl$_3$) δ 7.71 (d, J=8.0 Hz, 2H), 7.36 (d, J=8.4 Hz, 2H), 7.03 (d, J=8.4 Hz, 1H), 6.86-6.78 (m, 2H), 3.87 (s, 3H), 3.44 (t, J=7.2 Hz, 2H), 2.58 (t, J=7.2 Hz, 2H), 2.40-2.28 (m, 2H).

Step 4: 1-(4-Iodophenyl)-7-methoxy-2,3,4,5-tetrahydro-1H-benzo[c]azepine

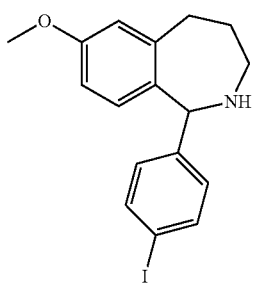 [SMILES: COc1ccc2c(c1)CCCNC2c1ccc(I)cc1]

To a solution of 1-(4-iodophenyl)-7-methoxy-4,5-dihydro-3H-2-benzazepine (From step 3, 3.1 g, 8.22 mmol) in ethanol (90 mL) was added NaBH$_4$ (0.62 g, 16.44 mmol) at 0° C. The resulting mixture was then warmed to 20° C., and stirred for 2 hours. The mixture was quenched with sat. aq. NH$_4$Cl (200 mL) and extracted with DCM (250 mL×2). The combined organic layers were washed with brine (200 mL), dried over anhydrous Na$_2$SO$_4$, filtered and concentrated to dryness to afford the title compound (3 g, 96%) as a yellow solid. The crude product was used for next step directly. $^1$H NMR (400 MHz, CDCl$_3$) δ 7.69 (d, J=8.0 Hz, 2H), 7.07 (d, J=8.4 Hz, 2H), 6.76 (s, 1H), 6.57-6.52 (m, 2H), 5.12 (s, 1H), 3.78 (s, 3H), 3.39-3.30 (m, 1H), 3.20-3.11 (m, 1H), 3.10-3.00 (m, 1H), 2.90-2.81 (m, 1H), 1.94-1.77 (m, 2H). LCMS: 380.1 [M+H]$^+$.

Step 5: 1-(4-iodophenyl)-4-methoxy-2-(2,2,2-trifluoroethyl)-2,3,4,5-tetrahydro-1H-benzo[c]azepine

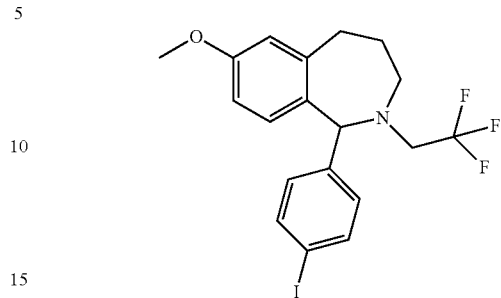

A mixture of 1-(4-iodophenyl)-7-methoxy-2,3,4,5-tetrahydro-1H-2-benzazepine (From step 4, 3.0 g, 7.91 mmol), 2,2,2-trifluoroethyl trifluoromethanesulfonate (9.18 g, 39.55 mmol) and DIPEA (11.02 mL, 63.28 mmol) in 1,4-dioxane (30 mL) was heated at 110° C. for 16 hours. The mixture was diluted with EtOAc (200 mL), washed with water (150 mL×2), sat. NaHCO$_3$ (150 mL) and brine (150 mL). The organic layer was dried over anhydrous Na$_2$SO$_4$, filtered and concentrated. The residue was purified by column chromatography (0-5% EtOAc in petroleum ether) to afford the title compound (2.6 g, 71%) as a yellow oil. $^1$H NMR (400 MHz, CDCl$_3$) δ 7.62 (d, J=8.0 Hz, 2H), 7.05-6.97 (m, 3H), 6.78 (d, J=2.4 Hz, 1H), 6.71 (dd, J=8.0, 2.4 Hz, 1H), 5.02 (s, 1H), 3.84 (s, 3H), 3.22-3.00 (m, 3H), 3.00-2.90 (m, 1H), 2.78-2.68 (m, 1H), 2.67-2.55 (m, 1H), 1.74-1.62 (m, 1H), 1.50-1.43 (m, 1H). LCMS: 462.2 [M+H]$^+$.

Step 6: 1-(4-Iodophenyl)-2-(2,2,2-trifluoroethyl)-2,3,4,5-tetrahydro-1H-benzo[c]azepin-7-ol

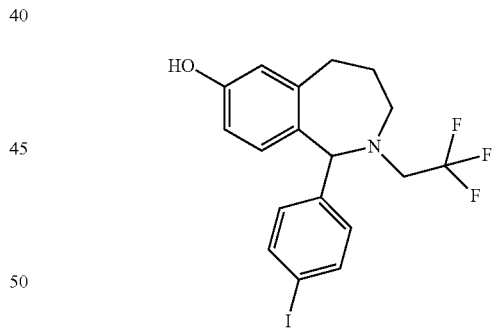

To a solution of 1-(4-iodophenyl)-7-methoxy-2-(2,2,2-trifluoroethyl)-1,3,4,5-tetrahydro-2-benzazepine (From step 5, 500.0 mg, 1.08 mmol) in dichloromethane (10 mL) was added tribromoborane (0.16 mL, 1.63 mmol) at −78° C. The reaction mixture was stirred and warmed up from −78° C. to room temperature for 2 hours. The solution was added into sat. aq. NaHCO$_3$ solution (30 mL). The solution was extracted with DCM (30 mL×2). The organic layer was dried over anhydrous Na$_2$SO$_4$ and concentrated. The residue was purified by column chromatography on silica gel (0-30% EtOAc in petroleum ether) to afford the title compound (250 mg, 52%) as a light yellow oil. $^1$H NMR (400 MHz, CDCl$_3$) δ 7.62 (d, J=8.4 Hz, 2H), 7.07-6.87 (m, 3H), 6.72 (d, J=2.0

Hz, 1H), 6.66-6.63 (m, 1H), 5.05-4.89 (m, 2H), 3.24-3.01 (m, 3H), 2.97-2.93 (m, 1H), 2.77-2.66 (m, 1H), 2.64-2.52 (m, 1H), 1.76-1.65 (m, 1H), 1.47-1.44 (m, 1H).

Step 7 1-(4-(2-(3-(Fluoromethyl)azetidin-1-yl) ethoxy)phenyl)-2-(2,2,2-trifluoroethyl)-2,3,4,5-tetrahydro-1H-benzo[c]azepin-7-ol

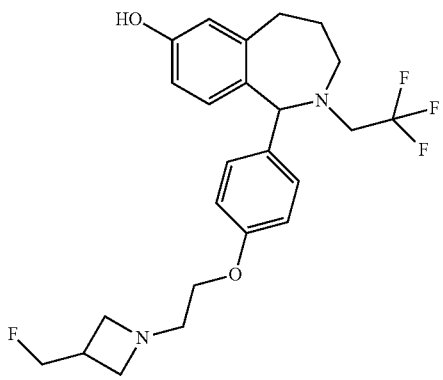 [SMILES: Oc1ccc2c(c1)CCCN(CC(F)(F)F)C2c1ccc(OCCN2CC(CF)C2)cc1]

To a solution of 2-[3-(fluoromethyl)azetidin-1-yl]ethanol (0.63 g, 4.7 mmol) in butyronitrile (10. mL, 17.16 mmol) was added 1-(4-iodophenyl)-2-(2,2,2-trifluoroethyl)-2,3,4,5-tetrahydro-1H-benzo[c]azepin-7-ol (From step 6, 700 mg, 1.57 mmol), CuI (0.89 g, 4.7 mmol) and K$_2$CO$_3$ (0.65 g, 4.7 mmol). The solution was purged with N$_2$ for 3 minutes and was stirred at 135° C. for 6 hours. The reaction mixture was concentrated to dryness. The residue was purified by column chromatography on silica gel (0-6% MeOH in DCM) to afford the title compound with 80% purity. The resulting residue was further purified by reverse phase chromatography (acetonitrile 48-78%/0.1% NH$_4$HCO$_3$ in water) to afford the racemic title compound as a light yellow solid (300 mg, 42%). $^1$H NMR (400 MHz, CDCl$_3$) δ 7.10 (d, J=8.0 Hz, 1H), 6.81 (d, J=8.0 Hz, 1H), 6.72 (d, J=8.0 Hz, 2H), 6.60-6.52 (m, 2H), 4.90 (s, 1H), 4.64-4.45 (m, 2H), 4.07-3.89 (m, 2H), 3.69 (q, J=7.2 Hz, 2H), 3.37 (q, J=7.2 Hz, 2H), 3.16-2.83 (m, 7H), 2.40-2.33 (m, 1H), 2.01-1.96 (m, 1H), 1.66-1.58 (m, 1H), 1.22-1.19 (m, 1H). LCMS: 453.1 [M+H]$^+$.

Step 8

1-(4-(2-(3-(Fluoromethyl)azetidin-1-yl)ethoxy)phenyl)-2-(2,2,2-trifluoroethyl)-2,3,4,5-tetrahydro-1H-benzo[c]azepin-7-ol (From step 7, 300 mg, 0.66 mmol) was purified by SFC (OD (250 mm×30 mm, 5 um), condition 0.1% NH$_4$OH in MeOH, flow rate 80 mL/min) to give separated 139 (second peak on SFC) as white solid (105.1 mg, 35%) and 140 (first peak on SFC) as light yellow solid (83.9 mg, 28%). The absolute structures of the two peaks were assigned arbitrarily.

Examples 143 and 144 (R)-1-(2,6-Difluoro-4-(1-(3-fluoropropyl)azetidin-3-yl)oxy)phenyl)-2-(2,2,2-trifluoroethyl)-1,2,3,4-tetrahydroisoquinolin-6-ol 143 and (S)-1-(2,6-Difluoro-4-((1-(3-fluoropropyl) azetidin-3-yl)oxy)phenyl)-2-(2,2,2-trifluoroethyl)-1, 2,3,4-tetrahydroisoquinolin-6-ol 144

Step 1: tert-Butyl 3-[3,5-difluoro-4-(6-hydroxy-1,2, 3,4-tetrahydroisoquinolin-1-yl)phenoxy]azetidine-1-carboxylate

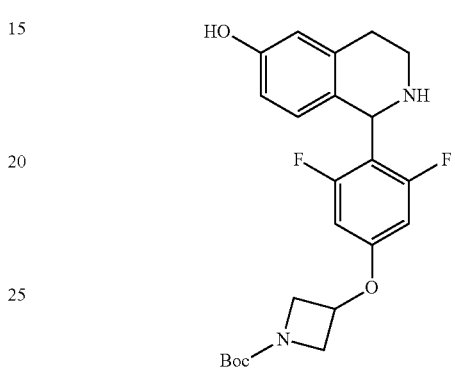

A mixture of 3-(2-aminoethyl)phenol (1.45 g, 10.57 mmol), tert-butyl 3-(3,5-difluoro-4-formyl-phenoxy)azetidine-1-carboxylate (2.98 g, 9.51 mmol)

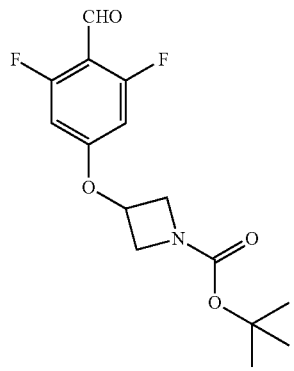 [SMILES: CC(C)(C)OC(=O)N1CC(Oc2cc(F)c(C=O)c(F)c2)C1]

and acetic acid (4.8 mL, 83.93 mmol) in anhydrous 1,4-dioxane (30 mL) was stirred at 90° C. for 16 hours under nitrogen atmosphere. The mixture was basified by saturated aqueous NaHCO$_3$ (20 mL) and was extracted with EtOAc (30 mL×3). The combined organic phases were dried over anhydrous Na$_2$SO$_4$, filtered and concentrated. The residue was then purified by flash column chromatography (eluting with 0~5% MeOH in DCM) to give the title compound (2.32 g, 47%) as a yellow solid. LCMS: 433.0 [M+H]$^+$. $^1$H NMR (400 MHz, CDCl$_3$) δ 6.59-6.52 (m, 3H), 6.28 (d, J=10.0 Hz, 2H), 5.46 (s, 1H), 4.84-4.75 (m, 1H), 4.31-4.26 (m, 2H), 4.02-3.96 (m, 2H), 3.43-3.97 (m, 1H), 3.18-3.06 (m, 1H), 3.04-2.92 (m, 1H), 2.73 (d, J=16.8 Hz, 1H), 1.45 (s, 9H).

Step 2: tert-Butyl 3-(3,5-difluoro-4-(6-hydroxy-2-(2,2,2-trifluoroethyl)-1,2,3,4-tetrahydroisoquinolin-1-yl)phenoxy)azetidine-1-carboxylate

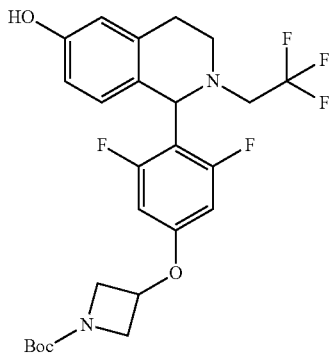 [SMILES: CC(C)(C)OC(=O)N1CC(Oc2cc(F)c(C3c4ccc(O)cc4CCN3CC(F)(F)F)c(F)c2)C1]

To a solution of tert-butyl 3-[3,5-difluoro-4-(6-hydroxy-1,2,3,4-tetrahydroisoquinolin-1-yl)phenoxy]azetidine-1-carboxylate (From step 1, 0.8 g, 1.85 mmol) in 1,4-dioxane (20 mL) was added DIPEA (0.64 mL, 3.7 mmol) followed by 2,2,2-trifluoroethyltrifluoromethanesulfonate (0.27 mL, 1.85 mmol). The resulting mixture was stirred at 80° C. for 15 hours. The reaction mixture was diluted with water (30 mL), extracted with EtOAc (30 mL×3). The combined organic phases were dried over anhydrous sodium sulfate, concentrated in vacuo. The residue was purified by flash chromatography on silica gel (eluting with 0~4% MeOH in DCM) to give the title compound (0.85 g, 85%) as a yellow solid. LCMS: 515.1 [M+H]$^+$. $^1$H NMR (400 MHz, CDCl$_3$) δ 6.64-6.51 (m, 3H), 6.24 (d, J=10.0 Hz, 2H), 5.86 (br., 1H), 5.19 (s, 1H), 4.83-4.73 (m, 1H), 4.34-4.23 (m, 2H), 4.03-3.95 (m, 2H), 3.32-3.23 (m, 1H), 3.16-2.97 (m, 3H), 2.96-2.86 (m, 1H), 2.75-2.71 (m, 1H), 1.45 (s, 9H).

Step 3: 1-(4-(Azetidin-3-yloxy)-2,6-difluorophenyl)-2-(2,2,2-trifluoroethyl)-1,2,3,4-tetrahydroisoquinolin-6-ol

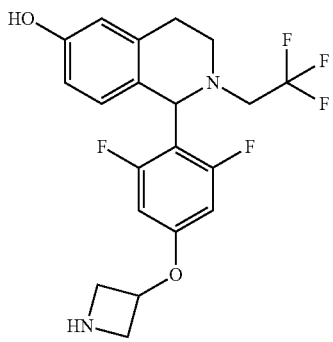 [SMILES: Oc1ccc2c(c1)CCN(CC(F)(F)F)C2c1c(F)cc(OC2CNC2)cc1F]

To the solution of tert-butyl 3-(3,5-difluoro-4-(6-hydroxy-2-(2,2,2-trifluoroethyl)-1,2,3,4-tetrahydroisoquinolin-1-yl)phenoxy)azetidine-1-carboxylate (From step 2, 850.0 mg, 1.65 mmol) in 1,4-dioxane (10 mL) was added sulfuric acid slowly (0.9 mL, 16.56 mmol) at 10° C. The reaction mixture was stirred at 10° C. for 0.5 hours. The solution was poured into saturated aqueous NaHCO$_3$ (20 mL) solution and extracted with EtOAc (20 mL×3). The combined organic layers were dried over anhydrous Na$_2$SO$_4$ and concentrated to give the title compound (680 mg, 99%) as a yellow solid. The crude compound was used directly for the next step. LCMS: 414.9 [M+H]$^-$. $^1$H NMR (400 MHz, CD$_3$OD) δ 6.52 (s, 1H), 6.51-6.44 (m, 2H), 6.42 (s, 1H), 6.40 (s, 1H), 5.12 (s, 1H), 5.06-5.00 (m, 1H), 3.98-3.89 (m, 2H), 3.67 (br., 1H), 3.64 (br., 1H), 3.29-3.23 (m, 1H), 3.15-2.97 (m, 3H), 2.92-2.82 (m, 1H), 2.73-2.65 (m, 1H).

Step 4: 1-(2,6-Difluoro-4-((1-(3-fluoropropyl)azetidin-3-yl)oxy)phenyl)-2-(2,2,2-trifluoroethyl)-1,2,3,4-tetrahydroisoquinolin-6-ol

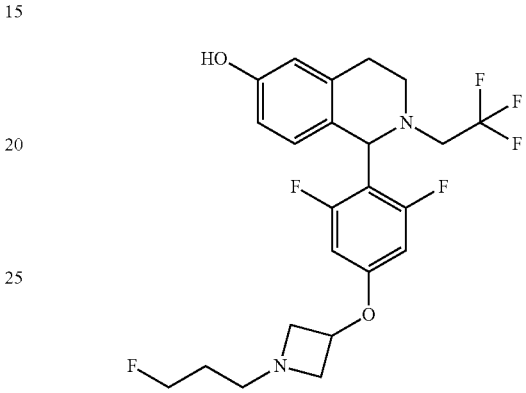

To a stirred mixture of DIPEA (0.62 mL, 3.48 mmol) and 1-(4-(azetidin-3-yloxy)-2,6-difluorophenyl)-2-(2,2,2-trifluoroethyl)-1,2,3,4-tetrahydroisoquinolin-6-ol (From step 3, 480.0 mg, 1.16 mmol) in DMF (10 mL) was added 1-iodo-3-fluoropropane (217.0 mg, 1.15 mmol). The reaction mixture was stirred at 15° C. for 16 hours. The reaction mixture was diluted with EtOAc (100 mL), washed with water (50 mL×5), dried over anhydrous Na$_2$SO$_4$, and concentrated in vacuo. The residue was purified on silica gel column (eluted with MeOH in DCM (0-4%)) to afford crude product which was further purified by preparative HPLC (acetonitrile 16-46%/0.225% FA in water). The desired fractions were collected, concentrated, then basified with solid NaHCO$_3$. The resulting suspension was extracted with EtOAc (50 mL×3), The combined organic phases were dried over anhydrous Na$_2$SO$_4$, filtered and concentrated in vacuo to give the title compound (290 mg, 53%) as a light-yellow solid. LCMS: 475.0 [M+H]$^+$. $^1$H NMR (400 MHz, CDCl$_3$) δ 6.63-6.56 (m, 2H), 6.55-6.49 (m, 1H), 6.27 (d, J=10.0 Hz, 2H), 5.18 (s, 1H), 4.74-4.68 (m, 1H), 4.55 (t, J=6.0 Hz, 1H), 4.43 (t, J=6.0 Hz, 1H), 3.86-3.73 (m, 2H), 3.33-3.23 (m, 1H), 3.17-2.97 (m, 5H), 2.96-2.86 (m, 1H), 2.76-2.72 (m, 1H), 2.66 (t, J=7.2 Hz, 2H), 1.86-1.68 (m, 2H).

Step 5

1-(2,6-Difluoro-4-((1-(3-fluoropropyl)azetidin-3-yl)oxy)phenyl)-2-2,2,2-trifluoroethyl)-1,2,3,4-tetrahydroisoquinolin-6-ol (From step 4, 280.0 mg, 0.59 mmol) was resolved by SFC separation (Column: Chiralpak AD-3; Mobile phase: A: CO$_2$, B: ethanol (0.1% NH$_4$OH); Flow Rate (mL/min): 75) to give 141 (First peak on SFC, 92 mg, 33%) and 142 (Second peak on SFC, 120 mg, 42%) both as white solids.

Examples 149 and 150 (S)-(1-(4-(2-(3-(Fluoromethyl)azetidin-1-yl)ethoxy)phenyl)-2-(2,2,2-trifluoroethyl)-1,2,3,4-tetrahydroisoquinolin-6-yl)methanol 149 and (R)-(1-(4-(2-(3-(fluoromethyl)azetidin-1-yl)ethoxy)phenyl)-2-(2,2,2-trifluoroethyl)-1,2,3,4-tetrahydroisoquinolin-6-yl)methanol 150

Step 1: Methyl 1-(4-(2-(3-(fluoromethyl)azetidin-1-yl)ethoxy)phenyl)-2-(2,2,2-trifluoroethyl)-1,2,3,4-tetrahydroisoquinoline-6-carboxylate

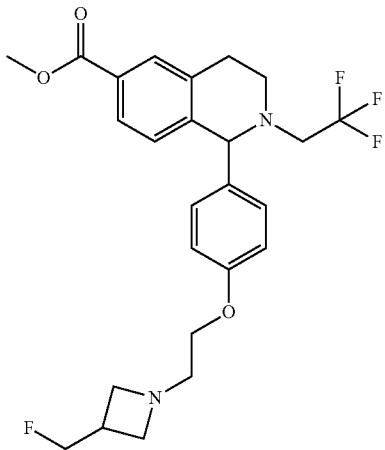 [SMILES: COC(=O)c1ccc2c(c1)CCN(CC(F)(F)F)C2c1ccc(OCCN2CC(CF)C2)cc1]

A mixture of 6-bromo-1-(4-(2-(3-(fluoromethyl)azetidin-1-yl)ethoxy)phenyl)-2-(2,2,2-trifluoroethyl)-1,2,3,4-tetrahydroisoquinoline (Intermediate 2, 1.0 g, 1.99 mmol), palladium acetate (223.9 mg, 1 mmol), triethylamine (0.55 mL, 3.99 mmol), 1,1'-bis(diphenyphosphino)ferrocene (1.11 g, 1.99 mmol) in methanol (20 mL) was stirred at 70° C. for 40 hours under CO (50 psi) atmosphere. The reaction mixture was filtered and the filtrate was concentrated in vacuo to give the title compound (0.90 g, 94%) as a yellow syrup, the crude product was used for next step directly. LCMS: 481.1 [M+H]$^+$.

Step 2 (1-(4-(2-(3-(Fluoromethyl)azetidin-1-yl)ethoxy)phenyl)-2-(2,2,2-trifluoroethyl)-1,2,3,4-tetrahydroisoquinolin-6-yl)methanol

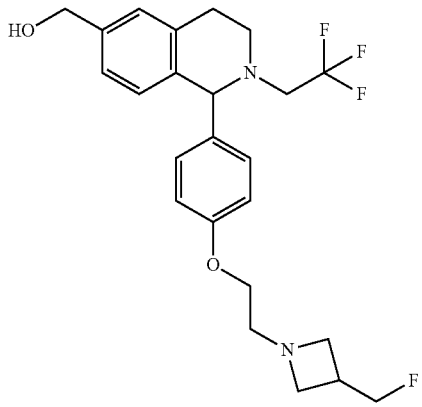 [SMILES: OCc1ccc2c(c1)CCN(CC(F)(F)F)C2c1ccc(OCCN2CC(CF)C2)cc1]

To a mixture of lithium aluminum hydride (165.8 mg, 4.37 mmol) in THF (10 mL) was added a solution of methyl 1-(4-(2-(3-(fluoromethyl)azetidin-1-yl)ethoxy)phenyl)-2-(2,2,2-trifluoroethyl)-1,2,3,4-tetrahydroisoquinoline-6-carboxylate (From step 1, 700.0 mg, 1.46 mmol) in THF (5 mL) slowly at 0° C. The resulting mixture was stirred at 15° C. for 3 hours, quenched by addition of H$_2$O (1 mL), followed by 15% aqueous NaOH (1 mL), dried over anhydrous MgSO$_4$, filtered and the filtrate was concentrated. The resulting residue was purified by reverse phase chromatography (acetonitrile 17-47/0.05% ammonia in water) to give the title compound (0.40 g, 61%) as a yellow solid. $^1$H NMR (400 MHz, CD$_3$OD) δ 7.18-7.10 (m, 3H), 6.98 (d, J=8.0 Hz, 1H), 6.85 (d, J=8.8 Hz, 2H), 6.64 (d, J=8.0 Hz, 1H), 4.74 (s, 1H), 4.55-4.50 (m, 3H), 4.41 (d, J=5.6 Hz, 1H), 3.98 (t, J=5.2 Hz, 2H), 3.52 (t, J=7.6 Hz, 2H), 3.30-3.26 (m, 1H), 3.21 (t, J=7.6 Hz, 2H), 3.07-3.02 (m, 3H), 2.91-2.81 (m, 5H). LCMS: 453.2 [M+H]$^+$.

Step 3

(1-(4-(2-(3-(Fluoromethyl)azetidin-1-yl)ethoxy)phenyl)-2-(2,2,2-trifluoroethyl)-1,2,3,4-tetrahydroisoquinolin-6-yl)methanol (From step 2, 400.0 mg, 0.44 mmol) was purified by SFC (OD 250 mm*30 mm, 5 um), supercritical CO$_2$/EtOH (0.1% NH$_3$H$_2$O) to give 149 as a white solid (157.6 mg, 38%) and 150 as white solid (52.1 mg, 13%).

Examples 153 and 154 (S)-1-(4-(2-(3-(Fluoromethyl)azetidin-1-yl)ethoxy)phenyl)-2-(2,2,2-trifluoroethyl)-1,2,3,4-tetrahydroisoquinolin-6-ol 153 and (R)-1-4-(2-(3-(Fluoromethyl)azetidin-1-yl)ethoxy)phenyl)-2-(2,2,2-trifluoroethyl)-1,2,3,4-tetrahydroisoquinolin-6-ol 154

Step 1: 1-(4-(2-(3-(Fluoromethyl)azetidin-1-yl)ethoxy)phenyl)-2-(2,2,2-trifluoroethyl)-1,2,3,4-tetrahydroisoquinolin-6-ol

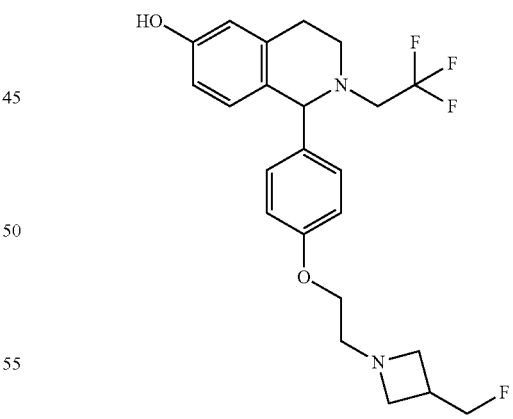

To a solution of 6-bromo-1-(4-(2-(3-(fluoromethyl)azetidin-1-yl)ethoxy)phenyl)-2-(2,2,2-trifluoroethyl)-1,2,3,4-tetrahydroisoquinoline (Intermediate 2, 400 mg, 0.80 mmol), di-tert-butyl-[2-(2,4,6-triisopropylphenyl)phenyl]phosphane (27 mg, 0.06 mmol) in 1,4-dioxane (5 mL) and water (5 mL) was added tris(dibenzylideneacetone)dipalladium (29 mg, 0.03 mmol) and potassium hydroxide (134 mg, 2.39 mmol) under nitrogen atmosphere. The resulting mixture was stirred at 90° C. for 15 hours and was concentrated under reduced pressure. The resulting residue was purified by reverse phase chromatography (acetonitrile 48-78/0.05% ammonia in water) to give the title compound as a light yellow solid (100 mg, 29%). ¹H NMR (400 MHz, CD₃OD) δ 7.14 (d, J=8.4 Hz, 2H), 6.85 (d, J=8.4 Hz, 2H), 6.53 (s, 1H), 6.48-6.41 (m, 2H), 4.65 (s, 1H), 4.53 (d, J=5.2 Hz, 1H), 4.42 (d, J=5.2 Hz, 1H), 3.99 (t, J=5.2 Hz, 2H), 3.53 (t, J=7.6 Hz, 2H), 3.27-3.19 (m, 3H), 3.12-2.95 (m, 3H), 2.89-2.73 (m, 5H). LCMS: 439.2 [M+H]⁺.

Step 2

1-(4-(2-(3-(Fluoromethyl)azetidin-1-yl)ethoxy)phenyl)-2-(2,2,2-trifluoroethyl)-1,2,3,4-tetrahydroisoquinolin-6-ol (From step 1, 100.0 mg, 0.23 mmol) was separated by SFC (AD 250 mm*30 mm, 5 um, supercritical CO₂/EtOH (0.1% NH₃·H₂O)) to give 153 as a white solid (first peak on SFC, 14.8 mg, 14%) and 154 as a white solid (second peak on SFC, 18 mg, 18%).

Example 155 and 156 (1S,3S)-1-(4-(2-(3-(Fluoromethyl)azetidin-1-yl)ethoxy)phenyl)-3-methyl-2-(2,2,2-trifluoroethyl)-1,2,3,4-tetrahydroisoquinoline 155 and (1R,3R)-1-(4-(2-(3-(Fluoromethyl)azetidin-1-yl)ethoxy)phenyl)-3-methyl-2-(2,2,2-trifluoroethyl)-1,2,3,4-tetrahydroisoquinoline 156

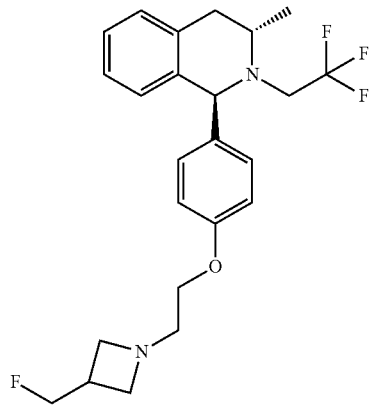

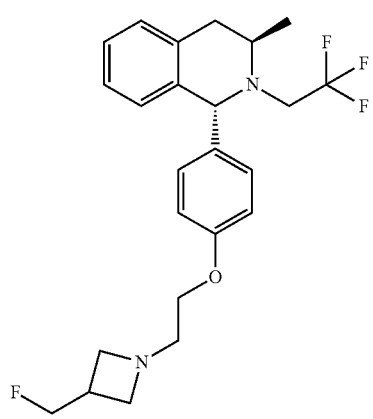

Step 1: (1,3-trans)-1-(4-(2-(3-(Fluoromethyl)azetidin-1-yl)ethoxy)phenyl)-3-methyl-2-(2,2,2-trifluoroethyl)-1,2,3,4-tetrahydroisoquinolin-6-yl trifluoromethanesulfonate

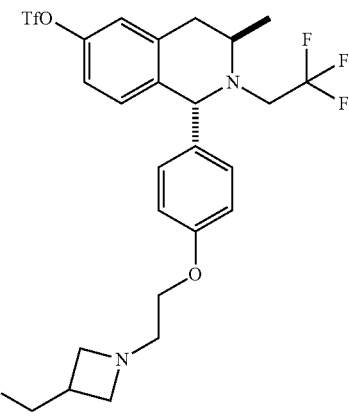

To a solution of (1,3-trans)-1-(4-(2-(3-(fluoromethyl)azetidin-1-yl)ethoxy)phenyl)-3-methyl-2-(2,2,2-trifluoroethyl)-1,2,3,4-tetrahydroisoquinolin-6-ol (From step 5 of Example 131, 250 mg, 0.55 mmol) in DCM (2 mL) was added triethylamine (0.1 mL, 0.72 mmol) and N-phenylbis(trifluoromethanesulfonimide) (237 mg, 0.66 mmol). The reaction mixture was stirred at 15° C. for 16 h. Water (30 mL) was added to the mixture and the mixture was extracted with DCM (30 mL×2). The combined organic layers were dried over anhydrous Na₂SO₄ and concentrated. The residue was purified by column chromatography on silica gel (0-10% MeOH in DCM) to afford the title compound (320 mg, 99%) as a colorless oil. LCMS: 585.0 [M+H]⁺.

Step 2: 155 and 156

To a solution of (1,3-trans)-1-(4-(2-(3-(fluoromethyl)azetidin-1-yl)ethoxy)phenyl)-3-methyl-2-(2,2,2-trifluoroethyl)-1,2,3,4-tetrahydroisoquinolin-6-yl trifluoromethanesulfonate (From step 1, 320.0 mg, 0.55 mmol) in DMF (5 mL) was added 1,3-bis(diphenylphosphino)propane (46 mg, 0.11 mmol) and palladium (II) acetate (25 mg, 0.11 mmol). The reaction mixture was purged with N₂ for 3 min. Et₃SiH (2.3 mL) was added into the mixture and the solution was purged with N₂ for 1 min again. The reaction mixture was stirred at 60° C. for 6 h. Water (30 mL) was added to the solution and the mixture was extracted with EtOAc (30 mL×2). The combined organic layers were dried over anhydrous Na₂SO₄ and concentrated. The residue was purified by column chromatography on silica gel (0-10% MeOH in DCM) to afford the title compound with 51% purity. The residue was further purified by reverse phase chromatography (acetonitrile 56-86%/0.1% NH₄OH in water) to afford the product (150 mg, 63%) as a light yellow oil. This product was separated by SFC (OD (250 mm*30 mm, 5 um), Condition: 0.1% NH₃H₂O-iPrOH Beginning B: 20%, End B: 20% Gradient Time (min), 100% B. Flow Rate 60 mL/min) to afford the title compound 155 (71.9 mg, 47%, Rt=3.68 min) as a light yellow oil and 156 (75 mg, 50%, Rt=2.93 min) as a yellow oil.

155: ¹H NMR (400 MHz, CD₃OD) δ 7.16-7.13 (m, 2H), 7.09 (d, J=8.4 Hz, 3H), 6.86 (d, J=7.2 Hz, 1H), 6.81 (d, J=9.2 Hz, 2H), 4.91 (s, 1H), 4.56-4.39 (dd, J=47.6, 5.6 Hz, 2H), 3.97 (t, J=5.2 Hz, 2H), 3.53 (t, J=7.6 Hz, 2H), 3.40-3.25 (m, 2H), 3.21 (t, J=7.6 Hz, 2H), 2.99-2.79 (m, 5H), 2.61-2.55 (m, 1H), 1.05 (d, J=6.8 Hz, 3H). LCMS: 437.1 [M+H⁺].

156: ¹H NMR (400 MHz, CD₃OD) δ 7.16-7.13 (m, 2H), 7.13-7.06 (m, 3H), 6.87 (d, J=7.6 Hz, 1H), 6.82 (d, J=8.4 Hz, 1H), 4.92 (s, 1H), 4.56-4.40 (dd, J=47.6, 6.0 Hz, 2H), 3.98 (t, J=5.2 Hz, 2H), 3.54 (t, J=7.6 Hz, 2H), 3.39-3.24 (m, 2H), 3.23 (t, J=7.6 Hz, 2H), 2.99-2.80 (m, 5H), 2.62-2.55 (m, 1H), 1.05 (d, J=6.8 Hz, 3H). LCMS: 437.1 [M+H]⁺.

Example 157 and 158 (S)-1-(4-(2-(3-(Fluoromethyl)azetidin-1-yl)ethoxy)phenyl)-3,3-dimethyl-2-(2,2,2-trifluoroethyl)-1,2,3,4-tetrahydroisoquinolin-6-ol 157 and (R)—1-(4-(2-(3-(Fluoromethyl)azetidin-1-yl)ethoxy)phenyl)-3,3-dimethyl-2-(2,2,2-trifluoroethyl)-1,2,3,4-tetrahydroisoquinolin-6-ol 158

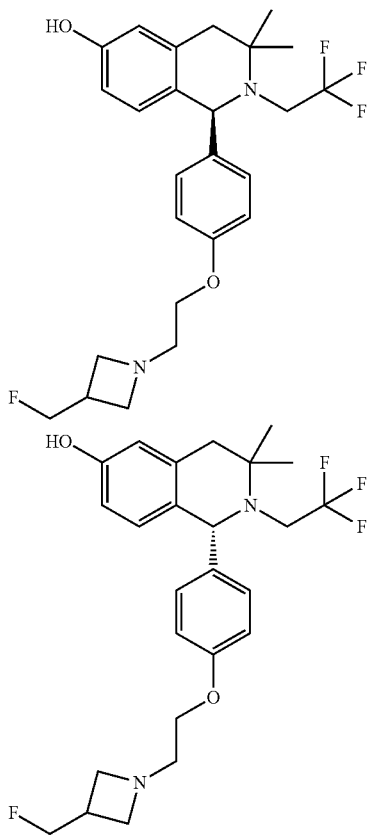

Following a similar procedure to that of Example 109, Examples 157/158 were prepared from 1-(3-methoxyphenyl)-2-methylpropan-2-amine. The enantiomers were separated by SFC (AD 250 mm*30 mm, 5 um; supercritical CO₂/EtOH (0.1% NH₃H₂O)=30/30 at 60 mL/min).

157: Rt=3.60 min. ¹HNMR (400 MHz, CD₃OD) δ 7.17 (d, J=8.4 Hz, 2H), 6.80 (d, J=8.4 Hz, 2H), 6.51-6.40 (m, 3H), 4.72 (s, 1H), 4.48 (dd, J=47.6, 5.6 Hz, 2H), 3.99 (t, J=5.2 Hz, 2H), 3.55-3.50 (m, 2H), 3.48-3.41 (m, 1H), 3.23-3.03 (m, 4H), 2.87-2.80 (m, 3H), 2.46 (d, J=15.6 Hz, 1H), 1.32 (s, 3H), 1.02 (s, 3H). LCMS: 467.1 [M+H]⁺.

158: Rt=4.42 min. ¹HNMR (400 MHz, CD₃OD) δ 7.17 (d, J=8.8 Hz, 2H), 6.80 (d, J=8.8 Hz, 2H), 6.50-6.40 (m, 3H), 4.72 (s, 1H), 4.48 (dd, J=47.6, 5.6 Hz, 2H), 3.99 (t, J=5.2 Hz, 2H), 3.55-3.50 (m, 2H), 3.48-3.40 (m, 1H), 3.25-3.00 (m, 4H), 2.87-2.80 (m, 3H), 2.45 (d, J=15.6 Hz, 1H), 1.32 (s, 3H), 1.02 (s, 3H). LCMS: 467.2 [M+H]⁺.

Example 159 and 160 ((1R,3R)-1-(4-(2-(3-(Fluoromethyl)azetidin-1-yl)ethoxy)phenyl)-3-methyl-2-(2,2,2-trifluoroethyl)-1,2,3,4-tetrahydroisoquinolin-6-yl)methanol 159 and ((1S,3S)-1-(4-(2-(3-(Fluoromethyl)azetidin-1-yl)ethoxy)phenyl)-3-methyl-2-(2,2,2-trifluoroethyl)-1,2,3,4-tetrahydroisoquinolin-6-yl)methanol 160

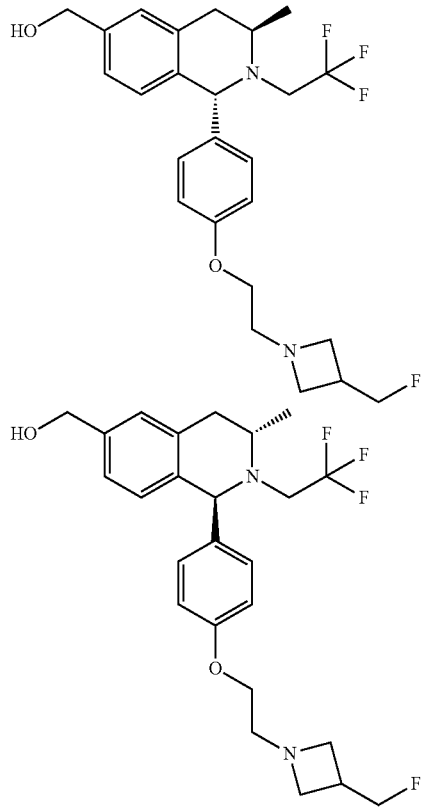

Step 1: (1,3-trans)-Methyl 1-(4-(2-(3-(fluoromethyl)azetidin-1-yl)ethoxy)phenyl)-3-methyl-2-(2,2,2-trifluoroethyl)-1,2,3,4-tetrahydroisoquinoline-6-carboxylate

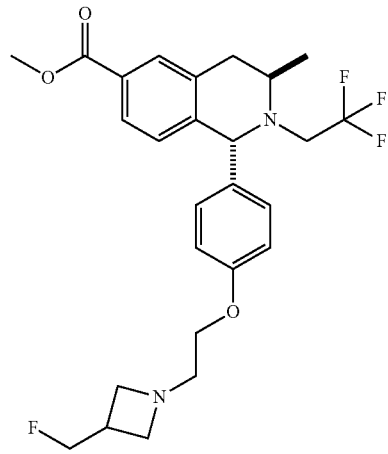 [SMILES: COC(=O)c1ccc2c(c1)C[C@@H](C)N(CC(F)(F)F)[C@@H]2c1ccc(OCCN2CC(CF)C2)cc1]

A solution of palladium(II) acetate (384 mg, 1.7 mmol), triethylamine (0.9 mL, 6.8 mmol), dppf (1.9 g, 3.4 mmol), (1,3-trans)-1-(4-(2-(3-(fluoromethyl)azetidin-1-yl)ethoxy)

phenyl)-3-methyl-2-(2,2,2-trifluoroethyl)-1,2,3,4-tetrahydroisoquinolin-6-yl trifluoromethanesulfonate (From step 1 of Example 156, 2.0 g, 3.4 mmol) in MeOH (20 mL) was stirred at 70° C. under CO (50 psi) for 40 h. The reaction mixture was filtered through a Celite® pad, and the filtrate was concentrated in vacuo. The residue was purified by chromatography on silica (0-10% MeOH in DCM) to afford the title compound (3 g, 99%) as a black oil. LCMS: 495.1 [M+H]$^+$.

Step 2: 159 and 160

To a solution of lithium aluminum hydride (230 mg, 6.0 mmol) in THF (10 mL) was added a solution of (1,3-trans)-methyl 1-(4-(2-(3-(fluoromethyl)azetidin-1-yl)ethoxy)phenyl)-3-methyl-2-(2,2,2-trifluoroethyl)-1,2,3,4-tetrahydroisoquinoline-6-carboxylate (From step 1, 1.0 g, 2.0 mmol) in THF (5 mL) slowly at 0° C. The mixture was stirred at 15° C. for 3 hours. The reaction was quenched by addition of 1 mL of H$_2$O, followed by 1 mL of 15% aqueous NaOH, dried over anhydrous MgSO$_4$. After being stirred at room temperature for 30 min, the solid was removed by filtration. The filtrate was concentrated. The resulting residue was purified by reverse phase chromatography (acetonitrile 50-80/0.05% ammonia in water) to afford the title compound (300 mg, 32%) as a white solid. A portion of this compound (250 mg, 0.54 mmol) was purified by SFC (AD 250 mm*30 mm, 5 um, 0.1% NH$_3$H$_2$O-EtOH 25%) to afford the title compounds 159 (Rt=3.84 min, 71 mg, 28%) and 160 (Rt=4.61 min, 72 mg, 29%) both as off-white solids.

159: $^1$H NMR (400 MHz, CDCl$_3$) δ 7.16 (s, 1H), 7.13-7.10 (m, 3H), 6.92 (d, J=8.0 Hz, 1H), 6.79 (d, J=8.4 Hz, 2H), 4.92 (s, 1H), 4.68 (s, 2H), 4.60-4.42 (dd, J=47.6, 6.0 Hz, 2H), 3.94 (t, J=5.2 Hz, 2H), 3.51 (t, J=7.6 Hz, 2H), 3.38-3.27 (m, 1H), 3.23-3.10 (m, 3H), 2.98-2.78 (m, 5H), 2.59-2.56 (m, 1H), 1.06 (d, J=6.8 Hz, 3H). LCMS: 467.2 [M+H]$^+$.

160: $^1$H NMR (400 MHz, CDCl$_3$) δ 7.16 (s, 1H), 7.12 (d, J=8.8 Hz, 3H), 6.92 (d, J=8.0 Hz, 1H), 6.80 (d, J=8.4 Hz, 2H), 4.92 (s, 1H), 4.68 (s, 2H), 4.59-4.42 ((dd, J=47.6, 5.6 Hz, 2H), 3.94 (t, J=5.2 Hz, 2H), 3.50 (t, J=7.6 Hz, 2H), 3.37-3.26 (m, 1H), 3.23-3.08 (m, 3H), 2.98-2.75 (m, 5H), 2.60-2.52 (m, 1H), 1.06 (d, J=6.4 Hz, 3H). LCMS: 467.2 [M+H]$^+$.

Example 161 2-((1R,3R)-1-(4-(2-(3-(Fluoromethyl) azetidin-1-yl)ethoxy)phenyl)-3-methyl-2-(2,2,2-trifluoroethyl)-1,2,3,4-tetrahydroisoquinolin-6-yl)propan-2-ol 161 and 2-((1S,3S)-1-(4-(2-(3-(Fluoromethyl)azetidin-1-yl)ethoxy)phenyl)-3-methyl-2-(2,2,2-trifluoroethyl)-1,2,3,4-tetrahydroisoquinolin-6-yl)propan-2-ol 162

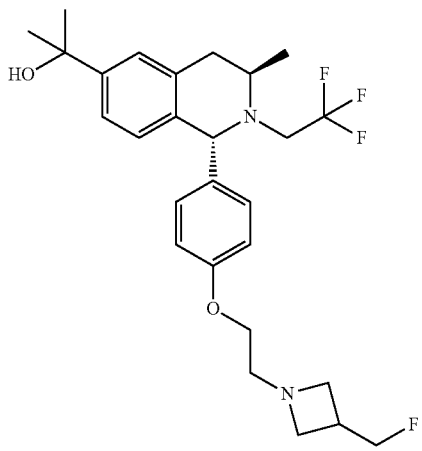

-continued

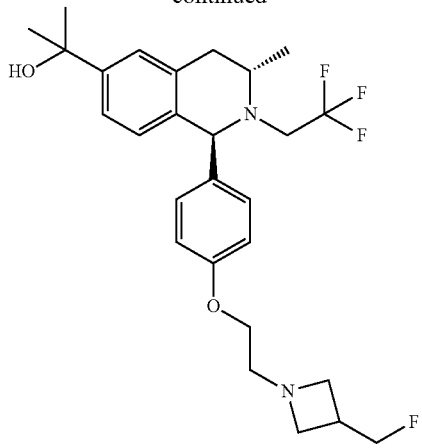

To a solution of (1,3-trans)-methyl 1-(4-(2-(3-(fluoromethyl)azetidin-1-yl)ethoxy)phenyl)-3-methyl-2-(2,2,2-trifluoroethyl)-1,2,3,4-tetrahydroisoquinoline-6-carboxylate From step 1 of Example 159, 300 mg, 0.6 mmol) in THF (5 mL) under a nitrogen atmosphere at −75° C. was added a solution of methyl magnesium bromide (3.0 M in THF, 0.5 mL, 1.5 mmol) dropwise. The reaction mixture was warmed up to room temperature and was stirred for 16 hours. Saturated aqueous NH$_4$Cl solution was added to the reaction mixture and the reaction mixture was extracted with EtOAc. The organic layer was dried over anhydrous MgSO$_4$, filtered and concentrated. The resulting residue was purified by reverse phase chromatography (acetonitrile 55-85/0.05% NH$_4$OH in water) to afford the title compound (100 mg, 33%). This product was purified by SFC (AD 250 mm*30 mm, 5 um, 0.1% NH$_3$H$_2$O-EtOH 25%) to afford 161 (Rt=3.61 min, 34 mg, 34%) and 162 (Rt=4.38 min, 36 mg, 36%) as off-white solids.

161: $^1$H NMR (400 MHz, CD$_3$OD) δ 7.28 (s, 1H), 7.22 (dd, J=8.4, 1.6 Hz, 1H), 7.16 (d, J=8.4 Hz, 2H), 6.89 (d, J=8.8 Hz, 2H), 6.81 (d, J=7.6 Hz, 1H), 4.91 (s, 1H), 4.64-4.48 (m, 2H), 4.43-4.35 (m, 2H), 4.25-4.18 (m, 4H), 3.67-3.62 (m, 2H), 3.34 (s, 1H), 3.30-3.21 (m, 2H), 2.97-2.85 (m, 2H), 2.67-2.62 (m, 1H), 1.52 (s, 6H), 1.05 (d, J=6.4 Hz, 3H). LCMS: 495.1 [M+H]$^+$.

162: $^1$H NMR (400 MHz, CD$_3$OD) δ7.28 (s, 1H), 7.22-7.21 (m, 1H), 7.16 (d, J=8.4 Hz, 2H), 6.89 (d, J=8.8 Hz, 2H), 6.81 (d, J=7.6 Hz, 1H), 4.91 (s, 1H), 4.64-4.50 (m, 2H), 4.43-4.35 (m, 2H), 4.25-4.15 (m, 4H), 3.67-3.60 (m, 2H), 3.34-3.21 (m, 3H), 2.97-2.85 (m, 2H), 2.68-2.60 (m, 1H), 1.51 (s, 6H), 1.05 (d, J=7.2 Hz, 3H). LCMS: 495.1 [M+H]$^+$.

Example 163 and 164 (1S,3S)-1-(4-(2-(3-(Fluoromethyl)azetidin-1-yl)ethoxy)phenyl)-3-methyl-2-(2,2,2-trifluoroethyl)-1,2,3,4-tetrahydroisoquinoline-6-carboxylic acid 163 and (1R,3R)-1-(4-(2-(3-(Fluoromethyl)azetidin-1-yl)ethoxy)phenyl)-3-methyl-2-(2,2,2-trifluoroethyl)-1,2,3,4-tetrahydroisoquinoline-6-carboxylic acid 164

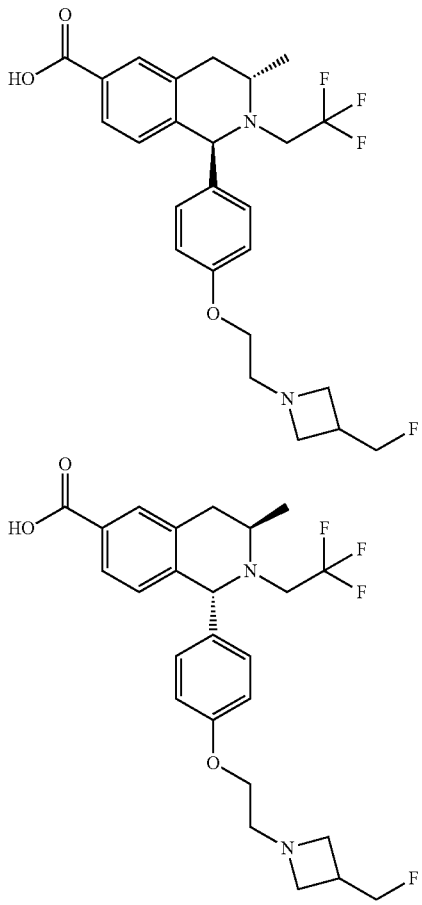

A solution of (1,3-trans)-methyl 1-(4-(2-(3-(fluoromethyl)azetidin-1-yl)ethoxy)phenyl)-3-methyl-2-(2,2,2-trifluoroethyl)-1,2,3,4-tetrahydroisoquinoline-6-carboxylate (From step 1 of Example 159, 1.0 g, 2.0 mmol) and lithium hydroxide hydrate (424 mg, 10.1 mmol) in THF/water (15 mL/3 mL) was stirred at 60° C. for 2 h. The reaction mixture was concentrated to dryness and the residue was taken up in water (30 mL) and 1M citric acid was added to the solution to make pH=2. The mixture was extracted with EtOAc (50 mL) and the organic layer was concentrated in vacuo. The resulting residue was purified by reverse phase chromatography (acetonitrile 15-65/0.225% FA in water) to afford the racemic compound (450 mg, 46%) as a white solid. This racemic product was purified by SFC (AD 250 mm*30 mm, 5 um, 0.1% NH$_3$H$_2$O-MeOH 30%) to afford 163 (44 mg, 9%) and 164 (60 mg, 12%).

163: $^1$H NMR (400 MHz, CD$_3$OD) δ 7.95 (s, 1H), 7.81-7.79 (m, 1H), 7.24 (d, J=8.8 Hz, 2H), 7.05-7.00 (m, 3H), 5.56 (s, 1H), 4.71-4.41 (m, 2H), 4.39-4.25 (m, 5H), 4.20-4.13 (m, 1H), 3.96-3.90 (m, 2H), 3.73-3.62 (m, 2H), 3.51-3.45 (m, 1H), 3.30-3.22 (m, 2H), 2.97-2.90 (m, 1H), 1.30 (d, J=6.8 Hz, 3H). LCMS: 481.0 [M+H]$^+$.

164: $^1$H NMR (400 MHz, CD$_3$OD) δ 7.96 (s, 1H), 7.82-7.80 (m, 1H), 7.25 (d, J=8.8 Hz, 2H), 7.05-7.02 (m, 3H), 5.60 (s, 1H), 4.71-4.41 (m, 2H), 4.39-4.25 (m, 5H), 4.20-4.13 (m, 1H), 3.96-3.90 (m, 2H), 3.73-3.62 (m, 2H), 3.51-3.45 (m, 1H), 3.30-3.22 (m, 2H), 2.97-2.90 (m, 1H), 1.30 (d, J=6.4 Hz, 3H). LCMS: 481.0 [M+H]$^+$.

Example 165 and 166 (1S,3S)-2-(2,2-Difluoro-3-hydroxypropyl)-1-(4-(2-(3-(fluoromethyl)azetidin-1-yl)ethoxy)phenyl)-3-methyl-1,2,3,4-tetrahydroisoquinolin-6-ol 165 and (1R,3R)-2-(2,2-Difluoro-3-hydroxypropyl)-1-(4-(2-(3-(fluoromethyl)azetidin-1-yl)ethoxy)phenyl)-3-methyl-1,2,3,4-tetrahydroisoquinolin-6-ol 166

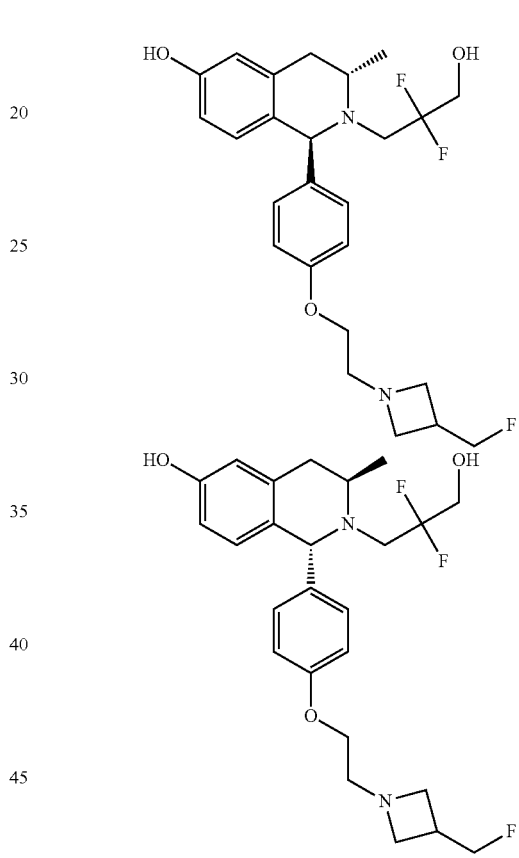

Following a similar procedure to that of Example 131/132, Examples 165/166 were prepared from 3-(2-aminopropyl)phenol. The Pictet-Spengler reaction yielded two products: (1,3-trans)-2-[3-[tert-butyl(diphenyl)silyl]oxy-2,2-difluoro-propyl]-1-(4-iodophenyl)-3-methyl-3,4-dihydro-1H-isoquinolin-6-ol (Minor product that is used to make examples 165/166) and (1,3-trans)-2-[3-[tert-butyl (diphenyl)silyl]oxy-2,2-difluoro-propyl]-1-(4-iodophenyl)-3-methyl-3,4-dihydro-1H-isoquinolin-8-ol (Major product that is used to make examples 167/168).

165: $^1$H NMR (400 MHz, CD$_3$OD) δ 7.07 (d, J=8.4 Hz, 2H), 6.79 (d, J=8.4 Hz, 2H), 6.65 (d, J=8.0 Hz, 1H), 6.56-6.53 (m, 2H), 4.84 (s, 1H), 4.46 (dd, J=47.6, 6.0 Hz, 2H), 4.00-3.94 (m, 2H), 3.82-3.64 (m, 2H), 3.53-3.49 (m, 2H), 3.22-3.08 (m, 4H), 2.86-2.55 (m, 6H), 1.01 (d, J=6.4 Hz, 3H). LCMS: 465.2 [M+H]$^+$.

166: $^1$H NMR (400 MHz, CD$_3$OD) δ 7.07 (d, J=8.4 Hz, 2H), 6.80 (d, J=8.4 Hz, 2H), 6.64 (d, J=8.0 Hz, 1H), 6.55-6.50 (m, 2H), 4.84 (s, 1H), 4.45 (dd, J=47.6, 6.0 Hz, 2H), 4.00-3.95 (m, 2H), 3.83-3.52 (m, 2H), 3.45-3.40 (m, 2H), 3.25-3.05 (m, 4H), 2.86-2.40 (m, 6H), 1.01 (d, J=6.4 Hz, 3H). LCMS: 465.2 [M+H]⁺.

Example 167 and 168 (1R,3R)-2-(2,2-Difluoro-3-hydroxypropyl)-1-(4-(2-(3-(fluoromethyl)azetidin-1-yl)ethoxy)phenyl)-3-methyl-1,2,3,4-tetrahydroisoquinolin-8-ol 167 and (1S,3S)-2-(2,2-Difluoro-3-hydroxypropyl)-1-(4-(2-(3-(fluoromethyl)azetidin-1-yl)ethoxy)phenyl)-3-methyl-1,2,3,4-tetrahydroisoquinolin-8-ol 168

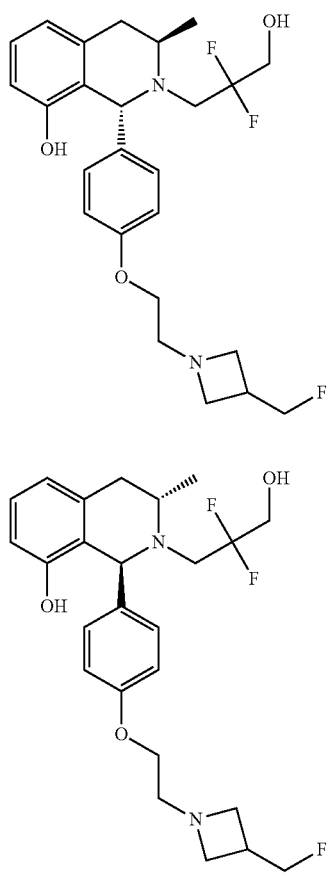 [SMILES: C[C@@H]1Cc2cccc(O)c2[C@@H](c2ccc(OCCN3CC(CF)C3)cc2)N1CC(F)(F)CO ; C[C@H]1Cc2cccc(O)c2[C@H](c2ccc(OCCN3CC(CF)C3)cc2)N1CC(F)(F)CO]

Following a similar procedure to that of Example 165/166, Examples 167/168 were prepared from (1,3-trans)-2-[3-[tert-butyl (diphenyl)silyl]oxy-2,2-difluoro-propyl]-1-(4-iodophenyl)-3-methyl-3,4-dihydro-1H-isoquinolin-8-ol.

167: ¹H NMR (400 MHz, CD₃OD) δ 7.06-7.02 (m, 3H), 6.76 (d, J=8.8 Hz, 2H), 6.66 (d, J=8.0 Hz, 1H), 6.60 (d, J=8.0 Hz, 1H), 5.22 (s, 1H), 4.47 (dd, J=47.6, 6.0 Hz, 2H), 3.97-3.80 (m, 4H), 3.56-3.52 (m, 2H), 3.25-3.03 (m, 4H), 2.91-2.81 (m, 3H), 2.58-2.52 (m, 3H), 1.01 (d, J=6.4 Hz, 3H). LCMS: 465.2 [M+H]⁺.

168: ¹HNMR (400 MHz, CD₃OD) δ 7.06-7.01 (m, 3H), 6.76 (d, J=8.8 Hz, 2H), 6.66 (d, J=8.0 Hz, 1H), 6.60 (d, J=8.0 Hz, 1H), 5.22 (s, 1H), 4.45 (dd, J=47.6, 6.0 Hz, 2H), 3.95-3.85 (m, 4H), 3.53-3.49 (m, 2H), 3.20-3.05 (m, 4H), 2.85-2.80 (m, 3H), 2.58-2.52 (m, 3H), 1.01 (d, J=6.4 Hz, 3H). LCMS: 465.2 [M+H]⁺.

Example 169 and 170 ((1S,3S)-1-(4-((1-(3-Fluoropropyl)azetidin-3-yl)amino)phenyl)-3-methyl-2-(2,2,2-trifluoroethyl)-1,2,3,4-tetrahydroisoquinolin-6-yl)methanol 169 and ((1R,3R)-1-(4-((1-(3-Fluoropropyl)azetidin-3-yl)amino)phenyl)-3-methyl-2-(2,2,2-trifluoroethyl)-1,2,3,4-tetrahydroisoquinolin-6-yl)methanol 170

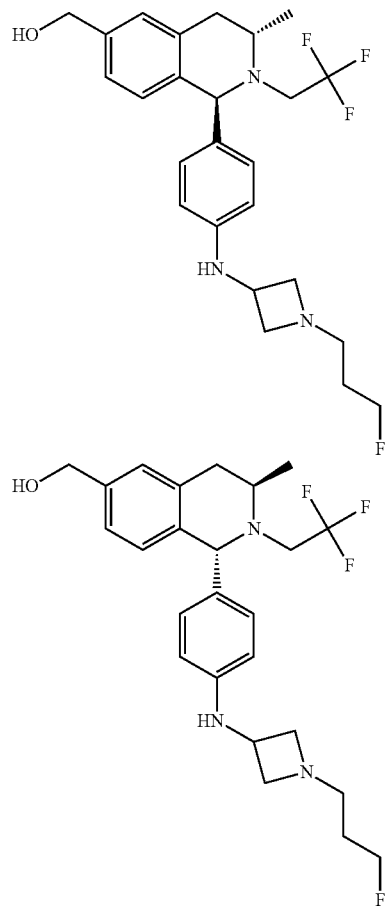

Step 1: tert-Butyl 3-((4-((1,3-trans)-6-hydroxy-3-methyl-2-(2,2,2-trifluoroethyl)-1,2,3,4-tetrahydroisoquinolin-1-yl)phenyl)amino)azetidine-1-carboxylate

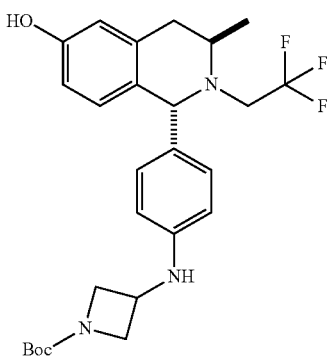 [SMILES: C[C@@H]1Cc2cc(O)ccc2[C@@H](c2ccc(NC3CN(C(=O)OC(C)(C)C)C3)cc2)N1CC(F)(F)F]

To a solution of (1,3-trans)-1-(4-iodophenyl)-3-methyl-2-(2,2,2-trifluoroethyl)-1,2,3,4-tetrahydroisoquinolin-6-ol (1.7 g, 3.8 mmol) in 1,4-dioxane (17 mL) was added Brettphos (408 mg, 0.8 mmol), 1-Boc-3-(amino)azetidine (982 mg, 5.7 mmol), Brettphos Pd G3 (172 mg, 0.2 mmol) and potassium phosphate, tribasic (2.4 g, 11 mmol). The reaction mixture was purged with $N_2$ for 3 min. The mixture was stirred at 100° C. under $N_2$ atmosphere (balloon) for 16 hours. Water (50 mL) was added to the mixture and the mixture was extracted with EtOAc (200 mL). The organic layers was dried over anhydrous sodium sulfate, and concentrated in vacuo. The crude product was purified by chromatography on silica (0-25% EtOAc in petroleum ether) to afford the title compound (1.3 g, 70%) as a yellow oil. $^1$H NMR (400 MHz, CDCl$_3$) δ 7.04 (d, J=8.4 Hz, 2H), 6.79 (d, J=8.0 Hz, 1H), 6.64-6.59 (m, 2H), 6.42 (d, J=8.4 Hz, 2H), 4.83 (s, 1H), 4.30-4.22 (m, 2H), 4.20-4.10 (m, 2H), 4.05-3.95 (m, 1H), 3.73-3.71 (m, 2H), 3.32-3.08 (m, 2H), 3.02-2.83 (m, 1H), 2.76-2.74 (m, 1H), 2.51-2.47 (m, 1H), 1.45 (s, 9H), 1.05 (d, J=6.4 Hz, 3H).

Step 2: (1,3-trans)-1-(4-(Azetidin-3-ylamino)phenyl)-3-methyl-2-(2,2,2-trifluoroethyl)-1,2,3,4-tetrahydroisoquinolin-6-ol

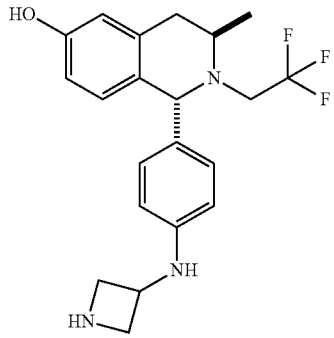 [SMILES: C[C@@H]1Cc2cc(O)ccc2[C@@H](c2ccc(NC3CNC3)cc2)N1CC(F)(F)F]

To a solution of tert-butyl 3-((4-((1,3-trans)-6-hydroxy-3-methyl-2-(2,2,2-trifluoroethyl)-1,2,3,4-tetrahydroisoquinolin-1-yl)phenyl)amino)azetidine-1-carboxylate (From step 1, 1.3 g, 2.6 mmol) in 1,4-dioxane (13 mL) was added sulfuric acid (14.4 mL, 26.5 mmol) dropwise in an ice bath. The reaction mixture was stirred at 25° C. for 1 h. Saturated aqueous NaHCO$_3$ solution (40 mL) was added to the reaction mixture and the mixture was extracted with EtOAc (100 mL×2). The combined organic layers were dried over sodium sulfate, and concentrated in vacuo to afford the title compound (1.0 g, 99%) as a yellow foam. LCMS: 392.0 [M+H]$^+$.

Step 3: (1,3-trans)-1-(4-((1-(3-Fluoropropyl)azetidin-3-yl)amino)phenyl)-3-methyl-2-(2,2,2-trifluoroethyl)-1,2,3,4-tetrahydroisoquinolin-6-ol

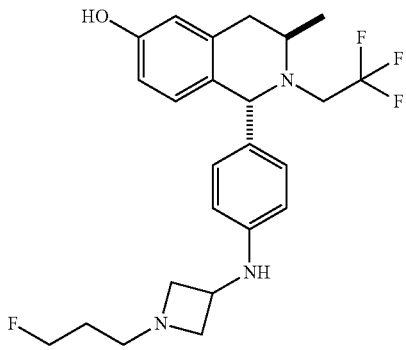 [SMILES: C[C@@H]1Cc2cc(O)ccc2[C@@H](c2ccc(NC3CN(CCCF)C3)cc2)N1CC(F)(F)F]

To a solution of (1,3-trans)-1-(4-(azetidin-3-ylamino)phenyl)-3-methyl-2-(2,2,2-trifluoroethyl)-1,2,3,4-tetrahydroisoquinolin-6-ol (From step 2, 1.0 g, 2.6 mmol), 1-iodo-3-fluoropropane (494 mg, 2.6 mmol) in N,N-dimethylformamide (10 mL) was added N,N-diisopropylethylamine (1.4 mL, 7.9 mmol). The mixture was stirred at 25° C. for 16 hours. Water was added to the reaction mixture and the mixture was extracted with EtOAc (50 mL×2). The combined organic layers were dried over anhydrous sodium sulfate, and concentrated in vacuo. The residue was purified by chromatography on silica (0-100% EtOAc in DCM) to afford the title compound (685 mg, 58%). LCMS: 452.1 [M+H]$^+$.

Step 4: (1,3-trans)-1-(4-((1-(3-Fluoropropyl)azetidin-3-yl)amino)phenyl)-3-methyl-2-(2,2,2-trifluoroethyl)-1,2,3,4-tetrahydroisoquinolin-6-yl trifluoromethanesulfonate

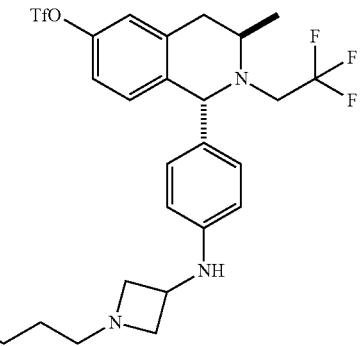

Following a similar procedure to that of Step 1 of Example 155, the title compound was prepared from (1,3-trans)-1-(4-((1-(3-Fluoropropyl)azetidin-3-yl)amino)phenyl)-3-methyl-2-(2,2,2-trifluoroethyl)-1,2,3,4-tetrahydroisoquinolin-6-ol. $^1$H NMR (400 MHz, CDCl$_3$) δ 7.07-6.94 (m, 5H), 6.45 (d, J=8.4 Hz, 2H), 4.88 (s, 1H), 4.57-4.40 (m, 2H), 4.20-4.10 (m, 2H), 3.81-3.75 (m, 2H), 3.37-3.35 (m, 1H), 3.15-3.13 (m, 1H), 2.98-2.88 (m, 4H), 2.66-2.54 (m, 3H), 1.80-1.70 (m, 1H), 1.07 (d, J=6.8 Hz, 3H). LCMS: 584.1 [M+H]$^+$.

Step 5: 169 and 170

To a solution of (1,3-trans)-1-(4-((1-(3-fluoropropyl)azetidin-3-yl)amino)phenyl)-3-methyl-2-(2,2,2-trifluoroethyl)-1,2,3,4-tetrahydroisoquinolin-6-yl trifluoromethanesulfonate (From step 4, 330 mg, 0.6 mmol) in 1,4-dioxane (10 mL) and water (2 mL) was added sodium carbonate (180 mg, 1.7 mmol), 2-dicyclohexylphosphino-2',6'-di-i-propoxy-1,1'-biphenyl (132 mg, 0.30 mmol), potassium difluoroboranylmethyl acetate fluoride (305 mg, 1.7 mmol), RuPhos-Pd-G2 (78 mg, 0.11 mmol) under the protection of nitrogen. The reaction mixture was stirred at 120° C. for 30 min under microwave irradiation. The reaction mixture was cooled to room temperature, filtered and concentrated under reduced pressure. The resulting residue was purified by reverse phase chromatography (acetonitrile 45-75%/0.05% NH$_4$OH in water) to afford the title compound (50 mg, 19%). This product was purified by SFC (OD 250 mm*30 mm, 5 um, 0.1% NH$_4$OH MeOH 40%) to afford 169 (5.1 mg, 10%) and 170 (6.3 mg, 13%) as off-white solids.

169: ¹H NMR (400 MHz, CDCl₃) δ 7.18-7.07 (m, 2H), 7.04-6.97 (d, J=8.0 Hz, 2H), 6.93 (d, J=8.0 Hz, 1H), 6.49-6.39 (m, 2H), 4.88 (s, 1H), 4.67 (s, 2H), 4.60-4.39 (m, 2H), 4.10 (s, 1H), 3.94 (s, 1H), 3.80-3.70 (m, 2H), 3.34-3.30 (m, 1H), 3.22-3.08 (m, 1H), 2.97-2.78 (m, 4H), 2.64-2.50 (m, 3H), 1.80-1.70 (m, 2H), 1.06 (d, J=6.4 Hz, 3H). LCMS: 466.1 [M+H]⁺.

170: ¹H NMR (400 MHz, CDCl₃) δ 7.17-7.05 (m, 2H), 7.04-6.97 (d, J=8.0 Hz, 2H), 6.93 (d, J=8.0 Hz, 1H), 6.47-6.39 (d, J=8.0 Hz, 2H), 4.88 (s, 1H), 4.67 (s, 2H), 4.60-4.39 (m, 2H), 4.15-4.07 (m, 1H), 3.94 (s, 1H), 3.73 (t, J=6.4 Hz, 2H), 3.40-3.28 (m, 1H), 3.22-3.08 (m, 1H), 3.00-2.78 (m, 4H), 2.64-2.50 (m, 3H), 1.80-1.70 (m, 2H), 1.06 (d, J=6.4 Hz, 3H). LCMS: 466.1 [M+H]⁺.

Example 171 and 172 2,2-Difluoro-3-((1S,3S)-1-(4-(2-(3-(fluoromethyl)azetidin-1-yl)ethoxy)phenyl)-6-(hydroxymethyl)-3-methyl-3,4-dihydroisoquinolin-2(1H)-yl)propan-1-ol 171 and 2,2-Difluoro-3-((1R,3R)-1-(4-(2-(3-(fluoromethyl)azetidin-1-yl)ethoxy)phenyl)-6-(hydroxymethyl)-3-methyl-3,4-dihydroisoquinolin-2(1H)-yl)propan-1-ol 172

171: ¹H NMR (400 MHz, CDCl₃) δ 7.16 (s, 1H), 7.13-7.05 (m, 3H), 6.85-6.75 (m, 3H), 4.89 (s, 1H), 4.65 (s, 2H), 4.60-4.39 (m, 2H), 3.94 2 3.92 (m, 2H), 3.86-3.60 (m, 2H), 3.50-3.47 (m, 3H), 3.24-3.04 (m, 3H), 2.98-2.76 (m, 5H), 2.62-2.59 (m, 1H), 1.09 (d, J=5.6 Hz, 3H). LCMS: 479.2 [M+H]⁺.

172: ¹H NMR (400 MHz, CDCl₃) δ 7.15 (s, 1H), 7.12-7.04 (m, 3H), 6.90-6.75 (m, 3H), 4.89 (s, 1H), 4.65 (s, 2H), 4.60-4.39 (m, 2H), 4.00-3.90 (m, 2H), 3.86-3.60 (m, 2H), 3.55-3.40 (s, 3H), 3.24-3.04 (m, 3H), 2.98-2.76 (m, 5H), 2.62-2.59 (m, 1H), 1.09 (d, J=5.6 Hz, 3H). LCMS: 479.2 [M+H]⁺.

Example 173 and 174 (1R,3R)-2-(2,2-Difluoro-3-hydroxypropyl)-1-(4-(2-(3-(fluoromethyl)azetidin-1-yl)ethoxy)phenyl)-3-methyl-1,2,3,4-tetrahydroisoquinoline-6-sulfonamide 173 and (1S,3S)-2-(2,2-Difluoro-3-hydroxypropyl)-1-(4-(2-(3-(fluoromethyl)azetidin-1-yl)ethoxy)phenyl)-3-methyl-1,2,3,4-tetrahydroisoquinoline-6-sulfonamide 174

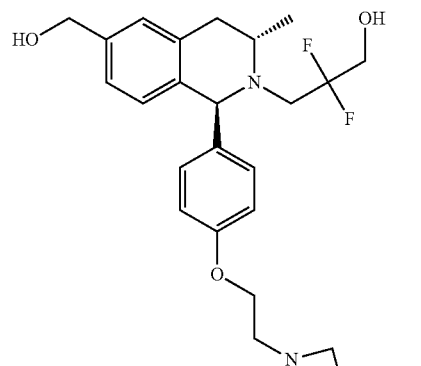

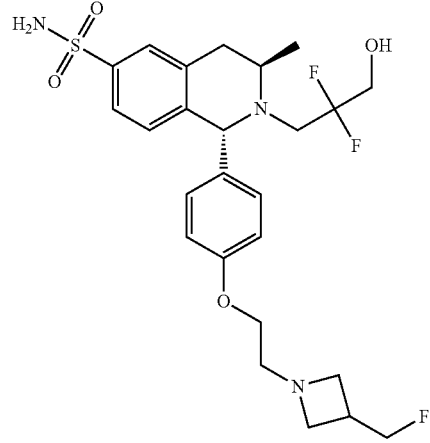

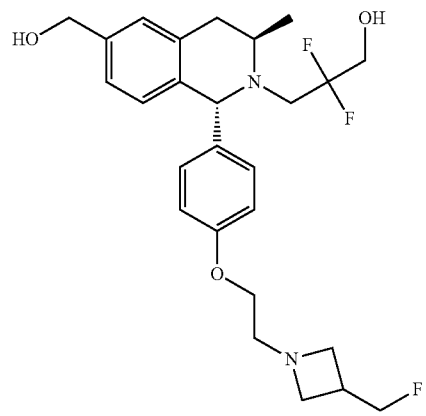

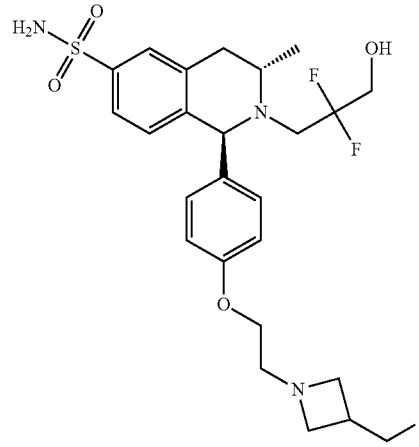

Following a similar procedure to that of Example 169/170, Examples 171/172 were prepared from (1,3-trans)-2-(3-((tert-butyl diphenylsilyl)oxy)-2,2-difluoropropyl)-1-(4-(2-(3-(fluoromethyl)azetidin-1-yl)ethoxy)phenyl)-3-methyl-1,2,3,4-tetrahydroisoquinolin-6-yl trifluoromethanesulfonate.

Step 1: (1,3-trans)-6-(Benzylthio)-2-(3-((tert-butyl diphenyl silyl)oxy)-2,2-difluoropropyl)-1-(4-(2-(3-(fluoromethyl)azetidin-1-yl)ethoxy)phenyl)-3-methyl-1,2,3,4-tetrahydroisoquinoline

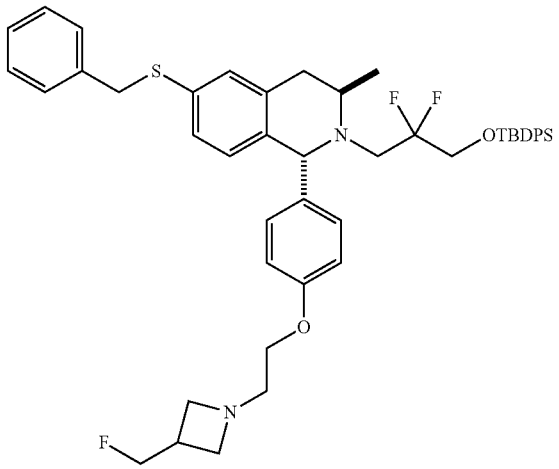

A mixture of (1,3-trans)-2-(3-((tert-butyldiphenylsilyl)oxy)-2,2-difluoropropyl)-1-(4-(2-(3-(fluoromethyl)azetidin-1-yl)ethoxy)phenyl)-3-methyl-1,2,3,4-tetrahydroisoquinolin-6-yl yl trifluoromethanesulfonate (1.0 g, 1.2 mmol), BnSH (297 mg, 2.4 mmol), DIPEA (0.56 mL, 3.59 mmol), Pd$_2$(dba)$_3$ (110 mg, 0.12 mmol) and Xantphos (139 mg, 0.24 mmol) in 1,4-dioxane (15 mL) was stirred at 120° C. for 3 hours. After being cooled to 25° C., the reaction mixture was diluted in water (50 mL), extracted with EtOAc (50 mL×2). The combined organic layers were dried over anhydrous Na$_2$SO$_4$, filtered and concentrated. The crude residue was purified by silica gel column chromatography (80% EtOAc in petroleum ether) to afford the title compound (700 mg, 72%) as a light yellow solid. LCMS: 809.3 [M+H]$^+$.

Step 2: (1,3-trans)-2-(3-((tert-Butyldiphenylsilyl)oxy)-2,2-difluoropropyl)-1-(4-(2-(3-(fluoromethyl)azetidin-1-yl)ethoxy)phenyl)-3-methyl-1,2,3,4-tetrahydroisoquinoline-6-sulfonamide

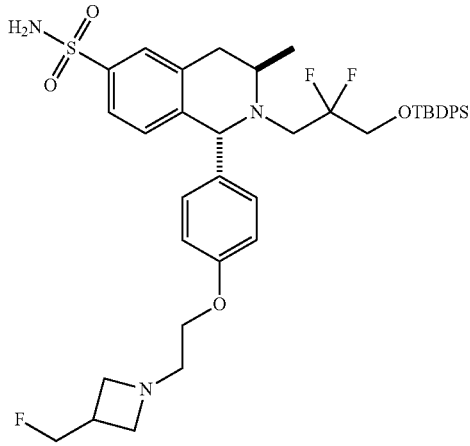

To a solution of (1,3-trans)-6-(benzylthio)-2-(3-((tert-butyl di phenyl silyl)oxy)-2,2-difluoropropyl)-1-(4-(2-(3-(fluoromethyl)azetidin-1-yl)ethoxy)phenyl)-3-methyl-1,2,3,4-tetrahydroisoquinoline (From step 1, 600 mg, 0.74 mmol) in HOAc (1 mL), THF (10 mL) and water (2 mL) was added 1,3-dichloro-5,5-dimethylhydantoin (438 mg, 2.22 mmol) slowly. The mixture was stirred at 0° C. for 1 hour. To the reaction mixture was added NH$_3$/MeOH (10 mL) and the mixture was stirred at 0° C. for 1 hour. Water (30 mL) was added and the mixture was extracted with EtOAc (30 mL×2). The combined organic layers were dried over anhydrous Na$_2$SO$_4$, filtered and concentrated. The crude residue was purified by silica gel column chromatography (10% MeOH in DCM) to afford the racemic products (150 mg, 31%) as a light yellow solid. LCMS: 766.1 [M+H]$^+$.

Step 3: 173 and 174

To a mixture of (1,3-trans)-2-(3-((tert-butyl diphenylsilyl)oxy)-2,2-difluoropropyl)-1-(4-(2-(3-(fluoromethyl)azetidin-1-yl)ethoxy)phenyl)-3-methyl-1,2,3,4-tetrahydroisoquinoline-6-sulfonamide (From step 2, 150 mg, 0.20 mmol) in THF (3 mL) was added TBAF (1.0 M in THF, 0.59 mL, 0.59 mmol). The reaction mixture was stirred at 25° C. for 1 hour. The reaction mixture was diluted in saturated NaHCO$_3$ solution (20 mL), extracted with EtOAc (20 mL×3). The combined organic layers were dried over anhydrous Na$_2$SO$_4$, filtered and concentrated. The residue was purified by reverse phase chromatography (acetonitrile 30-60/0.1% NH$_4$OH in water) to afford the racemic products (15 mg, 15%) as a white solid. This product was purified by chiral SFC (AD 250 mm*30 mm, 5 um; Supercritical CO$_2$/EtOH (0.1% NH$_3$.H$_2$O)=35/35 at 60 mL/min) to afford 173 and 174 (Both as white solids).

173: Rt=4.09 min. $^1$HNMR (400 MHz, CD$_3$OD) δ 7.61 (s, 1H), 7.52-7.49 (dd, J=8.0, 1.6 Hz, 1H), 6.99 (d, J=8.8 Hz, 2H), 6.94 (d, J=8.0 Hz, 1H), 6.73 (d, J=8.8 Hz, 2H), 4.91 (s, 1H), 4.40 (dd, J=47.6, 5.6 Hz, 2H), 3.86 (t, J=5.2 Hz, 2H), 3.75-3.65 (m, 1H), 3.57-3.49 (m, 1H), 3.45-3.40 (m, 2H), 3.35-3.25 (m, 1H), 3.22-3.05 (m, 3H), 2.90-2.82 (m, 1H), 2.80-2.70 (m, 3H), 2.65-2.61 (m, 2H), 1.05 (d, J=6.4 Hz, 3H); LCMS: 528.1 [M+H]$^+$.

174: Rt=4.49 min. $^1$HNMR (400 MHz, CD$_3$OD) δ 7.71 (s, 1H), 7.62 (dd, J=8.0, 1.6 Hz, 1H), 7.08 (d, J=8.8 Hz, 2H), 7.04 (d, J=8.4 Hz, 1H), 6.82 (d, J=8.8 Hz, 2H), 5.00 (s, 1H), 4.48 (dd, J=47.6, 5.6 Hz, 2H), 3.97 (t, J=5.2 Hz, 2H), 3.85-3.75 (m, 1H), 3.65-3.55 (m, 1H), 3.53-3.48 (m, 2H), 3.45-3.35 (m, 1H), 3.20-3.05 (m, 3H), 3.00-2.93 (m, 1H), 2.86-2.79 (m, 3H), 2.75-2.61 (m, 2H), 1.05 (d, J=6.4 Hz, 3H). LCMS: 528.1 [M+H]$^+$.

Example 175 and 176 1-(1R,3R)-2-(2,2-Difluoro-3-hydroxypropyl)-1-(4-(2-(3-(fluoromethyl)azetidin-1-yl)ethoxy)phenyl)-3-methyl-1,2,3,4-tetrahydroisoquinolin-6-yl)ethanone 175 and 1-((1S,3S)-2-(2,2-Difluoro-3-hydroxypropyl)-1-(4-(2-(3-(fluoromethyl)azetidin-1-yl)ethoxy)phenyl)-3-methyl-1,2,3,4-tetrahydroisoquinolin-6-yl)ethanone 176

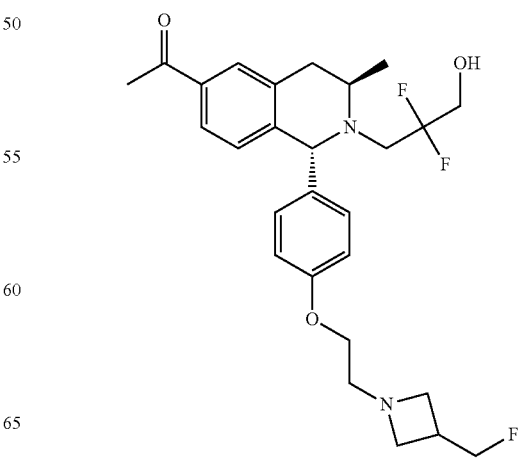

-continued

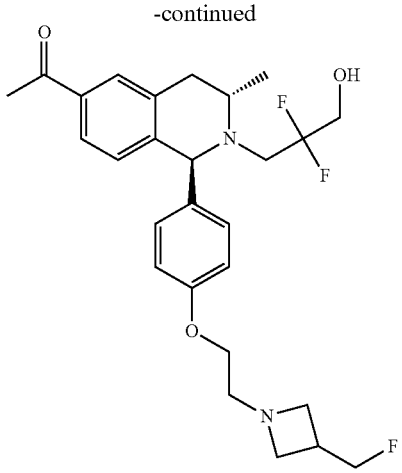

Step 1: 1-((1,3-trans)-2-(3-((tert-Butyldiphenylsilyl)oxy)-2,2-difluoropropyl)-1-(4-(2-(3-(fluoromethyl)azetidin-1-yl)ethoxy)phenyl)-3-methyl-1,2,3,4-tetrahydroisoquinolin-6-yl)ethanone

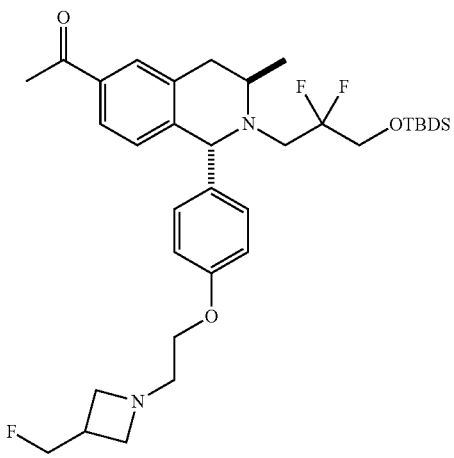

A mixture of (1,3-trans)-2-(3-((tert-butyldiphenyl silyl)oxy)-2,2-difluoropropyl)-1-(4-(2-(3-(fluoromethyl)azetidin-1-yl)ethoxy)phenyl)-3-methyl-1,2,3,4-tetrahydroisoquinolin-6-yl trifluoromethanesulfonate (1.0 g, 1.2 mmol), 1-(vinyloxy)butane (5.0 mL), Pd(OAc)$_2$ (27 mg, 0.12 mmol), 1,3-bis(diphenylphosphino)propane (50 mg, 0.12 mmol) and K$_2$CO$_3$ (332 mg, 2.4 mmol) in water (2 mL) and 1,4-dioxane (20 mL) was stirred at 100° C. for 16 hours under N$_2$. The reaction mixture was cooled to room temperature, filtered and concentrated under reduced pressure. The residue was passed through flash column (0-5% MeOH in DCM) to give an oil. This oil was dissolved in THF (20 mL) and to the solution was added 2 N HCl (1 mL, 1 mmol). The reaction mixture was stirred at 25° C. for 1 h. The solution was concentrated. Saturated aqueous NaHCO$_3$ solution (50 mL) was added and the mixture was extracted with EtOAc (50 mL×2). The combined organic layers were dried over anhydrous Na$_2$SO$_4$ and concentrated. The residue was purified by chromatography on silica (0-5% MeOH in DCM) to afford the title compound with about 70% purity as a yellow oil. The crude product was further purified by prep-HPLC (acetonitrile 45-75%/0.225% FA in water) to afford the title compound (0.3 g) as a light yellow oil. $^1$H NMR (400 MHz, CDCl$_3$) δ 7.72-7.49 (m, 6H), 7.43-7.21 (m, 7H), 6.96-6.84 (m, 2H), 6.70-6.56 (m, 2H), 4.94 (s, 1H), 4.53-4.33 (m, 2H), 3.97-3.79 (m, 3H), 3.76-3.57 (m, 1H), 3.44 (t, J=7.2 Hz, 2H), 3.30-3.18 (m, 1H), 3.15-3.00 (m, 3H), 2.88-2.60 (m, 7H), 2.59-2.44 (m, 4H), 1.01-0.90 (m, 12H). LCMS: 729.1 [M+H]$^+$.

Step 2: 175 and 176

To a solution of 1-((1,3-trans)-2-(3-((tert-butyldiphenylsilyl)oxy)-2,2-difluoropropyl)-1-(4-(2-(3-(fluoromethyl)azetidin-1-yl)ethoxy)phenyl)-3-methyl-1,2,3,4-tetrahydroisoquinolin-6-yl)ethanone (From step 1, 200 mg, 0.27 mmol) in THF (5 mL) was added TBAF (1.0 M in THF, 0.41 mL, 0.41 mmol). The reaction mixture was stirred at 25° C. for 16 h. The reaction mixture was diluted with EtOAc (10 mL), washed with aqueous 1 N NaOH solution (10 mL×3). The organic layer was dried over anhydrous Na$_2$SO$_4$, filtered, concentrated. The residue was purified by chromatography on silica (0-5% MeOH in DCM) to afford the title compound (100 mg with 75% purity). The residue was purified by prep-HPLC (acetonitrile 15-45%/0.225% FA in water) to afford the title compound (30 mg, 22%) as a light yellow oil. This oil was separated by SFC (AD (250 mm*30 mm, 5 um)) 0.1% NH$_3$H$_2$O, EtOH, 45%) to afford 175 (6.0 mg, 20%) and 176 (6.0 mg, 20%) both as white solids.

175: $^1$H NMR (400 MHz, CD$_3$OD) δ 7.81 (s, 1H), 7.70 (dd, J=8.0, 1.6 Hz, 1H), 7.08 (d, J=8.4 Hz, 2H), 6.99 (d, J=7.6 Hz, 1H), 6.83 (d, J=8.8 Hz, 2H), 5.00 (s, 1H), 4.56-4.39 (dd, J=47.6, 5.6 Hz, 2H), 3.97 (t, J=5.2 Hz, 2H), 3.87-3.74 (m, 1H), 3.67-3.56 (m, 1H), 3.52 (t, J=7.6 Hz, 2H), 3.42-3.35 (m, 1H), 3.25-3.08 (m, 3H), 2.97-2.93 (m, 1H), 2.91-2.77 (m, 3H), 2.76-2.62 (m, 2H), 2.59 (s, 3H), 1.06 (d, J=6.4 Hz, 3H). LCMS: 491.2 [M+H]$^+$.

176: $^1$H NMR (400 MHz, CD$_3$OD): δ 7.81 (s, 1H), 7.71 (d, J=8.0 Hz, 1H), 7.08 (d, J=8.8 Hz, 2H), 6.99 (d, J=8.0 Hz, 1H), 6.83 (d, J=8.8 Hz, 2H), 5.00 (s, 1H), 4.56-4.38 (dd, J=47.6, 5.6 Hz, 2H), 3.98 (t, J=5.2 Hz, 2H), 3.88-3.73 (m, 1H), 3.69-3.50 (m, 3H), 3.44-3.35 (m, 1H), 3.25-3.06 (m, 3H), 2.97-2.78 (m, 4H), 2.76-2.65 (m, 2H), 2.59 (s, 3H), 1.06 (d, J=6.8 Hz, 3H). LCMS: 491.2 [M+H]$^+$.

Example 177 and 178 2,2-Difluoro-3-((1R,3R)-1-(4-(2-(3-(fluoromethyl)azetidin-1-yl)ethoxy)phenyl)-6-((R)-1-hydroxyethyl)-3-methyl-3,4-dihydroisoquinolin-2(1H)-yl)propan-1-ol 177 and 2,2-Difluoro-3-((1R,3R)-1-(4-(2-(3-(fluoromethyl)azetidin-1-yl)ethoxy)phenyl)-6-((S)-1-hydroxyethyl)-3-methyl-3,4-dihydroisoquinolin-2(1H)-yl)propan-1-ol 178

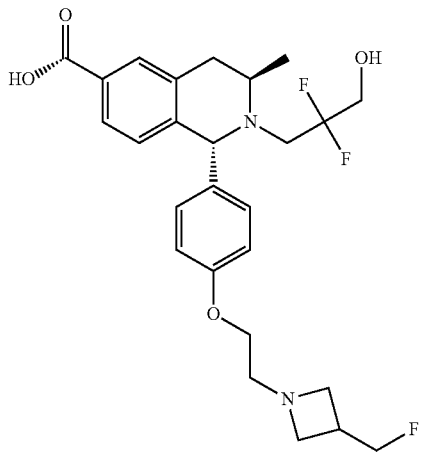

-continued

Step 1: 1-((1R,3R)-2-(3-((tert-butyl diphenylsilyl)oxy)-2,2-difluoropropyl)-1-(4-(2-(3-(fluoromethyl)azetidin-1-yl)ethoxy)phenyl)-3-methyl-1,2,3,4-tetrahydroisoquinolin-6-yl)ethanone & 1-((1S,3S)-2-(3-((tert-butyldiphenylsilyl)oxy)-2,2-difluoropropyl)-1-(4-(2-(3-(fluoromethyl)azetidin-1-yl)ethoxy)phenyl)-3-methyl-1,2,3,4-tetrahydroisoquinolin-6-yl)ethanone

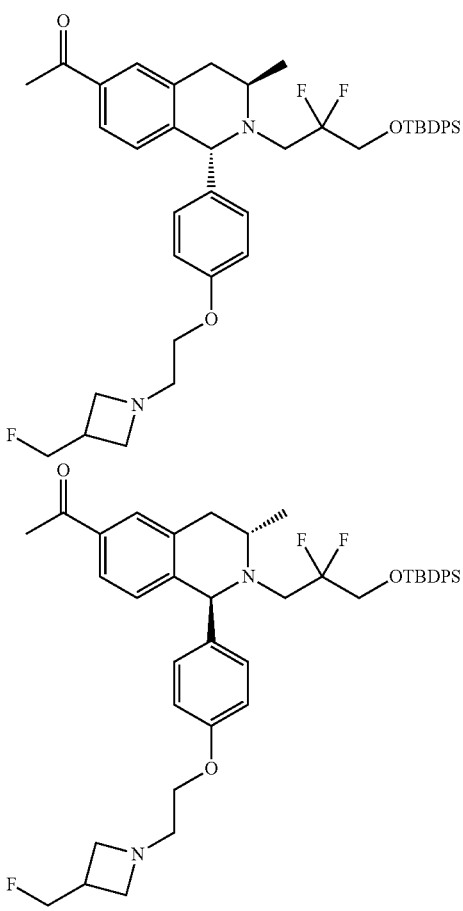

1-((1,3-trans)-2-(3-((tert-Butyl di phenyl silyl)oxy)-2,2-difluoropropyl)-1-(4-(2-(3-(fluoromethyl)azetidin-1-yl)ethoxy)phenyl)-3-methyl-1,2,3,4-tetrahydroisoquinolin-6-yl)ethanone (0.3 g, 0.41 mmol) was separated by SFC (AD (250 mm*30 mm, 5 um)), 0.1% NH$_3$H$_2$O IPA, 25%) to afford 1-((1R,3R)-2-(3-((tert-butyldiphenylsilyl)oxy)-2,2-difluoropropyl)-1-(4-(2-(3-(fluoromethyl)azetidin-1-yl)ethoxy)phenyl)-3-methyl-1,2,3,4-tetrahydroisoquinolin-6-yl)ethanone (140 mg, 47%) and 1-((1S,3S)-2-(3-((tert-butyldiphenylsilyl)oxy)-2,2-difluoropropyl)-1-(4-(2-(3-(fluoromethyl)azetidin-1-yl)ethoxy)phenyl)-3-methyl-1,2,3,4-tetrahydroisoquinolin-6-yl)ethanone (140 mg, 47%, contained about 20% cis) both as colorless oils. LCMS: 729.2 [M+H]$^+$.

Step 2: 1.41R,3R)-2-(3-((tert-Butyldiphenylsilyl)oxy)-2,2-difluoropropyl)-1-(4-(2-(3-(fluoromethyl)azetidin-1-yl)ethoxy)phenyl)-3-methyl-1,2,3,4-tetrahydroisoquinolin-6-yl)ethanol

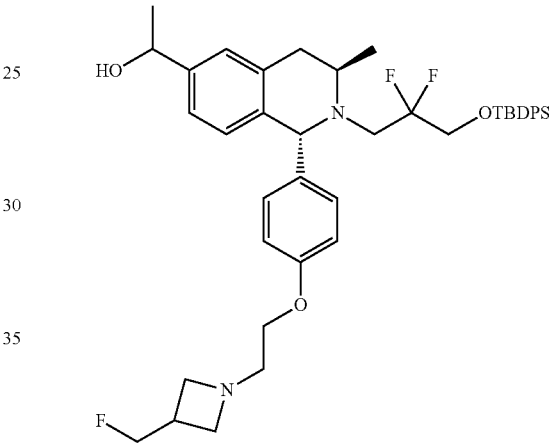

NaBH$_4$ (10 mg, 0.25 mmol) was added slowly to a stirred solution of 1-((1R,3R)-2-(3-((tert-butyldiphenylsilyl)oxy)-2,2-difluoropropyl)-1-(4-(2-(3-(fluoromethyl)azetidin-1-yl)ethoxy)phenyl)-3-methyl-1,2,3,4-tetrahydroisoquinolin-6-yl)ethanone (From step 1, 90.0 mg, 0.12 mmol) in MeOH (10 mL) at 25° C. The resulting mixture was stirred at 25° C. for 2 h. Water (10 mL) was added to the reaction mixture. The mixture was extracted with DCM (20 mL×2). The combined organic phases were dried over anhydrous Na$_2$SO$_4$, filtered and concentrated in vacuo to afford the title compound (90 mg, 99%) as a colorless oil. LCMS: 731.3 [M+H]$^+$.

Step 3: 177 and 178

To a solution of 1-((1R,3R)-2-(3-((tert-butyldiphenylsilyl)oxy)-2,2-difluoropropyl)-1-(4-(2-(3-(fluoromethyl)azetidin-1-yl)ethoxy)phenyl)-3-methyl-1,2,3,4-tetrahydroisoquinolin-6-yl)ethanol (From step 2, 90 mg, 0.12 mmol) in THF (2 mL) was added TBAF (1.0 M in THF, 0.18 mL, 0.18 mmol). The reaction mixture was stirred at 25° C. for 16 h. The reaction mixture was diluted with EtOAc (10 mL), washed with aqueous 1 N NaOH solution (10 mL×3). The organic layer was dried over anhydrous Na$_2$SO$_4$, filtered, concentrated. The residue was purified by TLC (80% EtOAc in petroleum ether) as a light yellow oil. This oil (80 mg, 0.16 mmol) was separated by SFC (AD (250 mm*30 mm, 5

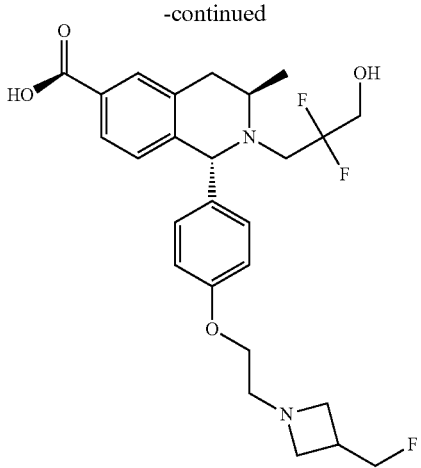

um)), 0.1% NH₃H₂O EtOH, 45%) to afford 177 (20 mg, 25%) and 178 (20 mg, 25%) both as white solids.

177: ¹H NMR (400 MHz, CD₃OD) δ 7.16 (s, 1H), 7.09-7.06 (m, 3H), 6.84-6.75 (m, 3H), 4.92 (s, 1H), 4.79-4.76 (m, 2H), 4.57-4.38 (m, 2H), 3.98-3.96 (m, 2H), 3.87-3.75 (m, 1H), 3.73-3.59 (m, 1H), 3.55-3.50 (m, 2H), 3.25-3.04 (m, 3H), 2.90-2.83 (m, 4H), 2.76-2.51 (m, 2H), 1.44 (d, J=6.0 Hz, 3H), 1.04 (d, J=6.0 Hz, 3H). LCMS: 493.1 [M+H]⁺.

178: ¹H NMR (400 MHz, CD₃OD) δ 7.16 (s, 1H), 7.14-7.01 (m, 3H), 6.81-6.79 (m, 3H), 4.92 (s, 1H), 4.80-4.78 (m, 2H), 4.57-4.36 (m, 2H), 3.98-3.96 (m, 2H), 3.88-3.70 (m, 1H), 3.69-3.58 (m, 1H), 3.52-3.49 (m, 2H), 3.22-3.19 (m, 2H), 3.15-3.04 (m, 1H), 2.85-2.83 (m, 4H), 2.76-2.52 (m, 2H), 1.44 (d, J=6.0 Hz, 3H), 1.04 (d, J=6.0 Hz, 3H). LCMS: 493.1 [M+H]⁺.

Example 179 and 180 2,2-Difluoro-3-((1S,3S)-1-(4-(2-(3-(fluoromethyl)azetidin-1-yl)ethoxy)phenyl)-6-((R)-1-hydroxyethyl)-3-methyl-3,4-dihydroisoquinolin-2(1H)-yl)propan-1-ol 179 and 2,2-Difluoro-3-((1S,3S)-1-(4-(2-(3-(fluoromethyl)azetidin-1-yl)ethoxy)phenyl)-6-((S)-1-hydroxyethyl)-3-methyl-3,4-dihydroisoquinolin-2(1H)-yl)propan-1-ol 180

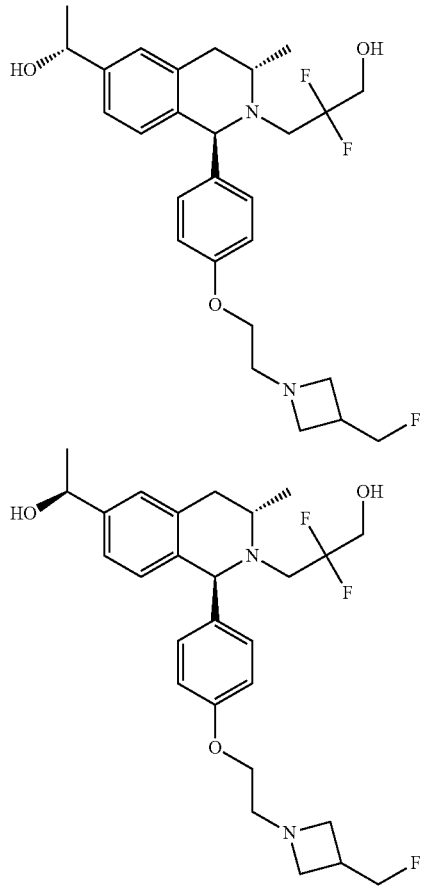

Following a similar procedure to that of Example 177 and 178, Examples 179 and 180 were synthesized from 1-((1S,3S)-2-(3-((tert-butyldiphenylsilyl)oxy)-2,2-difluoropropyl)-1-(4-(2-(3-(fluoromethyl)azetidin-1-yl)ethoxy)phenyl)-3-methyl-1,2,3,4-tetrahydroisoquinolin-6-yl)ethanone.

179: ¹H NMR (400 MHz, CD₃OD) δ 7.16 (s, 1H), 7.12-7.04 (m, 3H), 6.85-6.75 (m, 3H), 4.93-4.91 (m, 2H), 4.78 (q, J=6.4 Hz, 1H), 4.56-4.39 (m, 2H), 3.96 (t, J=5.2 Hz, 2H), 3.82-3.75 (m, 1H), 3.71-3.58 (m, 1H), 3.52 (t, J=8.0 Hz, 2H), 3.21 (t, J=7.6 Hz, 2H), 3.17-3.04 (m, 1H), 2.92-2.79 (m, 4H), 2.74-2.55 (m, 2H), 1.44 (d, J=6.4 Hz, 3H), 1.03 (d, J=6.4 Hz, 3H). LCMS: 493.1 [M+H]⁺.

180: ¹H NMR (400 MHz, CD₃OD) δ 7.16 (s, 1H), 7.13-7.04 (m, 3H), 6.85-6.77 (m, 3H), 4.93-4.91 (m, 2H), 4.79 (q, J=6.4 Hz, 1H), 4.55-4.40 (m, 2H), 3.97 (t, J=5.2 Hz, 2H), 3.80-3.70 (m, 1H), 3.70-3.60 (m, 1H), 3.52 (t, J=7.6 Hz, 2H), 3.21 (t, J=7.6 Hz, 2H), 3.18-3.04 (m, 1H), 2.92-2.79 (m, 4H), 2.74-2.55 (m, 2H), 1.44 (d, J=6.4 Hz, 3H), 1.04 (d, J=6.8 Hz, 3H). LCMS: 493.1 [M+H]⁺.

Example 901 Breast Cancer Cell ERa High Content Fluorescence Imaging Degradation Assay MCF7 breast cancer cells were seeded on day 1 at a density of 10,000 cells per well in 384 well poly-lysine coated tissue culture plate (Greiner #T-3101-4), in 50 µL/well RPMI (phenol red free), 10% FBS (Charcoal stripped), containing L-glutamine. On day 2, compounds were prepared at 2 compound source concentrations: 100 µM and 1 µM (ultimately to give 2 overlapping titration curves), in a Labcyte low dead volume plate, 10 µL/well, and 10 µL of DMSO in designated wells for backfill, and 5 µM Fulvestrant (control compound) in designated wells. Compounds and controls were dispensed using a Labcyte Echo acoustic dispenser to dispense compounds with a predefined serial dilution (1.8×, 10 point, in duplicate) and appropriate backfill and control compounds (final total volume transferred was 417.5 nL and compound dispense volume ranges from 2.5 nL to 417.5 nL; 0.84% DMSO (v/v) final), ultimately producing a concentration range from 0.05 nM to 835 nM. Cell plates were incubated at 37° C., for 4 hours. Fixation and permeabilization were carried out using a Biotek EL406 plate washer and dispenser as follows. Cells were fixed by addition of 15 µL of 16% paraformaldehyde (Electron Microscopy Sciences #15710-S) directly to the 50 µL cell culture medium in each well using the peristaltic pump 5 µL cassette on a Biotek EL406 (final concentration of formaldehyde was 3.7% w/v). Samples were incubated 30 minutes. Well contents was aspirated and 50 µL/well of Phosphate Buffered Saline (PBS) containing 0.5% w/v bovine serum albumen, 0.5% v/v Triton X-100 (Antibody Dilution Buffer) was added to each well. Samples were incubated for 30 minutes. Well contents were aspirated and washed 3 times with 100 µL/well of PBS. Immunofluorescence staining of estrogen receptor alpha (ESR1) was carried out using a Biotek EL406 plate washer and dispenser as follows. The well supernatant was aspirated from the wells and 25 µL/well of anti-ESR1 mAb (F10) (Santa Cruz sc-8002) diluted 1:1000 in Antibody Dilution Buffer was dispensed. Samples were incubated for 2 hours at room temperature. Samples were washed 4 times with 100 µL/well of PBS. 25 µL (microliters)/well of secondary antibody solution (Alexafluor® 488 conjugate anti-mouse IgG (LifeTechnologies #A21202) diluted 1:1000 and Hoechst 33342 1 µg/mL diluted in Antibody Dilution Buffer) were dispensed into each well. Samples were incubated for 2 hours at room temperature. Samples were washed 3 times with 100 µL/well of PBS using a Biotek EL406. Quantitative fluorescence imaging of ESR1 was carried out using a Cellomics Arrayscan V® (Thermo). Fluorescence images of the samples (Channel 1: XF53 Hoechst (DNA stain); Channel 2: XF53 FITC (ESR1 stain)) were acquired using a Cellomics VTI Arrayscan using the Bioapplication "Compartmental Analysis" using the auto-exposure (based on DMSO control wells) setting "peak target percentile" set to 25% target saturation for both channels. Channel 1 (DNA stain) was used to define the nuclear region (Circ). Measurements of "Mean_CircAvgIntCh2", which is the Alexafluor 488 fluorescence intensity (ESR1) within the nuclear region, was measured on a per cell basis and averaged over all the measured cells. Data analysis was carried out using Genedata Screener Software, with DMSO and 5 nM Fulvestrant treated samples being used to define the 0% and 100% changes in ESR1. The "Robust Fit" method was used to define the inflexion point of curve ($EC_{50}$) and the plateau of the maximal effect (Sinf). Degradation data for exemplary Formula I compounds is reported as ER-alpha MCF7 HCS S (%) values in Table 1.

Example 902 In Vitro Cell Proliferation Assay

Efficacy of estrogen receptor modulator compounds and chemotherapeutic compounds are measured by a cell proliferation assay employing the following protocol (Mendoza et al (2002) Cancer Res. 62:5485-5488).

The CellTiter-Glo® Luminescent Cell Viability Assay is a homogeneous method to determine the number of viable cells in culture based on quantitation of the ATP present, which signals the presence of metabolically active cells. The CellTiter-Glo® Assay is designed for use with multiwell plate formats, making it ideal for automated high-throughput screening (HTS), cell proliferation and cytotoxicity assays. The homogeneous assay procedure involves adding a single reagent (CellTiter-Glo® Reagent) directly to cells cultured in serum-supplemented medium. Cell washing, removal of medium or multiple pipetting steps are not required. The Cell Titer-Glo® Luminescent Cell Viability Assay, including reagents and protocol are commercially available (Promega Corp., Madison, Wis., Technical Bulletin TB288).

The assay assesses the ability of compounds to enter cells and inhibit cell proliferation. The assay principle is based on the determination of the number of viable cells present by quantitating the ATP present in a homogenous assay where addition of the Cell Titer-Glo® reagent results in cell lysis and generation of a luminescent signal through the luciferase reaction. The luminescent signal is proportional to the amount of ATP present.

Procedure: Day 1—Seed Cell Plates (384-well black, clear bottom, microclear, TC plates with lid from Falcon #353962), Harvest cells, Seed cells at 1000 cells per 54 µl per well into 384 well Cell Plates for 3 days assay. Cell Culture Medium: RPMI or DMEM high glucose, 10% Fetal Bovine Serum, 2 mM L-Glutamine, P/S. Incubate O/N (overnight) at 37° C., 5% $CO_2$.

Day 2—Add Drug to Cells, Compound Dilution, DMSO Plates (serial 1:2 for 9 points). Add 20 µl of compound at 10 mM in the 2nd column of 96 well plate. Perform serial 1:2 across the plate (10 µl+20 µl 100% DMSO) for a total of 9 points using Precision Media Plates 96-well conical bottom polypropylene plates from Nunc (cat. #249946) (1:50 dilution). Add 147 µl of Media into all wells. Transfer 3 µl of DMSO+compound from each well in the DMSO Plate to each corresponding well on Media Plate using Rapidplate® (Caliper, a Perkin-Elmer Co.). For 2 drug combination studies, transfer one drug 1.5 µl of DMSO+compound from each well in the DMSO Plate to each corresponding well on Media Plate using Rapidplate. Then, transfer another drug 1.5 µl to the medium plate.

Drug Addition to Cells, Cell Plate (1:10 dilution): Add 6 µl of media+compound directly to cells (54 µl of media on the cells already). Incubate 3 days at 37° C., 5% $CO_2$ in an incubator that will not be opened often.

Day 5—Develop Plates, Thaw Cell Titer Glo Buffer at room temperature: Remove Cell Plates from 37° C. and equilibrate to room temperature for about 30 minutes. Add Cell Titer-Glo® Buffer to Cell Titer-Glo® Substrate (bottle to bottle). Add 30 µl Cell Titer-Glo® Reagent (Promega cat. #G7572) to each well of cells. Place on plate shaker for about 30 minutes. Read luminescence on Analyst HT Plate Reader (half second per well).

Cell viability assays and combination assays: Cells were seeded at 1000-2000 cells/well in 384-well plates for 16 h. On day two, nine serial 1:2 compound dilutions were made in DMSO in a 96 well plate. The compounds were further diluted into growth media using a Rapidplate® robot (Zymark Corp., Hopkinton, Mass.). The diluted compounds were then added to quadruplicate wells in 384-well cell plates and incubated at 37° C. and 5% $CO_2$. After 4 days, relative numbers of viable cells were measured by luminescence using Cell Titer-Glo® (Promega) according to the manufacturer's instructions and read on a Wallac Multilabel Reader® (PerkinElmer, Foster City). EC50 values were calculated using Prism® 4.0 software (GraphPad, San Diego). Drugs in combination assays were dosed starting at 4+ $EC_{50}$ concentrations. If cases where the EC50 of the drug was ≥2.5 µM, the highest concentration used was 10 µM. Estrogen receptor modulator compounds and chemotherapeutic agents were added simultaneously or separated by 4 hours (one before the other) in all assays.

An additional exemplary in vitro cell proliferation assay includes the following steps:

1. An aliquot of 100 µl of cell culture containing about $10^4$ cells (see Table 3 for cell lines and tumor type) in medium was deposited in each well of a 384-well, opaque-walled plate.

2. Control wells were prepared containing medium and without cells.

3. The compound was added to the experimental wells and incubated for 3-5 days.

4. The plates were equilibrated to room temperature for approximately 30 minutes.

5. A volume of CellTiter-Glo® Reagent equal to the volume of cell culture medium present in each well was added.

6. The contents were mixed for 2 minutes on an orbital shaker to induce cell lysis.

7. The plate was incubated at room temperature for 10 minutes to stabilize the luminescence signal.

8. Luminescence was recorded and reported in graphs as RLU=relative luminescence units.

9. Analyze using the Chou and Talalay combination method and Dose-Effect Analysis with CalcuSyn® software (Biosoft, Cambridge, UK) in order to obtain a Combination Index.

Alternatively, cells were seeded at optimal density in a 96 well plate and incubated for 4 days in the presence of test compound. Alamar Blue™ was subsequently added to the assay medium, and cells were incubated for 6 h before reading at 544 nm excitation, 590 nm emission. $EC_{50}$ values were calculated using a sigmoidal dose response curve fit.

Alternatively, Proliferation/Viability was analyzed after 48 hr of drug treatment using Cell Titer-Glo® reagent (Promega Inc., Madison, Wis.). DMSO treatment was used as control in all viability assays. $IC_{50}$ values were calculated using XL fit software (IDBS, Alameda, Calif.)

The cell lines were obtained from either ATCC (American Type Culture Collection, Manassas, Va.) or DSMZ (Deutsche Sammlung von Mikroorganismen and Zellkulturen GmbH, Braunschweig, Del.). Cells were cultured in RPMI 1640 medium supplemented with 10% fetal bovine serum, 100 units/ml penicillin, 2 mM L-glutamine, and 100 mg/ml streptomycin (Life Technology, Grand Island, N.Y.) at 37° C. under 5% $CO_2$.

Example 903 MCF7 In Vitro Cell Proliferation Assay

MCF7 cells were washed with PBS and plated in RPMI 1640 (Gibco 11835-030 [-phenol+glutamine]) and 10% Charcoal Stripped FBS (Gibco 12676-029), in poly-lysine coated 384 well tissue culture plates (Greiner), at 25,000 cells/ml, 40 µl/well, and incubated overnight. Compounds were prepared in serial dilution in DMSO at 500-fold the final desired concentration using a Biomek-FX and diluted 50-fold in RPMI 1640. The control compound fulvestrant and negative control dimethylsulfoxide were also prepared in a similar manner. 5 ul of each individual compound concentration and each control compound was transferred to the cell plate. Fulvestrant was added to control wells at a final concentration of 100 nM. DMSO was added to negative control wells (0.2% v/v). Five microliters (5 µl) of 1 nM Estradiol (in phenol red free RPMI 1640 (Gibco 11835-030) was added to each well of the cell plate (except no estradiol control wells). Cells were incubated for 72 hours then lysed using Cell TiterGlo reagent (Promega #G7572) 40 µl/well and the luminescence was measured on an Envision (Perkin Elmer) plate reader. Data were analyzed using Genedata Screener software, using DMSO and Fulvestrant treated samples to define 0% and 100% inhibition and EC50 values were calculated using curve fitting using Robust method.

Example 904 ERa Co-Activator Peptide Antagonist Assay

Test compounds were prepared at 1 mM in DMSO and serially diluted in a 12 point, 1 to 3-fold titration using a Biomek FX in 384 well clear V-bottom polypropylene plates (Greiner cat #781280). A 3× compound intermediate dilution was prepared by mixing 1 mL of each concentration of the compound serial dilution with 32.3 mL of TR-FRET Coregulator Buffer E (Life Technologies PV4540). 2 mL of the 3× compound intermediate dilution was transferred to a 1536-well (Aurora Biotechnologies MaKO 1536 Black Plate, #00028905) using a Biomek FX. A Bioraptr Dispenser® (Beckman Coulter) was used to dispense: 2 mL per well of "3× ERa solution": 22 nM ERa (human estrogen receptor alpha, GST-tagged. ESR1 ligand binding domain, spanning residues S282-V595, either wild-type sequence or containing the mutations: Y537S or D538G) in TR-FRET Coregulator Buffer E containing 7.5 mM dithiothreitol (DTT); and 2 mL of 3× Assay mix (750 nM Fluorescein-PGC1a peptide sequence; Life Technologies PV4421), 12 nM Estradiol, 15 nM Anti-GST Tb-labeled antibody in TR-FRET Coregulator Buffer E (with 7.5 mM DTT). "No receptor" control wells received buffer without GST-ERa protein. Plates were centrifuged at 1800 rpm for 20 seconds in V-spin centrifuge and incubated for 2 hours at room temperature with the plates covered. Measurements were made using a Perkin Elmer EnVision Fluorescence Reader using TR-FRET setting (Top mirror: Perkin Elmer Lance/DELFIA Dual emission (PE #2100-4160); Excitation filter: Perkin Elmer UV (TFR) 340 nm (PE 42100-5010); Emission filters: Chroma 495 nm/1.0 nm and 520 nm/25 nm (Chroma #PV003 filters for LanthaScreen, 25 mm diameter for EnVision;) Excitation light: 100%; Delay: 100 us; Window time: 200; Number of sequential windows: 1; Time between flashes: 2000 us; Number of flashes: 100; Number of flashes ($2^{nd}$ detector): 100. Percentage inhibition values were calculated relative to no compound (DMSO only) controls and a "no ERa controls", Curve fitting and $IC_{50}$ calculations were carried out using Genedata Screener software.

Example 905 In Vivo Mouse Tumor Xenograft Efficacy

Mice: Female severe combined immunodeficiency mice (Fox Chase SCID®, C.B-17/IcrHsd, Harlan) or nude mice (Taconic Farms, Harlan) are 8 to 9 weeks old and had a BW range of 15.1 to 21.4 grams on Day 0 of the study. The animals are fed ad libitum water (reverse osmosis, 1 ppm Cl) and NIH 31 Modified and Irradiated Lab Diet® consisting of 18.0% crude protein, 5.0% crude fat, and 5.0% crude fiber. The mice are housed on irradiated ALPHA-Dri® Bed-O'Cobs® Laboratory Animal Bedding in static microisolators on a 12-hour light cycle at 21-22° C. (70-72° F.) and 40-60% humidity. PRC specifically complies with the recommendations of the Guide for Care and Use of Laboratory Animals with respect to restraint, husbandry, surgical procedures, feed and fluid regulation, and veterinary care. The animal care and use program at PRC is accredited by the Association for Assessment and Accreditation of Laboratory Animal Care International (AAALAC), which assures compliance with accepted standards for the care and use of laboratory animals.

Tumor Implantation: Xenografts are initiated with cancer cells. Cells are cultured in RPMI 1640 medium supplemented with 10% fetal bovine serum, 2 mM glutamine, 100 units/mL penicillin, 100 µg/mL streptomycin sulfate and 25 µg/mL gentamicin. The cells are harvested during exponential growth and resuspended in phosphate buffered saline (PBS) at a concentration of $5 \times 10^6$ or $10 \times 10^6$ cells/mL depending on the doubling time of the cell line. Tumor cells are implanted subcutaneously in the right flank, and tumor growth is monitored as the average size approached the target range of 100 to 150 mm3. Twenty-one days after tumor implantation, designated as Day 0 of the study, the mice are placed into four groups each consisting of ten mice with individual tumor volumes ranging from 75-172 mm3 and group mean tumor volumes from 120-121 mm3 (see Appendix A). Volume is calculated using the formula:

Tumor Volume (mm³)=($w^2 \times l$)/2, where $w$=width and $l$=length in mm of a tumor.

Tumor weight may be estimated with the assumption that 1 mg is equivalent to 1 mm3 of tumor volume.

Therapeutic Agents: Estrogen receptor modulator compounds and chemotherapeutic agents are typically prepared from dry powders, stored at room temperature, and protected from light. Drug doses are prepared weekly in 0.5% methylcellulose: 0.2% Tween 80 in deionized water ("Vehicle") and stored at 4° C. Vehicle (+) is solvent/buffer with ethynyl estradiol (ethinyl estradiol, EE2) at 0.1 mg/kg. Vehicle (−) is solvent/buffer without ethynyl estradiol. Doses of compounds are prepared on each day of dosing by diluting an aliquot of the stock with sterile saline (0.9% NaCl). All doses are formulated to deliver the stated mg/kg dosage in a volume of 0.2 mL per 20 grams of body weight (10 mL/kg).

Treatment: All doses are scaled to the body weights of the individual animals and provided by the route indicated.

Endpoint: Tumor volume is measured in 2 dimensions (length and width), using Ultra Cal IV calipers (Model 54 10 111; Fred V. Fowler Company), as follows: tumor volume (mm$^3$)=(length×width)×0.5 and analyzed using Excel version 11.2 (Microsoft Corporation). A linear mixed effect (LME) modeling approach is used to analyze the repeated measurement of tumor volumes from the same animals over time (Pinheiro J, et al. nlme: linear and nonlinear mixed effects models. R package version 3.1 92. 2009; Tan N, et al. Clin. Cancer Res. 2011; 17(6):1394-1404). This approach addresses both repeated measurements and modest dropouts due to any non-treatment-related death of animals before study end. Cubic regression splines are used to fit a nonlinear profile to the time courses of log 2 tumor volume at each dose level. These nonlinear profiles are then related to dose within the mixed model. Tumor growth inhibition as a percentage of vehicle control (% TGI) is calculated as the percentage of the area under the fitted curve (AUC) for the respective dose group per day in relation to the vehicle, using the following formula: % TGI=100×(1−AUC$_{dose}$/AUC$_{vch}$). Using this formula, a TGI value of 100% indicates tumor stasis, a TGI value of >1% but <100% indicates tumor growth delay, and a TGI value of >100% indicates tumor regression. Partial response (PR) for an animal is defined as a tumor regression of >50% but <100% of the starting tumor volume. Complete response (CR) was defined as 100% tumor regression (i.e., no measurable tumor) on any day during the study.

Toxicity: Animals are weighed daily for the first five days of the study and twice weekly thereafter. Animal body weights are measured using an Adventurer Pro® AV812 scale (Ohaus Corporation). Percent weight change is calculated as follows: body weight change (%)=[(weight$_{day\ new}$−weight$_{day\ 0}$)/weight$_{day\ 0}$]×100. The mice are observed frequently for overt signs of any adverse, treatment-related side effects, and clinical signs of toxicity recorded when observed. Acceptable toxicity is defined as a group mean body weight (BW) loss of less than 20% during the study and not more than one treatment-related (TR) death among ten treated animals. Any dosing regimen that results in greater toxicity is considered above the maximum tolerated dose (MTD). A death is classified as TR if attributable to treatment side effects as evidenced by clinical signs and/or necropsy, or may also be classified as TR if due to unknown causes during the dosing period or within 10 days of the last dose. A death is classified as NTR if there is no evidence that death was related to treatment side effects.

In-Vivo Xenograft Breast Cancer Model; (MCF-7; Tamoxifen-Sensitive):

Time release pellets containing 0.72 mg 17-0 Estradiol are subcutaneously implanted into nu/nu mice. MCF-7 cells were grown in RPMI containing 10% FBS at 5% CO$_2$, 37° C. Trypsinized cells are pelleted and re-suspended in 50% RPMI (serum free) and 50% Matrigel at 1×10$^7$ cells/mL. MCF-7 cells are subcutaneously injected (100 μL/animal) on the right flank 2-3 days post pellet implantation. Tumor volume (length×width$^2$/2) is monitored bi-weekly. When tumors reach an average volume of ~200 mm$^3$ animals are randomized and treatment is started. Animals are treated with vehicle or compound daily for 4 weeks. Tumor volume and body weight are monitored bi-weekly throughout the study.

In-Vivo Xenograft Breast Cancer Model; (Tamoxifen-Resistant Model):

Female nu/nu mice (with supplemental 17-β Estradiol pellets; 0.72 mg; 60 day slow release) bearing MCF-7 tumors (mean tumor volume 200 mm$^3$) are treated with tamoxifen (citrate) by oral gavage. Tumor volume (length×width$^2$/2) and body weight are monitored twice weekly. Following a significant anti-tumor response in which tumor volume remained static, evident tumor growth is first observed at approximately 100 days of treatment. At 120 days of treatment, tamoxifen dose is increased. Rapidly growing tumors are deemed tamoxifen resistant and selected for in vivo passage into new host animals. Tumor Fragments (~100 mm$^3$/animal) from the tamoxifen resistant tumors are subcutaneously implanted into the right flank of female nu/nu mice (with 17-β Estradiol pellets (0.72 mg; 60 day slow release)). Passaged tumors are maintained under constant Tamoxifen selection, and tumor volume (length×width$^2$/2) is monitored weekly. When tumor volume reached ~150-250 mm$^3$, animals are randomized into treatment groups (mean tumor volume 200 mm$^3$) and tamoxifen treatment is terminated. Animals are treated with vehicle or compound daily for 4 weeks. Tumor volume and body weight are monitored twice weekly for the duration of the study.

Example 906 Immature Uterine Wet Weight Assay

Female immature CD-IGS rats (21 days old upon arrival) are treated for three days. Animals are dosed daily for three days. For Antagonist Mode, Vehicle or test compound is administered orally by gavage followed 15 minutes later by an oral dose of 0.1 mg/kg Ethynyl Estradiol. For Agonist Mode, Vehicle or test compound is administered orally by gavage. On the fourth day 24 hours after dose, plasma is collected for pharmacokinetic analysis. Immediately following plasma collection, the animals are euthanized and the uterus removed and weighed.

Example 907 Adult Uterine Wet Weight-10 Day Assay

Female CD-IGS rats (69 days old, Charles River Laboratories) are purchased and split into groups. Group 1 is ovariectomized at the vendor (Charles River Laboratories) at 60 days of age and the study is started 2 weeks after surgery, while groups 2-8 were intact. Vehicle or test compound is administered orally for 10 days. Two hours after the 10$^{th}$ and final dose, cardiac punctures are performed and serum is collected for pharmacokinetic and estradiol analyses. Immediately following serum collection, the animals are euthanized and the uterus and ovaries removed and weighed. Uteri and ovaries from 2 animals per group are fixed in 10% neutral buffered formalin and paraffin embedded, sectioned and stained for H&E (SDPath). Stained tissues are analyzed and read by a board certified pathologist. Uteri and ovaries from 4 animals per group are flash frozen in liquid N$_2$ for transcriptional analysis, examining a select set of genes modulated by the estrogen receptor.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

We claim:
1. A compound selected from Formula I:

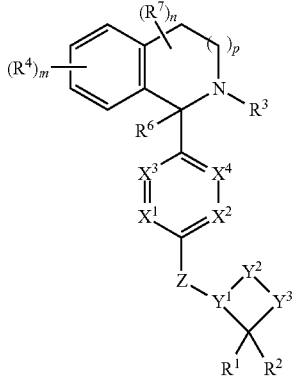

or a stereoisomer, tautomer, or pharmaceutically acceptable salt thereof, wherein:

$Y^1$ is —C($R^b$)— or N;
$Y^2$ is —CH$_2$— or —N($R^a$)—;
$Y^3$ is —N($R^a$)— or —C($R^b$)$_2$—;
where one of $Y^1$, $Y^2$ and $Y^3$ is N or —N($R^a$)—;
$R^a$ and $R^c$ are independently selected from H, $C_1$-$C_6$ alkyl, $C_1$-$C_6$ fluoroalkyl, allyl, propargyl, $C_3$-$C_6$ cycloalkyl, and $C_3$-$C_6$ heterocyclyl, optionally substituted with one or more groups independently selected from F, Cl, Br, I, CN, OH, OCH$_3$, and SO$_2$CH$_3$;
$R^b$ is independently selected from H, —O($C_1$-$C_3$ alkyl), $C_1$-$C_6$ alkyl, $C_1$-$C_6$ fluoroalkyl, allyl, propargyl, $C_3$-$C_6$ cycloalkyl, and $C_3$-$C_6$ heterocyclyl, optionally substituted with one or more groups independently selected from F, Cl, Br, I, CN, OH, OCH$_3$, and SO$_2$CH$_3$;
where at least one of $R^a$ and $R^b$ is —CH$_2$Cl, —CH$_2$F, —CHF$_2$, —CF$_3$, —CH$_2$CH$_2$F, —CH$_2$CHF$_2$, —CH$_2$CF$_3$, CH$_2$CH$_2$Cl, CH$_2$CH$_2$CH$_2$F, CH$_2$CH$_2$CHF$_2$, CH$_2$CH$_2$CF$_3$, or CH$_2$CH$_2$CH$_2$Cl;
$X^1$, $X^2$, $X^3$, and $X^4$ are independently selected from CR$^5$ and N; where none, one, or two of $X^1$, $X^2$, $X^3$, and $X^4$ is N;
Z is selected from O, S, S(O), S(O)$_2$, C(=O), CH(OH), $C_1$-$C_6$ alkyldiyl, CH(OH)—($C_1$-$C_6$ alkyldiyl), $C_1$-$C_6$ fluoroalkyldiyl, NR$^c$, NR$^c$—($C_1$-$C_6$ alkyldiyl), NR$^c$—($C_1$-$C_6$ fluoroalkyldiyl), O—($C_1$-$C_6$ alkyldiyl), and O—($C_1$-$C_6$ fluoroalkyldiyl);
$R^1$ and $R^2$ are independently selected from H, F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$Cl, —CH$_2$F, —CHF$_2$, —CH$_2$NH$_2$, —CH$_2$NHSO$_2$CH$_3$, —CH$_2$NHCH$_3$, —CH$_2$N(CH$_3$)$_2$, —CF$_3$, —CH$_2$CF$_3$, —CH$_2$CHF$_2$, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CONHCH$_2$CH$_3$, —CONHCH(CH$_3$)$_2$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, and morpholino;
$R^3$ is selected from $C_1$-$C_6$ alkyl, $C_1$-$C_6$ fluoroalkyl, allyl, propargyl, $C_3$-$C_6$ cycloalkyl, phenyl, $C_3$-$C_6$ heterocyclyl, $C_6$-$C_{20}$ aryl or $C_1$-$C_6$ heteroaryl, —CO—($C_1$-$C_6$ alkyl), —CO—($C_3$-$C_6$ cycloalkyl), —S(O)$_2$—($C_1$-$C_6$ alkyl), and —S(O)$_2$—($C_3$-$C_6$ cycloalkyl), optionally substituted with one or more groups independently selected from F, Cl, Br, I, CN, OH, OCH$_3$, and SO$_2$CH$_3$;
$R^4$ is independently selected from F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CH$_2$NH$_2$, —CH$_2$NHSO$_2$CH$_3$, —CH$_2$NHCH$_3$, —CH$_2$N(CH$_3$)$_2$, —CF$_3$, —CH$_2$CF$_3$, —CH$_2$CHF$_2$, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CONHCH$_2$CH$_3$, —CONHCH(CH$_3$)$_2$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, and morpholino; or two $R^4$ groups on vicinal carbon atoms form a five- or six-membered, fused carbocyclyl, heterocyclyl, or heteroaryl ring;
$R^5$ is selected from H, F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CH$_2$NH$_2$, —CH$_2$NHSO$_2$CH$_3$, —CH$_2$NHCH$_3$, —CH$_2$N(CH$_3$)$_2$, —CF$_3$, —CH$_2$CF$_3$, —CH$_2$CHF$_2$, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CONHCH$_2$CH$_3$, —CONHCH(CH$_3$)$_2$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, and morpholino;
$R^6$ is selected from H, F, and $C_1$-$C_6$ alkyl optionally substituted with one or more groups independently selected from F, Cl, Br, I, CN, OH, OCH$_3$, and SO$_2$CH$_3$;

$R^7$ is independently selected from F, and $C_1$-$C_6$ alkyl optionally substituted with one or more groups independently selected from F, Cl, Br, I, CN, OH, $OCH_3$, and $SO_2CH_3$;

m is selected from 0, 1, 2, 3, and 4;

n is selected from 0, 1, 2, 3, and 4; and p is 1 or 2;

where alkyldiyl, fluoroalkyldiyl, aryl, carbocyclyl, heterocyclyl, and heteroaryl are optionally substituted with one or more groups independently selected from F, Cl, Br, I, —CN, —$CH_3$, —$CH_2CH_3$, —$CH(CH_3)_2$, —$CH_2CH(CH_3)_2$, —$CH_2OH$, —$CH_2OCH_3$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —$CH_2OP(O)(OH)_2$, —$CH_2F$, —$CHF_2$, —$CF_3$, —$CH_2CF_3$, —$CH_2CHF_2$, —$CH(CH_3)CN$, —$C(CH_3)_2CN$, —$CH_2CN$, —$CH_2NH_2$, —$CH_2NHSO_2CH_3$, —$CH_2NHCH_3$, —$CH_2N(CH_3)_2$, —$CO_2H$, —$COCH_3$, —$CO_2CH_3$, —$CO_2C(CH_3)_3$, —$COCH(OH)CH_3$, —$CONH_2$, —$CONHCH_3$, —$CON(CH_3)_2$, —$C(CH_3)_2CONH_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —$OP(O)(OH)_2$, —$S(O)_2N(CH_3)_2$, —$SCH_3$, —$S(O)_2CH_3$, —$S(O)_3H$, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, and morpholino.

2. The compound of claim 1 having Formula Ia:

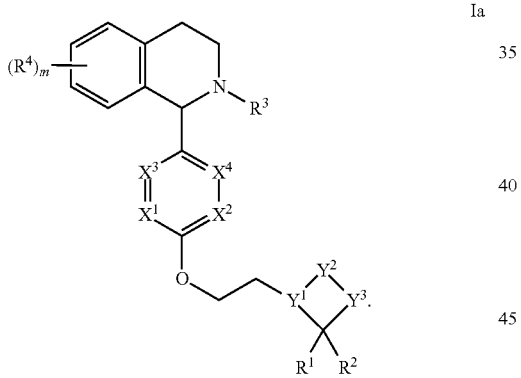

Ia

3. The compound of claim 2 having Formula Ib:

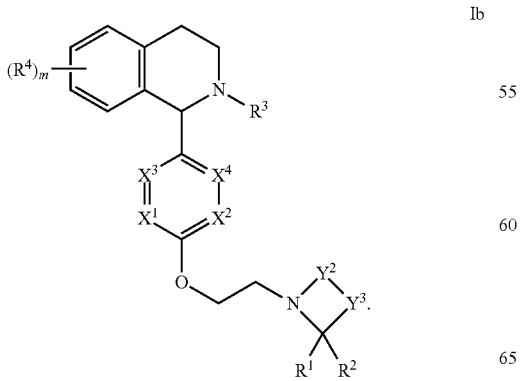

Ib

4. The compound of claim 1 having Formula Ic:

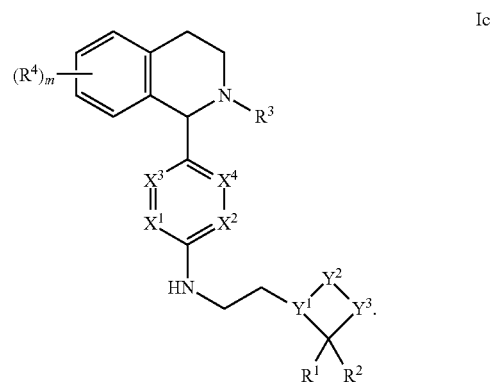

Ic

5. The compound of claim 4 having Formula Id:

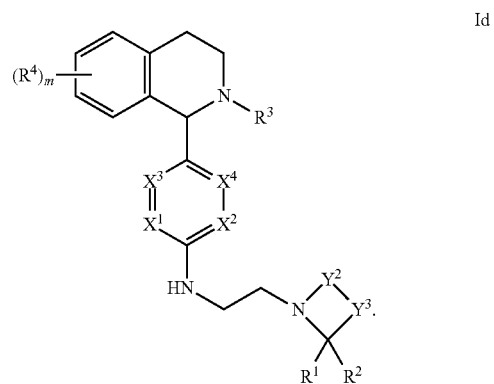

Id

6. The compound of claim 1 having Formula Ie:

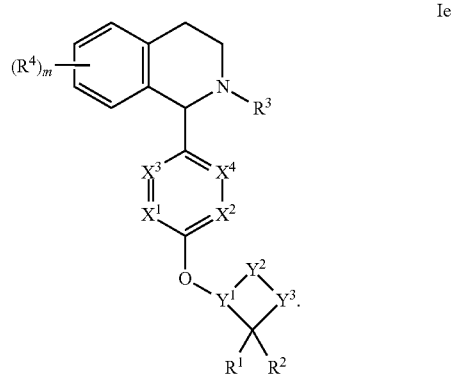

Ie

7. The compound of claim 6 having Formula If:

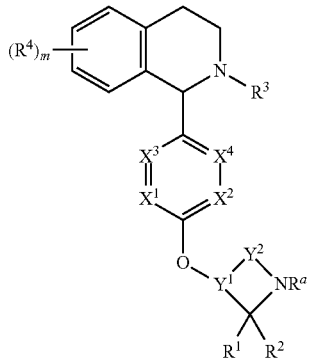

wherein $R^a$ is —CH$_2$Cl, —CH$_2$F, —CHF$_2$, —CF$_3$, —CH$_2$CH$_2$F, —CH$_2$CHF$_2$, —CH$_2$CF$_3$, or —CH$_2$CH$_2$CH$_2$F.

8. The compound of claim 1 having Formula Ig:

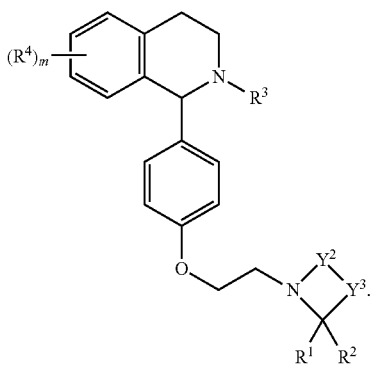

9. The compound of claim 8 having Formula Ih:

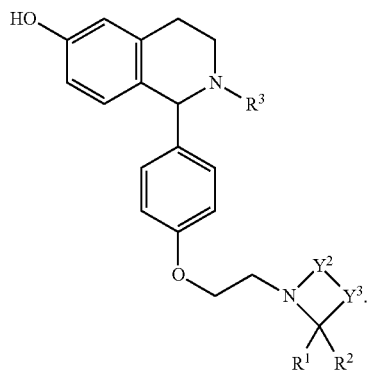

10. The compound of claim 9 selected from Formula Ii:

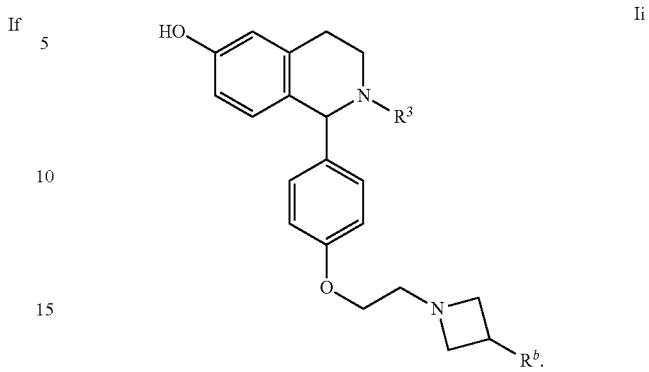

11. The compound of claim 1 wherein $R^a$ is selected from —CH$_2$Cl, —CH$_2$F, —CHF$_2$, —CF$_3$, —CH$_2$CH$_2$F, —CH$_2$CHF$_2$, —CH$_2$CF$_3$, and —CH$_2$CH$_2$CH$_2$F.

12. The compound of claim 1 wherein $Y^1$ is —C($R^b$)— and $Y^3$ is —N($R^a$)—.

13. The compound of claim 1 wherein $Y^1$ is N and $Y^3$ is —C($R^b$)$_2$—.

14. The compound of claim 1 wherein $Y^2$ is —CH$_2$—.

15. The compound of claim 1 wherein p is 1.

16. The compound of claim 1 wherein p is 2.

17. The compound of claim 1 wherein $Y^3$ is —N($R^a$)— and $R^a$ is —CH$_2$Cl, —CH$_2$F, —CHF$_2$, —CF$_3$, —CH$_2$CH$_2$F, —CH$_2$CHF$_2$, or —CH$_2$CF$_3$.

18. The compound of claim 1 wherein $X^1$, $X^2$, $X^3$, and $X^4$ are each CR$^5$ and R$^5$ is H or F.

19. The compound of claim 1 wherein one of $X^1$, $X^2$, $X^3$, and $X^4$ is N.

20. The compound of claim 1 wherein Z is O or O—(C$_1$-C$_6$ alkyldiyl).

21. The compound of claim 1 wherein $R^1$ and $R^2$ are H.

22. The compound of claim 1 wherein $R^3$ is C$_1$-C$_6$ fluoroalkyl.

23. The compound of claim 1 wherein $R^3$ is C$_6$-C$_{20}$ aryl.

24. The compound of claim 23 wherein $R^3$ is phenyl.

25. The compound of claim 1 wherein $R^4$ is OH, and m is 1.

26. The compound of claim 1 wherein two $R^4$ groups form a pyrazole ring.

27. The compound of claim 1 wherein $R^6$ is H.

28. The compound of claim 1 selected from the group consisting of:

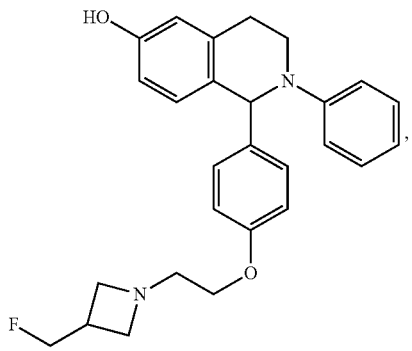

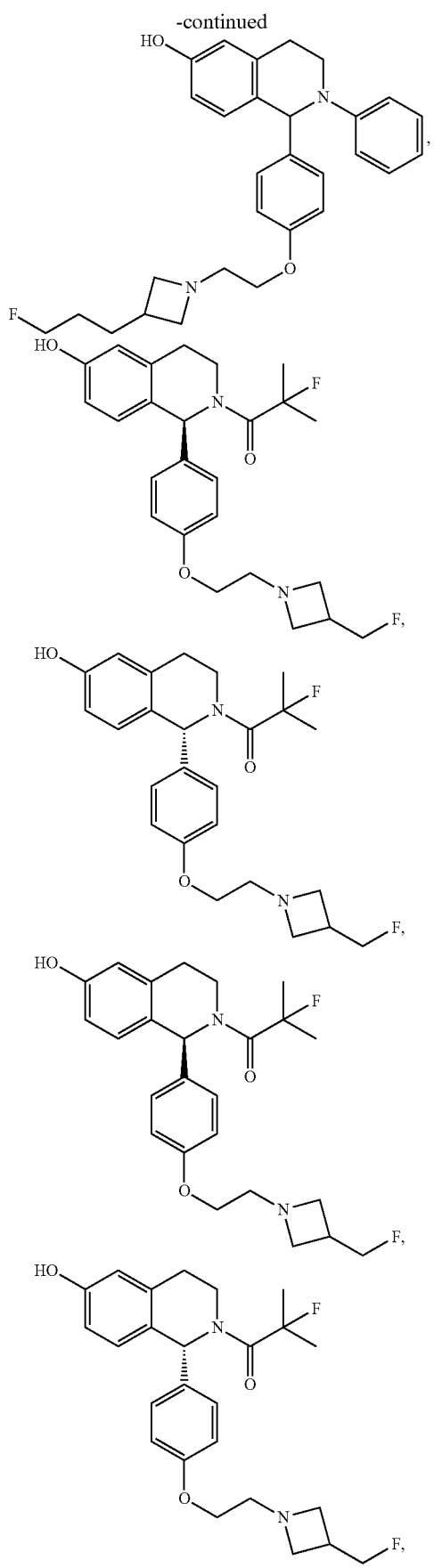
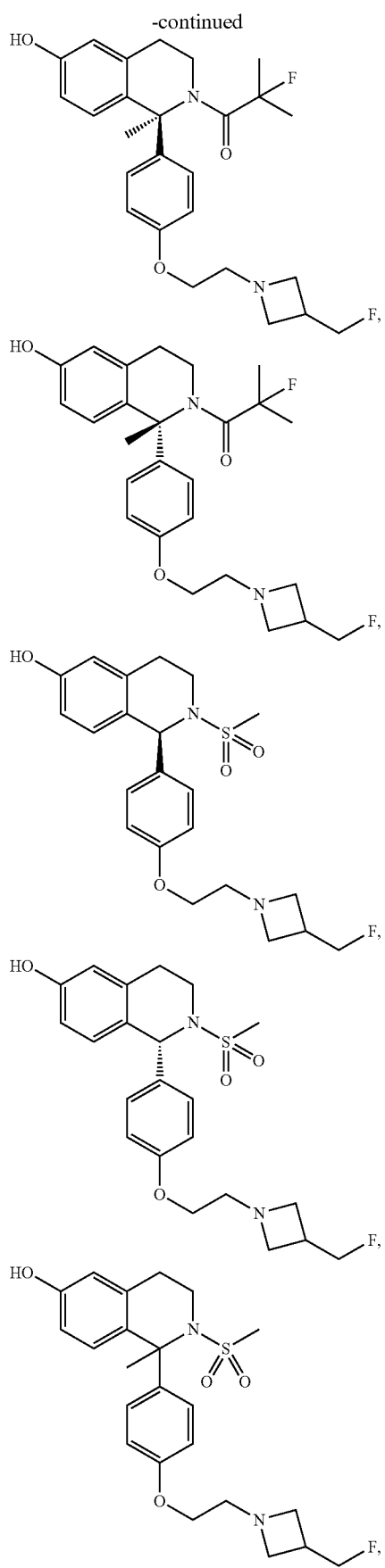

169
-continued
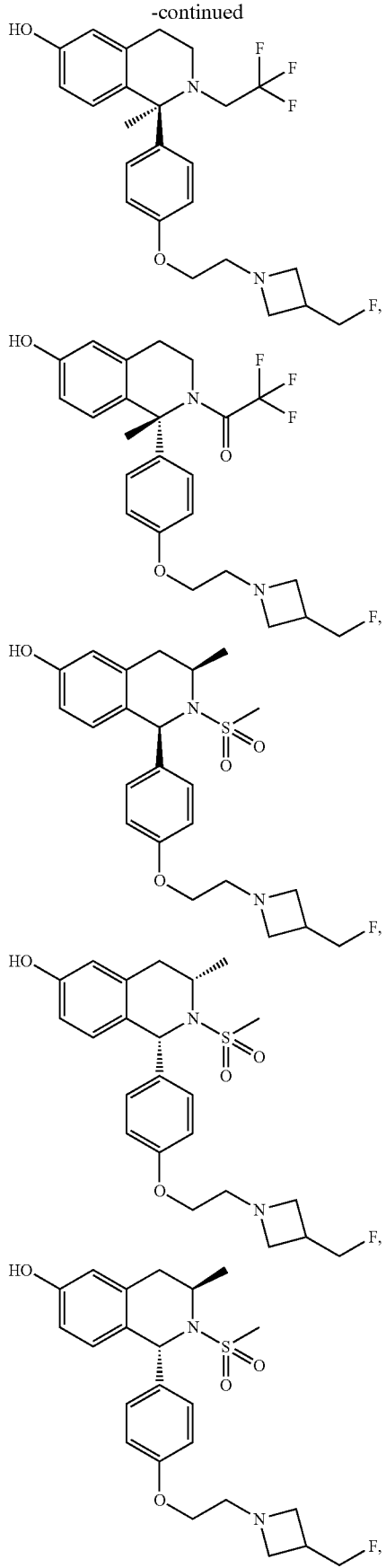
170
-continued
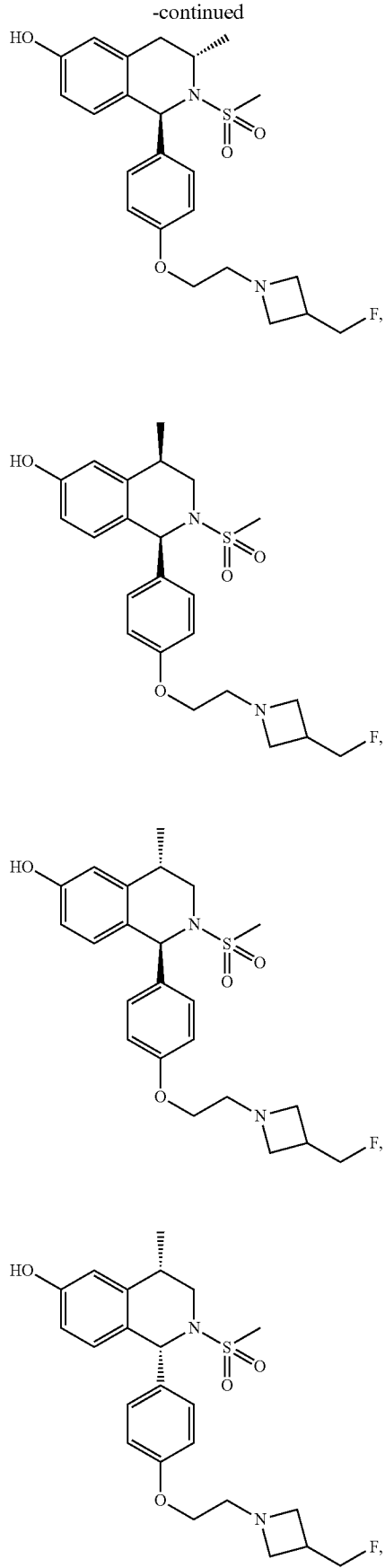

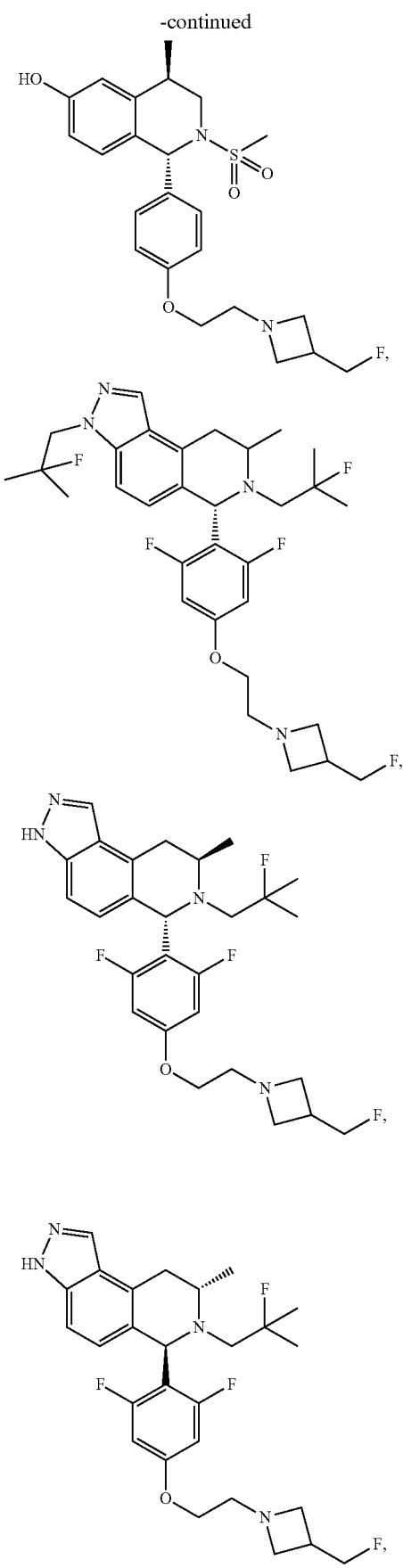
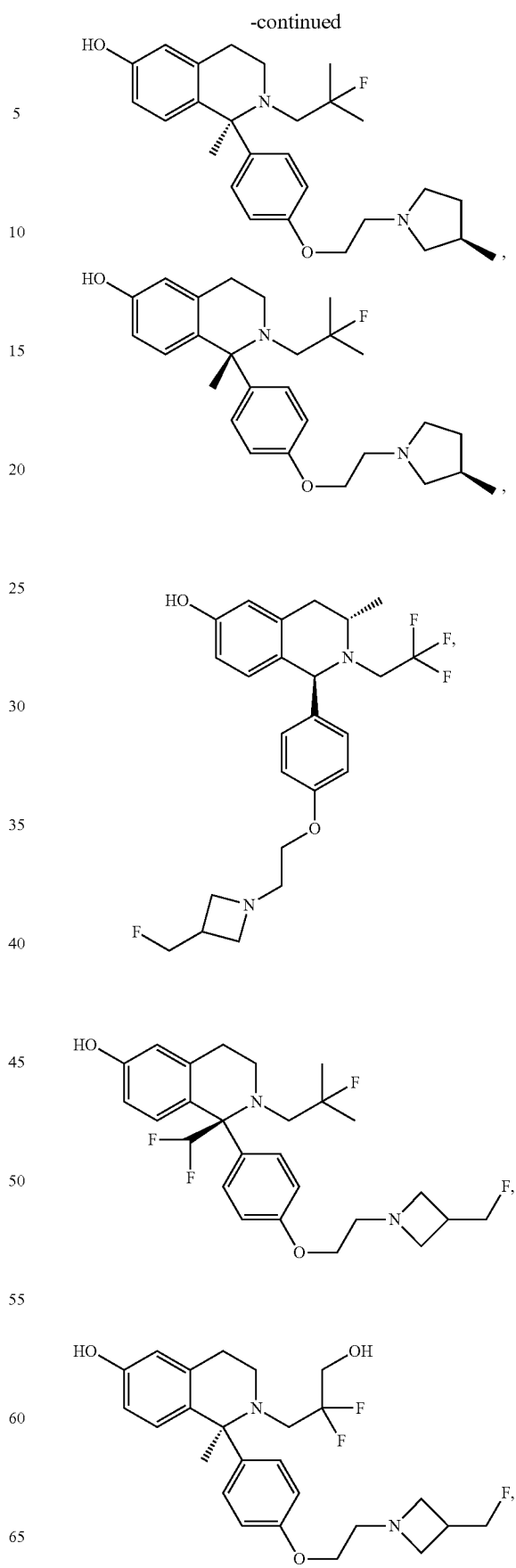

173
-continued
174
-continued
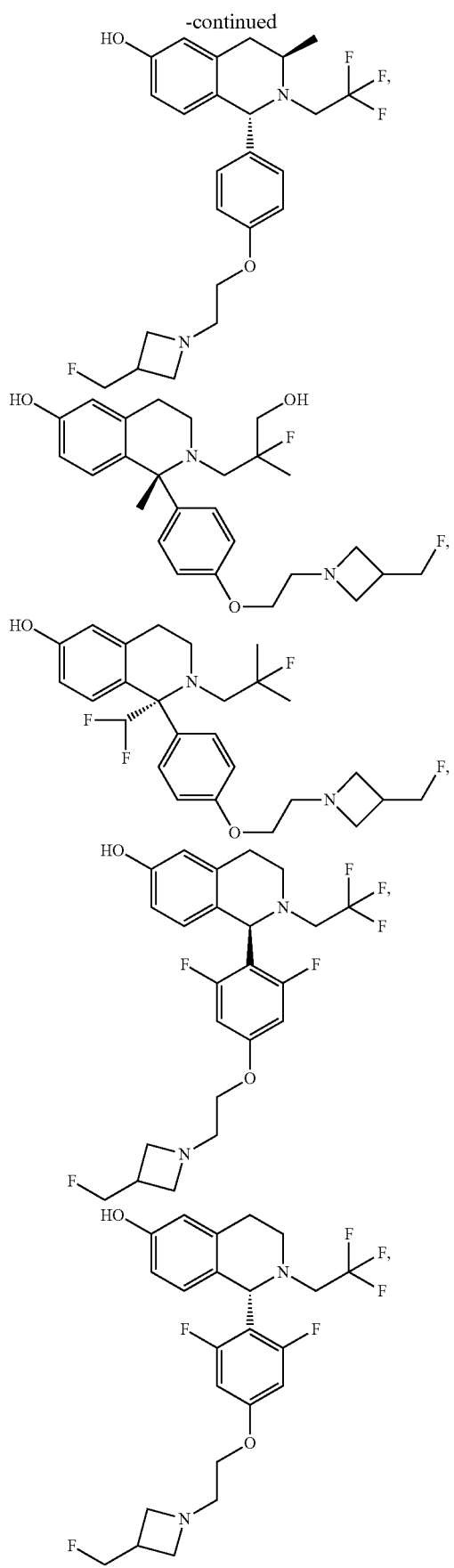
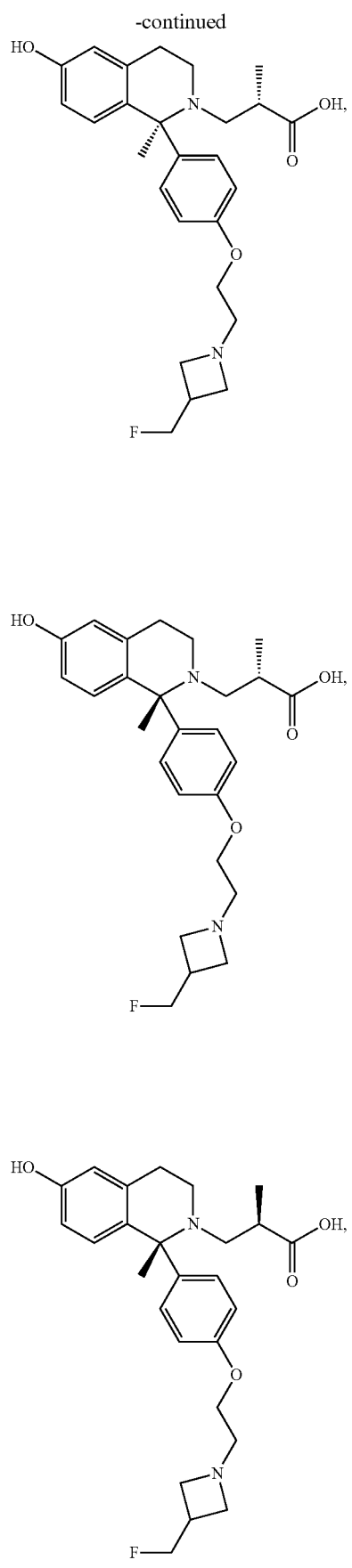

175
-continued
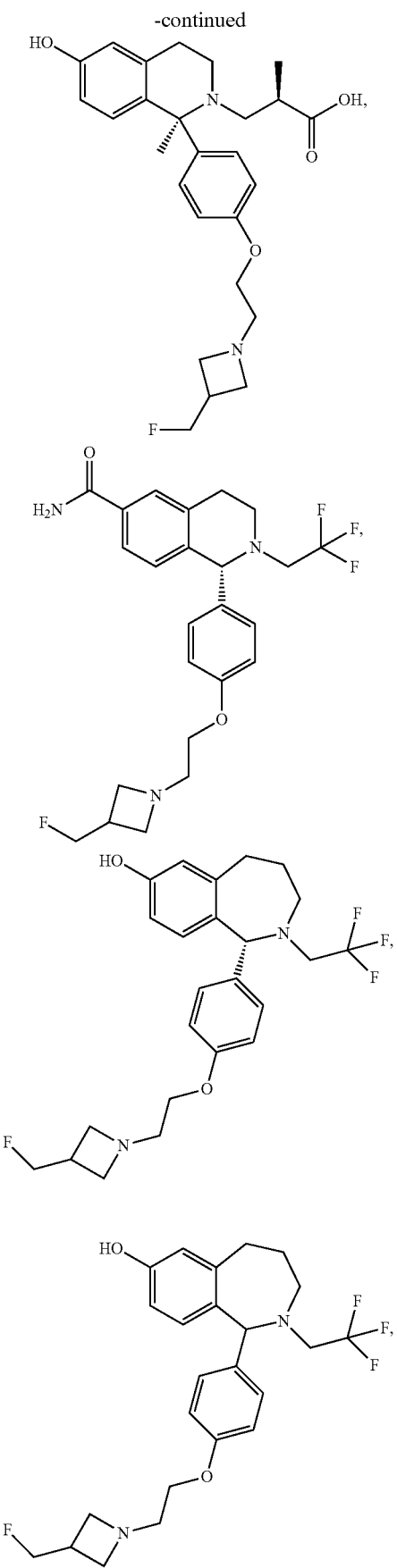
176
-continued
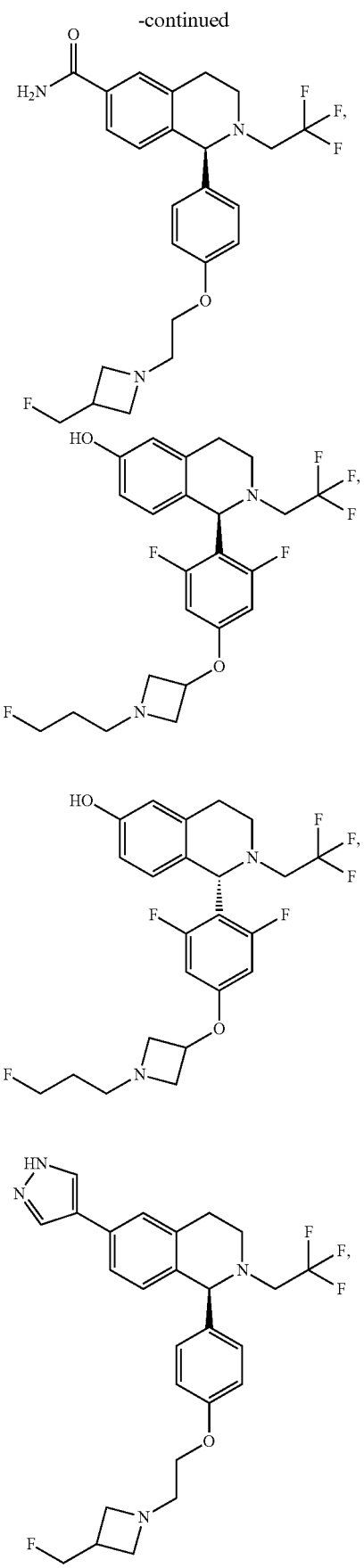

177
-continued
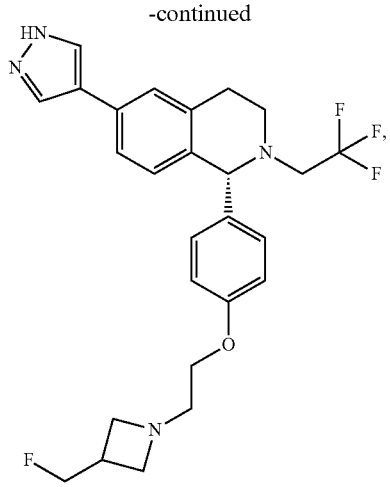
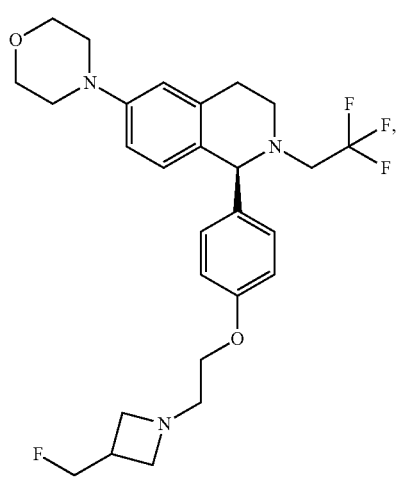
178
-continued
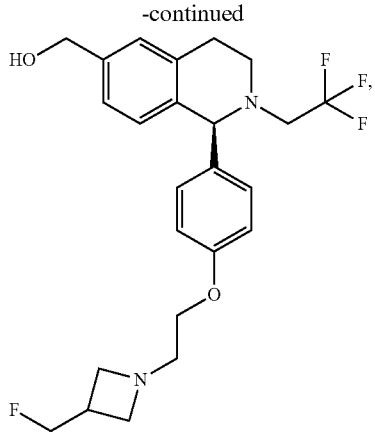
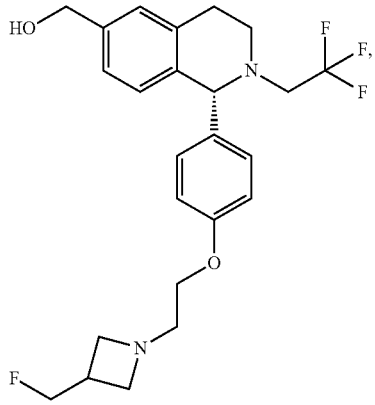
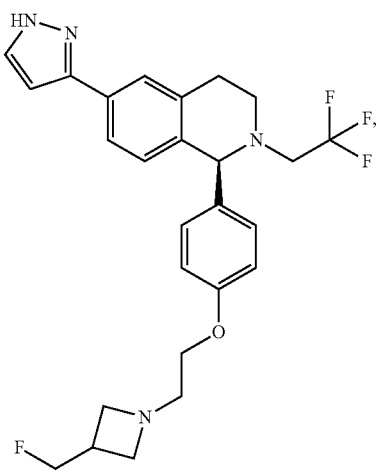

179
-continued
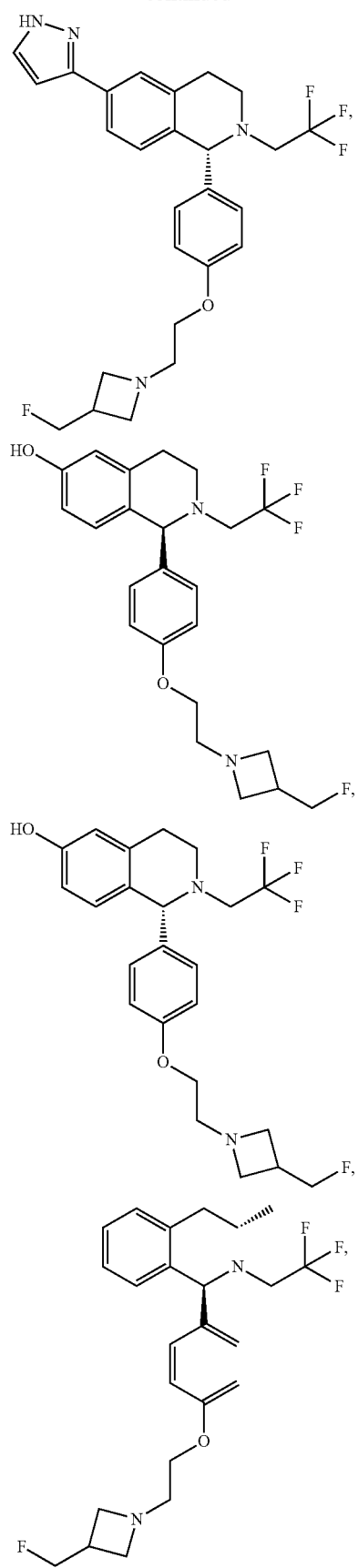
180
-continued
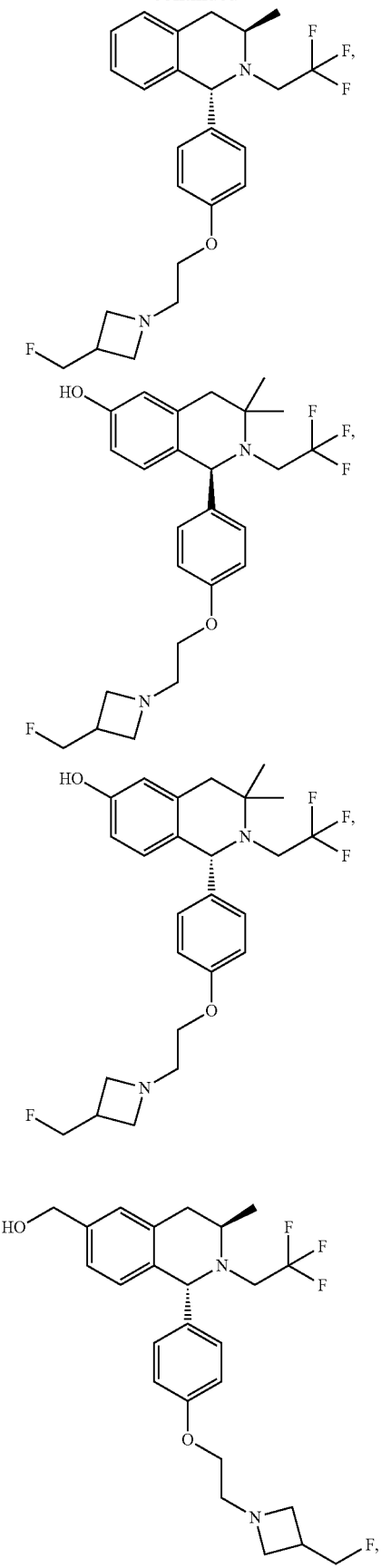

181
-continued
182
-continued
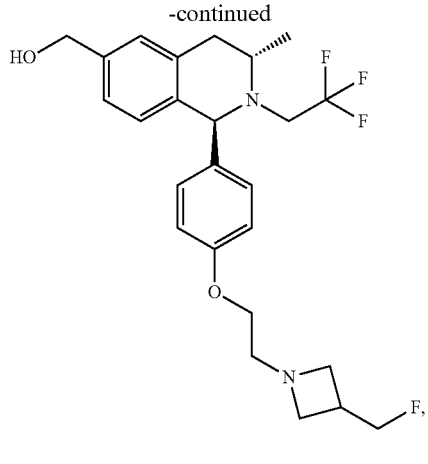
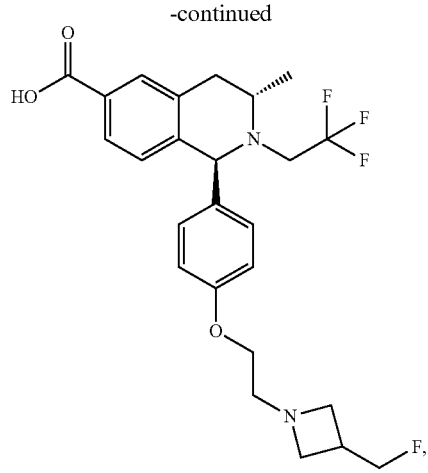
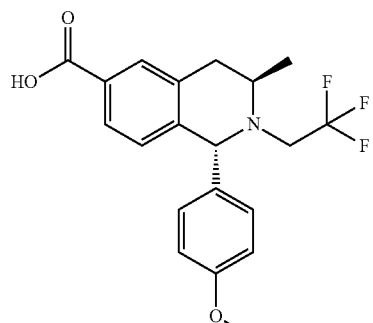
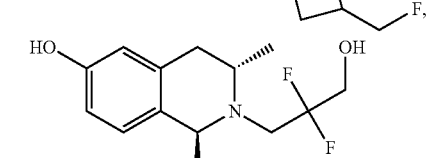
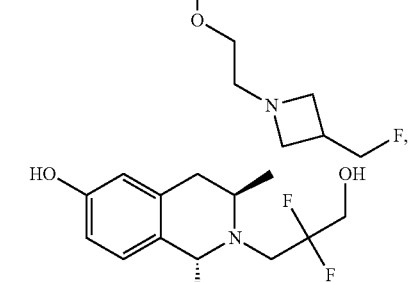
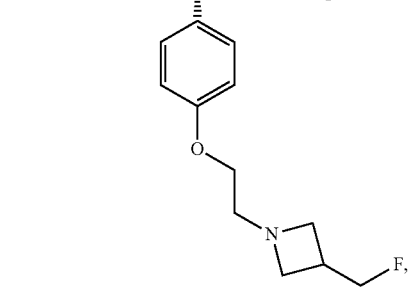

183
-continued
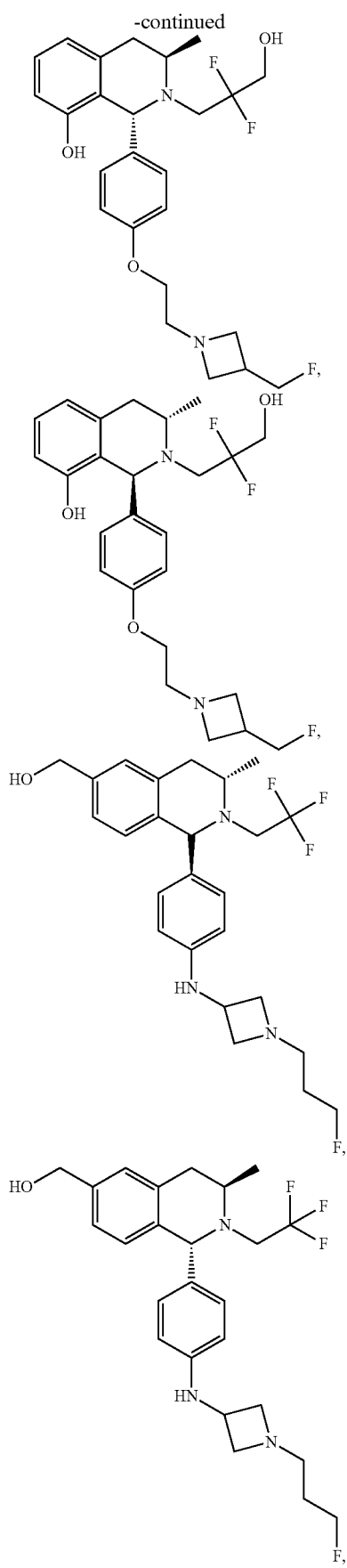
184
-continued
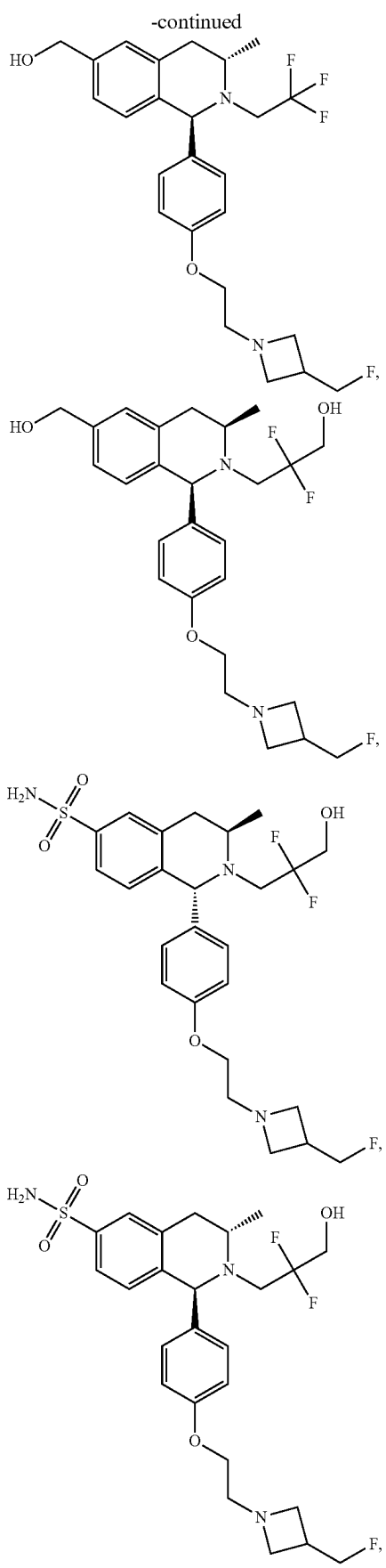

185
-continued

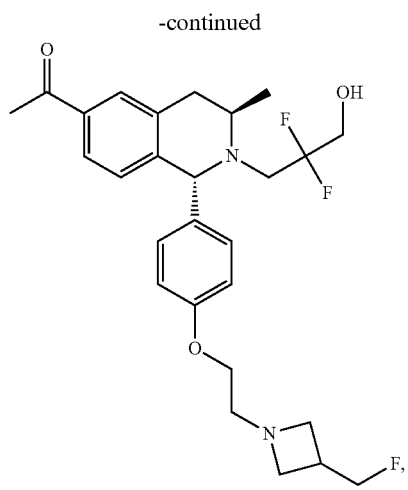

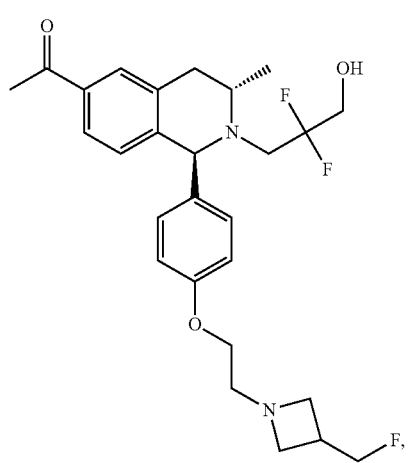

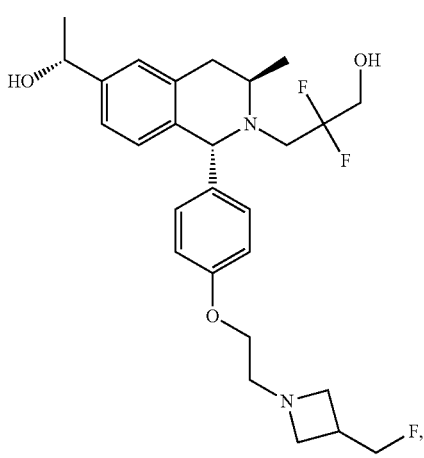

186
-continued

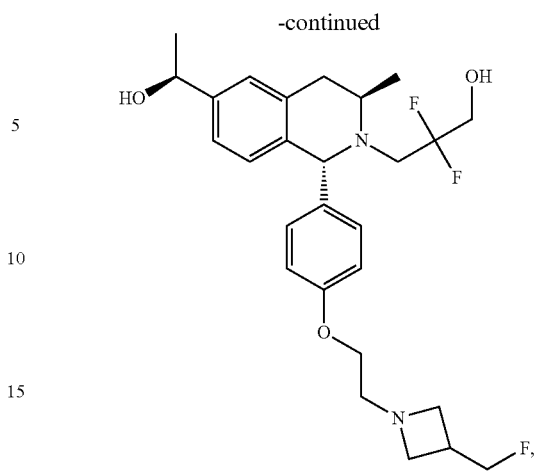

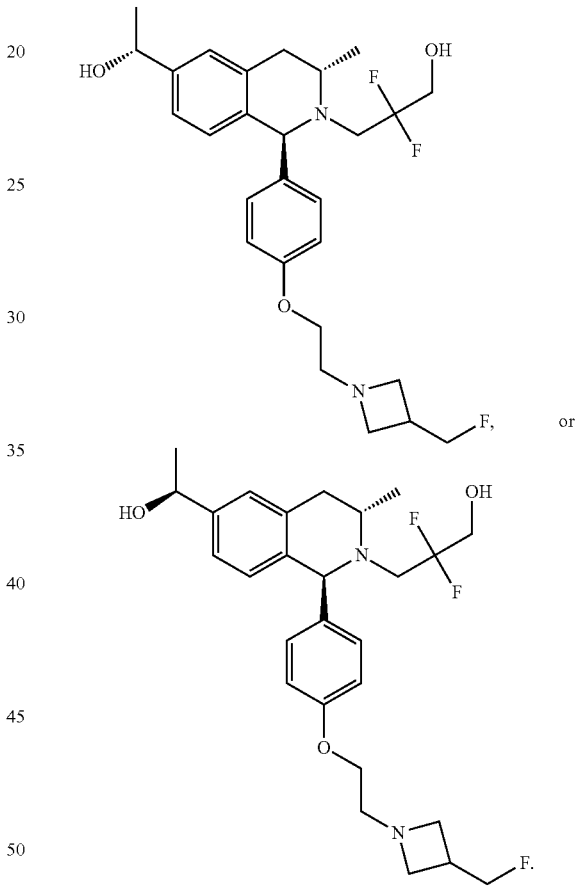

or

29. A pharmaceutical composition comprised of a compound of claim 1 and a pharmaceutically acceptable carrier, glidant, diluent, or excipient.

30. The pharmaceutical composition according to claim 29, further comprising a therapeutic agent.

31. A process for making a pharmaceutical composition which comprises combining a compound of claim 1 with a pharmaceutically acceptable carrier, glidant, diluent, or excipient.

32. A method of treating breast cancer in a patient having breast cancer, the method comprising administering a therapeutically effective amount of the pharmaceutical composition of claim 29 to said patient.

33. The method of claim 32 further comprising administering an additional therapeutic agent selected from an anti-inflammatory agent, an immunomodulatory agent, chemotherapeutic agent, an apoptosis-enhancer, a neurotropic factor, an agent for treating cardiovascular disease, an agent for treating liver disease, an anti-viral agent, an agent for treating blood disorders, an agent for treating diabetes, and an agent for treating immunodeficiency disorders.

* * * * *